United States Patent
Minamiguchi et al.

(10) Patent No.: US 9,889,136 B2
(45) Date of Patent: *Feb. 13, 2018

(54) TETRAHYDROPYRIDOPYRIMIDINE COMPOUND OR SALT THEREOF

(71) Applicant: TAIHO PHARMACEUTICAL CO., LTD., Chiyoda-ku (JP)

(72) Inventors: Kazuhisa Minamiguchi, Moriya (JP); Shigeo Okajima, Tsukuba (JP); Shinichi Aoki, Honjo (JP); Masanori Asai, Tsukuba (JP); Takahiro Asai, Tsukuba (JP); Hiroyoshi Yamanaka, Moriya (JP); Suguru Dohi, Bunkyo-ku (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,059

(22) Filed: Jul. 6, 2016

(65) Prior Publication Data

US 2016/0310496 A1    Oct. 27, 2016

Related U.S. Application Data

(63) Continuation of application No. 15/023,894, filed as application No. PCT/JP2015/065425 on May 28, 2015, now Pat. No. 9,662,333.

(30) Foreign Application Priority Data

May 29, 2014 (JP) ................................. 2014-111147

(51) Int. Cl.
| | |
|---|---|
| C07D 471/04 | (2006.01) |
| A61K 31/519 | (2006.01) |
| A61K 31/553 | (2006.01) |
| A61P 5/28 | (2006.01) |
| A61P 35/00 | (2006.01) |
| A61K 9/00 | (2006.01) |
| A61K 31/53 | (2006.01) |

(52) U.S. Cl.
CPC .......... *A61K 31/519* (2013.01); *A61K 9/0019* (2013.01); *A61K 31/53* (2013.01); *A61K 31/553* (2013.01); *C07D 471/04* (2013.01)

(58) Field of Classification Search
CPC ... C07D 471/04; A61K 31/553; A61K 31/519
USPC .......... 514/264.1, 264.11; 544/279; 122/122, 122/118
See application file for complete search history.

(56) References Cited

U.S. PATENT DOCUMENTS

| | | | |
|---|---|---|---|
| 9,662,333 B2* | 5/2017 | Minamiguchi | A61K 31/519 |
| 2005/0215572 A1 | 9/2005 | Kelly et al. | |
| 2005/0277643 A1 | 12/2005 | Kelly et al. | |
| 2006/0128710 A1 | 6/2006 | Lee et al. | |
| 2006/0160845 A1 | 7/2006 | Schlienger et al. | |

FOREIGN PATENT DOCUMENTS

| | | |
|---|---|---|
| JP | 2002-88073 A | 3/2002 |
| JP | 2007/517045 A | 6/2007 |
| JP | 2008-526888 A | 7/2008 |
| RU | EA 14495 B1 | 12/2010 |
| RU | EA 18721 B1 | 10/2013 |
| WO | 2005/066171 A1 | 7/2005 |
| WO | 2006-062981 A2 | 6/2006 |
| WO | 2006/118598 A1 | 11/2006 |

OTHER PUBLICATIONS

The National Cancer Institute National Cancer Institute at the National Institutes of Health, A to Z List of Cancers, <http:// https://www.cancer.gov/types> accessed Jun. 18, 2017.*
Helsen et al. Endocr Relat Cancer 2014, 21(4), T105-118.*
Russian Office Action (including Search Report), dated Dec. 27, 2016, in Russian Patent Application No. 2016125885 (with English Translation).
Pasi Koivisto, et al., "Androgen Receptor Gene Amplification: A Possible Molecular Mechanism for Androgen Deprivation Therapy Failure in Prostate Cancer," Cancer Research, vol. 57, Jan. 15, 1997, (7 pages).
Christopher W. Gregory, et al., "Androgen Receptor Stabilization in Recurrent Prostate Cancer is Associated with Hypersensitivity to Low Androgen," Cancer Research, vol. 61, Apr. 1, 2001, (8 pages).
Mary-Ellen Taplin, et al., "Mutation of the Androgen-Receptor Gene in Metastatic Androgen-Independent Prostate Cancer," The New England Journal of Medicine, vol. 332, No. 21, May 25, 1995, pp. 1393-1398.

(Continued)

*Primary Examiner* — Irina Neagu
(74) *Attorney, Agent, or Firm* — Oblon, McClelland, Maier & Neustadt, L.L.P.

(57) ABSTRACT

A method for inhibiting androgen activity, including administering an effective amount of a tetrahydropyridopyrimidine compound of formula (I) or a pharmaceutically acceptable salt thereof to a subject in need thereof, and a method for treating tumor, including administering an effective amount of a tetrahydropyridopyrimidine compound of formula (I) or a pharmaceutically acceptable salt thereof to a subject in need thereof

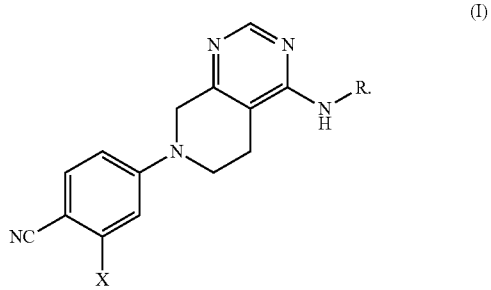

(I)

19 Claims, No Drawings

(56) References Cited

OTHER PUBLICATIONS

Xiao-Yan Zhao, et al., "Glucocorticoids can promote androgen-independent growth of prostate cancer cells through a mutated androgen receptor," Nature Medicine, vol. 6, No. 6, Jun. 2000, pp. 703-706.
Jiann-an Tan, et al., "Dehydroepiandrosterone Activates Mutant Androgen Receptors Expressed in the Androgen-Dependent Human Prostate Cancer Xenograft CWR22 and LNCaP Cells," Molecular Endocrinology, vol. 11, No. 4, 1997, pp. 450-459.
Charlie D Chen, et al., "Molecular determinants of resistance to antiandrogen therapy," Nature Medicine, vol. 10, No. 1, Jan. 2004, pp. 33-39.
Takahito Hara, et al., "Novel Mutations of Androgen Receptor: A Possible Mechanism of Bicalutamide Withdrawal Syndrome," Cancer Research, vol. 63, Jan. 1, 2003, (6 pages).
Ryan P. Trump, et al., "Design and Synthesis of an Array of Selective Androgen Receptor Modulators," Journal of Combinatorial Chemistry, vol. 9, No. 1, 2007, pp. 107-114.
International Search Report dated Jul. 21, 2016 in PCT/JP2015/065425 filed May 28, 2015.

\* cited by examiner

TETRAHYDROPYRIDOPYRIMIDINE COMPOUND OR SALT THEREOF

CROSS REFERENCE TO RELATED APPLICATIONS

This application is a continuation of U.S. patent application Ser. No. 15/023,894, filed Mar. 22, 2016, which is the National Stage of the International Patent Application No. PCT/JP2015/065425, filed May 28, 2015, the disclosures of which are incorporated herein by reference in their entireties. This application claims priority to Japanese Application Number 2014-111147, filed May 29, 2014.

TECHNICAL FIELD

The present invention relates to a novel tetrahydropyridopyrimidine compound which is useful as a pharmaceutical agent, in particular, an anti-androgen agent, and a salt thereof, and a pharmaceutical composition containing them.

BACKGROUND ART

Prostate cancer is the cancer with the highest incidence in men in western countries, and it is the second leading cause of cancer death. In Japan, according to westernization in food preferences and human population aging, the number of prostate cancer patients also increases over the years. In general, proliferation of prostate cancer cells is stimulated by androgen. As such, for treatment of unresectable progressive prostate cancer, patients are treated with surgical or chemical castration, and/or administration of an anti-androgen agent so-called androgen deprivation therapy. According to surgical or chemical castration, level of androgen circulating in human body is lowered so that the activity of an androgen receptor (it may be referred to as AR hereinbelow) is lowered. As the anti-androgen agent is administered, the binding of androgen to AR is inhibited, yielding lower AR activity. Those therapies are very effective for early stage treatment of most patients. However, cancer recurrence occurs within several years. Such recurrent prostate cancer is referred to as castration resistant prostate cancer (CRPC).

As a cause of castration resistant prostate cancer, amplification and overexpression of the AR gene have been confirmed and reported (Non-Patent Literatures 1 and 2). As a result of overexpression of AR, castration resistant prostate cancer exhibits high sensitivity even for androgen at an ultra-low concentration, which is caused by castration treatment. Namely, according to overexpression of AR, AR is activated to cause cancer proliferation. AR mutation has been also confirmed and reported as a cause of castration resistant prostate cancer (Non-Patent Literatures 3 to 5). According to a mutation in AR, estrogen or an anti-androgen agent itself, which is currently used, can function as an AR agonist, in addition to androgen.

Bicalutamide is the most generally used anti-androgen agent, and exhibits an inhibitory effect in hormone-sensitive prostate cancer as an antagonist for AR. However, the anti-androgen agent including bicalutamide, which is used for androgen deprivation therapy, has no effectiveness against castration resistant prostate cancer. The main reason is that, as AR is overexpressed in castration resistant prostate cancer, the AR antagonist activity is not fully exhibited and the AR agonist activity is shown (Non-Patent Literatures 6 and 7). As such, for inhibition of overexpressed AR in castration resistant prostate cancer, an anti-androgen agent having a more potent AR antagonist activity than a currently used anti-androgen agent and not having an AR agonist activity is needed. Furthermore, as the anti-androgen agent also has an effect of reducing AR expression, it can be a more effective therapeutic agent for castration resistant prostate cancer.

In a related art, 5,6,7,8-tetrahydropyrido[3,4-d]pyrimidine has been reported as an inhibitor for vanilloid receptor 1 (VR1) (Patent Literatures 1 to 3). In Patent Literature 1, a bicycloheteroarylamine compound useful for treatment of pain, inflammatory hyperalgesia, overactive bladder, and urinary incontinence based on inhibition of VR1 receptor is disclosed. Furthermore, in Patent Literatures 2 and 3, a bicycloheteroarylamine compound useful for treatment of inflammatory pain, for example, is disclosed, and an experimental data for thermal hyperalgeia is described. However, a compound having cyano benzene at position 7 of the 5,6,7,8-tetrahydropyrido[3,4-d]pyrimidine has not been reported in any one of those Patent Literatures 1 to 3. In addition, there are no descriptions regarding the data relating to an anti-tumor effect, and the AR antagonist activity or the activity of reducing AR expression is not described at all.

CITATION LIST

Patent Literature

Patent Literature 1: WO 2006/062981
Patent Literature 2: WO 2005/066171
Patent Literature 3: WO 2006/118598

Non-Patent Literature

Non-Patent Literature 1: Koivisto P et al., "Androgen receptor gene amplification: a possible molecular mechanism for androgen deprivation therapy failure in prostate cancer", Cancer Res 57: 314-319, 1997

Non-Patent Literature 2: Gregory C W et al., "Androgen receptor stabilization in recurrent prostate cancer is associated with hypersensitivity to low androgen", Cancer Res 61: 2892-2898, 2001

Non-Patent Literature 3: Taplin M E et al., "Mutation of the androgen-receptor gene in metastatic androgen-independent prostate cancer", N Engl J Med 332: 1393-1398, 1995

Non-Patent Literature 4: Zhao X Y et al., "Glucocorticoids can promote androgen-independent growth of prostate cancer cells through a mutated androgen receptor", Nat Med 6: 703-706, 2000

Non-Patent Literature 5: Tan J et al., "Dehydroepiandrosterone activates mutant androgen receptors expressed in the androgen-dependent human prostate cancer xenograft CWR22 and LNCaP cells", Mol Endocrinol 11: 450-459, 1997

Non-Patent Literature 6: Charlie D Chen et al., "Molecular determinants of resistance to antiandrogen therapy", Nature Medicine 10:33-39, 2004

Non-Patent Literature 7: Takahito Hara et al., "Novel Mutations of Androgen Receptor: A Possible Mechanism of Bicalutamide Withdrawal Syndrome", Cancer Res 63: 149-153, 2003

SUMMARY OF THE INVENTION

Problems to be Solved by the Invention

The present invention provide sa novel tetrahydropyridopyrimidine compound, which has a stronger antagonist activity for AR overexpressed in castration resistant prostate cancer than a currently prescribed anti-androgen agent such as bicalutamide, does not exhibit an agonistic activity for AR, and has an activity of lowering AR expression amount, or a pharmaceutically acceptable salt thereof.

Means for Solving the Problems

As a result of intensive studies, the inventors of the present invention found a novel compound group having 5,6,7,8-tetrahydropyrido[3,4-d]pyrimidine as a basic structure, a group represented by —NHR at position 4, and cyanobenzene at position 7. The compound group has an antagonist activity but no agonist activity for AR, and in addition to effectiveness for cells in which AR is expressed, it has a potent effect of inhibiting cell proliferation for cells in which AR is overexpressed. Furthermore, the compound group has, in addition to the antagonist activity for AR, an activity of lowering AR expression, and it exhibits an anti-tumor effect in a cancer-bearing mouse model with castration resistant prostate cancer. As such, the inventors of the present invention found that the compound group is effective as a pharmaceutical agent for treating cancer, and the present invention is completed accordingly.

Accordingly, the present invention provides the following [1] to [22].

[1] A tetrahydropyridopyrimidine compound represented by the following formula (I):

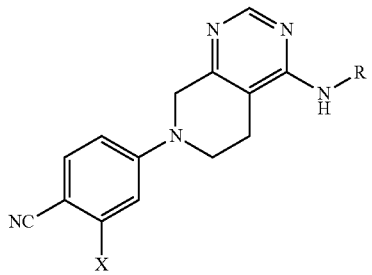

(I)

[in the formula,
X represents a halogen atom or a halogeno-$C_{1-3}$ alkyl group;
R represents a $C_{6-14}$ aryl group which is substituted with $R^1$ and may be substituted simultaneously with $R^2$, or a 5- or 6-membered heteroaryl group which is substituted with $R^1$ and may be substituted simultaneously with $R^2$;
$R^1$ represents a hydrogen atom, a phenyl group, a hydroxy-$C_{1-6}$ alkyl group, a hydroxy-$C_{3-7}$ cycloalkyl group, a $C_{1-6}$ alkoxy group which may be substituted with Ra, a $C_{3-7}$ cycloalkylaminosulfonyl group, a 3- to 7-membered monocyclic heterocycloalkylsulfonyl group, a halogeno-$C_{1-3}$ alkoxycarbonylamino group, a halogeno-$C_{1-3}$ alkylcarbonylamino group, a 3- to 7-membered monocyclic heterocycloalkanecarbonyl group substituted with a hydroxy-$C_{1-6}$ alkyl group, or —(CH$_2$)$_n$—C(=O)—NHRf;
$R^2$ represents a hydrogen atom, a halogen atom, or a halogeno-$C_{1-3}$alkyl group;
Ra represents a $C_{1-6}$ alkylpyrazolyl group, a triazolyl group, a tetrazolyl group, or a $C_{1-6}$ alkylsulfonylpiperazinyl group;
Rf represents a halogeno-$C_{1-3}$alkyl group, a hydroxy-$C_{1-6}$ alkyl group, a hydroxy-$C_{3-7}$cycloalkyl group, a hydroxy-$C_{3-7}$ cycloalkyl-$C_{1-6}$alkyl group, or a $C_{1-6}$ alkyl group substituted with Rfa;
Rfa represents a $C_{1-6}$ alkylpyrazolyl group, a halogeno-$C_{1-3}$ alkylthiazolyl group, an oxadiazolyl group, or a halogeno-$C_{1-3}$ alkyloxadiazolyl group; and
n represents an integer of from 0 to 3]
or a pharmaceutically acceptable salt thereof.

[2] The compound according to [1] or a pharmaceutically acceptable salt thereof, wherein X is a chlorine atom, a bromine atom, or a trifluoromethyl group.

[3] The compound according to [1] or [2] or a pharmaceutically acceptable salt thereof, wherein n is 0 or 1.

[4] The compound according to any one of [1] to [3] or a pharmaceutically acceptable salt thereof, wherein R is selected from the group consisting of the following groups:

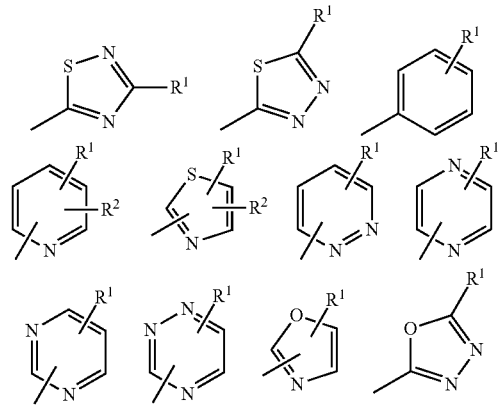

[5] The compound according to any one of [1] to [4] or a pharmaceutically acceptable salt thereof, wherein $R^1$ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanylsulfonyl group, a 2,2,2-trifluoroethoxycarbonylamino group, a 2,2,2-trifluoroethylcarbonylamino group, a piperidinecarbonyl group substituted with a hydroxy-isopropyl group, or —(CH$_2$)$_n$—C(=O)—NHRf;
Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with a trifluoromethyloxazolyl group; and n is 0 or 1.

[6] The compound according to any one of [1] to [5] or a pharmaceutically acceptable salt thereof, wherein R is selected from the group consisting of the following groups:

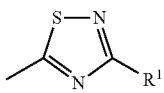

(in the formula, $R^1$ is a hydrogen atom);

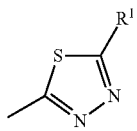

(in the formula, $R^1$ is —(CH$_2$)$_n$—C(=O)—NHRf,

Rf is a methyl group substituted with Rfa or an ethyl group substituted with Rfa, Rfa is a methylpyrazolyl group or an oxadiazolyl group, and n is 0);

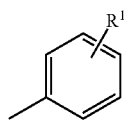

(in the formula, $R^1$ is a phenyl group, a hydroxy-ethyl group, a hydroxy-isopropyl group, a methoxy group, an isopropoxy group, an ethoxy group substituted with a methylpyrazolyl group, or an n-propoxy group substituted with a methylsulfonylpiperazinyl group);

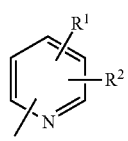

(in the formula, $R^1$ is a hydroxy-isopropyl group, a hydroxy-cyclopropyl group, a hydroxy-cyclobutyl group, an isopropoxy group, an ethoxy group substituted with a triazolyl group, a 2-methylpropoxy group substituted with a triazolyl group, a 2-methylpropoxy group substituted with a tetrazolyl group, a cyclopropylaminosulfonyl group, a 2,2,2-trifluoroethoxycarbonylamino group, a 2,2,2-trifluoroethylcarbonylamino group, or —(CH$_2$)$_n$—C(=O)—NHRf, $R^2$ is a hydrogen atom, a fluorine atom, or a chlorine atom, Rf is a 2,2-difluoroethyl group, a 2,2,2-trifluoroethyl group, a methyl group substituted with Rfa, or an ethyl group substituted with Rfa;

Rfa is a trifluoromethylthiazolyl group, an oxadiazolyl group, or a trifluoromethyloxadiazolyl group, and n is 0 or 1);

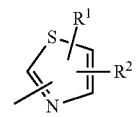

(in the formula, $R^1$ is a hydroxy-isopropyl group, a 1,4-oxazepanylsulfonyl group, or —(CH$_2$)$_n$—C(=O)—NHRf, $R^2$ is a hydrogen atom or a trifluoromethyl group, Rf is a 2,2,2-trifluoroethyl group or an ethyl group substituted with Rfa, Rfa is an oxadiazolyl group, and n is 0);

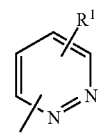

(in the formula, $R^1$ is a hydroxy-isopropyl group or —(CH$_2$)$_n$—C(=O)—NHRf, Rf is a 2,2-difluoroethyl group, a 2,2,2-trifluoroethyl group, a hydroxy-2-methylpropyl group, a hydroxycyclohexyl group, a hydroxycyclopropylmethyl group, and n is 0);

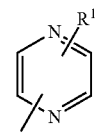

(in the formula, $R^1$ is —(CH$_2$)$_n$—C(=O)—NHRf,

Rf is a hydroxy-2-methylpropyl group, and n is 0);

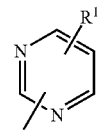

(in the formula, $R^1$ is —(CH$_2$)$_n$—C(=O)—NHRf,

Rf is a hydroxy-2-methylpropyl group, and n is 0);

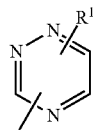

(in the formula,
R¹ is —(CH₂)ₙ—C(=O)—NHRf,
Rf is a 2,2,2-trifluoroethyl group, and
n is 0);

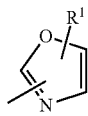

(in the formula,
R¹ is a piperidinecarbonyl group substituted with a hydroxy-isopropyl group; and

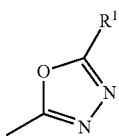

(in the formula,
R¹ is a piperidinecarbonyl group substituted with a hydroxy-isopropyl group).

[7] The compound according to any one of [1] to [5] or a pharmaceutically acceptable salt thereof, wherein
X is a chlorine atom, a bromine atom, or a trifluoromethyl group; and
R is selected from the group consisting of the following groups:

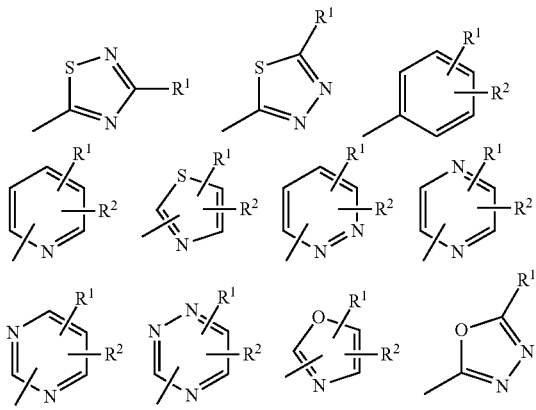

R¹ is a hydrogen atom, a phenyl group, a hydroxy-$C_{1-4}$ alkyl group, a hydroxy-$C_{3-5}$ cycloalkyl group, a $C_{1-4}$ alkoxy group which may be substituted with Ra, a $C_{3-5}$ cycloalkylaminosulfonyl group, a 7-membered monocyclic heterocycloalkylsulfonyl group, a fluoro-$C_{1-3}$ alkoxycarbonylamino group, a fluoro-$C_{1-3}$alkylcarbonylamino group, a 6-membered monocyclic heterocycloalkanecarbonyl group substituted with a hydroxy-$C_{1-4}$alkyl group, or —(CH₂)ₙ—C(=O)—NHRf;

R² is a hydrogen atom, a fluorine atom, a chlorine atom, or a trifluoromethyl group;
Ra is a $C_{1-4}$ alkylpyrazolyl group, a triazolyl group, a tetrazolyl group, or a $C_{1-4}$alkylsulfonylpiperazinyl group;
Rf is a fluoro-$C_{1-3}$alkyl group, a hydroxy-$C_{1-4}$alkyl group, a hydroxy-$C_{3-5}$cycloalkyl group, a hydroxy-$C_{3-5}$cycloalkyl-$C_{1-4}$alkyl group, or a $C_{1-4}$ alkyl group substituted with Rfa; Rfa is a $C_{1-4}$ alkylpyrazolyl group, a fluoro-$C_{1-3}$ alkylthiazolyl group, an oxadiazolyl group, or a fluoro-$C_{1-3}$ alkyloxadiazolyl group; and
n is 0 or 1.

[8] The compound according to [7] or a pharmaceutically acceptable salt thereof, wherein
X is a chlorine atom, a bromine atom, or a trifluoromethyl group; and
R is selected from the group consisting of the following groups:

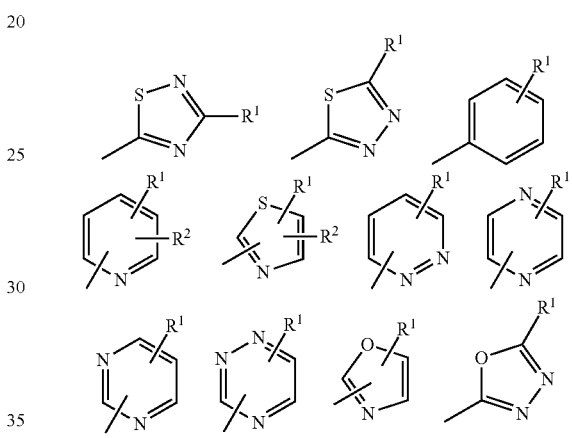

R¹ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanylsulfonyl group, a 2,2,2-trifluoroethoxycarbonylamino group, a 2,2,2-trifluoroethylcarbonylamino group, a piperidinecarbonyl group substituted with a hydroxy-isopropyl group, or —(CH₂)ₙ—C(=O)—NHRf;
R² is a hydrogen atom, a fluorine atom, a chlorine atom, or a trifluoromethyl group;
Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with a trifluoromethyl group; and
n is 0 or 1.

[9] The compound according to [8] or a pharmaceutically acceptable salt thereof, wherein
X is a chlorine atom or a trifluoromethyl group; and
R is selected from the group consisting of the following groups:

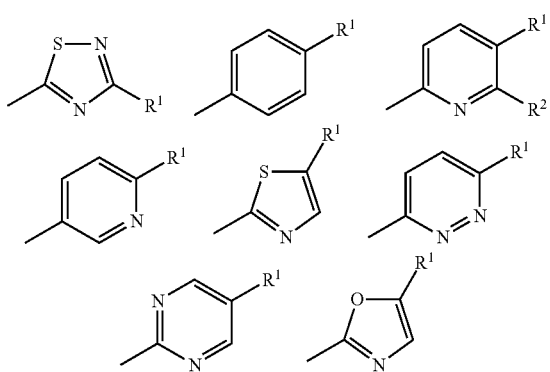

R¹ is a hydrogen atom, a hydroxy-isopropyl group, an isopropoxy group, a 2-methylpropoxy group substituted with a tetrazolyl group, an n-propoxy group substituted with a methylsulfonylpiperazinyl group, a 1,4-oxazepanylsulfonyl group, a piperidinecarbonyl group substituted with a hydroxy-isopropyl group, or —(CH$_2$)$_n$—C(=O)—NHRf;

R² is a hydrogen atom or a fluorine atom;

Rf is a 2,2,2-trifluoroethyl group, a hydroxy-2-methylpropyl group, a methyl group substituted with a trifluoromethylthiazolyl group, an ethyl group substituted with an oxadiazolyl group, or an ethyl group substituted with a trifluoromethyloxadiazolyl group; and n is 0.

[10] The compound according to [1] or a pharmaceutically acceptable salt thereof, which is selected from the group consisting of the following compounds (1) to (19):

(1) 4-(4-((1,2,4-thiadiazol-5-yl)amino)-5,6-dihydropyrido[3,4-d]pyrimidin-7(8H)-yl)-2-(trifluoromethyl)benzonitrile;

(2) 4-(4-((4-isopropoxyphenyl)amino)-5,6-dihydropyrido[3,4-d]pyrimidin-7 (8H)-yl)-2-(trifluoromethyl)benzonitrile;

(3) 4-(4-((6-fluoro-5-(2-hydroxypropan-2-yl)pyridin-2-yl)amino)-5, 6-dihydropyrido[3,4-d]pyrimidin-7 (8H)-yl)-2-(trifluoromethyl)benzonitrile;

(4) 2-chloro-4-(4-((6-(2-hydroxypropan-2-yl)pyridazin-3-yl)amino)-5, 6-dihydropyrido[3,4-d]pyrimidin-7 (8H)-yl)benzonitrile;

(5) 4-(4-((5-(2-hydroxypropan-2-yl)pyridin-2-yl)amino)-5, 6-dihydropyrido[3,4-d]pyrimidin-7(8H)-yl)-2-(trifluoromethyl)benzonitrile;

(6) 2-chloro-4-(4-((5-(2-hydroxypropan-2-yl)pyridin-2-yl)amino)-5, 6-dihydropyrido[3,4-d]pyrimidin-7 (8H)-yl)benzonitrile;

(7) 4-(4-((6-(2-hydroxypropan-2-yl)pyridazin-3-yl)amino)-5, 6-dihydropyrido[3,4-d]pyrimidin-7 (8H)-yl)-2-(trifluoromethyl)benzonitrile;

(8) 6-((7-(4-cyano-3-(trifluoromethyl)phenyl)-5,6,7,8,-tetrahydropyrido[3,4-d]pyrimidin-4-yl)amino)-N-(2,2,2-trifluoroethyl) nicotinamide;

(9) 4-(4-((6-isopropoxypyridin-3-yl)amino)-5,6-dihydropyrido[3,4-d]pyrimidin-7(8H)-yl)-2-(trifluoromethyl)benzonitrile;

(10) 4-(4-((6-(2-methyl-2-(1H-tetrazol-1-yl)propoxy)pyridin-3-yl)amino)-5,6-dihydropyrido[3,4-d]pyrimidin-7 (8H)-yl)-2-(trifluoromethyl)benzonitrile;

(11) 4-(4-((5-(2-methyl-2-(1H-tetrazol-1-yl)propoxy)pyridin-2-yl)amino)-5,6-dihydropyrido[3,4-d]pyrimidin-7 (8H)-yl)-2-(trifluoromethyl)benzonitrile;

(12) 4-(4-((4-(3-(4-(methylsulfonyl)piperazin-1-yl)propoxy)phenyl)amino)-5,6-dihydropyrido[3,4-d]pyrimidin-7(8H)-yl)-2-(trifluoromethyl)benzonitrile;

(13) 4-(4-((5-((1,4-oxazepan-4-yl)sulfonyl)thiazol-2-yl)amino)-5,6-dihydropyrido[3,4-d]pyrimidin-7(8H)-yl)-2-(trifluoromethyl)benzonitrile;

(14) 6-((7-(4-cyano-3-(trifluoromethyl)phenyl)-5,6,7,8-tetrahydropyrido[3,4-d]pyrimidin-4-yl)amino)-N-(2-hydroxy-2-methylpropyl)pyridazine-3-carboxamide;

(15) 2-((7-(4-cyano-3-(trifluoromethyl)phenyl)-5,6,7,8-tetrahydropyrido[3,4-d]pyrimidin-4-yl)amino)-N-(2-hydroxy-2-methylpropyl)pyrimidine-5-carboxamide;

(16) 6-((7-(4-cyano-3-(trifluoromethyl)phenyl)-5,6,7,8-tetrahydropyrido[3,4-d]pyrimidin-4-yl)amino)-N-((4-(trifluoromethyl)thiazol-2-yl)methyl)nicotinamide;

(17) (R)—N-(1-(1,3,4-oxadiazol-2-yl)ethyl)-6-((7-(4-cyano-3-(trifluoromethyl)phenyl)-5,6,7,8-tetrahydropyrido[3,4-d]pyrimidin-4-yl)amino)nicotinamide;

(18) (R)-6-((7-(4-cyano-3-(trifluoromethyl)phenyl)-5,6,7,8-tetrahydropyrido[3,4-d]pyrimidin-4-yl)amino)-N-(1-(5-(trifluoromethyl)-1,3,4-oxadiazol-2-yl)ethyl)nicotinamide; and

(19) 4-(4-((5-(4-(2-hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile.

[11] An anti-androgen agent comprising, as an active ingredient, the tetrahydropyridopyrimidine compound according to any one of [1] to [10] or a pharmaceutically acceptable salt thereof.

[12] An anti-tumor agent comprising, as an active ingredient, the tetrahydropyridopyrimidine compound according to any one of [1] to [10] or a pharmaceutically acceptable salt thereof.

[13] A pharmaceutical agent comprising, as an active ingredient, the tetrahydropyridopyrimidine compound according to any one of [1] to [10] or a pharmaceutically acceptable salt thereof.

[14] A pharmaceutical composition comprising the tetrahydropyridopyrimidine compound according to any one of [1] to [10] or a pharmaceutically acceptable salt thereof, and a pharmaceutically acceptable carrier.

[15] Use of the tetrahydropyridopyrimidine compound according to any one of [1] to [10] or a pharmaceutically acceptable salt thereof for producing an anti-androgen agent.

[16] Use of the tetrahydropyridopyrimidine compound according to any one of [1] to [10] or a pharmaceutically acceptable salt thereof for producing an anti-tumor agent.

[17] Use of the tetrahydropyridopyrimidine compound according to any one of [1] to [10] or a pharmaceutically acceptable salt thereof for producing a pharmaceutical agent.

[18] The tetrahydropyridopyrimidine compound according to any one of [1] to [10] or a pharmaceutically acceptable salt thereof for use in inhibiting androgen activity.

[19] The tetrahydropyridopyrimidine compound according to any one of [1] to [10] or a pharmaceutically acceptable salt thereof for use in treating tumor.

[20] The tetrahydropyridopyrimidine compound according to any one of [1] to [10] or a pharmaceutically acceptable salt thereof for use as a pharmaceutical agent.

[21] A method for inhibiting androgen activity, comprising administering an effective amount of the tetrahydropyridopyrimidine compound according to any one of [1] to [10] or a pharmaceutically acceptable salt thereof to a subject in need thereof.

[22] A method for treating tumor, comprising administering an effective amount of the tetrahydropyridopyrimidine compound according to any one of [1] to [10] or a pharmaceutically acceptable salt thereof to a subject in need thereof.

Effects of the Invention

The novel tetrahydropyridopyrimidine compound of the present invention or a salt thereof exhibits an antagonist activity against an androgen receptor (AR), and is effective for a disorder related with AR activation. Examples of a disorder related with AR activation include tumor, metastatic bone disease, prostatic hyperplasia, acne vulgaris, seborrhea, hypertrichosis, androgenetic alopecia, precocious puberty, and virillizing syndrome. Examples of the tumor include prostate cancer, breast cancer, ovarian cancer, bladder cancer, uterine cancer, pancreatic cancer, and hepatocellular cancer.

DESCRIPTION OF EMBODIMENTS

As described herein, examples of the "halogen atom" include a fluorine atom, a chlorine atom, a bromine atom, and an iodine atom.

As described herein, the "$C_{1-6}$alkyl group" indicates a linear or branched alkyl group having 1 to 6 carbon groups, and examples thereof include a methyl group, an ethyl group, an n-propyl group, an isopropyl group, an n-butyl group, a 2-methylpropyl group, a sec-butyl group, a tert-butyl group, an n-pentyl group, an isopentyl group, a tert-pentyl group, a neopentyl group, an n-hexyl group, and a texyl group. Furthermore, as described herein, the "$C_{1-4}$ alkyl group" and "$C_{1-3}$ alkyl group" each indicates, among the aforementioned "$C_{1-6}$ alkyl group", an alkyl group having 1 to 4 carbon atoms or 1 to 3 carbon atoms.

As described herein, the "halogeno-$C_{1-3}$alkyl group" indicates the aforementioned $C_{1-3}$ alkyl group which is substituted with 1 to 7 halogen atoms that are described above. Examples of the "halogeno-$C_{1-3}$alkyl group" include a fluoro-$C_{1-3}$alkyl group and a chloro-$C_{1-3}$alkyl group such as a fluoromethyl group, a difluoromethyl group, a trifluoromethyl group, a trichloromethyl group, a 2-fluoroethyl group, a 2,2-difluoroethyl group, a 2,2,2-trifluoroethyl group, a 2,2,2-trichloroethyl group, a monofluoro-n-propyl group, a perfluoro-n-propyl group, and a perfluoroisopropyl group.

As described herein, the "$C_{6-14}$ aryl group" indicates an aryl group having 6 to 14 carbon atoms, and examples thereof include a phenyl group, a naphthyl group, an antracenyl group, a phenanthryl group, and a fluorenyl group.

As described herein, the "heteroaryl group" indicates a monocyclic or polycyclic group having aromaticity which has 1 to 4 hetero atoms selected from of the group consisting of oxygen, nitrogen, and sulfur. Examples of the heteroaryl group include a furyl group, a thienyl group, a pyrrolyl group, an imidazolyl group, a pyrazolyl group, a diazolyl group, a triazolyl group, a tetrazolyl group, an oxazolyl group, an oxadiazolyl group, a triazinyl group, a thiazolyl group, a thiadiazolyl group, an isooxazolyl group, an isothiazolyl group, a pyridinyl group, a pyrazinyl group, a pyrimidinyl group, a pyridazinyl group, an indolyl group, a quinolyl group, an isoquinolyl group, a benzo[b]thienyl group, a benzimidazolyl group, a benzothiazolyl group, and a benzoxazolyl group.

As described herein, the "hydroxy-$C_{1-6}$alkyl group" indicates the aforementioned $C_{1-6}$ alkyl group which is substituted with 1 to 3 hydroxyl groups. Examples of the "hydroxy-$C_{1-6}$alkyl group" include a hydroxymethyl group, a 1-hydroxyethyl group, a 1,2-dihydroxyethyl group, a 1-hydroxypropyl group, a 1,2-dihydroxypropyl group, a 1,2,3-trihydroxypropyl group, a 1-hydroxybutyl group, a 2-hydroxypropan-2-yl group, and a 2-hydroxy-2-methylpropyl group.

As described herein, the "$C_{3-7}$ cycloalkyl group" indicates a cyclic alkyl group having 3 to 7 carbon atoms, and examples thereof include a cyclopropyl group, a cyclobutyl group, a cyclopentyl group, a cyclohexyl group, and a cycloheptyl group.

As described herein, the "hydroxy-$C_{3-7}$ cycloalkyl group" indicates the aforementioned $C_{3-7}$ cycloalkyl group which is substituted with 1 to 3 hydroxyl groups. Examples of the "hydroxy-$C_{3-7}$ cycloalkyl group" include a 1-hydroxycyclopropyl group, a 2-hydroxycyclopropyl group, a 1,2-dihydroxycyclopropyl group, a 1,2,3-trihydroxycyclopropyl group, a 1-hydroxycyclobutyl group, a 1-hydroxycyclopentyl group, a 1-hydroxycyclohexyl group, and a 4-hydroxycyclohexyl group.

As described herein, the "$C_{1-6}$ alkoxy group" indicates a linear or branched alkoxy group having 1 to 6 carbon groups, and examples thereof include a methoxy group, an ethoxy group, an n-propoxy group, an isopropoxy group, an n-butoxy group, a 2-methylpropoxy group (isobutoxy group), sec-butoxy group, a tert-butoxy group, an n-pentyloxy group, an isopentyloxy group, a tert-pentyloxy group, a neopentyloxy group, an n-hexyloxy group, and a texyloxy group. Furthermore, as described herein, the "$C_{1-4}$alkoxy group" and "$C_{1-3}$ alkoxy group" each indicates, among the aforementioned "$C_{1-6}$ alkoxy group", an alkoxy group having 1 to 4 carbon atoms or 1 to 3 carbon atoms.

As described herein, the "halogeno-$C_{1-3}$ alkoxy group" indicates the aforementioned $C_{1-3}$ alkoxy group which is substituted with 1 to 7 halogen atoms that are described above. Examples of the "halogeno-$C_{1-3}$alkoxy group" include a fluoro-$C_{1-3}$alkoxy group and a chloro-$C_{1-3}$alkoxy group such as a fluoromethoxy group, a difluoromethoxy group, a trifluoromethoxy group, a trichloromethoxy group, a 2-fluoroethoxy group, a 2,2-difluoroethoxy group, a 2,2,2-trifluoroethoxy group, a 2,2,2-trichloroethoxy group, a monofluoro-n-propoxy group, a perfluoro-n-propoxy group, and a perfluoroisopropoxy group.

As described herein, the "$C_{3-7}$ cycloalkylaminosulfonyl group" indicates a sulfonyl group having an amino group substituted with one $C_{3-7}$ cycloalkyl group described above. Examples of the "$C_{3-7}$cycloalkylaminosulfonyl group" include a cyclopropylaminosulfonyl group, a cyclobutylaminosulfonyl group, and a cyclopentylaminosulfonyl group.

As described herein, the "heterocycloalkyl group" indicates a 3- to 7-membered monocyclic alkyl group which has, instead of a carbon atom, 1 to 3 hetero atoms selected from the group consisting of oxygen, nitrogen, and sulfur. Examples thereof include an aziridinyl group, an azetidinyl group, a pyrrolidinyl group, an oxazolidinyl group, a thiazolidinyl group, a tetrahydrofuranyl group, a tetrahydrothiophenyl group, a piperidinyl group, a piperazinyl group, a morpholino group, a thiomorpholino group, an oxazinanyl group, a thiazinanyl group, an azepanyl group, a diazepanyl group, and an oxazepanyl group.

As described herein, the "heterocycloalkylsulfonyl group" indicates a sulfonyl group substituted with the aforementioned heterocycloalkyl group. Examples of the "heterocycloalkylsulfonyl group" include a piperidin-1-ylsulfonyl group, a morpholinosulfonyl group, a 1,4-thiazepan-4-ylsulfonyl group, and a 1,4-oxazepanylsulfonyl group.

As described herein, the "halogeno-$C_{1-3}$ alkoxycarbonylamino group" indicates an amino group which is substituted with one halogeno-$C_{1-3}$ alkoxycarbonyl group, and the "halogeno-$C_{1-3}$alkoxycarbonyl group" indicates a carbonyl group which is substituted with the aforementioned halogeno-$C_{1-3}$alkoxy group. Examples of the "halogeno-$C_{1-3}$ alkoxycarbonylamino group" include a trifluoromethoxycarbonylamino group, a trichloromethoxycarbonylamino group, a 2-fluoroethoxycarbonylamino group, a 2,2-difluoroethoxycarbonylamino group, and a 2,2,2-trifluoroethoxycarbonylamino group.

As described herein, the "halogeno-$C_{1-3}$ alkylcarbonylamino group" indicates an amino group which is substituted with one halogeno-$C_{1-3}$ alkylcarbonyl group, and the "halogeno-$C_{1-3}$alkylcarbonyl group" indicates a carbonyl group which is substituted with the aforementioned halogeno-$C_{1-3}$ alkyl group. Examples of the "halogeno-$C_{1-3}$ alkylcarbonylamino group" include a trifluoromethylcarbonylamino group, a trichloromethylcarbonylamino group, a 2-fluoroethylcarbonylamino group, a 2,2-difluoroethylcarbonylamino group, and a 2,2,2-trifluoroethylcarbonylamino group.

As described herein, the "heterocycloalkanecarbonyl group" indicates a carbonyl group which is substituted with the aforementioned heterocycloalkyl group, and examples thereof include a 4-piperidin-1-carbonyl group, a 4-piperazin-1-carbonyl group, an aziridine-1-carbonyl group, and a morpholine-4-carbonyl group.

As described herein, the "$C_{1-6}$alkylpyrazolyl group" indicates a pyrazolyl group which is substituted with one $C_{1-6}$ alkyl group described above, and examples of the "$C_{1-6}$ alkylpyrazolyl group" include a 1-methyl-1H-pyrazol-5-yl group, a 1-ethyl-1H-pyrazol-5-yl group, a 1-propyl-1H-pyrazol-5-yl group, a 1-methyl-1H-pyrazol-3-yl group, and a 1-methyl-1H-pyrazol-4-yl group.

As described herein, the "$C_{1-6}$ alkylsulfonylpiperazinyl group" indicates a piperazinyl group which is substituted with one $C_{1-6}$ alkylsulfonyl group, and the "$C_{1-6}$ alkylsulfonyl group" indicates a sulfonyl group substituted with the aforementioned $C_{1-6}$ alkyl group. Examples of the "$C_{1-6}$alkylsulfonylpiperazinyl group" include a 4-(methylsulfonyl)piperazin-1-yl group, a 4-(ethylsulfonyl)piperazin-1-yl group, a 4-(propylsulfonyl)piperazin-1-yl group, a 4-(isopropylsulfonyl)piperazin-1-yl group, a 4-(methylsulfonyl)piperazin-2-yl group, and a 4-(methylsulfonyl)piperazin-3-yl group.

As described herein, the "hydroxy-$C_{3-7}$cycloalkyl-$C_{1-6}$ alkyl group" indicates the aforementioned $C_{1-6}$ alkyl group which is substituted with one hydroxy-$C_{3-7}$ cycloalkyl group described above, and examples of the "hydroxy-$C_{3-7}$ cycloalkyl-$C_{1-6}$alkyl group" include a (1-hydroxycyclopropyl)methyl group, a (1-hydroxycyclobutyl)methyl group, a 2-(1-hydroxycyclopropyl)ethyl group, a (1,2-dihydroxycyclopropyl)methyl group, and a (1,2,3-trihydroxycyclopropyl)methyl group.

As described herein, the "halogeno-$C_{1-3}$ alkylthiazolyl group" indicates a thiazolyl group which is substituted with one halogeno-$C_{1-3}$ alkyl group described above, and examples thereof include a 4-(trifluoromethyl)thiazol-2-yl group, a 5-(trifluoromethyl)thiazol-2-yl group, a 4-(trichloromethyl)thiazol-2-yl group, and a 4-(2,2,2-trifluoroethyl)thiazol-2-yl group.

As described herein, the "halogeno-$C_{1-3}$ alkyloxadiazolyl group" indicates an oxadiazolyl group which is substituted with one halogeno-$C_{1-3}$ alkyl group described above, and examples thereof include a 5-(trifluoromethyl)-1,3,4-oxadiazol-2-yl group, a 5-(2,2,2-trifluoroethyl)-1,3,4-oxadiazol-2-yl group, a 5-(2-fluoroethyl)-1,3,4-oxadiazol-2-yl group, and a 4-(trifluoromethyl)-1,2,3-oxazol-5-yl group.

As described herein, the "pharmaceutically acceptable salt" can be any one which is in the form of a pharmaceutically acceptable salt, and examples thereof include a mineral acid salt such as hydrochloric acid salt, hydrogen bromide acid salt, sulfuric acid salt, nitric acid salt, and phosphoric acid salt, and an organic acid salt such as acetic acid salt, propionic acid salt, tartaric acid, salt, fumaric acid salt, maleic acid salt, succinic acid salt, malic acid salt, citric acid salt, methanesulfonic acid salt, p-toluenesulfonic acid salt, and trifuloroacetic acid salt.

As described herein, a group "may be substituted" with a substituent group means a state in which the group is substituted with a substituent group or the group is not substituted with a substituent group.

The tetrahydropyridopyrimidine compound of the present invention or a salt thereof is characterized in that it has a 5,6,7,8-tetrahydropyrido[3,4-d]pyrimidine skeleton, and a group represented by —NHR (R is as defined below) is present on position 4 and cyanobenzene is present on position 7 of the skeleton, and a cyano group is present on position 4 and a specific group X is present on position 3 of the cyanobenzene (X is as defined below). The tetrahydropyridopyrimidine compound of the present invention or a salt thereof has an antagonist activity for an androgen receptor (AR) and exhibits an anti-tumor effect. Meanwhile, the compound having, instead of the 5,6,7,8-tetrahydropyrido[3,4-d]pyrimidine skeleton, 5,6,7,8-tetrahydropyrido[4,3-d]pyrimidine or 5,6,7,8-tetrahydro[1,2,4]triazolo[4,3-a]pyrazine skeleton does not exhibit either the AR antagonist activity or anti-tumor effect. Furthermore, the compound having, instead of the cyanobenzene in which a cyano group is present on position 4 and substituent group X is present on position 3, another cyanobenzene does not exhibit the aforementioned effects.

In the aforementioned Patent Literatures 1 to 3, a compound having 5,6,7,8-tetrahydropyrido[3,4-d]pyrimidine skeleton is disclosed. However, in none of the Patent Literatures 1 to 3, a compound having a group represented by —NHR (R is as defined below) on position 4 and cyanobenzene on position 7 of the 5,6,7,8-tetrahydropyrido[3,4-d] pyrimidine is disclosed. Furthermore, the usefulness of the 5,6,7,8-tetrahydropyrido[3,4-d]pyrimidine compound as an anti-tumor agent is not disclosed at all in Patent Literatures 1 to 3, and the effect of the compound against AR is not suggested.

The tetrahydropyridopyrimidine compound of the present invention is represented by the following general formula (I).

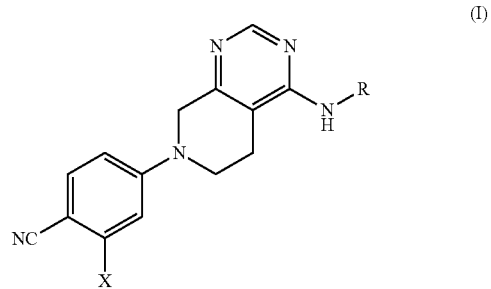

In the general formula (I), X represents a halogen atom, or a halogeno-$C_{1-3}$ alkyl group. Examples of the "halogen atom" represented by X include the aforementioned halogen atom, and it is preferably a chlorine atom or a bromine atom.

Examples of the "halogeno-$C_{1-3}$alkyl group represented by X include the aforementioned halogeno-$C_{1-3}$ alkyl group, and it is preferably a trifluoromethyl group. In the general formula (I), X is preferably a chlorine atom, a bromine atom, or a trifluoromethyl group, and more preferably a chlorine atom, or a trifluoromethyl group.

In the general formula (I), R represents a $C_{6-14}$ aryl group which is substituted with $R^1$ and may be substituted simultaneously with $R^2$, or a 5- or 6-membered heteroaryl group which is substituted with $R^1$ and may be substituted simultaneously with $R^2$.

The $C_{6-14}$ aryl group of "$C_{6-14}$ aryl group which is substituted with $R^1$ and may be substituted simultaneously with $R^2$" regarding R is the aforementioned $C_{6-14}$ aryl group, and it is preferably a phenyl group. The number of $R^1$ substituted on the "$C_{6-14}$ aryl group" is 1, and the number of $R^2$ is 0 or 1.

The heteroaryl group of "5- or 6-membered heteroaryl group which is substituted with $R^1$ and may be substituted simultaneously with $R^2$" regarding R is the aforementioned aryl group. The "5- or 6-membered heteroaryl group" is preferably a pyridinyl group, a pyrazinyl group, a pyrimidinyl group, a pyridazinyl group, a triazinyl group, a thiazolyl group, a thiadiazolyl group, an oxazolyl group, or an oxadiazolyl group. It is more preferably a pyridinyl group, a pyrimidinyl group, a pyridazinyl group, a thiazolyl group, an oxazolyl group, or a thiadiazolyl group. It is even more preferably a pyridinyl group, or a pyridazinyl group. The number of $R^1$ substituted on the "5- or 6-membered heteroaryl group" is 1, and the number of $R^2$ is 0 or 1.

In the general formula (I), R is preferably a group selected from the group consisting of the following groups.

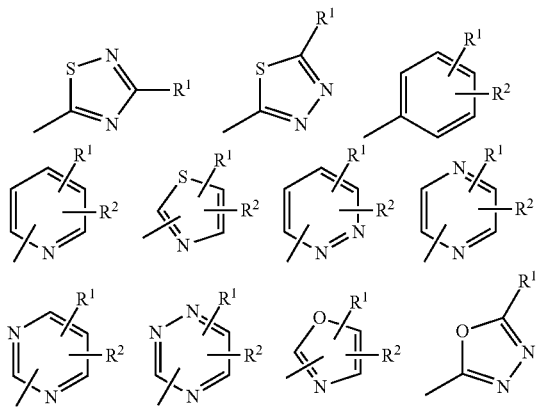

R is more preferably a group selected from the group consisting of the following groups.

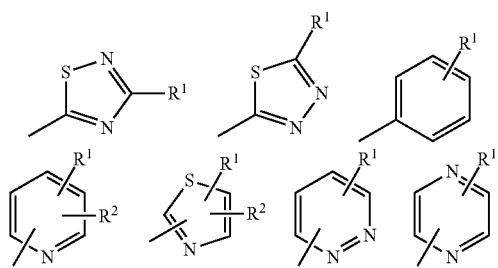

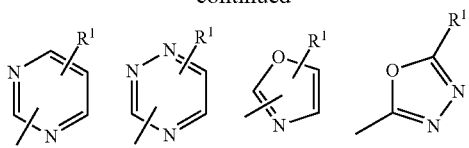

R is even more preferably a group selected from the group consisting of the following groups.

Regarding R of the general formula (I), $R^1$ is a hydrogen atom, a phenyl group, a hydroxy-$C_{1-6}$alkyl group, a hydroxy-$C_{3-7}$ cycloalkyl group, a $C_{1-6}$ alkoxy group which may be substituted with Ra, a $C_{3-7}$ cycloalkylaminosulfonyl group, a 3- to 7-membered monocyclic heterocycloalkylsulfonyl group, a halogeno-$C_{1-3}$ alkoxycarbonylamino group, a halogeno-$C_{1-3}$ alkylcarbonylamino group, a 3- to 7-membered monocyclic heterocycloalkanecarbonyl group substituted with a hydroxy-$C_{1-6}$alkyl group, or —$(CH_2)_n$—C(=O)—NHRf.

The "hydroxy-$C_{1-6}$alkyl group" represented by $R^1$ is the aforementioned hydroxy-$C_{1-6}$alkyl group, preferably the aforementioned $C_{1-4}$alkyl group substituted with 1 to 3 hydroxyl groups (hydroxy-$C_{1-4}$alkyl group), and more preferably an ethyl group substituted with 1 to 3 hydroxyl groups (hydroxy-ethyl group) or an isopropyl group substituted with 1 to 3 hydroxyl groups (hydroxy-isopropyl group). The number of the hydroxyl group is preferably 1. More preferably, the "hydroxy-$C_{1-6}$alkyl group" is a 1-hydroxyethyl group, or a 2-hydroxypropan-2-yl group.

The "hydroxy-$C_{3-7}$ cycloalkyl group" represented by $R^1$ is the aforementioned hydroxy-$C_{3-7}$cycloalkyl group, preferably a cyclic alkyl group with 3 to 5 carbon atoms substituted with 1 to 3 hydroxyl groups (hydroxy-$C_{3-5}$ cycloalkyl group), more preferably a cyclopropyl group substituted with 1 to 3 hydroxyl groups (hydroxy-cyclopropyl group) or a cyclobutyl group substituted with 1 to 3 hydroxyl groups (hydroxy-cyclobutyl group). The number of the hydroxyl group is preferably 1. More preferably, the "hydroxy-$C_{3-7}$ cycloalkyl group" is a 1-hydroxycyclopropyl group, or a 1-hydroxycyclobutyl group.

The "$C_{1-6}$ alkoxy group which may be substituted with Ra" represented by $R^1$ is the aforementioned $C_{1-6}$ alkoxy group which is substituted with 0 to 3 Ra, and it is preferably the aforementioned $C_{1-4}$ alkoxy group which is substituted with 0 to 3 Ra. The number of Ra is preferably 0 or 1.

Ra represents a $C_{1-6}$ alkylpyrazolyl group, a triazolyl group, a tetrazolyl group, or a $C_{1-6}$ alkylsulfonylpiperazinyl group. The "$C_{1-6}$ alkylpyrazolyl group" represented by Ra is a pyrazolyl group which is substituted with one $C_{1-6}$ alkyl group described above, preferably a pyrazolyl group which is substituted with one $C_{1-4}$alkyl group described above ($C_{1-4}$alkylpyrazolyl group), more preferably a pyrazolyl group which is substituted with one methyl group (methylpyrazolyl group), and even more preferably a 1-methyl-1H-pyrazol-5-yl group. The "$C_{1-6}$ alkylsulfonylpiperazinyl group" represented by Ra is a piperazinyl group which is substituted with one sulfonyl group substituted with the $C_{1-6}$ alkyl group described above, preferably a piperazinyl group which is substituted with one sulfonyl group substituted with the $C_{1-4}$ alkyl group described above ($C_{1-4}$ alkylsulfonylpiperazinyl group), and more preferably a piperazinyl group which is substituted with one sulfonyl group substituted with a methyl group (methylsulfonylpiperazinyl group).

The "$C_{1-6}$ alkoxy group which may be substituted with Ra" is preferably a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, or an n-propoxy group substituted with a methylsulfonylpiperazinyl group, and more preferably an isopropoxy group, a 2-methylpropoxy group substituted with a triazolyl group, a 2-methylpropoxy group substituted with a tetrazolyl group, or n-propoxy group substituted with a methylsulfonylpiperazinyl group.

The "$C_{3-7}$ cycloalkylaminosulfonyl group" represented by $R^1$ is the aforementioned $C_{3-7}$cycloalkylaminosulfonyl group, and it is preferably a sulfonyl group which is substituted with an amino group substituted with one cyclic alkyl group with 3 to 5 carbon atoms ($C_{3-5}$ cycloalkylaminosulfonyl group) and more preferably a cyclopropylaminosulfonyl group.

The "3- to 7-membered monocyclic heterocycloalkylsulfonyl group" represented by $R^1$ is a sulfonyl group substituted with the aforementioned heterocycloalkyl group, and it is preferably a sulfonyl group substituted with a 7-membered monocyclic heterocycloalkyl group and more preferably a 1,4-oxazepanylsulfonyl group.

The "halogeno-$C_{1-3}$alkoxycarbonylamino group" represented by $R^1$ is the aforementioned halogeno-$C_{1-3}$ alkoxycarbonylamino group, and it is preferably an amino group which is substituted with one carbonyl group substituted with the aforementioned fluoro-$C_{1-3}$alkoxy group (fluoro-$C_{1-3}$alkoxycarbonylamino group) and more preferably a 2,2,2-trifluoroethoxycarbonylamino group.

The "halogeno-$C_{1-3}$ alkylcarbonylamino group" represented by $R^1$ is the aforementioned halogeno-$C_{1-3}$ alkylcarbonylamino group, and it is preferably an amino group which is substituted with one carbonyl group substituted with the aforementioned fluoro-$C_{1-3}$ alkyl group (fluoro-$C_{1-3}$ alkylcarbonylamino group) and more preferably a 2,2,2-trifluoroethylcarbonylamino group.

The "3- to 7-membered monocyclic heterocycloalkanecarbonyl group substituted with a hydroxy-$C_{1-6}$ alkyl group" represented by $R^1$ is a carbonyl group which is substituted with a 3- to 7-membered monocyclic heterocycloalkane substituted with one hydroxy-$C_{1-6}$alkyl group described above, and it is preferably a 6-membered monocyclic heterocycloalkanecarbonyl group substituted with one hydroxy-$C_{1-4}$alkyl group described above, more preferably a piperidinecarbonyl group substituted with one hydroxy-isopropyl group described above, and even more preferably a 4-(2-hydroxypropan-2-yl)piperidinecarbonyl group.

In the group represented by "—$(CH_2)_n$—C(=O)—NHRf" regarding $R^1$, Rf is a halogeno-$C_{1-3}$ alkyl group, a hydroxy-$C_{1-6}$ alkyl group, a hydroxy-$C_{3-7}$ cycloalkyl group, a hydroxy-$C_{3-7}$cycloalkyl-$C_{1-6}$ alkyl group, or a $C_{1-6}$ alkyl group substituted with Rfa. n is an integer of from 0 to 3, preferably 0 or 1, and more preferably 0.

The "halogeno-$C_{1-3}$alkyl group" represented by Rf is the aforementioned halogeno-$C_{1-3}$ alkyl group, and it is preferably the aforementioned fluoro-$C_{1-3}$ alkyl group, more preferably a 2,2,2-trifluoroethyl group, or a 2,2-difluoroethyl group, and even more preferably a 2,2,2-trifluoroethyl group.

The "hydroxy-$C_{1-6}$alkyl group" represented by Rf is the aforementioned hydroxy-$C_{1-6}$alkyl group, and it is preferably a $C_{1-4}$alkyl group substituted with 1 to 3 hydroxyl groups (hydroxy-$C_{1-4}$ alkyl group), more preferably a 2-methylpropyl group substituted with 1 to 3 hydroxyl groups (hydroxy-2-methylpropyl group), and even more preferably a 2-hydroxy-2-methylpropyl group.

The "hydroxy-$C_{3-7}$ cycloalkyl group" represented by Rf is the aforementioned hydroxy-$C_{3-7}$cycloalkyl group, and it is preferably a cyclic alkyl group with 5 to 7 carbon atoms substituted with 1 to 3 hydroxyl groups (hydroxy-$C_{5-7}$ cycloalkyl group), more preferably a cyclohexyl group substituted with 1 to 3 hydroxyl groups (hydroxy-cyclohexyl group), and even more preferably a 4-hydroxycyclohexyl group.

The "hydroxy-$C_{3-7}$cycloalkyl-$C_{1-6}$alkyl group" represented by Rf is the aforementioned hydroxy-$C_{3-7}$ cycloalkyl-$C_{1-6}$alkyl group, and preferably the aforementioned $C_{1-4}$ alkyl group which is substituted with one cyclic alkyl group having 3 to 5 carbon atoms substituted with 1 to 3 hydroxyl groups (hydroxy-$C_{3-5}$ cycloalkyl group) (hydroxy-$C_{3-5}$ cycloalkyl-$C_{1-4}$ alkyl group), more preferably a methyl group which is substituted with one cyclopropyl group substituted with 1 to 3 hydroxyl groups (hydroxy-cyclopropyl group) (hydroxy-cyclopropylmethyl group), and more preferably a (1-hydroxycyclopropyl)methyl group.

The "$C_{1-6}$ alkyl group represented by Rfa" represented by Rf is the aforementioned $C_{1-6}$ alkyl group substituted with 1 to 3 Rfa, and preferably the aforementioned $C_{1-4}$ alkyl group which is substituted with 1 to 3 Rfa. The number of Rfa is preferably 1.

Rfa is a $C_{1-6}$ alkylpyrazolyl group, a halogeno-$C_{1-3}$ alkylthiazolyl group, an oxadiazolyl group, or a halogeno-$C_{1-3}$alkyloxadiazolyl group. The "$C_{1-6}$alkylpyrazolyl group" represented by Rfa is the aforementioned $C_{1-6}$ alkylpyrazolyl group, and it is preferably a $C_{1-4}$alkylpyrazolyl group, more preferably methylpyrazolyl group, and even more preferably a 1-methyl-1H-pyrazol-5-yl group. The "halogeno-$C_{1-3}$alkylthiazolyl group" represented by Rfa is the aforementioned halogeno-$C_{1-3}$alkylthiazolyl group, and it is preferably a thiazolyl group substituted with one fluoro-$C_{1-3}$ alkyl group described above (fluoro-$C_{1-3}$ alkylthiazolyl group), more preferably a thiazolyl group substituted with one trifluoromethyl group (trifluoromethylthiazolyl group), and even more preferably a 4-(trifluoromethyl)thiazol-2-yl group. The "halogeno-$C_{1-3}$ alkyloxazolyl group" represented by Rfa is the aforementioned halogeno-$C_{1-3}$alkyloxazolyl group, and it is preferably an oxadiazolyl group substituted with one fluoro-$C_{1-3}$alkyl group described above (fluoro-$C_{1-3}$ alkyloxazolyl group), more preferably an oxadiazolyl group substituted with one trifluoromethyl group (trifluoromethyloxazolyl group), and even more preferably a 5-(trifluoromethyl)-1,3,4-oxadiazol-2-yl group.

The "$C_{1-6}$alkyl group substituted with Rfa" is preferably the aforementioned $C_{1-4}$alkyl group which is substituted with any one of one $C_{1-4}$alkylpyrazolyl group described above, one fluoro-$C_{1-3}$ alkylthiazolyl group described above, one oxadiazolyl group, and one fluoro-$C_{1-3}$ alkyloxadiazolyl group described above. More preferably, it is a methyl group substituted with one trifluoromethylthiazolyl group described above, an ethyl group substituted with one methylthiazolyl group described above, an ethyl group substituted with one oxadiazolyl group described above, or an ethyl group substituted with one trifluoromethyloxadiazolyl group described above. Even more preferably, it is a 2-(1-methyl-1H-pyrazol-5-yl)ethyl group, a (4-(trifluoromethyl)thiazol-2-yl)methyl group, a 1-(1,3,4-oxadiazol-2-yl)ethyl group, or a 1-(5-(trifluoromethyl)-1,3,4-oxadiazol-2-yl)ethyl group. Even more preferably, it is a (4-(trifluoromethyl)thiazol-2-yl)methyl group.

Regarding the general formula (I), it is preferable that:

$R^1$ is a hydrogen atom, a phenyl group, a hydroxy-$C_{1-4}$alkyl group, a hydroxy-$C_{3-5}$ cycloalkyl group, a $C_{1-4}$ alkoxy group which may be substituted with Ra, a $C_{3-5}$ cycloalkylaminosulfonyl group, a 7-membered monocyclic heterocycloalkylsulfonyl group, a fluoro-$C_{1-3}$ alkoxycarbonylamino group, a fluoro-$C_{1-3}$ alkylcarbonylamino group, a 6-membered monocyclic heterocycloalkanecarbonyl group substituted with a hydroxy-$C_{1-4}$alkyl group, or —$(CH_2)_n$—$C(=O)$—NHRf;

Ra is a $C_{1-4}$ alkylpyrazolyl group, a triazolyl group, a tetrazolyl group, or a $C_{1-4}$ alkylsulfonylpiperazinyl group;

Rf is a halogeno-$C_{1-3}$ alkyl group, a hydroxy-$C_{1-4}$alkyl group, a hydroxy-$C_{5-7}$cycloalkyl group, a hydroxy-$C_{3-5}$cycloalkyl-$C_{1-4}$ alkyl group, or a $C_{1-4}$alkyl group substituted with Rfa;

Rfa is a $C_{1-4}$alkylpyrazolyl group, a fluoro-$C_{1-3}$ alkylthiazolyl group, an oxadiazolyl group, or a fluoro-$C_{1-3}$ alkyloxadiazolyl group; and n is 0 or 1.

Regarding the general formula (I), it is more preferable that:

$R^1$ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanylsulfonyl group, a 2,2,2-trifluoroethoxycarbonylamino group, a 2,2,2-trifluoroethylcarbonylamino group, a piperidinecarbonyl group substituted with a hydroxy-isopropyl group, or —$(CH_2)_n$—$C(=O)$—NHRf;

Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with trifluoromethyloxazolyl group; and n is 0 or 1.

In the general formula (I), $R^2$ represents a hydrogen atom, a halogen atom, or a halogeno-$C_{1-3}$alkyl group. Examples of the "halogen atom" include the aforementioned halogen atom, and it is preferably a fluorine atom or a chlorine atom. Examples of the "halogeno-$C_{1-3}$alkyl group" include the aforementioned halogeno-$C_{1-3}$alkyl group, and it is preferably a trifluoromethyl group. $R^2$ is preferably a hydrogen atom, a fluorine atom, a chlorine atom, or a trifluoromethyl group. More preferably, it is a hydrogen atom or a fluorine atom.

In the general formula (I), examples of the $C_{6-14}$ aryl group which is substituted with $R^1$ and may be substituted simultaneously with $R^2$ and the 5- or 6-membered heteroaryl group which is substituted with $R^1$ and may be substituted simultaneously with $R^2$ include the followings:

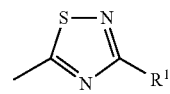

(in the formula, $R^1$ is a hydrogen atom);

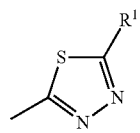

(in the formula,
$R^1$ is —$(CH_2)_n$—$C(=O)$—NHRf,
Rf is a $C_{1-6}$ alkyl group substituted with Rfa,
Rfa is a $C_{1-6}$ alkylpyrazolyl group, or an oxadiazolyl group, and
n is 0);

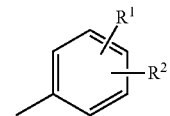

(in the formula,
$R^1$ is a phenyl group, a hydroxy-$C_{1-4}$alkyl group, a hydroxy-$C_{3-7}$ cycloalkyl group, or a $C_{1-6}$ alkoxy group which may be substituted with Ra,
$R^2$ is a hydrogen atom, a halogen atom, or a halogeno-$C_{1-3}$ alkyl group, and
Ra is a $C_{1-6}$ alkylpyrazolyl group, or a $C_{1-6}$ alkylsulfonylpiperazinyl group);

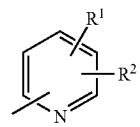

(in the formula,
$R^1$ is the aforementioned hydroxy-$C_{1-6}$alkyl group, hydroxy-$C_{3-7}$cycloalkyl group, $C_{1-6}$ alkoxy group which may be substituted with Ra, $C_{3-7}$ cycloalkylaminosulfonyl group, halogeno-$C_{1-3}$ alkoxycarbonylamino group, halogeno-$C_{1-3}$ alkylcarbonylamino group, or —$(CH_2)_n$—$C(=O)$—NHRf,
$R^2$ is a hydrogen atom or a halogen atom,
Ra is a triazolyl group, or a tetrazolyl group,
Rf is a halogeno-$C_{1-3}$ alkyl group or a $C_{1-6}$ alkyl group substituted with Rfa, Rfa is a halogeno-$C_{1-3}$ alkylthiadiazolyl group, an oxadiazolyl group, or a halogeno-$C_{1-3}$alkyloxadiazolyl group, and,
n is 0 or 1);

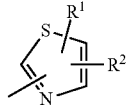

(in the formula,
$R^1$ is the aforementioned hydroxy-$C_{1-6}$alkyl group, 3- to 7-membered monocyclic heterocycloalkylsulfonyl group, or —$(CH_2)_n$—C(=O)—NHRf,
$R^2$ is a hydrogen atom, a halogen atom, or a halogeno-$C_{1-3}$ alkyl group,
Rf is a halogeno-$C_{1-3}$alkyl group, or a $C_{1-6}$ alkyl group substituted with Rfa,
Rfa is an oxadiazolyl group, and,
n is 0);

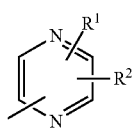

(in the formula,
$R^1$ is the aforementioned hydroxy-$C_{1-6}$ alkyl group, or —$(CH_2)_n$—C(=O)—NHRf,
$R^2$ is a hydrogen atom, a halogen atom, or a halogeno-$C_{1-3}$ alkyl group,
Rf is a halogeno-$C_{1-3}$alkyl group, a hydroxy-$C_{1-6}$alkyl group, a hydroxy-$C_{3-7}$ cycloalkyl group, or a hydroxy-$C_{37}$ cycloalkyl-$C_{1-6}$alkyl group, and,
n is 0);

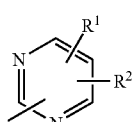

(in the formula,
$R^1$ is the aforementioned —$(CH_2)_n$—C(=O)—NHRf,
$R^2$ is a hydrogen atom, a halogen atom, or a halogeno-$C_{1-3}$ alkyl group,
Rf is a hydroxy-$C_{1-6}$alkyl group, and,
n is 0);

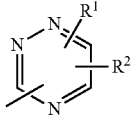

(in the formula,
$R^1$ is the aforementioned —$(CH_2)_n$—C(=O)—NHRf,
$R^2$ is a hydrogen atom, a halogen atom, or a halogeno-$C_{1-3}$ alkyl group,
Rf is a hydroxy-$C_{1-6}$alkyl group, and,
n is 0);

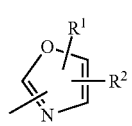

(in the formula,
$R^1$ is the aforementioned —$(CH_2)_n$—C(=O)—NHRf,
$R^2$ is a hydrogen atom, a halogen atom, or a halogeno-$C_{1-3}$ alkyl group,
Rf is a halogeno-$C_{1-3}$alkyl group, and,
n is 0);

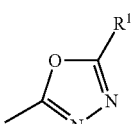

(in the formula,
$R^1$ is a 3- to 7-membered monocyclic cycloheteroalkanecarbonyl group which is substituted with the aforementioned hydroxy-$C_{1-6}$alkyl group,
$R^2$ is a hydrogen atom, a halogen atom, or a halogeno-$C_{1-3}$ alkyl group); and,

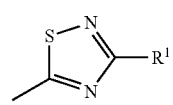

(in the formula, $R^1$ a 3- to 7-membered monocyclic cycloheteroalkanecarbonyl group which is substituted with the aforementioned hydroxy-$C_{1-6}$alkyl group).

Regarding the general formula (I), more preferred combination of R, $R^1$, and $R^2$ is described below:

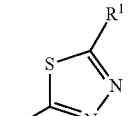

(in the formula, $R^1$ is a hydrogen atom);

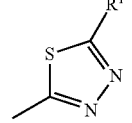

(in the formula,
$R^1$ represents —$(CH_2)_n$—C(=O)—NHRf,
Rf represents a methyl group substituted with Rfa or an ethyl group substituted with Rfa, Rfa is a methylpyrazolyl group or an oxadiazolyl group, and,
n is 0);

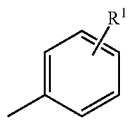

(in the formula,
R¹ is phenyl group, a hydroxy-ethyl group, a hydroxy-isopropyl group, a methoxy group, an isopropoxy group, an ethoxy group substituted with a methylpyrazolyl group, or an n-propoxy group substituted with a methylsulfonylpiperazinyl group);

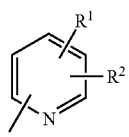

(in the formula,
R¹ is a hydroxy-isopropyl group, a hydroxy-cyclopropyl group, a hydroxy-cyclobutyl group, an isopropoxy group, an ethoxy group substituted with a triazolyl group, a 2-methylpropoxy group substituted with a triazolyl group, a 2-methylpropoxy group substituted with a tetrazolyl group, a cyclopropylaminosulfonyl group, a 2,2,2-trifluoroethoxycarbonylamino group, a 2,2,2-trifluoroethylcarbonylamino group, or —(CH$_2$)$_n$—C(═O)—NHRf,
R² is a hydrogen atom, a fluorine atom, or a chlorine atom,
Rf represents a 2,2-difluoroethyl group, a 2,2,2-trifluoroethyl group, a methyl group substituted with Rfa, or an ethyl group substituted with Rfa;
Rfa is a trifluoromethylthiazolyl group, an oxadiazolyl group, or a trifluoromethyloxadiazolyl group, and,
n is 0 or 1);

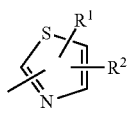

(in the formula,
R¹ is a hydroxy-isopropyl group, a 1,4-oxazepanylsulfonyl group, or —(CH$_2$)$_n$—C(═O)—NHRf,
R² is a hydrogen atom or a trifluoromethyl group,
Rf is a 2,2,2-trifluoroethyl group, or an ethyl group substituted with Rfa,
Rfa is an oxadiazolyl group, and,
n is 0);

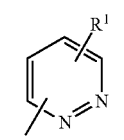

(in the formula,
R¹ is a hydroxy-isopropyl group or —(CH$_2$)$_n$—C(═O)—NHRf,

Rf is a 2,2-difluoroethyl group, a 2,2,2-trifluoroethyl group, a hydroxy-2-methylpropyl group, a hydroxycyclohexyl group, or a hydroxycyclopropylmethyl group, and
n is 0);

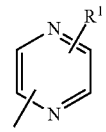

(in the formula,
R¹ is —(CH$_2$)—C(═O)—NHRf,
Rf is a hydroxy-2-methylpropyl group, and
n is 0);

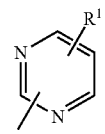

(in the formula,
R¹ is —(CH$_2$)$_n$—C(═O)—NHRf,
Rf is a hydroxy-2-methylpropyl group, and
n is 0);

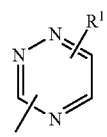

(in the formula,
R¹ is —(CH$_2$)$_n$—C(═O)—NHRf,
Rf is a 2,2,2-trifluoroethyl group, and
n is 0);

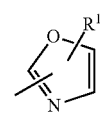

(in the formula,
R¹ is a piperidinecarbonyl group substituted with a hydroxy-isopropyl group); or

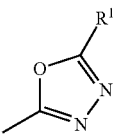

(in the formula,
R¹ is a piperidinecarbonyl group substituted with a hydroxy-isopropyl group).

Regarding the general formula (I), even more preferred combination of R, R¹, and R² is described below:

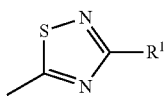

(in the formula, $R^1$ is a hydrogen atom);

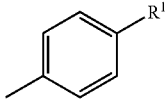

(in the formula, $R^1$ is an isopropoxy group, or an n-propoxy group substituted with a methylsulfonylpiperazinyl group);

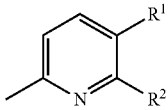

(in the formula,
$R^1$ is the aforementioned hydroxy-isopropyl group, a 2-methylpropoxy group substituted with a tetrazolyl group, or —$(CH_2)_n$—C(=O)—NHRf,
$R^2$ is a hydrogen atom or a fluorine atom,
Rf is a 2,2,2-trifluoroethyl group, a methyl group substituted with a trifluoromethylthiazolyl group, an ethyl group substituted with an oxadiazolyl group, or an ethyl group substituted with a trifluoromethyloxadiazolyl group, and
n is 0);

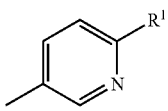

(in the formula, $R^1$ is an isopropoxy group, or a 2-methylpropoxy group substituted with a tetrazolyl group);

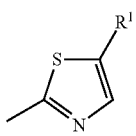

(in the formula, $R^1$ is a 1,4-oxazepanylsulfonyl group);

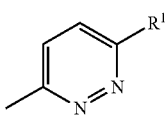

(in the formula,
$R^1$ is the aforementioned hydroxy-isopropyl group, or —$(CH_2)$n-C(=O)—NHRf,
Rf is the aforementioned hydroxy-2-methylpropyl group, and
n is 0);

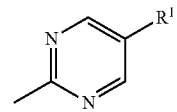

(in the formula,
$R^1$ is —$(CH_2)_n$—C(=O)—NHRf,
Rf is a hydroxy-2-methylpropyl group, and
n is 0); or

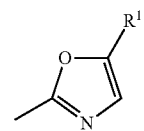

(in the formula, $R^1$ is a piperidinecarbonyl group substituted with a hydroxy-isopropyl group).

According to a preferred embodiment, in the general formula (I),
X is a chlorine atom, a bromine atom, or a trifluoromethyl group;
R is a group selected from the group consisting of the following groups;

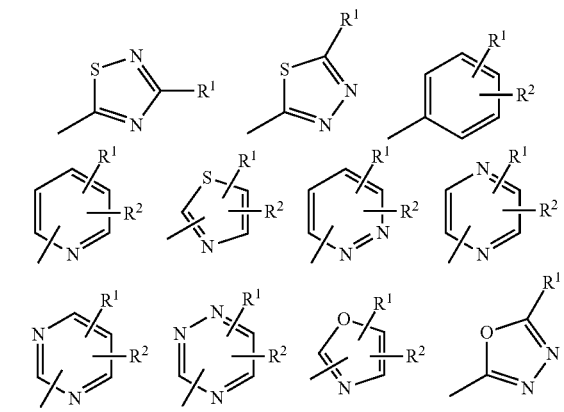

$R^1$ is a hydrogen atom, a phenyl group, a hydroxy-$C_{1-4}$alkyl group, a hydroxy-$C_{3-5}$ cycloalkyl group, a $C_{1-4}$ alkoxy group which may be substituted with Ra, a $C_{3-5}$ cycloalkylaminosulfonyl group, a 7-membered monocyclic heterocycloalkylsulfonyl group, a fluoro-$C_{1-3}$ alkoxycarbonylamino group, a fluoro-$C_{1-3}$alkylcarbonylamino group, a 6-membered monocyclic heterocycloalkanecarbonyl group substituted with a hydroxy-$C_{1-4}$ alkyl group, or —$(CH_2)_n$—C(=O)—NHRf;
$R^2$ is a hydrogen atom, a fluorine atom, a chlorine atom, or a trifluoromethyl group;
Ra is a $C_{1-4}$alkylpyrazolyl group, a triazolyl group, a tetrazolyl group, or a $C_{1-4}$ alkylsulfonylpiperazinyl group;
Rf is a fluoro-$C_{1-3}$alkyl group, a hydroxy-$C_{1-4}$ alkyl group, a hydroxy-$C_{3-5}$cycloalkyl group, a hydroxy-$C_{3-5}$cycloalkyl-$C_{1-4}$alkyl group, or a $C_{1-4}$alkyl group substituted with Rfa;

Rfa is a $C_{1-4}$ alkylpyrazolyl group, a fluoro-$C_{1-3}$ alkylthiazolyl group, an oxadiazolyl group, or a fluoro-$C_{1-3}$ alkyloxadiazolyl group; and n is 0 or 1.

According to a more preferred embodiment, in the general formula (I),

X is a chlorine atom, a bromine atom, or a trifluoromethyl group;

R is a group selected from the group consisting of the following groups;

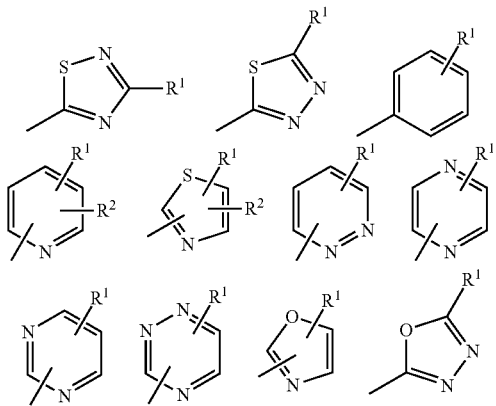

$R^1$ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanylsulfonyl group, a 2,2,2-trifluoroethoxycarbonylamino group, a 2,2,2-trifluoroethylcarbonylamino group, a piperidinecarbonyl group substituted with a hydroxy-isopropyl group, or —$(CH_2)_n$—C(=O)—NHRf;

$R^2$ is a hydrogen atom, a fluorine atom, a chlorine atom, or a trifluoromethyl group;

Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with a trifluoromethyl group; and n is 0 or 1.

According to an even more preferred embodiment, in the general formula (I),

X is a chlorine atom or a trifluoromethyl group;

R is a group selected from the group consisting of the following groups;

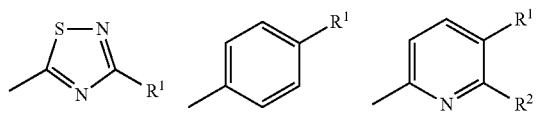

-continued

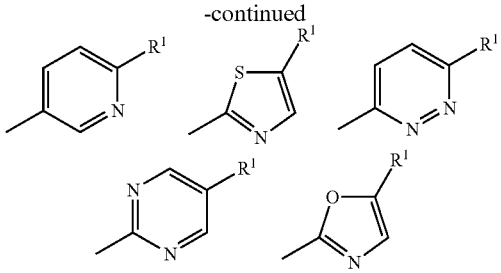

$R^1$ is a hydrogen atom, a hydroxy-isopropyl group, an isopropoxy group, a 2-methylpropoxy group substituted with a tetrazolyl group, an n-propoxy group substituted with a methylsulfonylpiperazinyl group, a 1,4-oxazepanylsulfonyl group, a piperidinecarbonyl group substituted with a hydroxy-isopropyl group, or —$(CH_2)_n$—C(=O)—NHRf;

$R^2$ is a hydrogen atom or a fluorine atom;

Rf is a 2,2,2-trifluoroethyl group, a hydroxy-2-methylpropyl group, a methyl group substituted with a trifluoromethylthiazolyl group, an ethyl group substituted with an oxadiazolyl group, or an ethyl group substituted with a trifluoromethyloxadiazolyl group; and n is 0.

Specific examples of the tetrahydropyridopyrimidine compound that are preferred in the present invention include the compounds described in the following (1) to (19).

(1) 4-(4-((1,2,4-thiadiazol-5-yl)amino)-5,6-dihydropyrido[3,4-d]pyrimidin-7(8H)-yl)-2-(trifluoromethyl)benzonitrile (Example 1)

(2) 4-(4-((4-isopropoxyphenyl)amino)-5,6-dihydropyrido[3,4-d]pyrimidin-7(8H)-yl)-2-(trifluoromethyl)benzonitrile (Example 2)

(3) 4-(4-((6-fluoro-5-(2-hydroxypropan-2-yl)pyridin-2-yl)amino)-5,6-dihydropyrido[3,4-d]pyrimidin-7(8H)-yl)-2-(trifluoromethyl)benzonitrile (Example 5)

(4) 2-chloro-4-(4-((6-(2-hydroxypropan-2-yl)pyridazin-3-yl)amino)-5,6-dihydropyrido[3,4-d]pyrimidin-7(8H)-yl)benzonitrile (Example 6)

(5) 4-(4-((5-(2-hydroxypropan-2-yl)pyridin-2-yl)amino)-5,6-dihydropyrido[3,4-d]pyrimidin-7(8H)-yl)-2-(trifluoromethyl)benzonitrile (Example 7)

(6) 2-chloro-4-(4-((5-(2-hydroxypropan-2-yl)pyridin-2-yl)amino)-5,6-dihydropyrido[3,4-d]pyrimidin-7(8H)-yl)benzonitrile (Example 9)

(7) 4-(4-((6-(2-hydroxypropan-2-yl)pyridazin-3-yl)amino)-5,6-dihydropyrido[3,4-d]pyrimidin-7(8H)-yl)-2-(trifluoromethyl)benzonitrile (Example 10)

(8) 6-((7-(4-cyano-3-(trifluoromethyl)phenyl)-5,6,7,8,-tetrahydropyrido[3,4-d]pyrimidin-4-yl)amino)-N-(2,2,2-trifluoroethyl)nicotinamide (Example 11)

(9) 4-(4-((6-isopropoxypyridin-3-yl)amino)-5,6-dihydropyrido[3,4-d]pyrimidin-7(8H)-yl)-2-(trifluoromethyl)benzonitrile (Example 13)

(10) 4-(4-((6-(2-methyl-2-(1H-tetrazol-1-yl)propoxy)pyridin-3-yl)amino)-5,6-dihydropyrido[3,4-d]pyrimidin-7(8H)-yl)-2-(trifluoromethyl)benzonitrile (Example 16)

(11) 4-(4-((5-(2-methyl-2-(1H-tetrazol-1-yl)propoxy)pyridin-2-yl)amino)-5,6-dihydropyrido[3,4-d]pyrimidin-7(8H)-yl)-2-(trifluoromethyl)benzonitrile (Example 17)

(12) 4-(4-((4-(3-(4-(methylsulfonyl)piperazin-1-yl)propoxy)phenyl)amino)-5,6-dihydropyrido[3,4-d]pyrimidin-7(8H)-yl)-2-(trifluoromethyl)benzonitrile (Example 18)

(13) 4-(4-((5-(((1,4-oxazepan-4-yl)sulfonyl)thiazol-2-yl)amino)-5,6-dihydropyrido[3,4-d]pyrimidin-7 (H)-yl)-2-(trifluoromethyl)benzonitrile (Example 20)
(14) 6-((7-(4-cyano-3-(trifluoromethyl)phenyl)-5,6,7,8-tetrahydropyrido[3,4-d]pyrimidin-4-yl)amino)-N-(2-hydroxy 2-methylpropyl)pyridazine-3-carboxamide (Example 32)
(15) 2-((7-(4-cyano-3-(trifluoromethyl)phenyl)-5,6,7,8-tetrahydropyrido[3,4-d]pyrimidin-4-yl)amino)-N-(2-hydroxy 2-methylpropyl)pyrimidine-5-carboxamide (Example 34)
(16) 6-((7-(4-cyano-3-(trifluoromethyl)phenyl)-5,6,7,8-tetrahydropyrido[3,4-d]pyrimidin-4-yl)amino)-N-((4-(trifluoromethyl)thiazol-2-yl)methyl)nicotinamide (Example 36)
(17) (R)—N-(1-(1,3,4-oxadiazol-2-yl)ethyl)-6-((7-(4-cyano-3-(trifluoromethyl)phenyl)-5,6,7,8-tetrahydropyrido[3,4-d]pyrimidin-4-yl)amino)nicotinamide (Example 38)
(18) (R)-6-((7-(4-cyano-3-(trifluoromethyl)phenyl)-5,6,7,8-tetrahydropyrido[3,4-d]pyrimidin-4-yl)amino)-N-(1-(5-(trifluoromethyl)-1,3,4-oxadiazol-2-yl)ethyl)nicotinamide (Example 40)
(19) 4-(4-((5-(4-(2-hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile (Example 42)

The tetrahydropyridopyrimidine compound of the present invention or a salt thereof can be produced by various methods. The compound represented by the general formula (I) can be produced according to a generally known method. The compound represented by the general formula (I) can be produced by the following Reaction schemes 1 to 6, for example. In Reaction schemes 1 to 6, X, R, $R^1$, $R^2$, Rf, and Ra are as defined above.

Reaction scheme 1

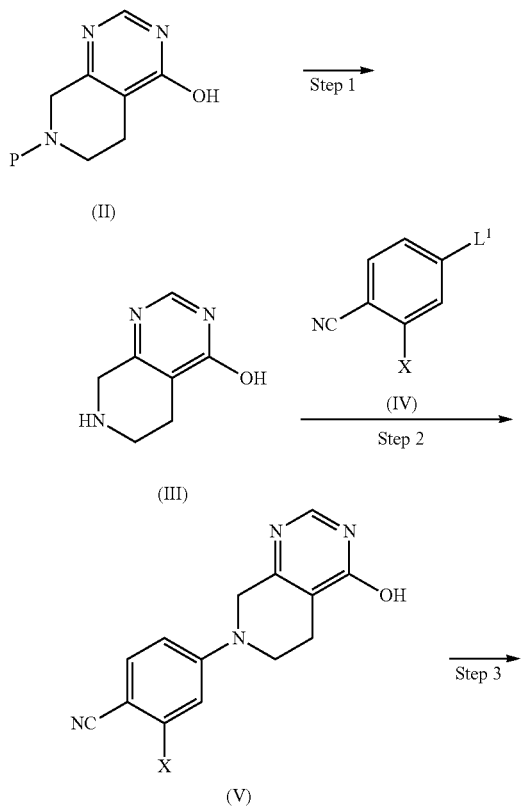

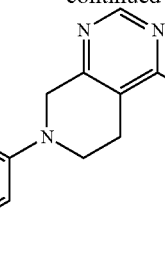

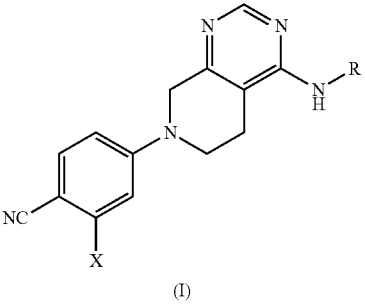

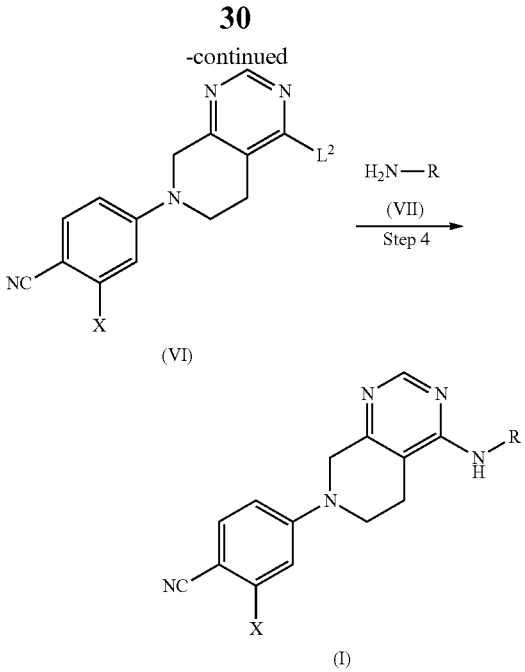

The present reaction scheme is a reaction scheme for synthesizing the general formula (I) from the formula (II).

(Step 1)

This step is a reaction for deprotecting the protecting group P of the compound of the formula (II) shown in Reaction scheme 1 above. As for the method for deprotection, it can be performed by a generally known method, for example, the method described in Protective Groups in Organic Synthesis, T. W. Greene, John Wiley & Sons (1981) or a method similar to it. Examples of the protecting group include a Boc group, a benzyloxycarbonyl group, and a benzyl group. When a benzyl group is used as a protecting group, examples of the catalyst for hydrogenolysis include palladium hydroxide, palladium/carbon, platinum, Raney nickel, platinum oxide, and rhodium-aluminum oxide. Preferably, it is palladium/carbon. The amount used of the reagent is, relative to 1 eqv. of the compound of the formula (II), 0.001 to 10 eqv., and preferably 0.05 to 2 eqv. Temperature for deprotecting reaction is 0 to 100° C., and preferably 40 to 80° C. The compound of the formula (III) obtained by this step can be separated and purified by a known means for separation and purification, for example, concentration, concentration under reduced pressure, crystallization, re-precipitation, and chromatography, or it can be subjected to the next step without any separation and purification.

(Step 2)

This step is a step for producing the compound represented by the formula (V) according to a nucleophilic substitution reaction between the amine represented by the formula (III) and the aromatic ring substituted with the leaving group $L^1$ represented by the formula (IV). Examples of the leaving group $L^1$ include, in addition to a halogen atom such as fluorine and chlorine, a methanesulfonyloxy group, a p-toluenesulfonyloxy group, and a trifluoromethylsulfonyloxy group. The solvent used for this step is not particularly limited as long as it does not cause any problem on the reaction. Examples of the solvent include toluene, acetonitrile, benzene, dioxane, THF, DMSO, DMF, pyridine, and a mixed solvent thereof. It is preferably DMSO. The equivalent of the aromatic ring represented by the formula (IV), which is used for this reaction, is 0.1 to excess mol and preferably 0.5 to 3 mol relative to 1 mol of the amine represented by the formula (III). For the reaction, a base may be either used or not used. When a base is used, examples of the base include pyridine, DBU, potassium carbonate, cesium carbonate, and a tertiary amine. Preferably, it is triethylamine. The temperature for the nucleophilic substitution reaction is 0 to 200° C., and preferably 0 to 50° C. The compound of the formula (V) obtained by this step can be separated and purified by a known means for separation and purification, for example, concentration, concentration under reduced pressure, crystallization, re-precipitation, and chromatography, or it can be subjected to the next step without any separation and purification.

(Step 3)

This step is a step for converting the free hydroxyl group of the compound of the formula (V) to a leaving group $L^2$. Examples of the leaving group $L^2$ include the same groups as $L^1$, and it is preferably a halogen atom. The conversion reaction is carried out without a solvent or in the presence of a solvent. Examples of the solvent which can be used for this step is not particularly limited as long as it does not cause any problem on the reaction. Examples of the solvent include DMF, NMP, DMA, toluene, dichloroethane, and acetonitrile. Examples of the base used for the reaction include triethylamine, diisopropylethylamine, N,N-dimethylaniline, and sodium hydrogen carbonate. The amount of the halogenating agent used for the reaction (e.g., phosphorus oxychloride, phosphorus pentachloride, and phosphorus tribromide) is, relative to 1 mol of the compound of the formula (V), 0.5 to 20 mol, and preferably 5 to 15 mol. The time of the conversion reaction is 0.1 to 48 hours, and preferably 0.5 to 24 hours. The reaction temperature is 0 to 200° C., and preferably 50 to 120° C. The compound of the formula (VI) obtained by this step can be separated and purified by a known means for separation and purification, for example, concentration, concentration under reduced pressure, crystallization, re-precipitation, and chromatography, or it can be subjected to the next step without any separation and purification.

(Step 4)

This step is a step for obtaining the compound of the general formula (I) by linking the compound of the formula (VI) to the compound of the formula (VII). The reaction of this step is performed by using a metal catalyst and a phosphine ligand in a suitable solvent, in the presence of various bases. As the metal catalyst, a metal complex having various ligands can be used, and examples thereof include tetrakistriphenylphosphine palladium (0), chlorobis(triphenylphosphine)palladium (II), tris (dibenzylideneacetone) dipalladium (0), and palladium acetate (II). Examples of the phosphine ligand include dppf, Xantphos, and XPhos. Examples of the base used for the reaction of this step include potassium carbonate, cesium carbonate, and sodium tert-butoxide. The solvent which can be used for this step is not particularly limited as long as it does not cause any problem on the reaction. Examples of the solvent include dioxane, ethyl acetate, and toluene. The amount of the metal catalyst used for the reaction is, relative to 1 mol of the compound of the formula (VI), 0.005 to 10 mol, and preferably 0.01 to 1 mol. The time of the reaction is 0.1 to 48 hours, and preferably 0.5 to 24 hours. The reaction temperature is 0 to 200° C., and preferably 50 to 120° C. The compound of the formula (I) obtained by this step can be separated and purified by a known means for separation and purification, for example, concentration, concentration under reduced pressure, crystallization, re-precipitation, and chromatography.

According to another method for this step, the compound represented by the general formula (I) can be obtained by using only a base without using the metal catalyst and phosphine ligand. Examples of the base include potassium carbonate. The amount of the base is, relative to 1 mol of the compound of the formula (VI), 0.005 to 10 mol, and preferably 1.0 to 5.0 mol. The solvent used for the reaction of this step is not particularly limited as long as it does not cause any problem on the reaction. Examples of the solvent include acetonitrile and dioxane. The time of the reaction is 0.1 to 48 hours, and preferably 0.5 to 24 hours. The reaction temperature is 0 to 200° C., and preferably 50 to 120° C. The compound of the general formula (I) obtained by this step can be separated and purified by a known means for separation and purification, for example, concentration, concentration under reduced pressure, crystallization, re-precipitation, and chromatography.

As another method for this step, the linking between the compound of the formula (VI) and the compound of the formula (VII) can be performed under irradiation of microwave. In that case, the aforementioned base can be used as a base of this step; however, it is also possible to use no base. The solvent used for the reaction of this step is not particularly limited as long as it does not cause any problem on the reaction. Examples of the solvent include acetonitrile. The time of the reaction is 0.01 to 10 hours, and preferably 0.1 to 1 hour. The reaction temperature is 0 to 200° C., and preferably 100 to 200° C. The compound of the general formula (I) obtained by this step can be separated and purified by a known means for separation and purification, for example, concentration, concentration under reduced pressure, crystallization, re-precipitation, and chromatography.

As another method for this step, the linking between the compound of the formula (VI) and the compound of the formula (VII) can be performed by using an acid instead of using the metal catalyst and phosphine ligand. The equivalent of the compound of the formula (VII) is, relative to 1 mol of the compound of the formula (VI), 0.1 to excess mol, and preferably 1 to 10 mol. Examples of the acid which is used include paratoluenesulfonic acid, camphorsulfonic acid, and hydrochloric acid. The amount of the acid is, relative to 1 mol of the compound of the formula (VI), 0.005 to excess mol, and preferably 0.1 to 10 mol. The solvent used for the reaction of this step is not particularly limited as long as it does not cause any problem on the reaction. Examples of the solvent include tert-butanol, 2-propanol, THF, and dioxane. The time of the reaction is 0.1 to 48 hours, and preferably 0.1 to 24 hours. The reaction temperature is 0 to 200° C., and preferably 50 to 180° C. The compound of the general formula (I) obtained by this step can be separated and purified by a known means for separation and purification, for example, concentration, concentration under reduced pressure, crystallization, re-precipitation, and chromatography.

Reaction scheme 2

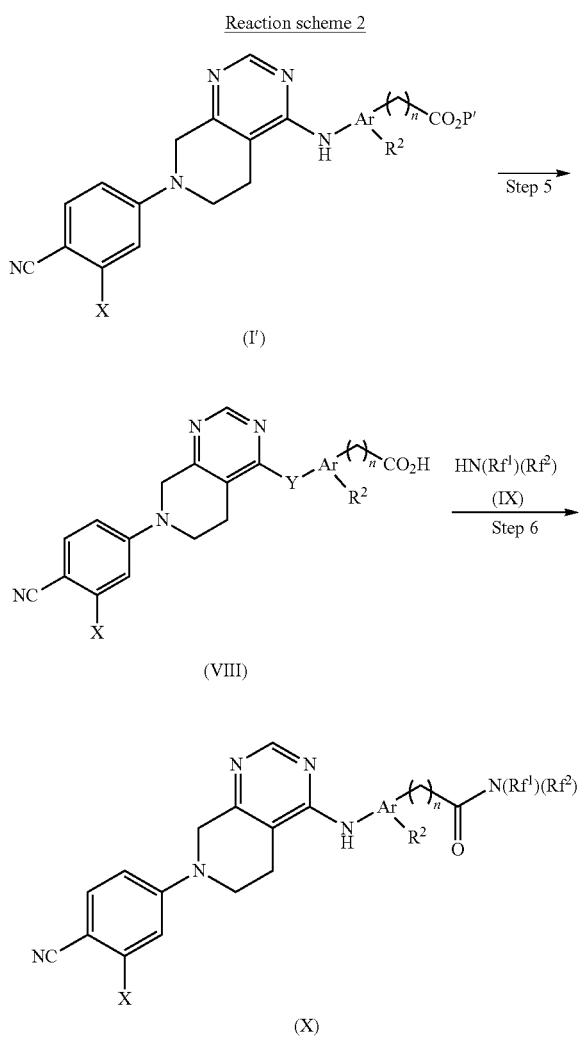

The present reaction scheme can be applied when $R^1$ substituted on R of the general formula (I) is —$(CH_2)_n$—C(=O)—NHRf, or a 3- to 7-membered monocyclic nitrogen-containing heterocycloalkyl group substituted with hydroxy-$C_{1-6}$ alkyl group.

(Step 5)

This step is a step for obtaining the compound represented by the formula (VIII) through hydrolysis of an ester group of the compound represented by the formula (I') by a commonly known method. In the formula (I'), Ar is a $C_{6-14}$ aryl group, or a 5- or 6-membered heteroaryl group, n is an integer of 0 to 3, and $R^2$ is as defined above. The compound of the formula (I') can be produced according to the process of the aforementioned Reaction scheme 1. As for the method for deprotecting the protecting group P', it can be performed by a generally known method, for example, the method described in Protective Groups in Organic Synthesis, T. W. Greene, John Wiley & Sons (1981) or a method similar to it. Examples of the protecting group P' include a methyl group and an ethyl group. In that case, deprotection under basic condition is preferable, and examples of the base include an inorganic base such as sodium hydroxide and potassium hydroxide. The amount used of the base is, relative to 1 mol of the compound of the formula (I'), 1 to 100 mol. The solvent used for the reaction of this step is not particularly limited as long as it does not cause any problem on the reaction. Examples of the solvent include water, methanol, ethanol, diethyl ether, and THF. The time of the reaction is 0.1 to 100 hours, and preferably 0.5 to 24 hours. Temperature for the reaction is 0 to 120° C., and preferably 0 to 90° C. The compound of the formula (VIII) obtained by this step can be separated and purified by a known means for separation and purification, for example, concentration, drying under reduced pressure, crystallization, re-precipitation, solvent extraction, and chromatography, or it can be subjected to the next step without any separation and purification.

(Step 6)

This step is a step for synthesizing the compound represented by the general formula (X) through condensation between the compound represented by the formula (VIII) and the amine represented by the formula (IX). The group represented by —$N(Rf^1)$ $(Rf^2)$ in the formula (IX) is —NHRf or a 3- to 7-membered monocyclic nitrogen-containing heterocycloalkyl group substituted with hydroxy-$C_{16}$ alkyl group. The solvent used for the reaction of this step is not particularly limited as long as it does not cause any problem on the reaction. Examples of the solvent include DMF, toluene, dichloromethane, acetonitrile, THF, and DMSO. It is preferably DMF or methanol. Examples of the condensing agent include DCC, WSC/1-hydroxybenzotriazole (hereinbelow, HOBt), DMT-MM, and HATU. It is preferably WSC/HOBt, DMT-MM, or HATU. The number of the equivalents of the condensing agent is, relative to 1 eqv. of the compound of the formula (VIII), 0.2 to 5.0 eqv., and preferably 1.0 to 1.5 eqv. Furthermore, a base such as DIPEA can be used, if necessary. Temperature for the reaction is 0 to 100° C., and preferably 10 to 40° C. Time for the reaction is 0.1 to 24 hours, and preferably 0.5 to 16 hours. The compound of the formula (X) obtained by this step can be separated and purified by a known means for separation and purification, for example, concentration, drying under reduced pressure, crystallization, re-precipitation, solvent extraction, and chromatography.

Reaction scheme 3

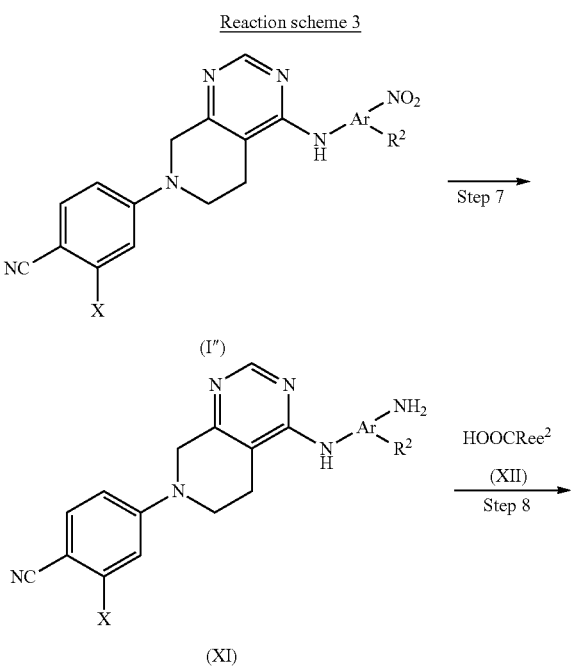

-continued

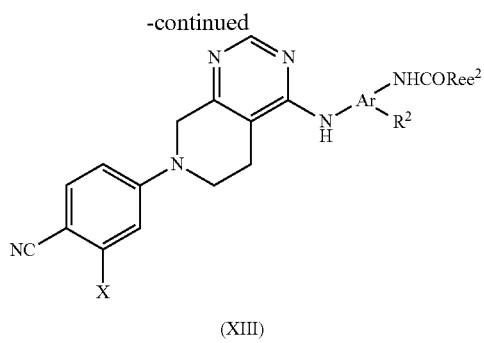

(XIII)

The present reaction scheme can be applied when $R^1$ substituted on R of the general formula (I) is a halogeno-$C_{1-3}$ alkylcarbonylamino group.

(Step 7)

This step is a reaction for obtaining the compound represented by the formula (XI) through a commonly known contact reduction of the nitro group of the compound represented by the formula (I''). The compound of the formula (I'') can be produced according to the process of the aforementioned Reaction scheme 1. The solvent used for the reaction of this step is not particularly limited as long as it does not cause any problem on the reaction. Examples of the solvent include methanol, ethanol, 1-propanol, 2-propanol, tert-butyl alcohol, dimethoxyethane, diethylene glycol dimethyl ether, diisopropyl ether, diethyl ether, THF, dioxane, ethyl acetate, and butyl acetate. It is preferably methanol or ethanol. Examples of the catalyst used for this step include palladium/carbon, palladium hydroxide/carbon, platinum, Raney nickel, platinum oxide, and rhodium-aluminum oxide. Preferably, it is palladium/carbon. The number of the equivalents of the catalyst is, relative to 1 eqv. of the compound of the formula (I''), 0.001 to 10 eqv., and preferably 0.01 to 5.0 eqv. Temperature for the reducing reaction is 0 to 100° C., and preferably 20 to 60° C. Time for the reaction is 0.1 to 72 hours, and preferably 6 to 72 hours. The compound of the formula (XI) obtained by this step can be separated and purified by a known means for separation and purification, for example, concentration, concentration under reduced pressure, crystallization, re-precipitation, and chromatography, or it can be subjected to the next step without any separation and purification.

(Step 8)

This step is an amidation between the compound represented by the general formula (XI) and the carboxylic acid represented by the formula (XII). $Ree^2$ is a halogeno-$C_{1-3}$alkyl group. The solvent used for the reaction of this step is not particularly limited as long as it does not cause any problem on the reaction. Examples of the solvent include DMF, toluene, dichloromethane, acetonitrile, THF, and DMSO. It is preferably DMF or methanol. Examples of the condensing agent which is used for this step include DCC, WSC/HOBt, DMT-MM, and HATU. It is preferably WSC/HOBt, DMT-MM, or HATU. The number of the equivalents of the condensing agent is, relative to 1 eqv. of the compound of the formula (XI), 0.2 to 5.0 eqv., and preferably 1.0 to 1.5 eqv. Furthermore, a base such as DIPEA can be used, if necessary. Temperature for the amidation reaction is 0 to 100° C., and preferably 10 to 40° C. Time for the reaction is 0.1 to 24 hours, and preferably 0.5 to 16 hours. The compound of the formula (XIII) obtained by this step can be separated and purified by a known means for separation and purification, for example, concentration, concentration under reduced pressure, crystallization, re-precipitation, and chromatography.

Reaction scheme 4

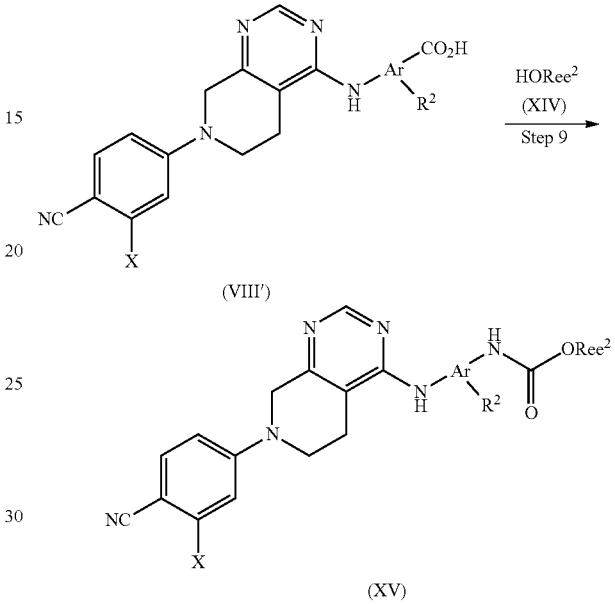

The present reaction scheme can be applied when $R^1$ substituted on R of the general formula (I) is a halogeno-$C_{1-3}$ alkoxycarbonylamino group. $Ree^2$ has the same meaning as the aforementioned $Ree^2$.

(Step 9)

This step is a step for obtaining the compound represented by the formula (XV) from the compound represented by the formula (VIII'). This step is a Cutius transition reaction between the compound represented by the formula (VIII') and an alcohol represented by the formula (XIV). Examples of the base which is used for this step include triethylamine and N,N-diisopropylamine. The amount used of the base is, relative to 1 eqv. of the compound of the formula (VIII'), 1 to 10 eqv., for example. Examples of an azidation reagent include sodium azide and DPPA. The amount used of the azidation reagent is, relative to 1 eqv. of the compound of the formula (VIII'), 1 to 5 eqv. The amount used of the alcohol represented by the formula (XIV) is, relative to 1 eqv. of the compound of the formula (VIII'), generally 1 to 10 eqv. and preferably 2 to 5 eqv. Examples of the solvent used for this step include dichloromethane, chloroform, THF, toluene, and dioxane. Temperature for the reaction is 0° C. to 200° C. Time for the reaction is 0 to 24 hours. If necessary, the reaction can be performed under irradiation of microwave. The compound of the formula (XV) obtained by this step can be separated and purified by a known means for separation and purification, for example, concentration, concentration under reduced pressure, crystallization, re-precipitation, and chromatography.

Reaction scheme 5

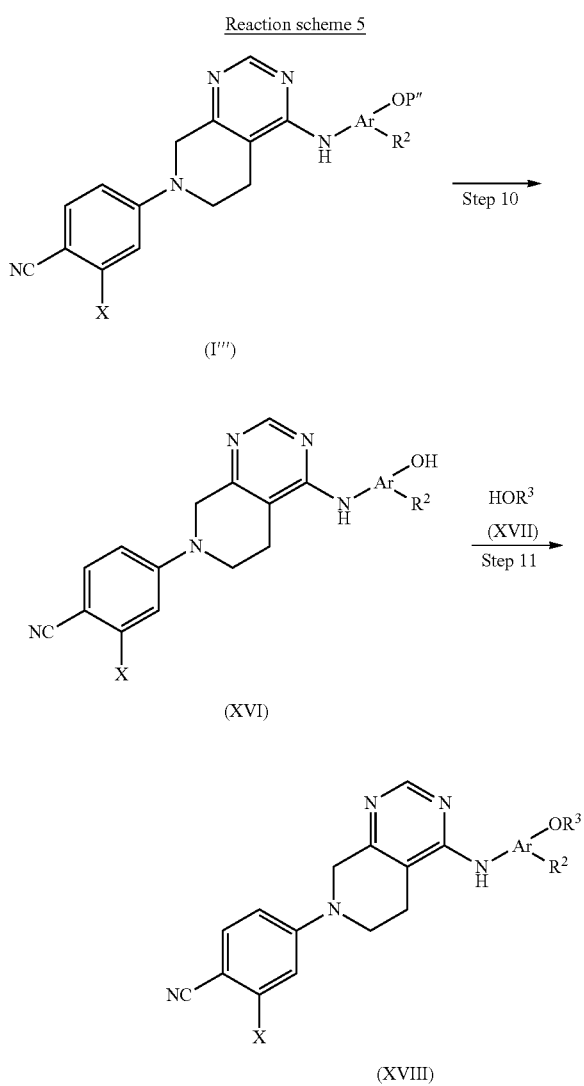

The present reaction scheme can be applied when $R^1$ substituted on R of the general formula (I) is a $C_{1-6}$ alkoxy group which may be substituted with Ra. —$OR^3$ indicates a $C_{1-6}$ alkoxy group which may be substituted with Ra.

(Step 10)

This step is a reaction for deprotecting the protecting group P''' of the formula (I''''). The compound of the formula (I'''') can be produced according to the process of the aforementioned Reaction scheme 1. As for the method for deprotection, it can be performed by a generally known method, for example, the method described in Protective Groups in Organic Synthesis, T. W. Greene, John Wiley & Sons (1981) or a method similar to it. Examples of the protecting group P''' include a benzyloxymethyl group (BOM), methoxyethoxymethyl group (MEM), tert-butyl group, and a benzyl group. When a benzyl group is used as a protecting group P''', examples of the catalyst for hydrogenolysis include palladium hydroxide, palladium/carbon, platinum, Raney nickel, platinum oxide, and rhodium-aluminum oxide. Preferably, it is palladium/carbon. The solvent used for the reaction of this step is not particularly limited as long as it does not cause any problem on the reaction. Examples of the solvent include methanol, ethanol, 1-propanol, 2-propanol, tert-butyl alcohol, dimethoxyethane, diethylene glycol dimethyl ether, diisopropyl ether, diethyl ether, THF, dioxane, ethyl acetate, and butyl acetate. It is preferably methanol or ethanol. The amount used of the catalyst is, relative to 1 eqv. of the compound of the formula (I''''), 0.001 to 10 eqv., and preferably 0.05 to 2 eqv. Temperature for the reaction is 0 to 100° C., and preferably 40 to 80° C. The compound of the formula (XVI) obtained by this step can be separated and purified by a known means for separation and purification, for example, concentration, concentration under reduced pressure, re-precipitation, crystallization, and chromatography, or it can be subjected to the next step without any separation and purification.

(Step 11)

This step relates to a method for producing the compound of the formula (XVIII) from the compound of the formula (XVI). This step can be performed by a known method, that is, a so-called Mitsunobu reaction (Synthesis, 1981, 1-28). The amount of the compound represented by the formula (XVII) which is used for this step is, relative to 1 eqv. of the compound of the formula (XVI), 0.5 to 5 eqv. and preferably 1 to 3 eqv. Examples of the azo compound used for this reaction include diethyl azodicarboxylate, diisopropyl azodicarboxylate, and 1,1'-azobis(N,N-dimethylformamide). The amount of the azo compound which is used is, relative to 1 eqv. of the compound of the formula (XVI), 1 to 5 eqv., and preferably 1.1 to 3 eqv. Examples of the phosphine compound which is used include triphenylphosphine and tributylphosphine. The amount of the phosphine compound which is used is, relative to 1 eqv. of the compound of the formula (XVI), 1 to 5 eqv., and preferably 1.1 to 3 eqv. The solvent which can be used for this step is not particularly limited as long as it does not cause any problem on the reaction. Examples of the solvent include THF, dioxane, diethyl ether, chloroform, dichloromethane, toluene, DMF, and dimethyl sulfoxide. Those solvents can be used as a mixture in which they are mixed at an appropriate ratio. The reaction temperature is between room temperature and reflux temperature. The time of the reaction is 1 to 4 hours. The compound of the formula (XVIII) obtained by this step can be separated and purified by a known means for separation and purification, for example, concentration, concentration under reduced pressure, crystallization, re-precipitation, and chromatography.

Furthermore, the reaction of this step can be performed by using a reagent such as (cyanomethylene)trimethylphosphrane and (cyanomethylene)tributylphosphrane (Tsunoda Reagent). The amount of the reagent which is used is, relative to 1 eqv. of the compound of the formula (XVI), 1 to 5 eqv., and preferably 1.1 to 3 eqv. Examples of the solvent which is used for the reaction include the aforementioned solvent for this step. The reaction temperature is between room temperature and reflux temperature. The reaction time is 1 to 48 hours. The compound of the formula (XVIII) obtained by this step can be separated and purified by a known means for separation and purification, for example, concentration, concentration under reduced pressure, re-precipitation, solvent extraction, crystallization, and chromatography.

Reaction scheme 6

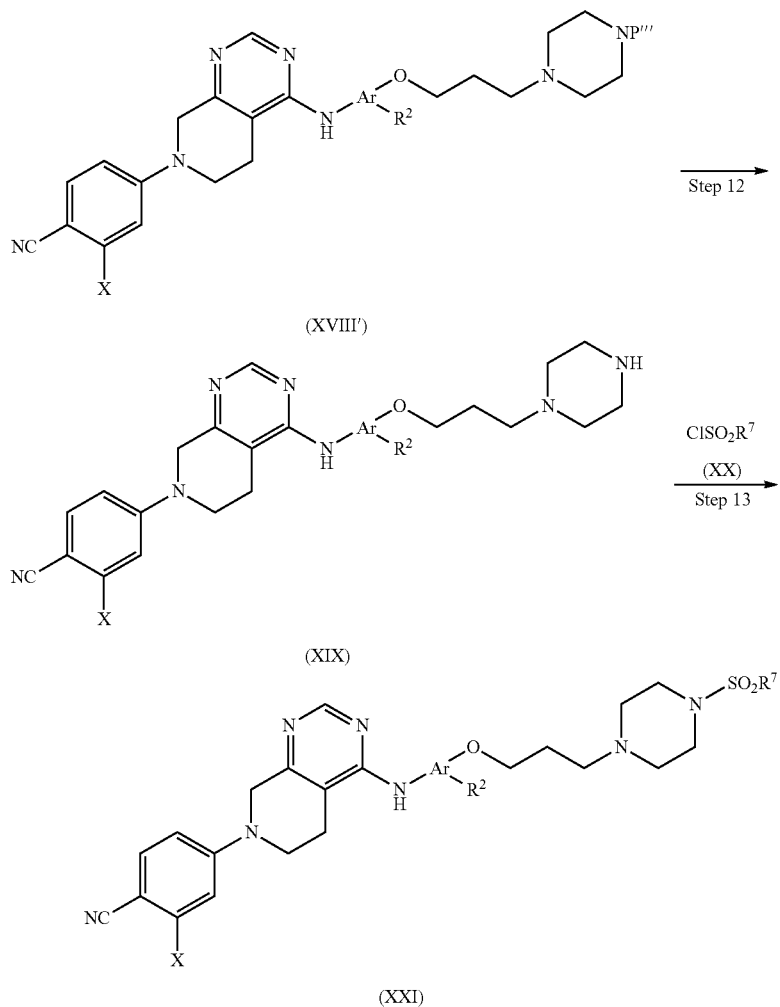

The present reaction scheme can be applied when $R^1$ substituted on R of the general formula (I) is a $C_{1-6}$ alkoxy group which may be substituted with Ra in which Ra is a $C_{1-6}$ alkylsulfonylpiperazinyl group. Herein, an n-propyl group is exemplified as a $C_{1-6}$ alkoxy group. $R^7$ is a $C_{1-6}$ alkyl group.

(Step 12)

This step is a reaction for deprotecting the protecting group P''' of the compound of the formula (XVIII'). As for the method for deprotection, it can be performed by a generally known method, for example, the method described in Protective Groups in Organic Synthesis, T. W. Greene, John Wiley & Sons (1981) or a method similar to it. Examples of the protecting group P''' include a tert-butoxycarbonyl group, a p-methoxycarbobenzoxy group, and a trityl group. It is preferably a tert-butoxycarbonyl group.

When the protecting group P''' is a tert-butoxycarbonyl group, deprotection can be achieved by using an acid. The solvent used for the reaction of this step is not particularly limited as long as it does not cause any problem on the reaction. Examples of the solvent include chloroform, dichloromethane, dioxane, THF, ethyl acetate, methanol, and water. Furthermore, examples of the acid used for this step include mineral acid such as hydrochloric acid and sulfuric acid and an organic acid such as trifluoroacetic acid and paratoluenesulfonic acid. Temperature for the reaction is 0 to 100° C., and preferably room temperature to 60° C. The time of the reaction is 1 to 48 hours, preferably a 1 to 6 hours. The compound of the formula (XIX) obtained by this step can be separated and purified by a known means for separation and purification, for example, concentration, concentration under reduced pressure, re-precipitation, solvent extraction, crystallization, and chromatography, or it can be subjected to the next step without any separation and purification.

(Step 13)

This step relates to a method for producing the compound represented by the formula (XXI) by using the compound represented by the formula (XIX). The reaction of this step can be performed by using sulfonyl chloride represented by the formula (XX) in an aprotic solvent in the presence of a base. The amount of the compound represented by the formula (XX) which is used is, relative to 1 eqv. of the compound of the formula (XIX), 0.5 to 5 eqv., and preferably 1 to 3 eqv. Examples of the base include triethylamine, diisopropylethylamine, pyridine, DMAP, and DBU. It is preferably triethylamine. The solvent which can be used for this step is not particularly limited as long as it does not cause any problem on the reaction. Examples of the solvent include THF, dioxane, diethyl ether, chloroform, dichloromethane, toluene, and DMF. It is preferably dichloromethane. The reaction temperature is 0 to 100° C., and preferably 0 to 50° C. The time of the reaction is 0.5 to 48 hours, and preferably 1 to 6 hours. The compound of the formula (XXI) obtained by this step can be separated and purified by a known means for separation and purification, for example, concentration, concentration under reduced pressure, re-precipitation, solvent extraction, crystallization, and chromatography.

The tetrahydropyridopyrimidine compound represented by the general formula (I) (hereinbelow, it may be also referred to as the "compound of the formula (I) of the present invention"), which is obtained by the process described above, may have an optical isomer or a geometric isomer depending on the type of a substituent group, and any of those is also included in the compound of the formula (I) of the present invention. The isomers may be subjected to resolution or used as a mixture of the isomers by themselves. Furthermore, tautomers shown below are present for the tetrahydropyridopyrimidine compound represented by the general formula (I), and any of those tautomers is also included in the compound of the formula (I) of the present invention.

used as a material for formulation are used, and for a solid formulation, for example, there may be mentioned a vehicle, a lubricating agent, a binding agent, and a disintegrating agent, and for a liquid formulation, there may be mentioned a solvent, a dissolution aid, a suspending agent, an isotonic agent, a buffer agent, a stabilizing agent, a pH controlling agent, a surfactant, a wetting agent, a preservative, and a pain relieving agent. Furthermore, the pharmaceutical agent may contain formulation additives such as a preservative, an anti-oxidant, a coloring agent, a sweetening agent, and a flavoring agent, if necessary.

The pharmaceutically acceptable carrier or formulation additives can be those that are generally used in the pertinent field. Examples of the vehicle include lactose, white sugar, sodium chloride, glucose, starch, calcium carbonate, kaolin, microcrystalline cellulose, and silicic acid; examples of the binding agent include water, ethanol, propanol, sweet syrup, glucose solution, starch solution, gelatin solution, carboxymethyl cellulose, hydroxypropyl cellulose, hydroxypropyl starch, methyl cellulose, ethyl cellulose, shellac, calcium phosphate, and polyvinylpyrrolidone; examples of the disintegrating agent include dry starch, sodium alginate, agar powder, sodium hydrogen carbonate, calcium carbonate, sodium lauryl sulfate, stearic acid monoglyceride, and lactose; examples of the lubricating agent include purified

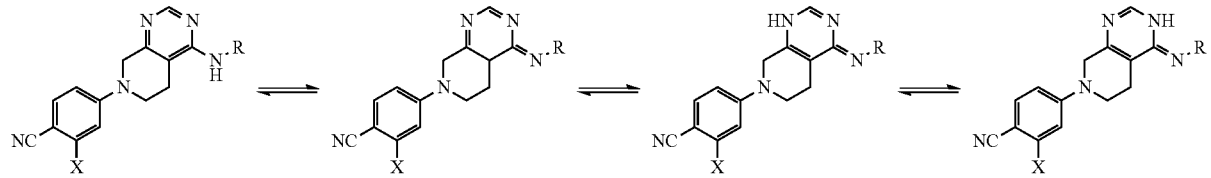

Furthermore, a solvate represented by a hydrate, a non-crystalline (amorphous) or crystalline polymorph is also encompassed by the compound of the formula (I) of the present invention.

The compound of the formula (I) of the present invention may form a salt according to a commonly known method. As for the type of the salt of the compound of the formula (I) of the present invention, any of the aforementioned pharmaceutically acceptable salts is possible.

The compound of the formula (I) of the present invention or a salt thereof can be separated and purified by a known means for separation and purification, for example, concentration, solvent extraction, filtration, recrystallization, or various chromatographies.

When the compound of the formula (I) of the present invention or a pharmaceutically acceptable salt thereof is used as a pharmaceutical agent, various administration forms can be adopted depending on purpose of prevention or treatment. Examples of the administration form include oral and parenteral administration forms, for example, an oral preparation, an injection, a suppository, an external preparation, and a patch. Preferably, an oral preparation is used. Each of those administration forms can be produced by a formulation method that is generally known to a person skilled in the art.

The pharmaceutical agent can be a pharmaceutical composition containing an effective amount of the compound of the formula (I) of the present invention or a pharmaceutically acceptable salt, and a pharmaceutically acceptable carrier. As for the pharmaceutically acceptable carrier, various organic or inorganic carrier substances that are generally talc, stearic acid salt, borax, and polyethylene glycol; examples of the coloring agent include titanium oxide and iron oxide; and examples of the flavoring agent include white sugar, orange peel, citric acid, and tartaric acid.

For producing a solid formulation for oral administration, the compound of the formula (I) of the present invention or a pharmaceutically acceptable salt thereof is added with a vehicle, and if necessary, with a binding agent, a disintegrating agent, a lubricating agent, a coloring agent, a flavoring agent, or the like, and prepared as a tablet, a coated tablet, a granule, a powder, or a capsule, for example, according to a commonly used method.

For producing a liquid formulation for oral administration, the compound of the formula (I) of the present invention or a pharmaceutically acceptable salt thereof is added with a flavoring agent, a buffer agent, a stabilizing agent, a corrigent, or the like, and prepared as a internal liquid medicine, a syrup, or an elixir, for example. In that case, the flavoring agent may be the same as those described above; examples of the buffer agent include sodium citrate; and examples of the stabilizing agent include tragacanth, gum Arabic, and gelatin.

For producing an injection, the compound of the formula (I) of the present invention or a pharmaceutically acceptable salt thereof is added with a pH controlling agent, a buffer agent, a stabilizing agent, an isotonic agent, a local anesthetic, or the like, and prepared as an intramuscular or intravenous injection according to a commonly used method. In that case, examples of the pH controlling agent and buffer agent include sodium citrate, sodium acetate, and sodium phosphate; examples of the stabilizing agent include sodium pyrosulfite, EDTA, thioglycolic acid, and thiolactic acid; examples of the local anesthetic include procaine hydrochloride and lidocaine hydrochloride; and examples of the isotonic agent include sodium chloride and glucose.

For producing a suppository, the compound of the formula (I) of the present invention or a pharmaceutically acceptable salt thereof is added with a known carrier for formulation, e.g., polyethylene glycol, lanolin, kakao fat, and a fatty acid triglyceride, and if necessary, a surfactant such as Tween (registered trademark), and production is performed according to a common method.

For producing an external preparation such as an ointment, a cream, a gel, or a paste, the compound of the formula (I) of the present invention or a pharmaceutically acceptable salt thereof is added with, if necessary, a commonly used base, a stabilizing agent, a wetting agent, or a preservative, and mixing and formulating are performed according to a common method. Examples of the base include fluid paraffin, white vaseline, white beeswax, octyl dodecyl alcohol, and paraffin. Examples of the preservative include methyl paraoxybenzoate, ethyl paraoxybenzoate, and propyl paraoxybenzoate.

For producing a patch, the ointment, cream, gel, or paste, for example, are coated on a common support according to a common method. Examples of the support include a woven or non-woven fabric consisting of cotton, staple fiber, or chemical fiber, or a film or a foamed sheet of soft vinyl chloride, polyethylene, and polyurethane.

The amount of the compound of the formula (I) of the present invention or a pharmaceutically acceptable salt thereof which needs to be blended in each administration unit form described above varies depending on symptom, weight, age, or sex of a subject for application, or a formulation type, for example. However, in terms of the amount of the compound of the formula (I) of the present invention, it is preferably 0.05 to 1000 mg for an oral preparation, 0.01 to 500 mg for an injection, and 1 to 1000 mg for a suppository. Furthermore, the daily dose of above administration form varies depending on species, symptom, weight, age, or sex of a subject for application. However, in terms of the amount of the compound of the formula (I) of the present invention, it is preferably 0.05 to 5000 mg, and preferably 0.1 to 1000 mg per day for an adult, and it is preferably administered once or in about 2 to 4 divided doses per day. With regard to the compound of the formula (I) of the present invention or a pharmaceutically acceptable salt, any one type of the compound or a salt may be used singly or a plurality of types may be used in combination.

As described herein, the anti-androgen activity means an activity of suppressing the androgen activity, and a compound, a composition, or a pharmaceutical agent having the anti-androgen activity is referred to as an anti-androgen agent. The compound of the formula (I) of the present invention or a pharmaceutically acceptable salt thereof acts as an antagonist for an androgen receptor (AR) and suppresses the response of AR to androgen, thus exhibiting the anti-androgen activity. Furthermore, as the compound of the formula (I) of the present invention or a salt thereof also has an activity of lowering AR expression, it can exhibit an anti-androgen activity based on it. By having the anti-androgen activity, the compound of the formula (I) of the present invention or a pharmaceutically acceptable salt thereof exhibits the effect of suppressing an occurrence or progress of various disorders, an occurrence of tumor, or progress or recurrence of a progressive or recurrent tumor.

Thus, according to another embodiment, provided by the present invention is an anti-androgen agent which contains, as an active ingredient, the compound of the formula (I) of the present invention or a pharmaceutically acceptable salt. Also provided by the present invention is use of the compound of the formula (I) of the present invention or a pharmaceutically acceptable salt thereof for producing an anti-androgen agent. Also provided by the present invention is use of the compound of the formula (I) of the present invention or a pharmaceutically acceptable salt thereof as an anti-androgen agent. Also provided by the present invention is the compound of the formula (I) of the present invention or a pharmaceutically acceptable salt thereof for use as an anti-androgen agent.

According to another embodiment, provided by the present invention is a pharmaceutical agent which contains, as an active ingredient, the compound of the formula (I) of the present invention or a pharmaceutically acceptable salt. Also provided by the present invention is use of the compound of the formula (I) of the present invention or a pharmaceutically acceptable salt thereof for producing a pharmaceutical agent. Also provided by the present invention is use of the compound of the formula (I) of the present invention or a pharmaceutically acceptable salt thereof as a pharmaceutical agent. Also provided by the present invention is the compound of the formula (I) of the present invention or a pharmaceutically acceptable salt thereof for use as a pharmaceutical agent.

According to another embodiment, provided by the present invention is a pharmaceutical composition which contains the compound of the formula (I) of the present invention or a pharmaceutically acceptable salt, and a pharmaceutically acceptable carrier.

According to a preferred embodiment, the pharmaceutical agent or pharmaceutical composition is used as an anti-androgen agent. Furthermore, according to a preferred embodiment, the pharmaceutical agent or pharmaceutical composition is a therapeutic agent for a disorder related with AR activation. Furthermore, according to a preferred embodiment, the pharmaceutical agent or pharmaceutical composition is an anti-tumor agent.

Meanwhile, according to another embodiment, provided by the present invention is a method of suppressing androgen activity including administering an effective amount of the compound of the formula (I) of the present invention or a pharmaceutically acceptable salt thereof to a subject. Also provided by the present invention is a method for treating a disorder related with AR activation including administering an effective amount of the compound of the formula (I) of the present invention or a pharmaceutically acceptable salt thereof to a subject. Also provided by the present invention is a method for treating tumor including administering an effective amount of the compound of the formula (I) of the present invention or a pharmaceutically acceptable salt thereof to a subject.

With regard to a method for suppressing androgen activity, a method for treating a disorder related with AR activation, and a method for treating tumor according to the present invention, examples of the subject include a human or a non-human animal in need of the method. Examples of the non-human animal include primates such as a monkey and a chimpanzee, and mammals such as a mouse, a rat, a hamster, a guinea pig, a dog, a cat, a cow, a horse, a sheep, a goat, and a pig; however, it is not limited thereto.

The effective amount or administration regimen of the compound of the formula (I) of the present invention or a pharmaceutically acceptable salt thereof administered to the above subject can be suitably determined by a person skilled in the art depending on, for example, species, symptom, weight, age, or sex, of the subject. For example, when the subject is an adult human, it is usually administered at 0.05 to 5000 mg, and preferably 0.1 to 1000 mg per day in terms of the amount of the compound of the formula (I) of the present invention, and it is preferably administered once or in about 2 to 4 divided doses per day.

Examples of the disorder related with AR activation include tumor, metastatic bone disease, prostatic hyperplasia, acne vulgaris, seborrhea, hypertrichosis, androgenetic alopecia, precocious puberty, and virillizing syndrome. Examples of the tumor include prostate cancer, breast cancer, ovarian cancer, bladder cancer, uterine cancer, pancreatic cancer, and hepatocellular cancer. It is preferably prostate cancer. Meanwhile, the tumor also includes resistant, recurrent, or metastatic tumor. Thus, specific examples of the prostate cancer include, in addition to common prostate cancer, castration resistant prostate cancer (CRPC), hormone resistant prostate cancer (HRPC), PSA recurrent prostate cancer, taxan resistant prostate cancer, and radiation resistant prostate cancer. It is preferably castration resistant prostate cancer.

Examples of a conventional anti-androgen agent include bicalutamide. However, as they have an agonist activity for AR, the effect is not maintained for a long period of time, and recurrent cancer is observed 2 to 5 years after the response. Furthermore, in CRPC, overexpression of AR is believed to be a cause of recurrence. The compound of the formula (I) of the present invention or a salt thereof has a potent antagonist activity for AR but no agonist activity therefor, and it exhibits a strong AR antagonist activity for cells in which AR is overexpressed. Furthermore, by having the activity of reducing AR expression in addition to the antagonist activity for AR, the compound of the formula (I) of the present invention or a salt thereof is effective for cancer having overexpressed AR such as CRPC.

EXAMPLES

Hereinbelow, the present invention is described specifically by way of Examples and Test Examples. However, they are described solely for exemplification, and the scope of the present invention is not limited to them.

Production Example

For the following examples given below, various reagents used were commercially available products, unless specifically described otherwise. For silica gel column chromatography, Purif-Pack (registered trademark) SI manufactured by MORITEX Corporation, KP-Sil (registered trademark) Silica pre-packed column manufactured by Biotage, or HP-Sil (registered trademark) Silica pre-packed column manufactured by Biotage were used. For basic silica gel column chromatography, Purif-Pack (registered trademark) NH manufactured by MORITEX Corporation or KP-NH (registered trademark) pre-packed column manufactured by Biotage were used. For basic silica gel column chromatography, Purif-Pack (registered trademark) NH manufactured by MORITEX Corporation or KP-NH (registered trademark) pre-packed column manufactured by Biotage were used.

Reverse phase preparative HPLC column chromatography was performed at the following conditions.

Column: YMC-Actus Triart C18 manufactured by YMC, 30×50 mm, 5 μm

UV detection: 254 nm

Column flow rate: 40 mL/min

Mobile phase: water/acetonitrile (0.1% formic acid)

Injection volume: 1.0 mL

Gradient water/acetonitrile 10%→60% (7 minutes)

For $^1$H-NMR spectrum measurement, AL400 (400 MHz; JEOL Ltd. (JEOL)), Mercury400 (400 MHz; Agilent Technologies, Inc.) type spectrometer, or Inova400 (400 MHz; Agilent Technologies, Inc.) type spectrometer equipped with OMNMR probe (Protasis) was used. For obtaining $^1$H-NMR spectrum, measurement was made using TMS (tetramethylsilane) as an internal standard, and chemical shift was represented in terms of δ value (ppm). With regard to the chemical shift, number of protons, absorption pattern, and coupling constant (J value) were described in parentheses. With regard to the absorption pattern, the following symbols were used: s=singlet, d=doublet, t=triplet, q=quartet, sept=septet, dd=double doublet, dt=double triplet, dq=double quartet, m=multiplet, br-s=broad singlet.

For mass spectrum, low resolution mass spectrometer (LRMS) was used, and the measurement was performed by electrospray ionization method (hereinbelow, ESI).

With regard to the structural formula of compounds, the following symbols may be used: Me=methyl, Et=ethyl, tBu=tert-butyl, Ph=phenyl, Bn=benzyl, Ac=acetyl, Boc=tert-butoxy carbonyl, TFA=trifluoroacetic acid, MsOH=methanesulfonic acid.

With regard to the solvent and reagent, the following abbreviations may be used:

DMSO=dimethyl sulfoxide;

DMF=N,N-dimethylformamide;

THF=tetrahydrofuran;

dba=dibenzylideneacetone;

dppf=1,1-bis(diphenylphosphino)ferrocene;

XantPhos=4,5-bis(diphenylphosphino)-9,9-dimethylxanthene;

Boc$_2$O=di-tert-butyl dicarbonate;

DMAP=4-dimethylaminopyridine;

TFA=trifluoroacetic acid;

DIPEA=diisopropylethylamine;

DMT-MM=4-(4,6-dimethoxy-1,3,5-triazin-2-yl)-4-methylmorpholinum chloride;

HATU=O-(7-azabenzotriazol-1-yl)-N,N,N',N'-tetramethyluroniumhexafluorophosphate;

HOBt=1-hydroxybenzotriazole;

WSC=EDCI=1-ethyl-3-(3-dimethylaminopropyl)carbodiimide;

DBU=1,8-diazabicyclo[5,4,0]undecene;

NMP=N-methyl-2-pyrrolidone;

DMA=dimethylacetamide;

DCC=N,N'-dicyclohexylcarbodiimide;

DPPA=diphenylphosphoryl azide;

LDA=lithium diisopropylamide.

Reference Example 1-1

4-(4-Hydroxy-5,6-dihydropyrido[3,4-d]pyrimidin-7(8H)-yl)-2-(trifluoromethyl)benzonitrile

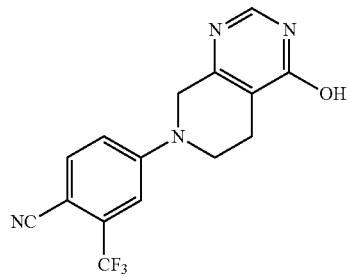 [SMILES: N#Cc1ccc(N2CCc3c(O)ncnc3C2)cc1C(F)(F)F]

Commercially available 7-benzyl-5,6,7,8-tetrahydropyrido[3,4-d]pyrimidin-4-ol (12.6 g), 10% palladium/carbon (2 g), and ammonium formate (16.5 g) were suspended in methanol (200 mL), followed by stirring overnight at 60° C. The reaction solution was filtered through Celite and concentrated, and then used for the next reaction without any purification. It was suspended with 4-fluoro-2-(trifluoromethyl)benzonitrile (10 g) in DMSO (150 mL) and stirred overnight at room temperature. The reaction solution was added with water (200 mL) and the solid was separated by filtering. It was further suspended and washed with 100 mL of ethyl acetate, followed by drying by heating to obtain the target compound (7.1 g).

$^1$H-NMR (DMSO-$d_6$) δ12.35 (1H, br-s), 8.09 (1H, S), 7.85 (1H, d, J=8.0 Hz), 7.39 (1H, s), 7.32 (1H, d, J=8.0 Hz), 4.34 (2H, s), 3.71 (2H, t, J=4.0), 2.56 (2H, t, J=4.0 Hz); LRMS (ESI) m/z 321 [M+H]$^+$.

Reference Example 1-2

4-(4-Chloro-5,6-dihydropyrido[3,4-d]pyrimidin-7(8H)-yl)-2-(trifluoromethyl)benzonitrile

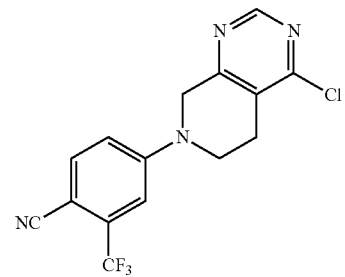 [SMILES: N#Cc1ccc(N2CCc3c(Cl)ncnc3C2)cc1C(F)(F)F]

The solid (12.3 g) obtained from Reference Example 1-1 was suspended in dichloroethane (60 mL), and added with phosphorus oxychloride (36 mL) and triethylamine (12 mL), followed by stirring for 30 minutes at 90° C. The reaction solution was added to water (300 mL) and extracted with chloroform (300 mL × three times) of which pH had been adjusted to 7 using sodium carbonate. After drying over magnesium sulfate, it was concentrated, and suspended and washed with ethyl acetate to obtain 9.4 g (72%) of the target compound.

$^1$H-NMR (DMSO-$d_6$) δ8.89 (1H, s), 7.89 (1H, d, J=8.0 Hz), 7.47 (1H, s), 7.40 (1H, d, J=8.0 Hz), 4.73 (2H, s), 3.90 (2H, t, J=4.0), 2.94 (2H, t, J=4.0 Hz); LRMS (ESI) m/z 339 [M+H]$^+$.

Reference Example 1-3

2-Chloro-4-(4-chloro-5,6-dihydropyrido[3,4-d]pyrimidin-7(8H)-yl)benzonitrile

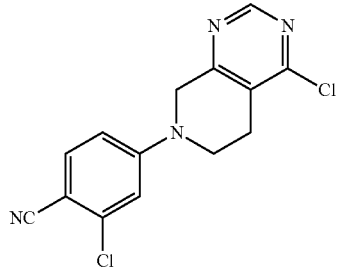 [SMILES: N#Cc1ccc(N2CCc3c(Cl)ncnc3C2)cc1Cl]

Commercially available 5,6,7,8-tetrahydropyrido[3,4-d]pyrimidin-4-ol hydrochloride (10.0 g), 2-chloro-4-fluorobenzonitrile (8.1 g), and triethylamine (22 mL) were added to DMSO (183 mL) and stirred for 2 days at room temperature. After adding water (400 mL), the reaction solution was adjusted to have a pH of 4 to 6 using conc. hydrochloric acid, and the precipitated solid was collected by filtration. The obtained solid was suspended and washed with ethyl acetate followed by drying. It was used for the next reaction without purification. The obtained solid (6.4 g) was refluxed for 10 minutes in phosphorus oxychloride (15 mL). After concentration under reduced pressure, it was added with water (400 mL) and the aqueous layer was adjusted to have a pH of 8 by using sodium carbonate. The precipitated solid was collected by filtration, followed by drying. It was suspended and washed with toluene to obtain 5.8 g (two step yield 47%) of the target compound.

$^1$H-NMR (DMSO-$d_6$) δ8.87 (1H, s), 7.70 (1H, d, J=8.9 Hz), 7.32 (1H, d, J=2.3 Hz), 7.12 (1H, dd, J=8.9, 2.3 Hz), 4.66 (2H, s), 3.83 (2H, t, J=5.8 Hz), 2.90 (2H, t, J=5.8 Hz); LRMS (ESI) m/z 306 [M+H]$^+$.

Reference Example 2-1

Methyl 6-((7-(4-cyano-3-(trifluoromethyl)phenyl)-5,6,7,8-tetrahydropyrido[3,4-d]pyrimidin-4-yl)amino)nicotinate

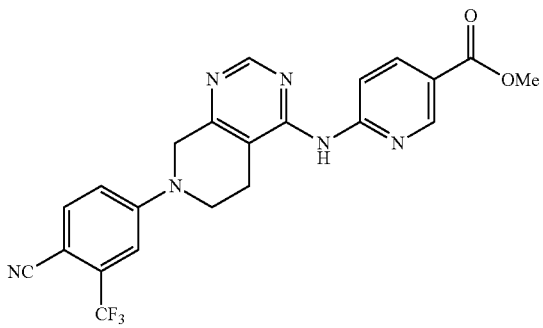 [SMILES: COC(=O)c1ccc(Nc2ncnc3c2CCN(c2ccc(C#N)c(C(F)(F)F)c2)C3)nc1]

The compound (10.0 g) obtained from Reference Example 1-2, methyl 6-aminonicotinate (4.49 g), Pd(dba)$_2$ (1.70 g), dppf (1.64 g), and cesium carbonate (24.1 g) were suspended in dioxane (120 mL) and stirred overnight at 80° C. under nitrogen atmosphere. The reaction solution was cooled to room temperature, and the solid obtained by adding water was collected by filtration, and purified by silica gel column chromatography to obtain 9.42 g (70%) of the target compound.

$^1$H-NMR (DMSO-d$_6$) δ9.63 (1H, s), 8.82 (1H, s), 8.65 (1H, s), 8.27-8.21 (2H, m), 7.85 (1H, d, J=8.8 Hz), 7.42 (1H, d, J=2.0 Hz), 7.35 (1H, dd, J=8.8, 2.0 Hz), 4.57 (2H, s), 3.85-3.80 (5H, m), 2.91 (2H, t, 5.2 Hz); LRMS (ESI) m/z 455 [M+H]$^+$.

Reference Example 2-2

6-((7-(4-Cyano-3-(trifluoromethyl)phenyl)-5,6,7,8-tetrahydropyrido[3,4-d]pyrimidin-4-yl)amino)nicotinic acid

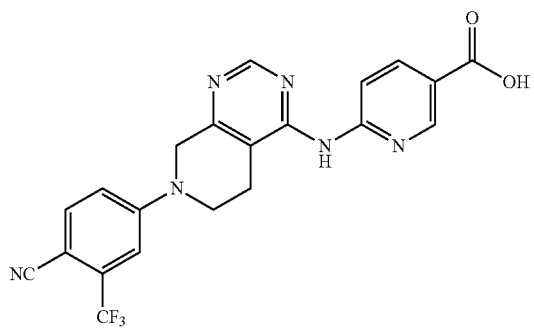

The compound (9.21 g) obtained from Reference Example 2-1 was suspended in methanol (100 mL), and added with 5.0 mol/L aqueous solution of sodium hydroxide (11 mL), followed by stirring overnight at 40° C. The reaction solution was cooled to room temperature, and the pH was adjusted to about 3 by using 5.0 mol/L hydrochloric acid. The precipitated solid was collected by filtration, and after washing with distilled water and air drying, 8.24 g (92%) of the target compound was obtained. The compound was directly used for the next step without performing any purification.

$^1$H-NMR (DMSO-d$_6$) δ9.59 (1H, s), 8.83 (1H, d, J=2.0 Hz), 8.67 (1H, s), 8.27-8.23 (2H, m), 7.87 (1H, d, J=8.8 Hz), 7.45 (1H, d, J=2.0 Hz), 7.38 (1H, dd, J=2.4, 8.8 Hz), 4.60 (2H, s), 3.86 (2H, t, J=5.6 Hz), 2.93 (2H, t, J=5.6 Hz); LRMS (ESI) m/z 441 [M+H]$^+$.

Reference Example 3

2-(6-Aminopyridin-3-yl)propan-2-ol

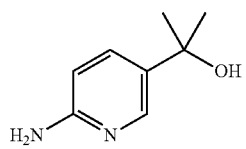

Methyl 6-aminonicotinate (5.0 g) was suspended in THF (500 mL), and added with methyl lithium at −78° C., followed by stirring for 15 hours while the temperature was naturally increased. The reaction mixture was added with a saturated aqueous solution of ammonium chloride in an ice bath, and extraction was performed 3 times with chloroform/methanol=5/1. The organic layer was combined together, and dried over anhydrous sodium sulfate. The insoluble matters were separated by filtration, and the filtrate was concentrated and dried. The obtained solid was purified by silica gel column chromatography to obtain 2.2 g (44%) of the target compound.

$^1$H-NMR (DMSO-d$_6$) δ7.97 (1H, d, J=2.4 Hz), 7.43 (1H, dd, J=8.8, 2.4 Hz), 6.36 (1H, d, J=8.8 Hz), 5.66 (2H, br-s), 4.82 (1H, s), 1.36 (6H, s); LRMS (ESI) m/z 153 [M+H]$^+$.

Production Example A 2-(6-Aminopyridazin-3-yl)propan-2-ol

Step 1

Synthesis of ethyl 6-aminopyridazine-3-carboxylate

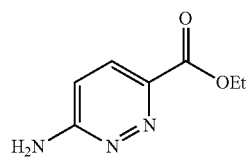 [SMILES: CCOC(=O)c1ccc(N)nn1]

To ethanol (800 mL), sodium (7.2 g) was slowly added and stirred for 2 hours at room temperature. After confirming that all sodium was dissolved, commercially available methyl 6-aminopyridazine-3-carboxylate (40.0 g) was added and further stirred at room temperature for 1 hour. To the reaction solution, hydrogen chloride (4.0 mol/L ethyl acetate solution, about 80 mL) was added in dropwise manner to adjust the pH to about 5. The obtained reaction solution was concentrated and dried, and after suspending and washing with distilled water followed by collecting by filtration and air drying, 39.9 g (99%) of the target compound was obtained.

$^1$H-NMR (DMSO-d$_6$) δ7.73 (1H, d, J=9.2 Hz), 7.14 (2H, br-s), 6.77 (1H, d, J=9.2 Hz), 4.29 (2H, q, J=7.2 Hz), 1.29 (3H, t, J=7.2 Hz); LRMS (ESI) m/z 168 [M+H]$^+$.

Step 2

Synthesis of 2-(6-aminopyridazin-3-yl)propan-2-ol

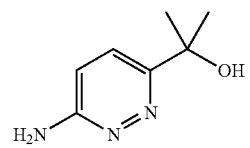

By performing the same operation as Reference Example 3 and using the compound (4.00 g) obtained from step 1 instead of methyl 6-aminonicotinate, 1.21 g (33%) of the target compound was obtained as an oily product.

$^1$H-NMR (DMSO-d$_6$) δ7.45 (1H, d, J=9.2 Hz), 6.73 (1H, d, J=9.2 Hz), 6.14 (2H, br-s), 5.12 (1H, s), 1.41 (6H, s); LRMS (ESI) m/z 154 [M+H]$^+$.

Production Example B 6-((7-(4-Cyano-3-(trifluoromethyl)phenyl)-5,6,7,8-tetrahydropyrido[3,4-d]pyrimidin-4-yl)amino)pyridazine-3-carboxylic acid Step 1

Synthesis of methyl 6-((7-(4-cyano-3-(trifluoromethyl)phenyl)-5,6,7,8-tetrahydropyrido[3,4-d]pyrimidin-4-yl)amino)pyridazine-3-carboxylate

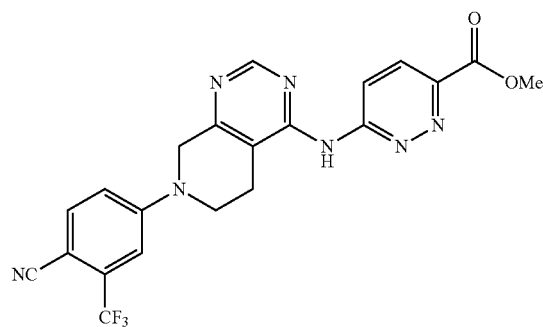 [SMILES: COC(=O)c1ccc(Nc2ncnc3c2CCN(c2ccc(C#N)c(C(F)(F)F)c2)C3)nn1]

By performing the same operation as Reference Example 2-1 and using a commercially available methyl 6-aminopyridazine-3-carboxylate (100 mg) instead of methyl 6-aminonicotinate, 38 mg (28%) of the target compound was obtained.

$^1$H-NMR (DMSO-d$_6$) δ10.39 (1H, s), 8.65 (1H, s), 8.48 (1H, d, J=9.6 Hz), 8.16 (1H, d, J=9.6 Hz), 7.86 (1H, d, J=8.8 Hz), 7.44 (1H, d, J=2.8 Hz), 7.37 (1H, dd, J=8.8, 2.0 Hz), 4.60 (2H, s), 3.91 (3H, s), 3.85 (2H, t, J=6.0 Hz), 2.97 (2H, t, 5.6 Hz); LRMS (ESI) m/z 456 [M+H]$^+$.

Step 2

Synthesis of 6-((7-(4-cyano-3-(trifluoromethyl)phenyl)-5,6,7,8-tetrahydropyrido[3,4-d]pyrimidin-4-yl)amino)pyridazine-3-carboxylic acid

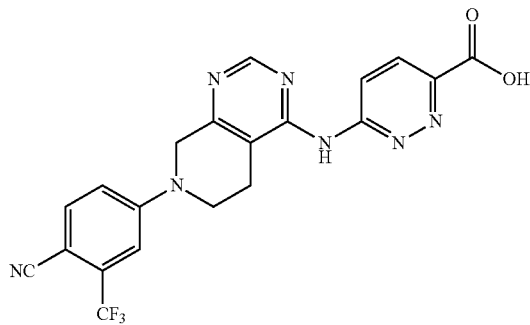 [SMILES: N#Cc1ccc(N2CCc3c(ncnc3Nc3ccc(C(=O)O)nn3)C2)cc1C(F)(F)F]

By performing the same operation as Reference Example 2-2 and using the compound (2.30 g) obtained from step 1 instead of the compound obtained from Reference Example 2-1, 2.04 g (91%) of the target compound was obtained.

$^1$H-NMR (DMSO-d$_6$) δ10.32 (1H, s), 8.64 (1H, s), 8.45 (1H, d, J=9.6 Hz), 8.13 (1H, d, J=9.2 Hz), 7.86 (1H, d, J=8.8 Hz), 7.44 (1H, d, J=2.4 Hz), 7.37 (1H, dd, J=8.8, 2.4 Hz), 4.60 (2H, s), 3.85 (2H, t, J=5.6 Hz), 2.97 (2H, t, 6.0 Hz); LRMS (ESI) m/z 442 [M+H]$^+$.

Production Example C 5-((7-4-Cyano-3-(trifluoromethyl)phenyl-5,6,7,8-tetrahydropyrido[3,4-d]pyrimidin-4-yl)amino)pyrazine-2-carboxylic acid Step 1

Synthesis of 5-((7-4-cyano-3-(trifluoromethyl)phenyl-5,6,7,8-tetrahydropyrido[3,4-d]pyrimidin-4-yl)amino)pyrazine-2-carboxylic acid methyl ester

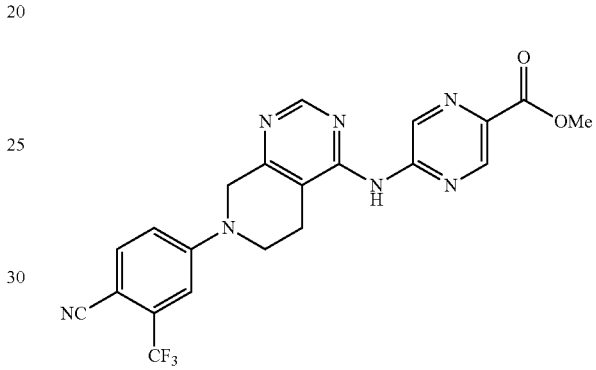

By performing the same operation as Reference Example 2-1 and using the compound (700 mg) obtained from Reference Example 1-2 and 5-aminopyrazine-2-carboxylic acid methyl ester (320 mg) instead of methyl 6-aminonicotinate, 360 mg (38%) of the target compound was obtained (yield 66%).

$^1$H-NMR (CDCl$_3$) δ9.99 (1H, s), 8.99 (1H, s), 8.79 (1H, s), 7.70 (1H, d, J=8.8 Hz), 7.56 (1H, s), 7.09 (1H, dd, J=2.6 Hz, 8.9 Hz), 4.57 (2H, s), 4.03 (3H, s), 3.90 (2H, t, J=5.7 Hz), 2.94 (2H, t, 5.5 Hz); LRMS (ESI) m/z 456 [M+H]$^+$.

Step 2

Synthesis of 5-((7-4-cyano-3-(trifluoromethyl)phenyl-5,6,7,8-tetrahydropyrido[3,4-d]pyrimidin-4-yl)amino)pyrazine-2-carboxylic acid

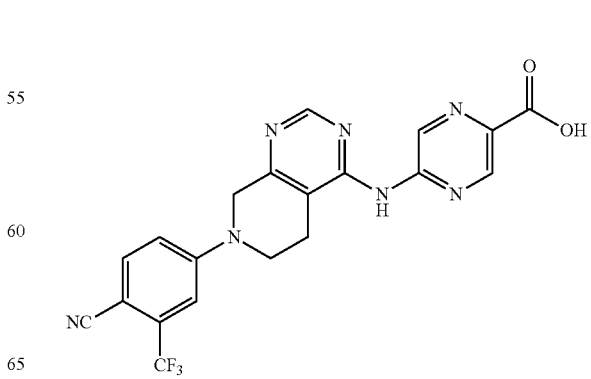

By performing the same operation as Reference Example 2-2 for the compound (360 mg) obtained from step 1, 310 mg of the target compound was obtained (yield 89%).

$^1$H-NMR (DMSO-d$_6$) δ10.06 (1H, br-s), 9.39 (1H, s), 8.92 (1H, s), 8.70 (1H, s), 7.89 (1H, d, J=8.8 Hz), 7.47 (1H, d, J=2.2 Hz), 7.40 (1H, dd, J=2.7 Hz, 9.0 Hz), 4.63 (2H, s), 3.87 (2H, t, J=5.6 Hz), 2.94 (2H, m); LRMS (ESI) m/z 442 [M+H]$^+$.

Production Example D 2-((7-4-Cyano-3-(trifluoromethyl)phenyl-5,6,7,8-tetrahydropyrido[3,4-d]pyrimidin-4-yl)amino)pyrimidine-5-carboxylic acid Step 1

Synthesis of 2-aminopyrimidine-5-carboxylic acid methyl ester

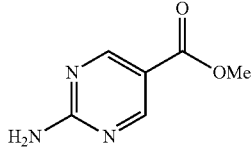

3,3-Dimethoxy-2-methoxycarbonylpropen-1-ol sodium salt (3.0 g), which had been synthesized according to the method described in Synthesis, 2002, 6, 720, and guanidine hydrochloride were dissolved in DMF (24 mL) and stirred at 100° C. for 1 hour. After cooling to room temperature, water was added to precipitate a solid, which was then collected by filtration and dried under reduced pressure to obtain 720 mg (30%) of the target compound.

$^1$H-NMR (DMSO-d$_6$) δ8.69 (2H, s), 7.57 (2H, s), 3.78 (3H, s); LRMS (ESI) m/z 154 [M+H]$^+$.

Step 2

Synthesis of methyl 2-((7-4-cyano-3-(trifluoromethyl)phenyl-5,6,7,8-tetrahydropyrido[3,4-d]pyrimidin-4-yl)amino)pyrimidine-5-carboxylate

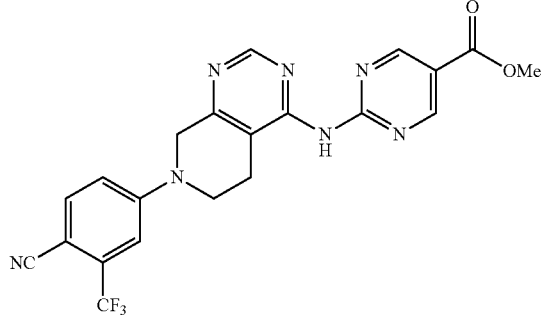 [SMILES: COC(=O)c1cnc(Nc2ncnc3c2CCN(c2ccc(C#N)c(C(F)(F)F)c2)C3)nc1]

By performing the same operation as Reference Example 2-1 and using the compound (300 mg) obtained from Reference Example 1-2 and 5-2-aminopyrimidine-5-carboxylic acid methyl ester (164 mg) obtained from step 1 instead of methyl 6-aminonicotinate, 128 mg of the target compound was obtained (yield 32%).

$^1$H-NMR (CDCl$_3$) δ9.11 (2H, s), 8.94 (1H, s), 8.01 (1H, s), 7.71 (1H, d, J=8.8 Hz), 7.23 (1H, s), 7.07 (1H, d, J=8.8 Hz), 4.63 (2H, s), 3.97 (3H, s), 3.78 (2H, t, J=5.7 Hz), 2.92 (2H, t, 5.5 Hz); LRMS (ESI) m/z 456 [M+H]$^+$.

Step 3

Synthesis of 2-((7-4-cyano-3-(trifluoromethyl)phenyl-5,6,7,8-tetrahydropyrido[3,4-d]pyrimidin-4-yl)amino)pyrimidine-5-carboxylic acid

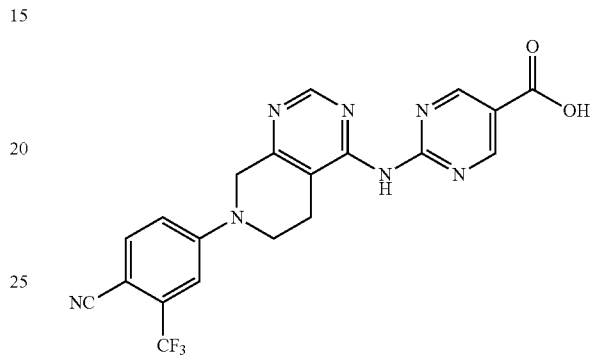

By performing the same operation as Reference Example 2-2 for the compound (120 mg) obtained from step 2, 114 mg of the target compound was obtained (yield 99%).

$^1$H-NMR (DMSO-d$_6$) δ10.65 (1H, s), 8.94 (2H, m), 8.82 (1H, s), 7.88 (1H, d, J=8.8 Hz), 7.43 (1H, s), 7.36 (1H, d, J=9.0 Hz), 4.69 (2H, s), 3.78 (2H, t, J=5.5 Hz), 2.77 (2H, m); LRMS (ESI) m/z 442 [M+H]$^+$.

Production Example E 5-((7-(4-Cyano-3-(trifluoromethyl)phenyl)-5,6,7,8-tetrahydropyrido[3,4-d]pyrimidin-4-yl)amino)-1,3,4-thiadiazol-2-carboxylic acid

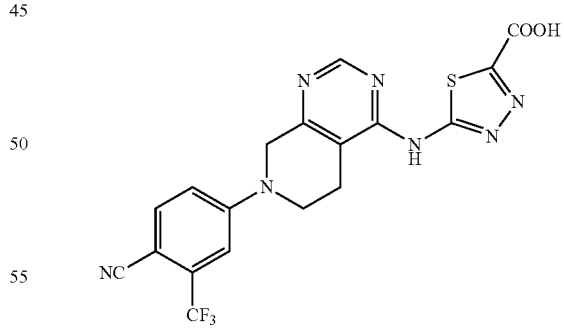

By performing the same operation as Reference Examples 2-1 and 2-2 and using ethyl 5-amino-1,3,4-thiadiazol-2-carboxylate (92 mg) instead of methyl 6-aminonicotinate, 141 mg of the target compound was obtained (two step yield 72%).

$^1$H-NMR (DMSO-d$_6$) δ8.80 (1H, s), 7.88 (1H, d, J=8.4 Hz), 7.46 (1H, br-s), 7.39 (1H, d, J=8.4 Hz), 4.62 (2H, s), 3.88 (2H, t, J=5.2 Hz), 2.97 (2H, t, J=5.2 Hz); LRMS (ESI) m/z 448 [M+H]$^+$.

Example 1

4-(4-((1,2,4-Thiadiazol-5-yl)amino)-5,6-dihydropyrido[3,4-d]pyrimidin-7(8H)-yl)-2-(trifluoromethyl)benzonitrile

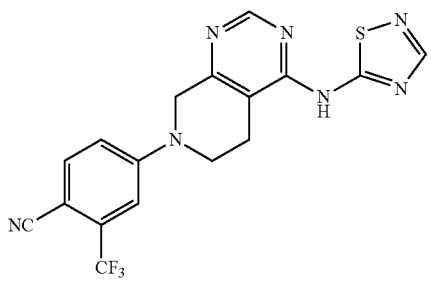 [SMILES: N#Cc1ccc(N2CCc3c(ncnc3Nc3ncns3)C2)cc1C(F)(F)F]

By performing the same operation as Reference Example 2-1 and using the compound (100 mg) obtained from Reference Example 1-2, 5-amino-1,2,4-thiadiazole (45 mg) instead of methyl 6-aminonicotinate, Pd$_2$(dba)$_3$ (30 mg) instead of Pd(dba)$_2$, and Xantphos (17 mg) instead of dppf, 10 mg of the target compound was obtained (yield 8%).

$^1$H-NMR (DMSO-d$_6$) δ8.88 (1H, s), 8.31 (1H, s), 7.71 (1H, d, J=8.8 Hz), 7.26 (1H, s), 7.10 (1H, d, J=8.8 Hz), 4.59 (2H, s), 3.89 (2H, t, J=5.9 Hz), 2.96 (2H, t, J=5.9 Hz); LRMS (ESI) m/z 404 [M+H]$^+$.

Example 2

4-(4-((4-Isopropoxyphenyl)amino)-5,6-dihydropyrido[3,4-d]pyrimidin-7(8H)-yl)-2-(trifluoromethyl)benzonitrile

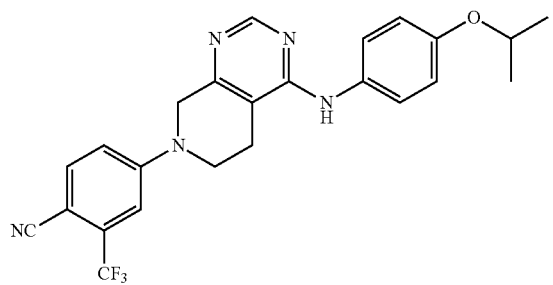

The compound (19 mg) obtained from Reference Example 1-2 and 4-isopropoxyaniline (10 mg) were dissolved in acetonitrile (1.5 mL) and reacted for 10 minutes at 180° C. under irradiation of microwave. After concentrating the solvent, it was purified by silica gel column chromatography to obtain the target compound (17 mg, 60%).

$^1$H-NMR (CDCl$_3$) δ8.55 (1H, s), 7.69 (1H, d, J=8.7 Hz), 7.45-7.36 (2H, m), 7.24 (1H, d, J=2.4 Hz), 7.06 (1H, dd, J=8.7, 2.4 Hz), 6.96-6.88 (2H, m), 6.31 (1H, s), 4.53 (1H, sept, J=6.1 Hz), 4.48 (2H, s), 3.87 (2H, t, J=6.1 Hz), 2.75 (2H, t, J=5.7 Hz), 1.35 (6H, d, J=6.1 Hz); LRMS (ESI) m/z 454 [M+H]$^+$.

Example 3

4-(4-((4-Methoxyphenyl)amino)-5,6-dihydropyrido[3,4-d]pyrimidin-7(8H)-yl)-2-(trifluoromethyl)benzonitrile

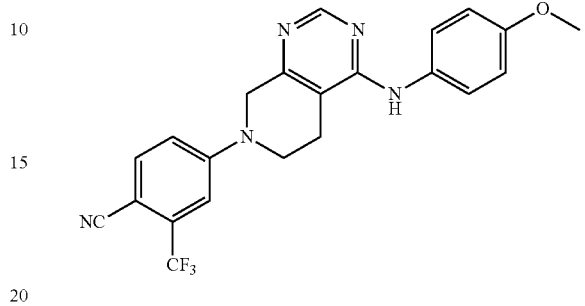

The solid (600 mg) obtained from Reference Example 1-2 and p-anisidine (262 mg) were suspended in acetonitrile (12 mL) and stirred for 20 minutes at 180° C. under irradiation of microwave. The obtained reaction solution was concentrated and dried, followed by purification by silica gel column chromatography to obtain the target compound (555 mg).

$^1$H-NMR (DMSO-d$_6$) δ9.89 (1H, br-s), 8.68 (1H, s), 7.96 (1H, d, J=8.0 Hz), 7.48-7.42 (3H, m), 7.37 (1H, dd, J=8.0, 4.0 Hz), 6.99 (1H, d, J=20.0 Hz), 4.68 (2H, s), 3.93 (2H, t, J=4.0 Hz), 3.17 (3H, s), 2.83 (2H, t, 4.0 Hz); LRMS (ESI) m/z 426 [M+H]$^+$.

Example 4

4-(4-((1,1'-Biphenyl)-3-ylamino)-5,6-dihydropyrido[3,4-d]pyrimidin-7(8H)-yl)-2-(trifluoromethyl)benzonitrile

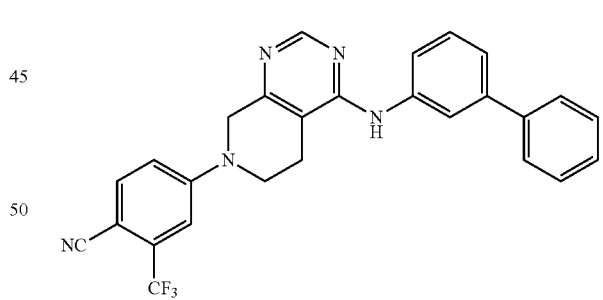

The solid (100 mg) obtained from Reference Example 1-2 and 3-aminobiphenyl (125 mg) were suspended in acetonitrile (2.0 mL), and added with potassium carbonate (182 mg), followed by stirring for 8 hours at 80° C. The obtained reaction solution was concentrated and dried, followed by purification by silica gel column chromatography to obtain the target compound (15 mg).

$^1$H-NMR (DMSO-d$_6$) δ8.63 (1H, s), 8.46 (1H, s), 7.95 (1H, t, J=2.0 Hz), 7.87 (1H, d, J=9.3 Hz), 7.75 (1H, d, J=8.3 Hz), 7.67-7.62 (2H, m), 7.51-7.33 (7H, m), 4.53 (2H, s), 3.91 (2H, t, J=5.6 Hz), 2.84 (2H, t, 5.6 Hz); LRMS (ESI) m/z 472 [M+H]$^+$.

Example 5

4-(4-((6-Fluoro-5-(2-hydroxypropan-2-yl)pyridin-2-yl)amino)-5,6-dihydropyrido[3,4-d]pyrimidin-7(8H)-yl)-2-(trifluoromethyl)benzonitrile

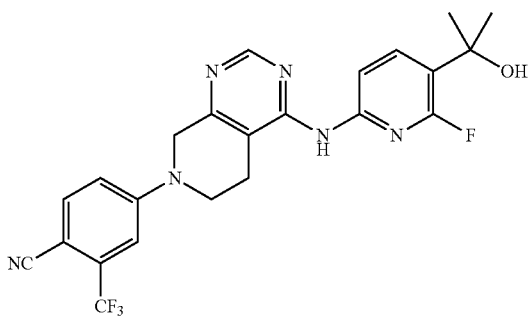 [SMILES: CC(C)(O)c1ccc(Nc2ncnc3c2CCN(c2ccc(C#N)c(C(F)(F)F)c2)C3)nc1F]

Step 1

Synthesis of 5-bromo-6-fluoropyridin-2-amine

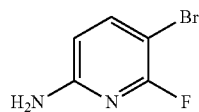

6-Fluoropyridin-2-amine (2.40 g) was dissolved in acetonitrile (45 mL), and under light blocking conditions, N-bromosuccinimide (3.81 g) was added under ice cooling, followed by stirring for 3 days and nights at room temperature under light blocking conditions. The obtained reaction solution was concentrated and dried, followed by purification by silica gel column chromatography to obtain 3.22 g (79%) of the target compound.

$^1$H-NMR (CDCl$_3$) δ7.61 (1H, t), 6.27 (1H, dd, J=8.4, 0.8 Hz), 4.63 (2H, br-s); LRMS (ESI) m/z 191 [M+H]$^+$.

Step 2

Synthesis of methyl 6-amino-2-fluoronicotinate

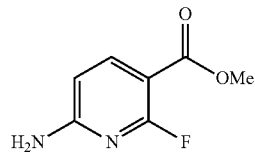

The solid (500 mg) obtained from step 1, palladium acetate (II) (118 mg), dppf (290 mg), and triethylamine (1.1 mL) were suspended in methanol (10 mL) and N,N-dimethylformamide (30 mL), and under atmosphere of carbon monoxide (0.4 MPa), stirred for 18 hours at 75° C. The reaction solution was filtered through Celite and concentrated under reduced pressure. The obtained oily product was dissolved in ethyl acetate and washed with distilled water and saturated brine, followed by drying over anhydrous sodium sulfate. The insoluble matters were separated by filtration, and the filtrate was concentrated and dried. The obtained solid was purified by silica gel column chromatography to obtain 133 mg (30%) of the target compound.

$^1$H-NMR (DMSO-d$_6$) δ7.91 (1H, dd, J=10.0, 8.4 Hz), 7.22 (2H, br-s), 6.34 (1H, dd, J=8.8, 2.0 Hz), 3.73 (3H, s); LRMS (ESI) m/z 171 [M+H]$^+$.

Step 3

Synthesis of 2-(6-amino-2-fluoropyridin-3-yl)propan-2-ol

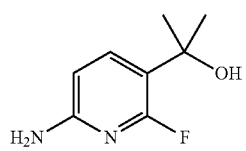

The solid (200 mg) obtained from step 2 was dissolved in tetrahydrofuran (4 mL) and added with methyl magnesium bromide (3.0 mol/L tetrahydrofuran solution, 1.96 mL) under ice cooling, followed by stirring for 5 hours. The reaction solution was added with a saturated aqueous solution of ammonium chloride, and extracted with ethyl acetate. The organic layer was washed with distilled water and saturated brine, followed by drying over anhydrous magnesium sulfate. The insoluble matters were separated by filtration, and the filtrate was concentrated under reduced pressure. The obtained oily product was purified by silica gel column chromatography to obtain 32 mg (16%) of the target compound as an oily product. The compound was used directly for the next step without performing any further purification.

LRMS (ESI) m/z 171 [M+H]$^+$.

Step 4

Synthesis of 4-(4-((6-fluoro-5-(2-hydroxypropan-2-yl)pyridin-2-yl)amino)-5,6-dihydropyrido[3,4-d]pyrimidin-7(8H)-yl)-2-(trifluoromethyl)benzonitrile

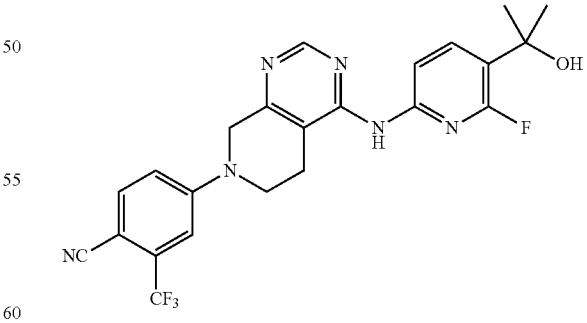

By performing the same operation as Reference Example 2-1 and using the oily product obtained from step 3 instead of methyl 6-aminonicotinate, 25 mg (30%) of the target compound was obtained.

$^1$H-NMR (DMSO-d$_6$) δ9.25 (1H, s), 8.56 (1H, s), 8.04-7.97 (2H, m), 7.83 (1H, d, J=8.8 Hz), 7.41 (1H, d, J=2.4 Hz), 7.34 (1H, dd, J=8.8, 2.0 Hz), 5.32 (1H, s), 4.53 (2H, s), 3.82 (2H, t, J=5.2 Hz), 2.84 (2H, t, 5.6 Hz), 1.44 (6H, s); LRMS (ESI) m/z 473 [M+H]⁺.

Example 6

2-Chloro-4-(4-((6-(2-hydroxypropan-2-yl)pyridazin-3-yl)amino)-5,6-dihydropyrido[3,4-d]pyrimidin-7(8H)-yl) benzonitrile

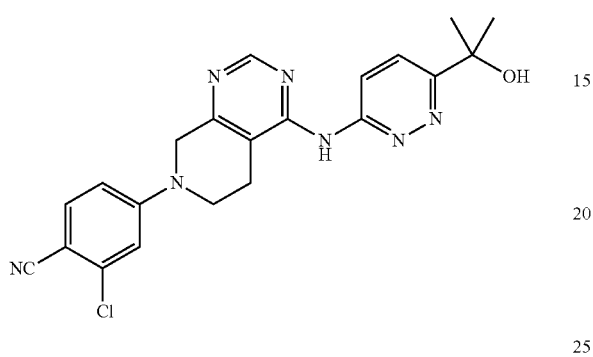

By performing the same operation as Reference Example 2-1 and using the solid (1.85 g) obtained from Reference Example 1-3 instead of the compound obtained from Reference Example 1-2 and the oily product (975 mg) obtained from Production Example A instead of methyl 6-aminonicotinate, 650 mg (yield 25%) of the target compound was obtained.

¹H-NMR (DMSO-d₆) δ9.74 (1H, s), 8.52 (1H, s), 8.19 (1H, d, J=9.2 Hz), 7.84 (1H, d, J=9.6 Hz), 7.67 (1H, d, J=8.8 Hz), 7.30 (1H, d, J=2.4 Hz), 7.11 (1H, dd, J=8.8, 2.4 Hz), 5.41 (1H, s), 4.50 (2H, s), 3.80 (2H, t, J=5.2 Hz), 2.89 (2H, t, J=5.2 Hz), 1.51 (6H, s); LRMS (ESI) m/z 422 [M+H]⁺.

Example 7

4-(4-((5-(2-Hydroxypropan-2-yl)pyridin-2-yl)amino)-5,6-dihydropyrido[3,4-d]pyrimidin-7(8H)-yl)-2-(trifluoromethyl)benzonitrile

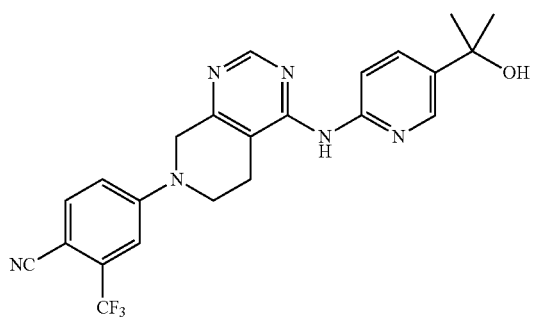

By performing the same operation as Reference Example 2-1 and using the solid (50 mg) obtained from Reference Example 1-2 and the solid (25 mg) obtained from Reference Example 3 instead of methyl 6-aminonicotinate, 17 mg (26%) of the target compound was obtained.

¹H-NMR (DMSO-d₆) δ9.04 (1H, s), 8.53 (1H, s), 8.41 (1H, d, J=2.4 Hz), 8.02 (1H, d, J=8.5 Hz), 7.86 (1H, d, J=8.8 Hz), 7.82 (1H, dd, J=8.5, 2.4 Hz), 7.43 (1H, d, J=2.4 Hz), 7.37 (1H, dd, J=8.8, 2.4 Hz), 5.14 (1H, s), 4.54 (2H, s), 3.85 (2H, t, J=5.6 Hz), 2.86 (2H, t, 5.4 Hz), 1.45 (6H, s); LRMS (ESI) m/z 455 [M+H]⁺.

Example 8

4-(4-((5-(2-Hydroxypropan-2-yl)-4-(trifluoromethyl)thiazol-2-yl)amino)-5,6-dihydropyrido[3,4-d]pyrimidin-7(8H)-yl)-2-(trifluoromethyl)benzonitrile

Step 1

Synthesis of 2-((tert-butoxycarbonyl)amino)-4-(trifluoromethyl)thiazol-5-carboxylic acid ethyl ester

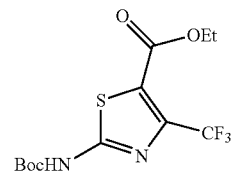

2-Amino-4-(trifluoromethyl)thiazol-5-carboxylic acid ethyl ester (1.0 g) was dissolved in THF and added with Boc₂O (1.0 g) and DMAP (25 mg), followed by stirring at 60° C. for 1 hour. The reaction solution was concentrated and dried and then purified by silica gel column chromatography to obtain the target compound (1.14 g, 80%).

¹H-NMR (CDCl₃) δ8.63 (1H, br-s), 4.36 (2H, q, J=7.1 Hz), 1.55 (9H, s), 1.36 (3H, t, J=7.1 Hz); LRMS (ESI) m/z 285 [M-tert-butyl+H]⁺.

Step 2

Synthesis of tert-butyl (5-(2-hydroxypropan-2-yl)-4-(trifluoromethyl)thiazol-2-yl)carbamate

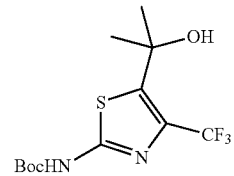

The compound (450 mg) obtained from step 1 was dissolved in THF and added dropwise with methyl lithium (3.0 mol/L diethoxymethane solution; 1.76 mL) at −78° C. under argon gas atmosphere, followed by stirring for 40 minutes. The reaction solution was added dropwise with a saturated aqueous solution of ammonium chloride and extracted with ethyl acetate and washed with saturated brine. It was dried over sodium sulfate and concentrated, and then purified by silica gel column chromatography to obtain the target compound (410 mg, 95%).

$^1$H-NMR (CDCl$_3$) δ8.05 (1H, br-s), 2.36 (1H, s), 1.71 (6H, s), 1.51 (9H, s); LRMS (ESI) m/z 271 [M-tert-butyl+H]$^+$.

Step 3

Synthesis of 2-(2-amino-4-(trifluoromethyl)thiazol-5-yl)propan-2-ol

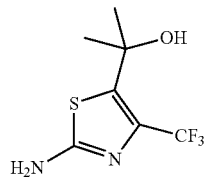

The compound (250 mg) obtained from step 2 was dissolved in methylene chloride (5 mL) and added with TFA (1 mL), followed by stirring at 0° C. for 60 hours and at room temperature for 7 hours. A saturated aqueous solution of sodium bicarbonate was added dropwise thereto, followed by extraction with ethyl acetate. After drying over sodium sulfate and concentration, it was purified by silica gel column chromatography to obtain the target compound (50 mg, 29%).

$^1$H-NMR (CDCl$_3$) δ4.89 (2H, br-s), 2.31 (1H, s), 1.68 (6H, s); LRMS (ESI) m/z 227 [M+H]$^+$.

Step 4

Synthesis of 4-(4-((5-(2-hydroxypropan-2-yl)-4-(trifluoromethyl)thiazol-2-yl)amino)-5,6-dihydropyrido[3,4-d]pyrimidin-7(8H)-yl)-2-(trifluoromethyl)benzonitrile

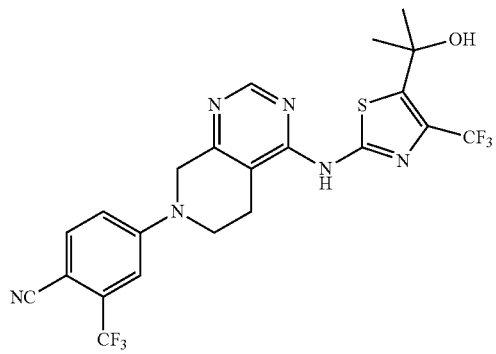 [SMILES: CC(C)(O)c1sc(Nc2ncnc3c2CCN(c2ccc(C#N)c(C(F)(F)F)c2)C3)nc1C(F)(F)F]

By performing the same operation as Reference Example 2-1 and using the compound (37 mg) obtained from step 3 instead of methyl 6-aminonicotinate and performing the reaction at 150° C. for 25 minutes under irradiation of microwave instead of overnight stirring at 80° C., the target compound was obtained (48 mg, 62%).

$^1$H-NMR (DMSO-d$_6$) δ11.29 (1H, s), 8.73 (1H, s), 7.87 (1H, d, J=8.8 Hz), 7.46 (1H, d, J=2.4 Hz), 7.38 (1H, dd, J=2.4, 8.8 Hz), 6.14 (1H, s), 4.59 (2H, s), 3.86 (2H, t, J=5.2 Hz), 2.92 (2H, t, J=5.2 Hz), 1.58 (6H, s); LRMS (ESI) m/z 529 [M+H]$^+$.

Example 9

2-Chloro-4-(4-((5-(2-hydroxypropan-2-yl)pyridin-2-yl)amino)-5,6-dihydropyrido[3,4-d]pyrimidin-7(8H)-yl)benzonitrile

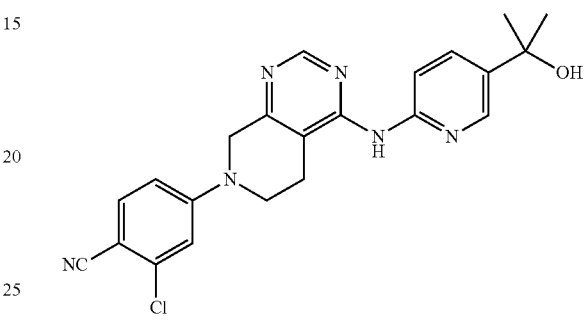

By performing the same operation as Reference Example 2-1 and using the compound (3.0 g) obtained from Reference Example 1-3 instead of the compound obtained from Reference Example 1-2 and the compound (1.59 g) obtained from Reference Example 3 instead of methyl 6-aminonicotinate, the target compound was obtained (1.0 g, 23%).

$^1$H-NMR (DMSO-d$_6$) δ9.04 (1H, s), 8.53 (1H, s), 8.42 (1H, d, J=2.6 Hz), 8.03 (1H, d, J=8.8 Hz), 7.83 (1H, dd, J=2.6, 8.8 Hz), 7.69 (1H, d, J=8.8 Hz), 7.31 (1H, d, J=2.6 Hz), 7.11 (1H, dd, J=2.6, 8.8 Hz), 5.14 (1H, s), 4.48 (2H, s), 3.80 (2H, t, J=5.7 Hz), 2.85 (2H, t, J=5.7 Hz), 1.46 (6H, s); LRMS (ESI) m/z 421 [M+H]$^+$.

Example 10

4-(4-((6-(2-Hydroxypropan-2-yl)pyridazin-3-yl)amino)-5,6-dihydropyrido[3,4-d]pyrimidin-7(8H)-yl)-2-(trifluoromethyl)benzonitrile

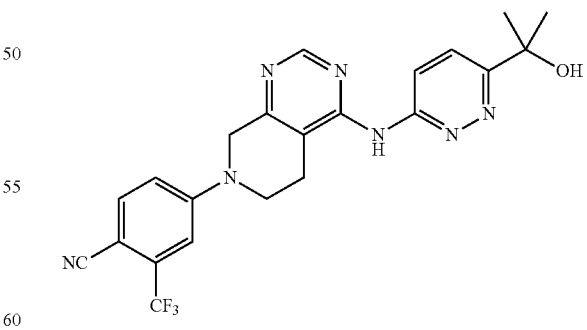

By performing the same operation as Reference Example 2-1 and using the compound (30 mg) obtained from Production Example A instead of methyl 6-aminonicotinate and performing the reaction at 150° C. for 25 minutes under irradiation of microwave instead of overnight stirring at 80° C., the target compound was obtained (30 mg, 36%).

¹H-NMR (DMSO-d₆) δ9.74 (1H, s), 8.52 (1H, s), 8.19 (1H, d, J=9.2 Hz), 7.88-7.81 (1H, m), 7.43 (1H, d, J=2.2 Hz), 7.37 (1H, dd, J=2.2, 8.8 Hz), 5.40 (1H, s), 4.56 (2H, s), 3.87 (2H, t, J=5.7 Hz), 2.91 (2H, t, J=5.7 Hz), 1.51 (6H, s); LRMS (ESI) m/z 456 [M+H]⁺.

Example 11

6-((7-(4-Cyano-3-(trifluoromethyl)phenyl)-5,6,7,8,-tetrahydropyrido[3,4-d]pyrimidin-4-yl)amino)-N-(2,2,2-trifluoroethyl)nicotinamide

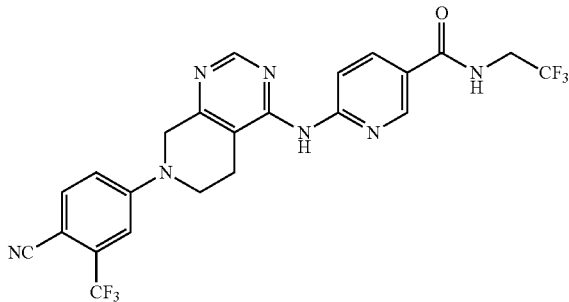 [SMILES: N#Cc1ccc(N2CCc3c(ncnc3Nc3ccc(C(=O)NCC(F)(F)F)cn3)C2)cc1C(F)(F)F]

The compound (8.24 g) obtained from Reference Example 2-2 and DMT-MM (10.36 g) were suspended in methanol (20 mL) and N,N-dimethylformamide (40 mL), and added with 2,2,2-trifluoroethylamine (3.71 g), followed by stirring overnight at room temperature. The reaction solution was added with distilled water and extracted three times with ethyl acetate. The organic layer was collected together, washed with distilled water and saturated brine, and dried over anhydrous sodium sulfate. The insoluble matters were separated by filtration, and the filtrate was concentrated and dried. The obtained solid was purified by silica gel column chromatography to obtain 6.80 g (70%) of the target compound.

¹H-NMR (DMSO-d₆) δ9.53 (1H, s), 9.13 (1H, t, J=6.2 Hz), 8.84-8.81 (1H, m), 8.64 (1H, s), 8.27-8.20 (1H, m), 7.85 (1H, d, J=8.8 Hz), 7.43 (1H, d, J=2.6 Hz), 7.36 (1H, dd, J=9.0, 2.4 Hz), 4.57 (2H, s), 4.15-4.04 (2H, m), 3.84 (2H, t, J=6.0 Hz), 2.91 (2H, t, 5.2 Hz); LRMS (ESI) m/z 522 [M+H]⁺.

Example 12

4-(4-((5-(1-Hydroxycyclopropyl)pyridin-2-yl)amino)-5,6-dihydropyrido[3,4-d]pyrimidin-7(8H)-yl)-2-(trifluoromethyl)benzonitrile

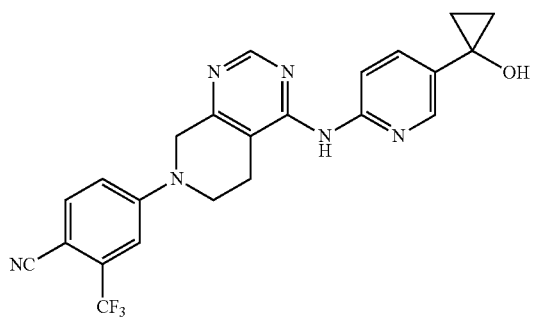 [SMILES: N#Cc1ccc(N2CCc3c(ncnc3Nc3ccc(C4(O)CC4)cn3)C2)cc1C(F)(F)F]

Step 1

Synthesis of 1-(6-chloropyridin-3-yl)cyclopropanol

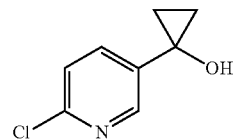 [SMILES: OC1(c2ccc(Cl)nc2)CC1]

Methyl 6-chloronicotinamide (1 g) was suspended in diethyl ether (20 mL), and added with titanium tetraisopropoxide (1.76 mL) at room temperature under nitrogen atmosphere, followed by stirring for 30 minutes. The reaction solution was cooled to −78° C., and added with ethyl magnesium bromide (3 M, 6.8 mL), followed by stirring for 4 hours at −78° C. After further stirring overnight at room temperature, the reaction solution was added with water and extracted three times with chloroform. After drying over sodium sulfate followed by concentration and purification by silica gel column chromatography, the target compound was obtained as an oily product (283 mg, 29%).

¹H-NMR (CDCl₃) δ9.33 (1H, d, J=2.6 Hz), 7.69 (1H, dd, J=8.1, 2.6 Hz), 7.28 (1H, d, J=8.1 Hz), 0.95 (4H, t, J=7.3 Hz); LRMS (ESI) m/z 170 [M+H]⁺.

Step 2

Synthesis of 1-(6-aminopyridin-3-yl)cyclopropanol

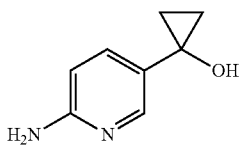

The compound (283 mg) obtained from step 1, benzophenone imine (363 mg), Pd₂(dba)₃ (76 mg), XantPhos (145 mg), and cesium carbonate (761 mg) were dissolved in THF (10 mL) and stirred for 3 days at 60° C. After filtering the reaction solution, the residues were washed with ethyl acetate and the filtrate was concentrated under reduced pressure. The obtained residues were suspended in THF (5 mL), and added with 2 N hydrochloric acid, followed by stirring at room temperature for 2 hours. The reaction solution was added with a saturated aqueous solution of sodium hydrogen carbonate and extracted three times with chloroform. After drying over sodium sulfate and concentration, the obtained residues were purified by silica gel column chromatography to obtain the target compound (98 mg, 39%).

¹H-NMR (CDCl₃) δ8.71 (1H, d, J=2.3 Hz), 8.03 (1H, dd, J=8.6, 2.3 Hz), 6.50 (1H, d, J=8.6 Hz), 1.22 (4H, t, J=7.3 Hz); LRMS (ESI) m/z 151 [M+H]⁺.

Step 3

Synthesis of 4-(4-((5-(1-hydroxycyclopropyl)pyridin-2-yl)amino)-5,6-dihydropyrido[3,4-d]pyrimidin-7(8H)-yl)-2-(trifluoromethyl)benzonitrile

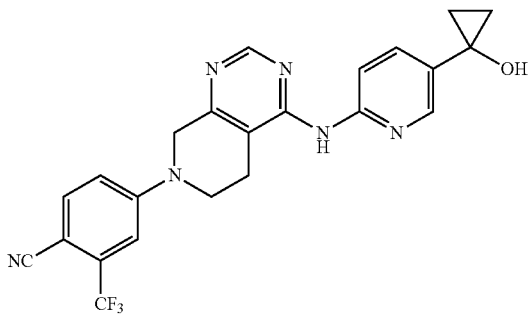 [SMILES: N#Cc1ccc(N2CCc3c(ncnc3Nc3ccc(C4(O)CC4)cn3)C2)cc1C(F)(F)F]

By reacting the compound (50 mg) obtained from Reference Example 1-2 and the compound (27 mg) obtained from step 2 according to Reference Example 2-1, the target compound was obtained (9.0 mg, 13%).

$^1$H-NMR (DMSO-$d_6$) δ9.61 (1H, s), 8.89 (1H, d, J=1.9 Hz), 8.65 (1H, s), 8.27 (1H, dd, J=8.8, 1.9 Hz), 8.22 (1H, d, J=9.1 Hz), 7.86 (1H, d, J=9.1 Hz), 7.43 (1H, d, J=2.3 Hz), 7.36 (1H, dd, J=8.8, 2.3 Hz), 4.58 (2H, s), 3.84 (2H, t, J=5.6 Hz), 2.91 (2H, t, J=5.6 Hz), 1.07 (4H, t, J=7.3 Hz); LRMS (ESI) m/z 453 [M+H]$^+$.

Example 13

4-(4-((6-Isopropoxypyridin-3-yl)amino)-5,6-dihydropyrido[3,4-d]pyrimidin-7(8H)-yl)-2-(trifluoromethyl)benzonitrile

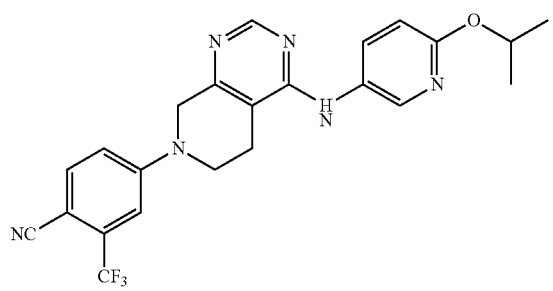 [SMILES: CC(C)Oc1ccc(Nc2ncnc3c2CCN(c2ccc(C#N)c(C(F)(F)F)c2)C3)cn1]

By performing the same operation as Reference Example 2-1 and using 6-isopropoxypyridin-3-amine (54 mg) instead of methyl 6-aminonicotinate, 43 mg (32%) of the target compound was obtained.

$^1$H-NMR (DMSO-$d_6$) δ8.64 (1H, s), 8.35 (1H, s), 8.28 (1H, d, J=2.9 Hz), 7.85 (2H, m), 7.43 (1H, d, J=2.6 Hz), 7.36 (1H, dd, J=8.8, 2.6 Hz), 6.72 (1H, d, J=8.8 Hz), 5.18 (1H, quin, J=6.1 Hz), 4.49 (2H, s), 3.88 (2H, t, J=5.7 Hz), 2.76 (2H, t, 5.5 Hz), 1.26 (6H, d, J=6.2 Hz); LRMS (ESI) m/z 455 [M+H]$^+$.

Example 14

4-(4-((4-(2-(1-Methyl-1H-pyrazol-5-yl)ethoxy)phenyl)amino)-5,6-dihydropyrido[3,4-d]pyrimidin-7(8H)-yl)-2-(trifluoromethyl)benzonitrile

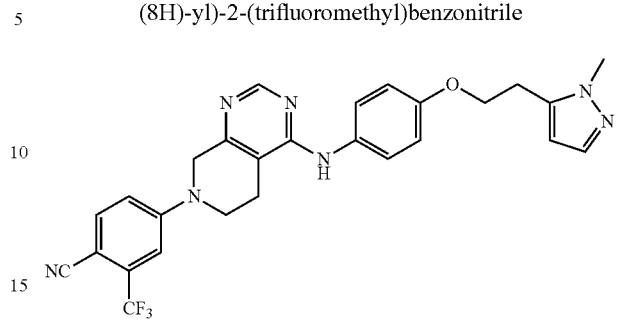

Step 1

Synthesis of 2-(1-methyl-1H-pyrazol-5-yl)ethanol

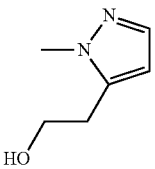

1-Methyl-1H-pyrazole (3.57 g) was dissolved in THF (50 mL), and added with tert-butyllithium (30.5 mL, 1.6 mol/L pentane solution) at −78° C., followed by stirring under nitrogen atmosphere at −60° C. for 30 minutes and at −10° C. for 40 minutes. The reaction solution was added dropwise with a THF solution (50 mL) of oxirane (2.42 g) at −10° C. The reaction solution was stirred overnight at room temperature, and added with a saturated aqueous solution of ammonium chloride, followed by extraction three times with chloroform. The organic layer was dried over sodium sulfate, followed by concentration and purification by silica gel column chromatography to obtain the target compound (2.42 g, 45%).

$^1$H-NMR (DMSO-$d_6$) δ7.24 (1H, d, J=1.8 Hz), 6.02 (1H, d, J=1.8 Hz), 4.76 (1H, t, J=5.3 Hz), 3.71 (3H, s), 3.60 (2H, td, J=6.9, 5.3 Hz), 2.74 (2H, t, J=6.9 Hz); LRMS (ESI) m/z 127 [M+H]$^+$.

Step 2

Synthesis of 4-(4-((4-(benzyloxy)phenyl)amino)-5,6-dihydropyrido[3,4-d]pyrimidin-7(8H)-yl)-2-(trifluoromethyl)benzonitrile

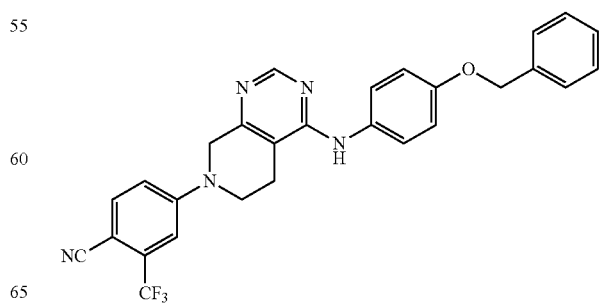

By performing the same operation as Reference Example 2-1 and using 4-(benzyloxy)aniline (706 mg) instead of methyl 6-aminonicotinate, the target compound was obtained (1.39 g, 94%).

$^1$H-NMR (MeOH-d$_4$) δ8.30 (1H, s), 7.76 (1H, d, J=9.0 Hz), 7.47-7.24 (9H, m), 7.02-6.97 (2H, m), 5.09 (2H, s), 4.45 (2H, s), 3.89 (2H, t, J=5.8 Hz), 2.80 (2H, t, J=5.8 Hz); LRMS (ESI) m/z 502 [M+H]$^+$.

Step 3

Synthesis of 4-(4-((4-hydroxyphenyl)amino)-5,6-dihydropyrido[3,4-d]pyrimidin-7(8H)-yl)-2-(trifluoromethyl)benzonitrile

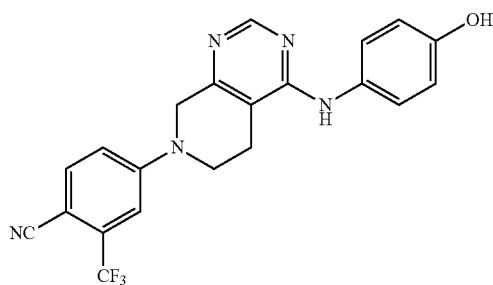 [SMILES: N#Cc1ccc(N2CCc3c(ncnc3Nc3ccc(O)cc3)C2)cc1C(F)(F)F]

The compound (1.39 g) obtained from step 2, 10% palladium/carbon (containing 50% water, 300 mg), and ammonium formate (872 mg) were suspended in methanol (30 mL) and stirred overnight at 60° C. The reaction solution was filtered and the residues were washed with chloroform-methanol. Water was added thereto, followed by extraction four times with chloroform-methanol (3:1). After drying over sodium sulfate followed by concentration, the target compound was obtained (971 mg, 85%).

$^1$H-NMR (DMSO-d$_6$) δ9.25 (1H, br-s), 8.43 (1H, s), 8.33 (1H, s), 7.87 (1H, d, J=8.8 Hz), 7.46-7.30 (4H, m), 6.73 (1H, d, J=8.3 Hz), 4.48 (2H, s), 3.88 (2H, t, J=5.6 Hz), 2.75 (2H, t, J=5.6 Hz); LRMS (ESI) m/z 412 [M+H]$^+$.

Step 4

Synthesis of 4-(4-((4-(2-(1-methyl-1H-pyrazol-5-yl)ethoxy)phenyl)amino)-5,6-dihydropyrido[3,4-d]pyrimidin-7(8H)-yl)-2-(trifluoromethyl)benzonitrile

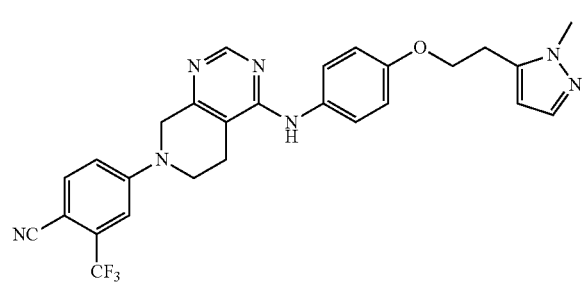 [SMILES: Cn1nccc1CCOc1ccc(Nc2ncnc3c2CCN(c2ccc(C#N)c(C(F)(F)F)c2)C3)cc1]

The compound (802 mg) obtained from step 3, cyanomethylenetributylphosphrane (Tsunoda Reagent, 565 mg), and 2-(1-methyl-1H-pyrazol-5-yl)ethanol (246 mg) obtained from step 1 were dissolved in toluene (10 mL)-tetrahydrofuran (8 mL), and stirred overnight at 95° C. The solvent was concentrated and purification by silica gel column chromatography was performed to obtain the target compound (724 mg, 71%).

$^1$H-NMR (CDCl$_3$) δ8.55 (1H, s), 7.69 (1H, d, J=8.8 Hz), 7.47-7.39 (3H, m), 7.24 (1H, d, J=2.4 Hz), 7.06 (1H, dd, J=8.8, 2.4 Hz), 6.96-6.90 (2H, m), 6.32 (1H, br-s), 6.14 (1H, d, J=1.5 Hz), 4.49 (2H, s), 4.22 (2H, t, J=6.6 Hz), 3.89 (3H, s), 3.87 (2H, t, J=5.6 Hz), 3.13 (2H, t, J=6.6 Hz), 2.76 (2H, t, J=5.6 Hz); LRMS (ESI) m/z 520 [M+H]1.

Example 15

4-(4-((6-(2-(1H-1,2,3-Triazol-1-yl)ethoxy)pyridin-3-yl)amino)-5,6-dihydropyrido[3,4-d]pyrimidin-7(8H)-yl)-2-(trifluoromethyl)benzonitrile

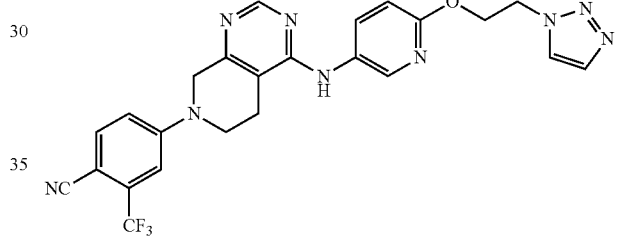

Step 1

Synthesis of 2-(2-(1H-1,2,3-triazol-1-yl)ethoxy)-5-nitropyridine

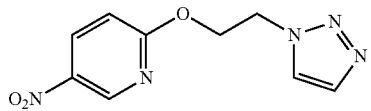 [SMILES: O=[N+]([O-])c1ccc(OCCn2ccnn2)nc1]

2-Chloro-5-nitropyridine (300 mg) was dissolved in THF, and added with sodium hydride (151 mg, 60%) at 0° C., followed by stirring for 10 minutes. After further added with 2-(1H-1,2,3-triazol-1-yl)ethanol, it was stirred for 2 hours at 0° C. The reaction solution was added with water and extracted with ethyl acetate three times. The organic layer was washed with water and saturated brine, followed by drying over sodium sulfate and concentration. The obtained residues were purified by silica gel column chromatography to obtain the target compound (376 mg, 90%).

¹H-NMR (DMSO-d₆) δ9.05 (1H, d, J=2.9 Hz), 8.47 (1H, dd, J=9.2, 2.9 Hz), 8.20 (1H, s), 7.73 (1H, s), 7.07 (1H, d, J=9.2 Hz), 4.87-4.78 (4H, m); LRMS (ESI) m/z 236 [M+H]⁺.

Step 2

Synthesis of 6-(2-(1H-1,2,3-triazol-1-yl)ethoxy)pyridin-3-amine

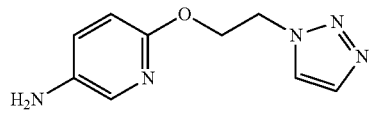

The compound (270 mg) obtained from step 1 was dissolved in methanol (8 mL) and added with 10% palladium/carbon (135 mg, containing 50% water). Under hydrogen atmosphere, it was stirred overnight at atmospheric pressure. The reaction solution was filtered through Hyflo Super-Cel, and the solvent was concentrated to obtain the target compound as a colorless oily product (200 mg).

¹H-NMR (DMSO-d₆) δ8.11 (1H, d, J=1.0 Hz), 7.70 (1H, d, J=1.0 Hz), 7.46 (1H, d, J=2.9 Hz), 6.97 (1H, dd, J=8.4, 2.9 Hz), 6.49 (1H, d, J=8.4 Hz), 4.77 (2H, s), 4.70 (2H, t, J=5.3 Hz), 4.48 (2H, t, J=5.3 Hz); LRMS (ESI) m/z 206 [M+H]⁺.

Step 3

Synthesis of 4-(4-((6-(2-(1H-1,2,3-triazol-1-yl)ethoxy)pyridin-3-yl)amino)-5,6-dihydropyrido[3,4-d]pyrimidin-7(8H)-yl)-2-(trifluoromethyl)benzonitrile

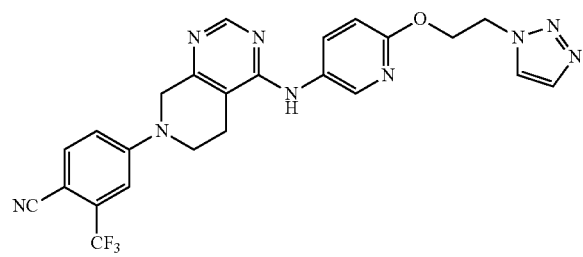 [SMILES: N#Cc1ccc(N2CCc3c(ncnc3Nc3ccc(OCCn4ccnn4)nc3)C2)cc1C(F)(F)F]

By reacting the compound (50 mg) obtained from Reference Example 1-2 and the compound (36 mg) obtained from step 2 according to Reference Example 2-1, the target compound was obtained (28 mg, 37%).

¹H-NMR (DMSO-d₆) δ8.69 (1H, s), 8.38 (1H, s), 8.33 (1H, d, J=2.6 Hz), 8.19 (1H, s), 7.92 (1H, dd, J=8.8, 2.6 Hz), 7.87 (1H, d, J=8.8 Hz), 7.73 (1H, s), 7.44 (1H, d, J=2.2 Hz), 7.38 (1H, dd, J=8.8, 2.2 Hz), 6.79 (1H, d, J=8.8 Hz), 4.79 (2H, t, J=5.2 Hz), 4.65 (2H, t, J=5.2 Hz), 4.51 (2H, s), 3.89 (2H, t, J=5.6 Hz), 2.78 (2H, t, J=5.6 Hz); LRMS (ESI) m/z 508 [M+H]⁺.

Example 16

4-(4-((6-(2-Methyl-2-(1H-tetrazol-1-yl)propoxy)pyridin-3-yl)amino)-5,6-dihydropyrido[3,4-d]pyrimidin-7(8H)-yl)-2-(trifluoromethyl)benzonitrile

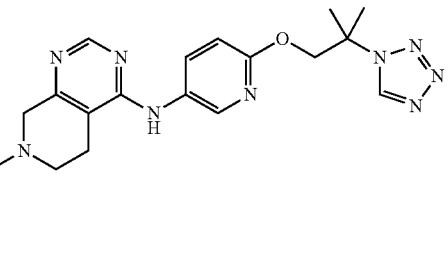

Step 1

Synthesis of 2-methyl-2-(1H-tetrazol-1-yl)propan-1-ol

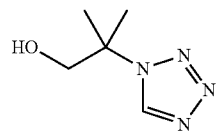

2-Amino-2-methylpropan-1-ol (30 g), triethyl orthoformate (64.8 g), and sodium azide (26.3 g) were suspended in acetic acid (150 mL) and stirred overnight at reflux conditions. The reaction solution was added with conc. hydrochloric acid (40 mL) and the produced insoluble matters were removed by filtration. The filtrate was concentrated under reduced pressure to remove the solvent, and the obtained residues were purified by silica gel column chromatography to obtain a solid. The obtained solid was suspended in toluene, and after filtering and washing with toluene, it was dried under reduced pressure to obtain the target compound (28.5 g, 60%).

¹H-NMR (DMSO-d₆) δ9.39 (1H, s), 5.24 (1H, t, J=5.6 Hz), 3.59 (2H, d, J=5.6 Hz), 1.56 (6H, s); LRMS (ESI) m/z 143 [M+H]⁺.

Step 2

Synthesis of 6-(2-methyl-2-(1H-tetrazol-1-yl)propoxy)pyridin-3-amine

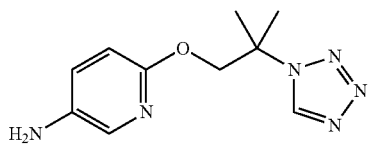 [SMILES: CC(C)(COc1ccc(N)cn1)n1cnnn1]

By performing the same operation as step 1 and step 2 of Example 15 and using 2-methyl-2-(1H-tetrazol-1-yl)propan-1-ol (2.82 g) obtained from step 1 instead of 2-(1H-1,2,3-triazol-1-yl)ethanol, the target compound was obtained (3.84 g, two step yield 86%).

$^1$H-NMR (DMSO-d$_6$) δ9.54 (1H, s), 7.42 (1H, d, J=2.9 Hz), 6.96 (1H, dd, J=8.8, 2.9 Hz), 6.46 (1H, d, J=8.8 Hz), 4.79 (2H, br-s), 4.40 (2H, s), 1.72 (6H, s); LRMS (ESI) m/z 235 [M+H]$^+$.

Step 3

Synthesis of 4-(4-((6-(2-methyl-2-(1H-tetrazol-1-yl) propoxy)pyridin-3-yl)amino)-5,6-dihydropyrido[3,4-d]pyrimidin-7(8H)-yl)-2-(trifluoromethyl)benzonitrile

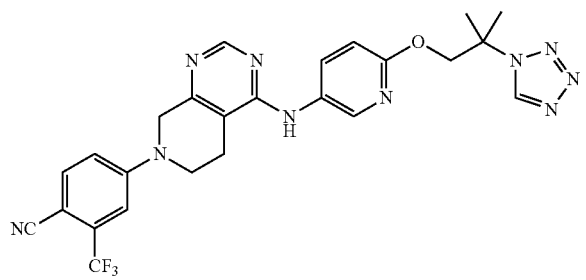 [SMILES: CC(C)(COc1ccc(Nc2ncnc3c2CCN(c2ccc(C#N)c(C(F)(F)F)c2)C3)cn1)n1cnnn1]

By reacting the compound (2.0 g) obtained from Reference Example 1-2 and the compound (1.52 g) obtained from step 2 according to Reference Example 2-1, the target compound was obtained (1.49 g, 47%).

$^1$H-NMR (DMSO-d$_6$) δ9.60 (1H, s), 8.68 (1H, s), 8.39 (1H, s), 8.27 (1H, d, J=2.7 Hz), 7.92 (1H, dd, J=8.8, 2.7 Hz), 7.87 (1H, d, J=8.8 Hz), 7.44 (1H, d, J=2.5 Hz), 7.38 (1H, dd, J=9.1, 2.5 Hz), 6.75 (1H, d, J=9.1 Hz)), 4.57 (2H, s), 4.50 (2H, br-s) 3.89 (2H, t, J=5.6 Hz), 2.77 (2H, t, J=5.6 Hz) 1.76 (6H, s); LRMS (ESI) m/z 537 [M+H]$^+$.

Example 17

4-(4-((5-(2-Methyl-2-(1H-tetrazol-1-yl)propoxy) pyridin-2-yl)amino)-5,6-dihydropyrido[3,4-d]pyrimidin-7(8H)-yl)-2-(trifluoromethyl)benzonitrile

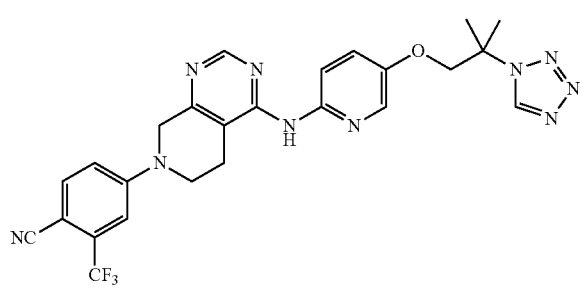 [SMILES: CC(C)(COc1ccc(Nc2ncnc3c2CCN(c2ccc(C#N)c(C(F)(F)F)c2)C3)nc1)n1cnnn1]

Step 1

Synthesis of 2-bromo-5-(2-methyl-2-(1H-tetrazol-1-yl)propoxy)pyridine

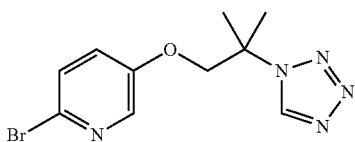 [SMILES: CC(C)(COc1ccc(Br)nc1)n1cnnn1]

2-Methyl-2-(1H-tetrazol-1-yl)propan-1-ol (3.27 g) obtained from step 1 of Example 16, 6-bromopyridin-3-ol (4.00 g), and cyanomethylenetributylphosphrane (Tsunoda Reagent, 9.99 g) were dissolved in toluene (100 mL) and stirred overnight under reflux. The solvent was concentrated and purification by silica gel column chromatography was performed to obtain the target compound (5.08 g, 74%).

$^1$H-NMR (DMSO-d$_6$) δ9.60 (1H, s), 8.08 (1H, d, J=3.3 Hz), 7.53 (1H, d, J=8.8 Hz), 7.36 (1H, dd, J=8.8, 3.3 Hz), 4.39 (2H, s), 1.76 (6H, s); LRMS (ESI) m/z 298 [M+H]$^+$.

Step 2

Synthesis of tert-butyl (5-(2-methyl-2-(1H-tetrazol-1-yl)propoxy)pyridin-2-yl)carbamate

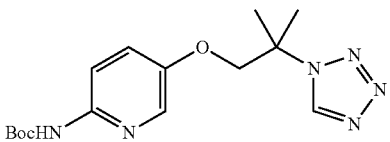 [SMILES: CC(C)(C)OC(=O)Nc1ccc(OCC(C)(C)n2cnnn2)cn1]

The compound (4 g) obtained from step 1, tert-butylcarbamate (4.72 g), Pd$_2$(dba)$_3$ (1.23 g), XantPhos (2.33 g) and sodium tert-butoxide (2.58 g) were dissolved in dioxane (100 mL) and stirred overnight under reflux. The reaction solution was added with water and extracted three times with chloroform. After drying over sodium sulfate and concentration, the obtained residues were purified by silica gel column chromatography to obtain the target compound (3.36 g, 74%).

$^1$H-NMR (DMSO-d$_6$) δ9.59 (1H, s), 9.58 (1H, br-s), 7.89 (1H, d, J=3.0 Hz), 7.66 (1H, d, J=9.1 Hz), 7.33 (1H, dd, J=9.1, 3.0 Hz), 4.32 (2H, s), 1.75 (6H, s), 1.44 (9H, s); LRMS (ESI) m/z 335 [M+H]$^+$.

Step 3

Synthesis of 5-(2-methyl-2-(1H-tetrazol-1-yl)propoxy)pyridin-2-amine

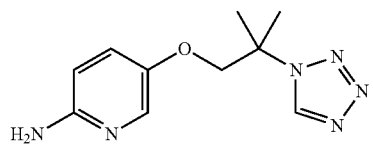

The compound (185 mg) obtained from step 2 was dissolved in 4 N hydrochloric acid-dioxane solution (3 mL) and stirred overnight under reflux. The reaction solution was added with a saturated aqueous solution of sodium hydrogen carbonate and extracted three times with chloroform. After drying over sodium sulfate and concentration, the target compound was obtained as a yellow oily product (130 mg, 100%).

$^1$H-NMR (DMSO-$d_6$) δ9.60 (1H, s), 7.56 (1H, d, J=3.0 Hz), 7.01 (1H, dd, J=8.9, 3.0 Hz), 6.36 (1H, d, J=8.9 Hz), 5.52 (2H, br-s), 4.18 (2H, s), 1.76 (6H, s); LRMS (ESI) m/z 235 [M+H]$^+$.

Step 4

Synthesis of 4-(4-((5-(2-methyl-2-(1H-tetrazol-1-yl)propoxy)pyridin-2-yl)amino)-5,6-dihydropyrido[3,4-d]pyrimidin-7(8H)-yl)-2-(trifluoromethyl)benzonitrile

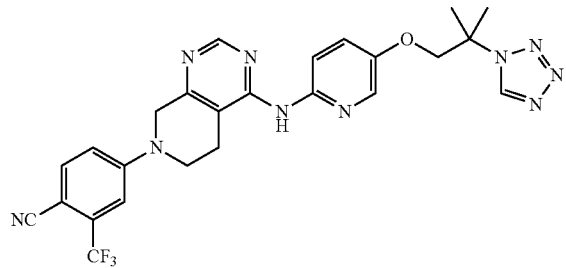 [SMILES: CC(C)(COc1ccc(Nc2ncnc3c2CCN(c2ccc(C#N)c(C(F)(F)F)c2)C3)nc1)n1cnnn1]

By reacting the compound (1.6 g) obtained from Reference Example 1-2 and the compound (1.14 g) obtained from step 3 according to Reference Example 2-1, the target compound was obtained (0.80 g, 32%).

$^1$H-NMR (DMSO-$d_6$) δ9.62 (1H, s), 9.02 (1H, s), 8.49 (1H, s), 8.01 (1H, d, J=3.1 Hz), 7.99 (1H, d, J=9.1 Hz), 7.86 (1H, d, J=8.8 Hz), 7.46-7.34 (3H, m), 4.53 (2H, br-s), 4.37 (2H, s), 3.85 (2H, t, J=5.7 Hz), 2.84 (2H, t, J=5.7 Hz) 1.77 (6H, s); LRMS (ESI) m/z 537 [M+H]$^+$.

Example 18

4-(4-((4-(3-(4-(Methylsulfonyl)piperazin-1-yl)propoxy)phenyl)amino)-5,6-dihydropyrido[3,4-d]pyrimidin-7(8H)-yl)-2-(trifluoromethyl)benzonitrile

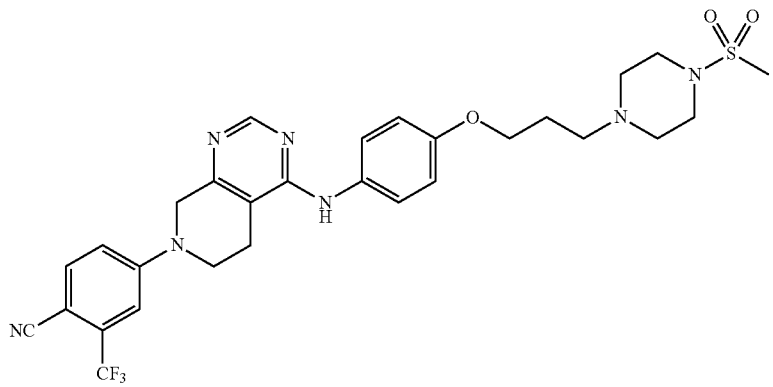 [SMILES: CS(=O)(=O)N1CCN(CCCOc2ccc(Nc3ncnc4c3CCN(c3ccc(C#N)c(C(F)(F)F)c3)C4)cc2)CC1]

Step 1

Synthesis of tert-butyl 4-(3-(4-((7-(4-cyano-3-(trifluoromethyl)phenyl)-5,6,7,8-tetrahydropyrido[3,4-d]pyrimidin-4-yl)amino)phenoxy)propyl)piperazin-1-carboxylate

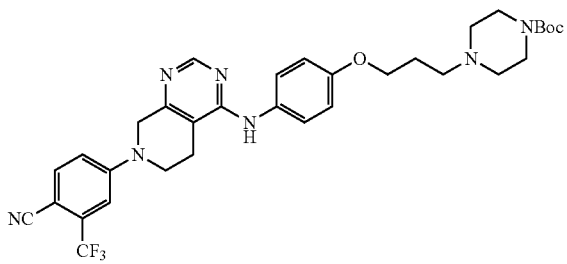 [SMILES: CC(C)(C)OC(=O)N1CCN(CCCOc2ccc(Nc3ncnc4c3CCN(c3ccc(C#N)c(C(F)(F)F)c3)C4)cc2)CC1]

By performing the same operation as Example 14 (step 4) and using tert-butyl 4-(3-hydroxypropyl)piperazin-1-carboxylate (65 mg) instead of 2-(1-methyl-1H-pyrazol-5-yl)ethanol, the target compound was obtained (140 mg, 92%).

$^1$H-NMR (CDCl$_3$) δ8.61 (1H, s), 7.69 (1H, d, J=8.8 Hz), 7.34-7.31 (1H, m), 7.29-7.22 (2H, m), 7.06 (2H, dd, J=8.8, 2.7 Hz), 6.70 (1H, d, J=8.3, 2.2 Hz), 6.50 (1H, s), 4.49 (2H, s), 4.05 (2H, t, J=6.2 Hz), 3.87 (2H, t, J=5.6 Hz), 3.48-3.38 (4H, m), 2.79 (2H, t, J=5.6 Hz), 2.54 (2H, t, J=7.2 Hz), 2.46-2.35 (4H, m), 2.04-1.92 (2H, m); LRMS (ESI) m/z 638 [M+H]$^+$.

Step 2

Synthesis of 4-(4-((4-(3-(4-(methylsulfonyl)piper-azin-1-yl)propoxy)phenyl)amino)-5,6-dihydropyrido[3,4-d]pyrimidin-7(8H)-yl)-2-(trifluoromethyl)benzonitrile

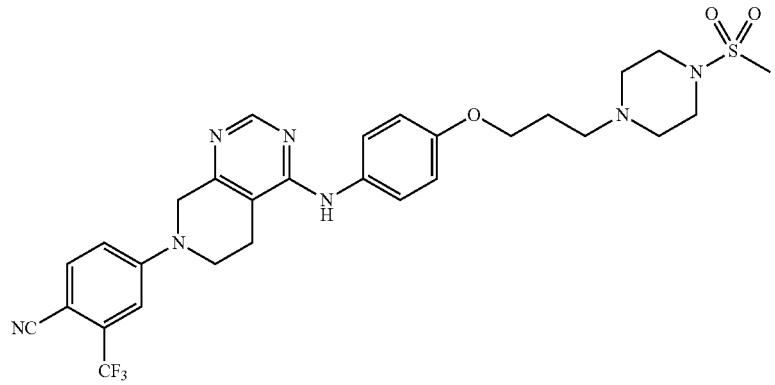 [SMILES: CS(=O)(=O)N1CCN(CCCOc2ccc(Nc3ncnc4c3CCN(c3ccc(C#N)c(C(F)(F)F)c3)C4)cc2)CC1]

The compound (140 mg) obtained from step 1 was added with 10% hydrochloric acid-methanol solution, followed by stirring for 3 hours at 50° C. The solvent was concentrated to obtain a de-Boc product (132 mg). A part (30 mg) of the obtained solid was suspended in dichloromethane, and added sequentially with triethylamine (22 μL) and methanesulfonyl chloride (5 μL), followed by stirring for 2 hours at room temperature. The reaction solution was added with water and extracted three times with chloroform. After drying over sodium sulfate and concentration, purification by silica gel column chromatography was performed to obtain the target compound (6.7 mg, 21%).

$^1$H-NMR (CDCl$_3$) δ8.54 (1H, s), 7.68 (1H, d, J=8.8 Hz), 7.45-7.36 (2H, m), 7.23 (1H, d, J=2.7 Hz), 7.06 (1H, dd, J=8.8, 2.7 Hz), 6.95-6.89 (2H, m), 6.32 (1H, s), 4.48 (2H, s), 4.03 (2H, t, J=6.1 Hz), 3.87 (2H, t, J=5.7 Hz), 3.72 (1H, q, J=7.0 Hz), 3.30-3.23 (4H, m), 2.83-2.73 (2H, m), 2.78 (3H, s), 2.63-2.55 (5H, m) 2.02-1.93 (2H, m); LRMS (ESI) m/z 616 [M+H]$^+$.

Example 19

6-((7-(4-Cyano-3-(trifluoromethyl)phenyl)-5,6,7,8-tetrahydropyrido[3,4-d]pyrimidin-4-yl)amino)-N-cyclopropylpyridine-3-sulfonamide

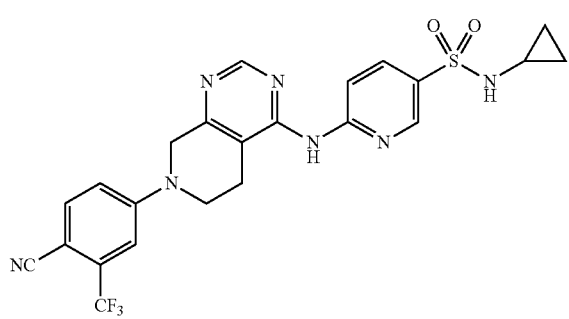 [SMILES: N#Cc1ccc(N2CCc3c(ncnc3Nc3ccc(S(=O)(=O)NC4CC4)cn3)C2)cc1C(F)(F)F]

Step 1

Synthesis of 6-chloro-N-cyclopropylpyridine-3-sulfonamide

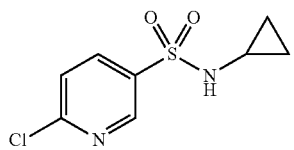 [SMILES: O=S(=O)(NC1CC1)c1ccc(Cl)nc1]

6-Chloropyridine-3-sulfonyl chloride (300 mg) and triethylamine (0.59 mL) were dissolved in dichloromethane (6 mL), and added with cyclopropylamine (121 mg) and dimethylaminopyridine (5 mg), followed by stirring overnight at room temperature. The reaction solution was added with water and extracted three times with chloroform. After drying over sodium sulfate and concentration, the target compound was obtained (442 mg).

$^1$H-NMR (DMSO-d$_6$) δ8.78 (1H, d, J=2.6 Hz), 8.24 (1H, br-s), 8.20 (1H, dd, J=8.4, 2.6 Hz), 7.81 (1, d, J=8.4 Hz), 2.25-2.17 (1H, m), 0.56-0.49 (2H, m), 0.40-0.36 (2H, m); LRMS (ESI) m/z 233 [M+H]$^+$.

Step 2

Synthesis of 6-amino-N-cyclopropylpyridine-3-sulfonamide

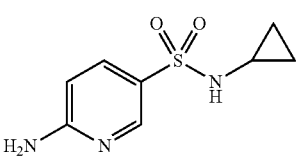 [SMILES: Nc1ccc(S(=O)(=O)NC2CC2)cn1]

The compound (200 mg) obtained from step 1 was dissolved in ethanol (2 mL) and added with 28% ammonia water (2 mL), followed by stirring for 1 hour at 140° C. under irradiation of microwave. After concentrating the reaction solution, the obtained residues were purified by silica gel column chromatography to obtain the target compound (90 mg, two step yield 66%).

¹H-NMR (CDCl₃) δ8.27 (1H, d, J=2.2 Hz), 7.65 (1H, dd, J=8.8, 2.6 Hz), 7.60 (1H, d, J=2.6 Hz), 6.87 (2H, s), 6.52 (1H, d, J=8.8 Hz), 2.13-2.05 (1H, m), 0.52-0.45 (2H, m), 0.39-0.33 (2H, m); LRMS (ESI) m/z 214 [M+H]⁺.

Step 3

Synthesis of 6-((7-(4-cyano-3-(trifluoromethyl)phenyl)-5,6,7,8-tetrahydropyrido[3,4-d]pyrimidin-4-yl)amino)-N-cyclopropylpyridine-3-sulfonamide

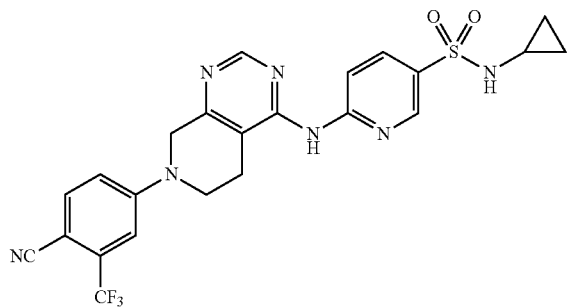 [SMILES: N#Cc1ccc(N2CCc3c(ncnc3Nc3ccc(S(=O)(=O)NC4CC4)cn3)C2)cc1C(F)(F)F]

By reacting the compound (50 mg) obtained from Reference Example 1-2 and the compound (38 mg) obtained from step 2 according to Reference Example 2-1, the target compound was obtained (21 mg, 28%).

¹H-NMR (DMSO-d₆) δ9.74 (1H, s), 8.68 (1H, s), 8.67 (1H, dd, J=2.6, 0.8 Hz), 8.33 (1H, dd, J=8.8, 0.8 Hz), 8.12 (1H, dd, J=8.8, 2.6 Hz), 7.95 (1H, d, J=2.8 Hz), 7.88 (1H, d, J=8.8 Hz), 7.45 (1H, d, J=2.2 Hz), 7.39 (1H, dd, J=8.8, 2.8 Hz), 4.61 (2H, s), 3.86 (2H, t, J=5.8 Hz), 2.94 (2H, t, J=5.8 Hz), 2.24-2.15 (1H, m), 0.57-0.49 (2H, m), 0.43-0.36 (2H, m); LRMS (ESI) m/z 516 [M+H]⁺.

Example 20

4-(4-((5-((1,4-Oxazepan-4-yl)sulfonyl)thiazol-2-yl)amino)-5,6-dihydropyrido[3,4-d]pyrimidin-7(8H)-yl)-2-(trifluoromethyl)benzonitrile

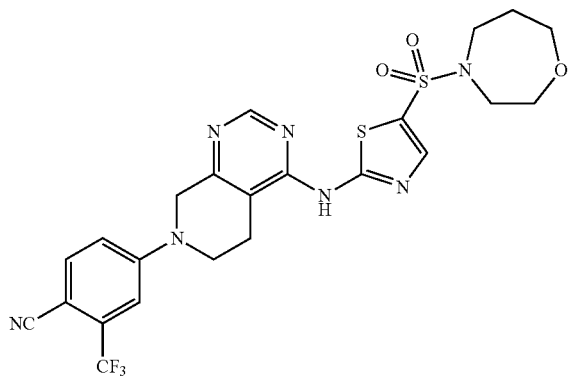 [SMILES: N#Cc1ccc(N2CCc3c(ncnc3Nc3ncc(S(=O)(=O)N4CCCOCC4)s3)C2)cc1C(F)(F)F]

Step 1

Synthesis of N-(5-((1,4-oxazepan-4-yl)sulfonyl)thiazol-2-yl)acetamide

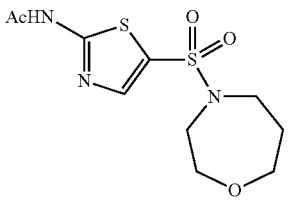 [SMILES: CC(=O)Nc1ncc(S(=O)(=O)N2CCCOCC2)s1]

2-(Acetylamino)-1,3-thiazol-5-sulfonyl chloride (200 mg) was dissolved in DMF (5 mL) and added with 1,4-oxazepane hydrochloride (170 mg) and DIPEA (424 μL), followed by stirring for 6 hours at room temperature. The reaction solution was added with an aqueous solution of ammonium chloride, and the precipitates were collected by filtration to obtain the target compound (200 mg, 79%).

¹H-NMR (DMSO-d₆) δ13.03 (1H, br-s), 8.31 (1H, s), 3.99-3.95 (4H, m), 3.71-3.58 (4H, m), 2.52 (3H, s), 2.16-2.10 (2H, m); LRMS (ESI) m/z 306 [M+H]⁺.

Step 2

Synthesis of 5-((1,4-oxazepan-4-yl)sulfonyl)thiazol-2-amine

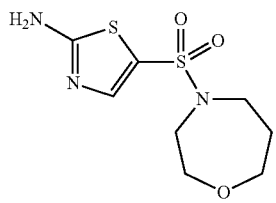 [SMILES: Nc1ncc(S(=O)(=O)N2CCCOCC2)s1]

The compound (183 mg) obtained from step 1 was dissolved in ethanol (4 mL) and added with 4.0 mol/L hydrochloric acid (dioxane solution, 1.2 mL), followed by stirring for 4.5 hours at 70° C. After concentrating the reaction solution, ammonia water was added under ice cooling and the precipitates were collected by filtration to obtain the target compound (110 mg, 70%).

¹H-NMR (DMSO-d₆) δ7.88 (2H, br-s), 7.45 (1H, s), 3.67-3.64 (4H, m), 3.39-3.27 (4H, m), 1.84-1.78 (2H, m); LRMS (ESI) m/z 264 [M+H]⁺.

Step 3

Synthesis of 4-(4-((5-(((1,4-oxazepan-4-yl)sulfonyl)thiazol-2-yl)amino)-5,6-dihydropyrido[3,4-d]pyrimidin-7(8H)-yl)-2-(trifluoromethyl)benzonitrile

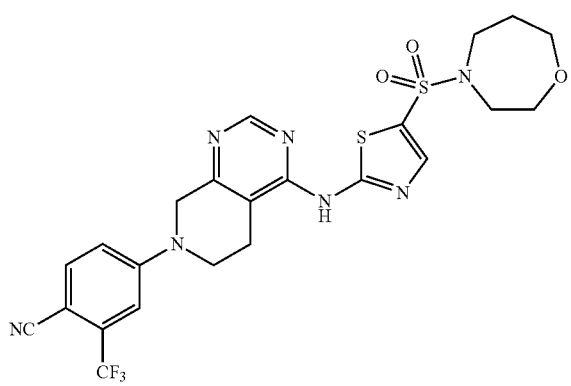 [SMILES: N#Cc1ccc(N2CCc3c(ncnc3Nc3ncc(S(=O)(=O)N4CCCOCC4)s3)C2)cc1C(F)(F)F]

By performing the same operation as Reference Example 2-1 and using the compound (47 mg) obtained from step 2 instead of methyl 6-aminonicotinate and carrying out the reaction for 30 minutes at 150° C. under microwave irradiation instead of stirring overnight at 80° C., the target compound was obtained (10 mg, 12%).

$^1$H-NMR (DMSO-d$_6$) δ11.97 (1H, br-s), 8.81 (1H, s), 8.03 (1H, s), 7.87 (1H, d, J=8.8 Hz), 7.45 (1H, d, 2.0 Hz), 7.38 (1H, dd, J=2.0, 8.8 Hz), 4.61 (2H, s), 3.86 (2H, t, 5.6 Hz), 3.69-3.63 (4H, m), 3.42-3.30 (4H, m), 2.94 (2H, t, 5.6 Hz), 1.84-1.78 (2H, m); LRMS (ESI) m/z 566 [M+H]$^+$.

Example 21

2,2,2-Trifluoroethyl (6-((7-(4-cyano-3-(trifluoromethyl)phenyl)-5,6,7,8,-tetrahydropyrido[3,4-d]pyrimidin-4-yl)amino)pyridin-3-yl)carbamate

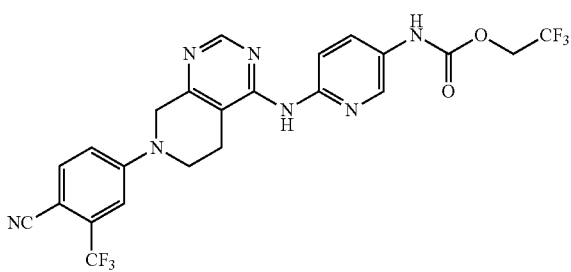 [SMILES: N#Cc1ccc(N2CCc3c(ncnc3Nc3ccc(NC(=O)OCC(F)(F)F)cn3)C2)cc1C(F)(F)F]

The compound (100 mg) obtained from Reference Example 2-2, diphenylphosphoryl azide (188 mg), 2,2,2-trifluoroethanol (68 mg), and N,N-diisopropylethylamine (88 mg) were suspended in dioxane (2.5 mL) and stirred for 2 hours at 125° C. under microwave irradiation. The obtained reaction solution was concentrated and dried, and purification by silica gel column chromatography was performed to obtain the target compound 5.8 mg (2.4%).

$^1$H-NMR (DMSO-d$_6$) δ10.24 (1H, s), 9.08 (1H, s), 8.51 (1H, s), 8.42 (1H, s), 8.07 (1H, d, J=9.2 Hz), 7.89-7.82 (2H, m), 7.43 (1H, d, J=1.8 Hz), 7.36 (1H, dd, J=8.8, 2.6 Hz), 4.79 (2H, q, J=9.2 Hz), 4.53 (2H, s), 3.84 (2H, t, J=5.9 Hz), 2.85 (2H, t, 5.1 Hz); LRMS (ESI) m/z 538 [M+H]$^+$.

Example 22

2-(6-((7-(4-Cyano-3-(trifluoromethyl)phenyl)-5,6,7,8-tetrahydropyrido[3,4-d]pyrimidin-4-yl)amino)pyridin-3-yl)-N-(2,2,2-trifluoroethyl)acetamide

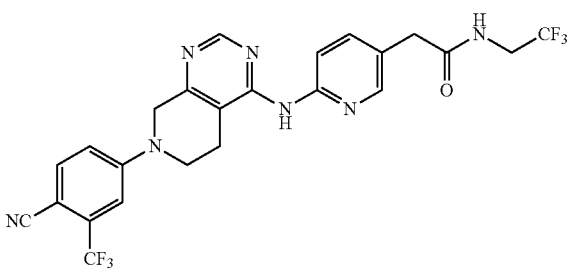 [SMILES: N#Cc1ccc(N2CCc3c(ncnc3Nc3ccc(CC(=O)NCC(F)(F)F)cn3)C2)cc1C(F)(F)F]

Step 1

Synthesis of 2-(6-((7-(4-cyano-3-(trifluoromethyl)phenyl)-5,6,7,8-tetrahydropyrido[3,4-d]pyrimidin-4-yl)amino)pyridin-3-yl)acetic acid

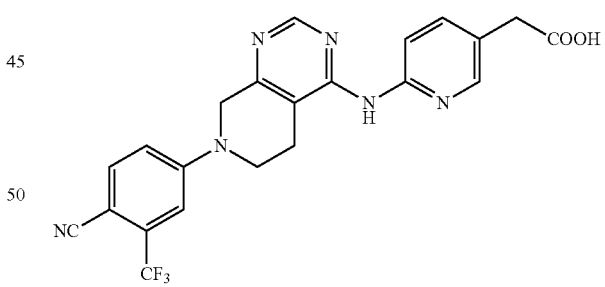

By performing the same operation as Reference Examples 2-1 and 2-2 and using ethyl 2-(6-aminopyridin-3-yl)acetate (175 mg) instead of methyl 6-aminonicotinate, the target compound was obtained (94 mg, two step yield 26%).

$^1$H-NMR (DMSO-d$_6$) δ9.73 (1H, br-s), 8.64 (1H, s), 8.27 (1H, d, J=1.1 Hz), 8.03 (1H, d, J=8.8 Hz), 7.89 (1H, d, J=8.8 Hz), 7.84 (1H, dd, J=8.8, 1.1 Hz), 7.45 (1H, d, J=2.1 Hz), 7.39 (1H, dd, J=8.8, 2.1 Hz), 4.60 (2H, s), 3.88 (2H, t, J=5.2 Hz), 3.66 (2H, s), 2.91 (2H, t, J=5.2 Hz); LRMS (ESI) m/z 455 [M+H]$^+$.

Step 2

Synthesis of 2-(6-((7-(4-cyano-3-(trifluoromethyl)phenyl)-5,6,7,8-tetrahydropyrido[3,4-d]pyrimidin-4-yl)amino)pyridin-3-yl)-N-(2,2,2-trifluoroethyl)acetamide

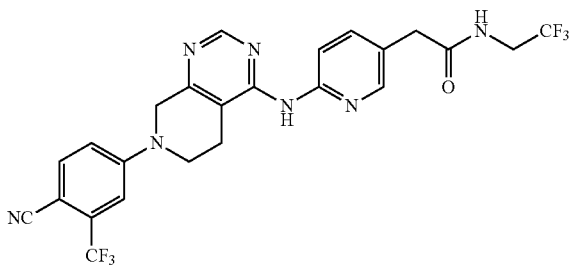 [SMILES: N#Cc1ccc(N2CCc3c(ncnc3Nc3ccc(CC(=O)NCC(F)(F)F)cn3)C2)cc1C(F)(F)F]

By performing the same operation as Example 11 and using the compound (30 mg) obtained from step 1 instead of the compound obtained from Reference Example 2-2, the target compound was obtained (29 mg, 83%).
$^{1}$H-NMR (DMSO-$d_6$) δ9.10 (1H, br-s), 8.79 (1H, t, J=6.2 Hz), 8.54 (1H, s), 8.20 (1H, d, J=2.2 Hz), 8.07 (1H, d, J=8.4 Hz), 7.87 (1H, d, J=8.8 Hz), 7.66 (1H, dd, J=8.4, 2.4 Hz), 7.44 (1H, d, J=2.2 Hz), 7.37 (1H, dd, J=8.8, 2.4 Hz), 4.55 (2H, s), 3.98-3.82 (4H, m), 3.52 (2H, s), 2.88 (2H, t, J=5.5 Hz); LRMS (ESI) m/z 536 [M+H]$^+$.

Example 23

N-(6-((7-(4-Cyano-3-(trifluoromethyl)phenyl)-5,6,7,8-tetrahydropyrido[3,4-d]pyrimidin-4-yl)amino)pyridin-3-yl)-3,3,3-trifluoropropanamide

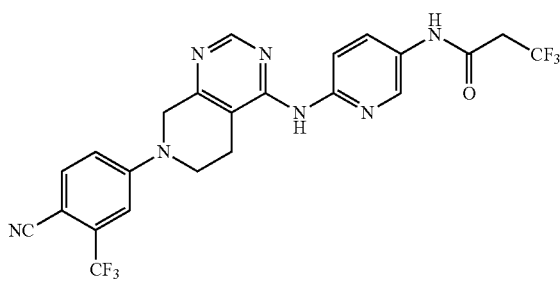 [SMILES: N#Cc1ccc(N2CCc3c(ncnc3Nc3ccc(NC(=O)CC(F)(F)F)cn3)C2)cc1C(F)(F)F]

Step 1

4-(4-((5-Nitropyridin-2-yl)amino)-5,6-dihydropyrido[3,4-d]pyrimidin-7(8H)-yl)-2-(trifluoromethyl)benzonitrile

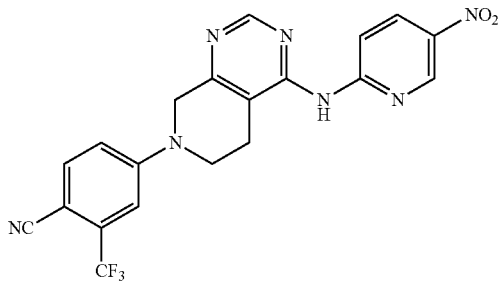 [SMILES: N#Cc1ccc(N2CCc3c(ncnc3Nc3ccc([N+](=O)[O-])cn3)C2)cc1C(F)(F)F]

By performing the same operation as Reference Example 2-1 and using 5-nitropyridin-2-amine (986 mg) instead of methyl 6-aminonicotinate, the target compound was obtained (810 mg, 31%).
$^{1}$H-NMR (DMSO-$d_6$) δ10.11 (1H, s), 9.14 (1H, d, J=2.9 Hz), 8.71 (1H, s), 8.54 (1H, dd, J=9.3, 2.7 Hz), 8.27 (1H, d, J=9.5 Hz), 7.86 (1H, d, J=8.8 Hz), 7.43 (1H, d, J=2.2 Hz), 7.37 (1H, dd, J=8.8, 2.6 Hz), 4.61 (2H, s), 3.84 (2H, t, J=5.7 Hz), 2.94 (2H, t, 5.7 Hz); LRMS (ESI) m/z 442 [M+H]$^+$.

Step 2

4-(4-((5-Aminopyridin-2-yl)amino)-5,6-dihydropyrido[3,4-d]pyrimidin-7(8H)-yl)-2-(trifluoromethyl)benzonitrile

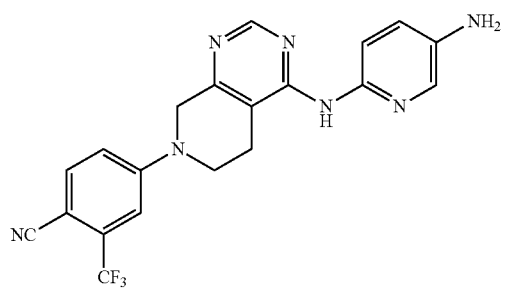 [SMILES: N#Cc1ccc(N2CCc3c(ncnc3Nc3ccc(N)cn3)C2)cc1C(F)(F)F]

The compound (100 mg) obtained from step 1 and 10% palladium/carbon (10 mg) were suspended in methanol (2.0 mL) and stirred for 2 days at room temperature under hydrogen atmosphere. The obtained suspension was filtered through Celite, and the filtrate was concentrated and dried to obtain 12 mg (13%) of the target compound.
$^{1}$H-NMR (DMSO-$d_6$) δ8.67 (1H, s), 8.40 (1H, s), 7.86 (1H, d, J=8.8 Hz), 7.72 (1H, d, J=2.9 Hz), 7.67 (1H, d, J=8.8 Hz), 7.43 (1H, d, J=2.6 Hz), 7.36 (1H, dd, J=8.8, 2.6 Hz), 7.00 (1H, dd, J=8.6, 2.7 Hz), 5.12 (2H, s), 4.49 (2H, s), 3.85 (2H, t, J=5.9 Hz), 2.78 (2H, t, 5.5 Hz); LRMS (ESI) m/z 412 [M+H]$^+$.

Step 3

N-(6-((7-(4-Cyano-3-(trifluoromethyl)phenyl)-5,6,7,8-tetrahydropyrido[3,4-d]pyrimidin-4-yl)amino)pyridin-3-yl)-3,3,3-trifluoropropanamide

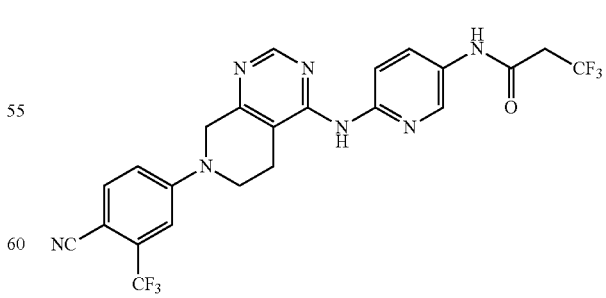

By performing the same operation as Example 11 and using 3,3,3-trifluoropropanoic acid (7.0 mg) instead of 6-((7-(4-cyano-3-(trifluoromethyl)phenyl)-5,6,7,8-tetrahydropyrido[3,4-d]pyrimidin-4-yl)amino)nicotinic acid and the compound (15 mg) obtained from step 3 instead of 2,2,2-trifluoroethylamine, 2.8 mg (15%) of the target compound was obtained.

¹H-NMR (DMSO-d₆) δ10.51 (1H, s), 9.14 (1H, s), 8.57 (1H, d, J=2.6 Hz), 8.53 (1H, s), 8.12 (1H, d, J=8.8 Hz), 7.91 (1H, dd, J=8.8, 2.6 Hz), 7.86 (1H, d, J=8.8 Hz), 7.43 (1H, d, J=2.6 Hz), 7.37 (1H, dd, J=9.0, 2.4 Hz), 4.54 (2H, s), 3.85 (2H, t, J=5.8 Hz), 3.53 (2H, q, J=11.2 Hz), 2.86 (2H, t, 5.5 Hz); LRMS (ESI) m/z 522 [M+H]+.

Example 24

6-((7-(4-Cyano-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide

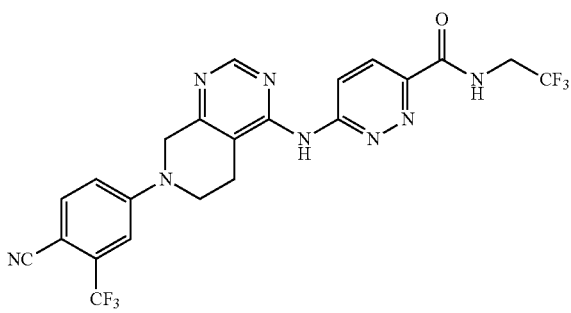

By performing the same operation as Example 11 and using the compound (5.0 mg) obtained from Production Example B instead of the compound obtained from Reference Example 2-2 and HATU (8.6 mg) and DIPEA (8.1 μL) instead of DMT-MM, the target compound was obtained (1.22 mg) (yield 21%).

¹H-NMR (DMSO-d₆) δ9.53 (1H, t, J=6.5 Hz), 8.62 (1H, s), 8.49-8.42 (2H, m), 8.15 (1H, d, J=9.6 Hz), 7.85 (1H, d, J=8.9 Hz), 7.45 (1H, s), 7.36 (1H, d, J=8.9 Hz), 4.59 (2H, s), 4.09 (2H, m), 3.85 (2H, t, J=5.5 Hz), 2.96 (2H, m) LRMS (ESI) m/z 523 [M+H]⁺.

Example 25

3-((7-(4-Cyano-3-(trifluoromethyl)phenyl)-5,6,7,8-tetrahydropyrido[3,4-d]pyrimidin-4-yl)amino)-N-(2,2,2-trifluoroethyl)-1,2,4-triazine-6-carboxamide

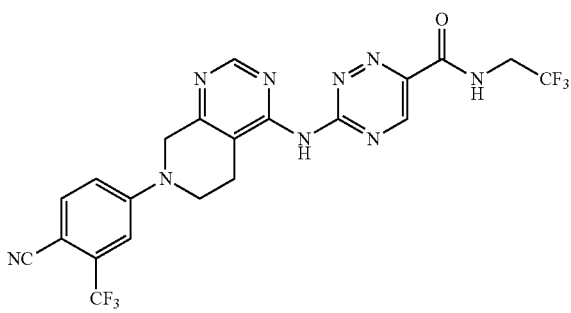 [SMILES: N#Cc1ccc(N2CCc3c(ncnc3Nc3ncc(C(=O)NCC(F)(F)F)nn3)C2)cc1C(F)(F)F]

Step 1

Synthesis of 6-bromo-1,2,4-triazine-3-amine

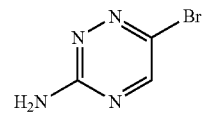

1,2,4-Triazin-3-amine (5.00 g) was dissolved in acetonitrile (45 mL) and distilled water (75 mL), and under light blocking conditions, N-bromosuccinimide (10.0 g) was added under ice cooling, followed by stirring overnight at room temperature under light blocking conditions. The obtained reaction solution was added with distilled water (100 mL) and extracted three times with ethyl acetate (150 mL). The obtained organic layer was combined, and after washing with saturated brine, dried over anhydrous sodium sulfate. The insoluble matters were separated by filtration, and the filtrate was concentrated and dried to obtain 2.64 g (yield 29%) of the target compound.

¹H-NMR (DMSO-d₆) δ8.38 (1H, s), 7.45 (2H, br-s); LRMS (ESI) m/z 175 [M+H]⁺.

Step 2

Synthesis of methyl 3-amino-1,2,4-triazine-6-carboxylate

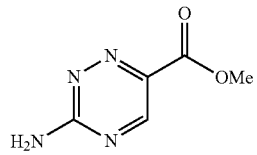 [SMILES: COC(=O)c1cnc(N)nn1]

By performing the same operation as Example 5 and using the compound (1.0 g) obtained from step 1 of this example instead of the compound obtained from step 1 of Example 5, 728 mg of the target compound was obtained (yield 83%).

¹H-NMR (DMSO-d₆) δ8.64 (1H, s), 3.85 (3H, s); LRMS (ESI) m/z 155 [M+H]⁺.

Step 3

Synthesis of 3-amino-N-(2,2,2-trifluoroethyl)-1,2,4-triazine-6-carboxamide

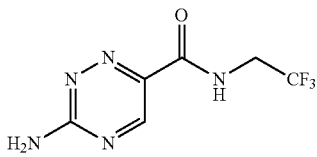 [SMILES: Nc1ncc(C(=O)NCC(F)(F)F)nn1]

The compound (100 mg) obtained from step 2 was dissolved in methanol (6.5 mL), and added with 2 N aqueous solution of sodium hydroxide (4 mL), followed by stirring for 3 hours. The reaction solution was adjusted to have a pH of 4 using 2 N hydrochloric acid, and then concentrated and dried under reduced pressure. The obtained residues and 2,2,2-trifluoroethylamine (102 μL) were dissolved in a mixed solvent of DMF (3 mL) and methanol (3 mL), added with DMT-MM, followed by stirring overnight. The reaction solution was added with distilled water and extracted three times with ethyl acetate. The organic layer was combined, washed with distilled water and saturated brine, and dried over anhydrous sodium sulfate. The insoluble matters were separated by filtration, and the filtrate was concentrated and dried. Then, purification by silica gel column chromatography was performed to obtain the target compound (56 mg) (yield 39%).

LRMS (ESI) m/z 222 [M+H]$^+$.

Step 4

Synthesis of 3-((7-(4-cyano-3-(trifluoromethyl)phenyl)-5,6,7,8-tetrahydropyrido[3,4-d]pyrimidin-4-yl)amino)-N-(2,2,2-trifluoroethyl)-1,2,4-triazine-6-carboxamide

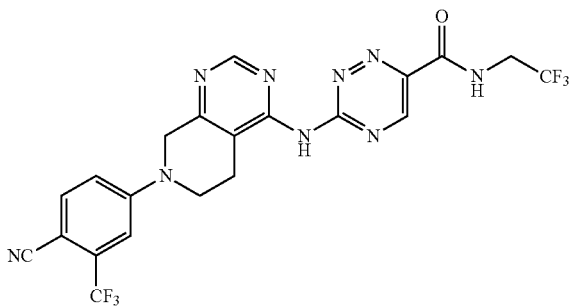 [SMILES: N#Cc1ccc(N2CCc3c(ncnc3Nc3ncc(C(=O)NCC(F)(F)F)nn3)C2)cc1C(F)(F)F]

By performing the same operation as Reference Example 2-1 and using the compound (30 mg) obtained from Reference Example 1-2 and the compound (23 mg) obtained from step 3 instead of methyl 6-aminonicotinate and stirring for 30 minutes at 140° C. under irradiation of microwave instead of overnight stirring at 80° C., 32 mg of the target compound was obtained (yield 70%).

$^1$H-NMR (DMSO-d$_6$) δ9.62 (1H, t, J=6.4 Hz), 8.99 (1H, s), 8.79 (1H, s), 8.28 (1H, s), 7.85 (1H, d, J=8.8 Hz), 7.41 (1H, s), 7.36 (1H, dd, J=8.8, 2.6 Hz), 4.68 (2H, s), 4.14 (2H, m), 3.79 (2H, m), 2.81 (2H, t, J=5.5 Hz); LRMS (ESI) m/z 524 [M+H]$^+$.

Example 26

2-((7-(4-Cyano-3-(trifluoromethyl)phenyl)-5,6,7,8-tetrahydropyrido[3,4-d]pyrimidin-4-yl)amino)-N-(2,2,2-trifluoroethyl)-4-(trifluoromethyl)thiazol-5-carboxamide

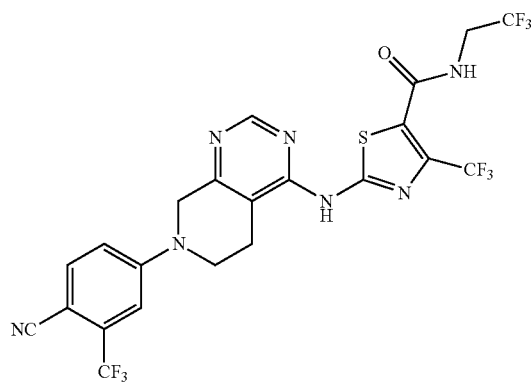 [SMILES: N#Cc1ccc(N2CCc3c(ncnc3Nc3nc(C(F)(F)F)c(C(=O)NCC(F)(F)F)s3)C2)cc1C(F)(F)F]

Step 1

Synthesis of ethyl 2-((7-(4-cyano-3-(trifluoromethyl)phenyl)-5,6,7,8-tetrahydropyrido[3,4-d]pyrimidin-4-yl)amino)-4-(trifluoromethyl) thiazol-5-carboxylate

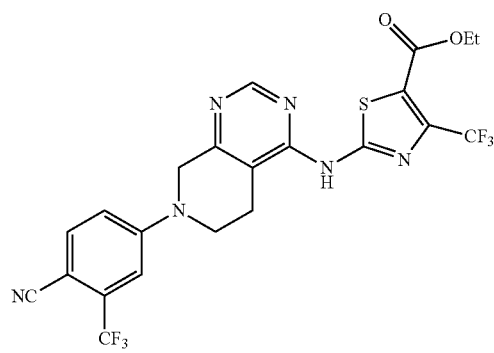

By performing the same operation as Reference Example 2-1 and using ethyl 2-amino-4-(trifluoromethyl)thiazol-5-carboxylate (341 mg) instead of methyl 6-aminonicotinate and having the reaction for 30 minutes at 150° C. under irradiation of microwave instead of overnight stirring at 80° C., the target compound was obtained (670 mg, 100%).

$^1$H-NMR (DMSO-d$_6$) δ8.59 (1H, s), 7.79 (1H, d, 8.8 Hz), 7.40 (1H, d, 2.4 Hz), 7.33 (1H, dd, J=2.4, 8.8 Hz), 4.43 (2H, s), 4.19 (2H, q, 7.0 Hz), 3.79 (2H, t, J=5.9 Hz), 2.80 (2H, t, J=5.9 Hz), 1.25 (3H, t, J=7.0 Hz); LRMS (ESI) m/z 543 [M+H]$^+$.

Step 2

Synthesis of 2-((7-(4-cyano-3-(trifluoromethyl)phenyl)-5,6,7,8-tetrahydropyrido[3,4-d]pyrimidin-4-yl)amino)-4-(trifluoromethyl)thiazol-5-carboxylic acid

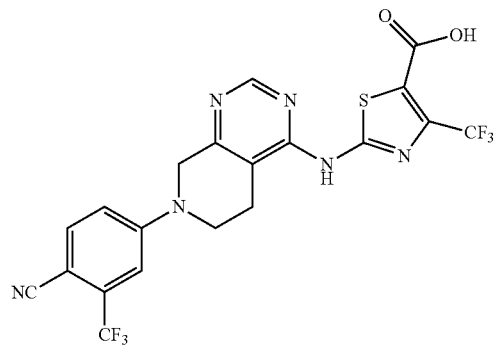 [SMILES: N#Cc1ccc(N2CCc3c(ncnc3Nc3nc(C(F)(F)F)c(C(=O)O)s3)C2)cc1C(F)(F)F]

The compound (670 mg) obtained from step 1 was suspended in ethanol (10 mL), and added with 2.0 mol/L aqueous solution of sodium hydroxide (4.8 mL), followed by stirring for 6 hours at 60° C. The reaction solution was concentrated, diluted with distilled water, and adjusted to have a pH of about 5 by using 2.0 mol/L hydrochloric acid. The precipitates were collected by filtration to obtain the target compound (275 mg, 45%).

LRMS (ESI) m/z 515 [M+H]$^+$.

Step 3

Synthesis of 2-((7-(4-cyano-3-(trifluoromethyl)phenyl)-5,6,7,8-tetrahydropyrido[3,4-d]pyrimidin-4-yl)amino)-N-(2,2,2-trifluoroethyl)-4-(trifluoromethyl)thiazol-5-carboxamide

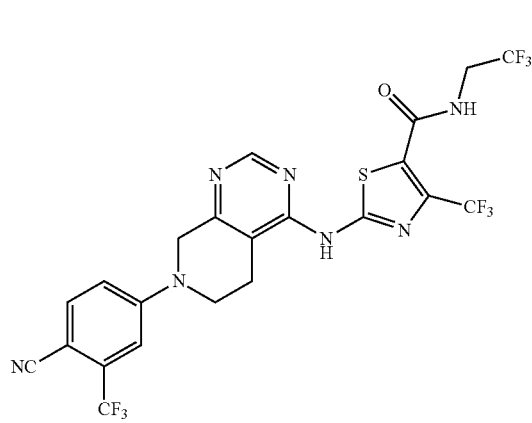 [SMILES: N#Cc1ccc(N2CCc3c(ncnc3Nc3nc(C(F)(F)F)c(C(=O)NCC(F)(F)F)s3)C2)cc1C(F)(F)F]

By performing the same operation as Example 11 and using the compound (40 mg) obtained from step 2 instead of the compound obtained from Reference Example 2-2 and HOBt (13 mg) and WSC (16 mg) instead of DMT-MM, the target compound was obtained (11 mg, 24%).

$^1$H-NMR (DMSO-$d_6$) δ12.02 (1H, s), 9.43 (1H, t, J=6.2 Hz), 8.83 (1H, s), 7.88 (1H, d, J=8.8 Hz), 7.48 (1H, d, J=2.4 Hz), 7.40 (1H, dd, J=2.4, 8.8 Hz), 4.63 (2H, s), 4.11-4.01 (2H, m), 3.88 (2H, t, J=5.7 Hz), 2.96 (2H, t, J=5.7 Hz); LRMS (ESI) m/z 596 [M+H]$^+$.

Example 27

6-((7-(4-Cyano-3-(trifluoromethyl)phenyl)-5,6,7,8-tetrahydropyrido[3,4-d]pyrimidin-4-yl)amino)-N-(2,2-difluoroethyl)nicotinamide

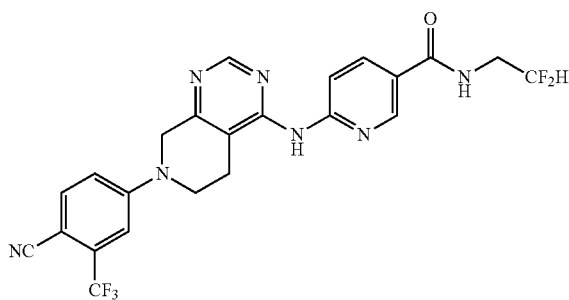 [SMILES: N#Cc1ccc(N2CCc3c(ncnc3Nc3ccc(C(=O)NCC(F)F)cn3)C2)cc1C(F)(F)F]

By performing the same operation as Example 11 and using 2,2-difluoroethylamine instead of 2,2,2-trifluoroethylamine and HATU and DIPEA instead of DMT-MM, the target compound was obtained (yield 58%).

$^1$H-NMR (DMSO-$d_6$) δ9.48 (1H, s), 8.90 (1H, t, J=5.8 Hz), 8.80 (1H, s), 8.62 (1H, s), 8.25-8.16 (2H, m), 7.84 (1H, d, J=8.9 Hz), 7.42 (1H, s), 7.35 (1H, d, J=8.9 Hz), 6.10 (1H, t, J=56 Hz), 4.56 (2H, s), 3.83 (2H, t, J=5.5 Hz), 3.66 (2H, m), 2.90 (2H, m) LRMS (ESI) m/z 504 [M+H]$^+$.

Example 28

6-((7-(4-Cyano-3-(trifluoromethyl)phenyl)-5,6,7,8-tetrahydropyrido[3,4-d]pyrimidin-4-yl)amino)-N-(2,2-difluoroethyl)pyridazine-3-carboxamide

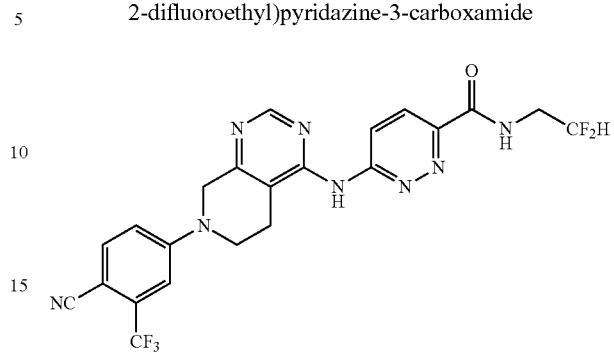

By performing the same operation as Example 11 and using the compound (5.0 mg) obtained from Production Example B instead of the compound obtained from Reference Example 2-2, 2,2-difluoroethylamine instead of 2,2,2-trifluoroethylamine, and HATU (8.6 mg) and DIPEA (8.1 µL) instead of DMT-MM, the target compound was obtained (3.52 mg) (yield 62%).

$^1$H-NMR (DMSO-$d_6$) δ10.22 (1H, br-s), 9.26 (1H, t, J=6.2 Hz), 8.62 (1H, s), 8.44 (1H, d, J=9.6 Hz), 8.14 (1H, d, J=8.9 Hz), 7.85 (1H, d, J=8.9 Hz), 7.43 (1H, s), 7.36 (1H, d, J=8.9 Hz), 6.14 (1H, t, J=56 Hz), 4.59 (2H, s), 3.85 (2H, m), 3.73 (2H, m), 2.96 (2H, m) LRMS (ESI) m/z 505 [M+H]$^+$.

Example 29

6-((7-(3-Chloro-4-cyanophenyl)-5,6,7,8-tetrahydropyrido[3,4-d]pyrimidin-4-yl)amino)-N-((1r,4r)-4-hydroxycyclohexyl)pyridazine-3-carboxamide

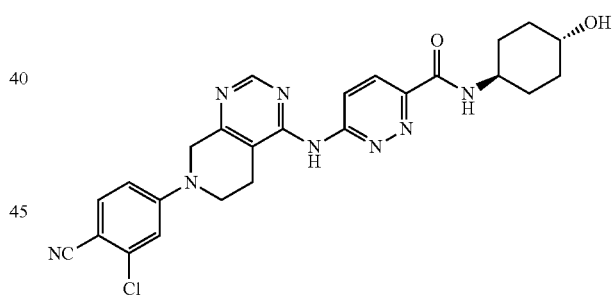

Step 1

Synthesis of methyl 6-((7-benzyl-5,6,7,8-tetrahydropyrido[3,4-d]pyrimidin-4-yl)amino)pyridazine-3-carboxylate

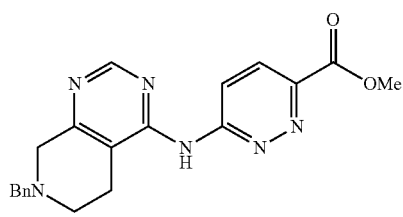 [SMILES: COC(=O)c1ccc(Nc2ncnc3c2CCN(Cc2ccccc2)C3)nn1]

By performing the same operation as Reference Example 2-1 and using methyl 6-aminopyridazine-3-carboxylate (353 mg) instead of methyl 6-aminonicotinate and commercially available 7-benzyl-4-chloro-5,6,7,8-tetrahydropyrido[3,4-d]pyrimidine (500 mg) instead of the compound obtained from Reference Example 1-2, the target compound was obtained (267 mg, 37%).

$^1$H-NMR (DMSO-d$_6$) δ8.56 (1H, s), 8.52 (1H, d, J=9.5 Hz), 8.17 (1H, d, J=9.5 Hz), 7.37 (1H, s), 7.59-7.32 (5H, m), 3.93 (3H, s), 3.68 (2H, s), 3.50 (2H, s), 2.83 (2H, t, J=5.5 Hz), 2.74 (2H, t, J=5.5 Hz); LRMS (ESI) m/z 377 [M+H]+.

Step 2

Synthesis of methyl 6-((7-(3-chloro-4-cyanophenyl)-5,6,7,8-tetrahydropyrido[3,4-d]pyrimidin-4-yl)amino)pyridazine-3-carboxylate

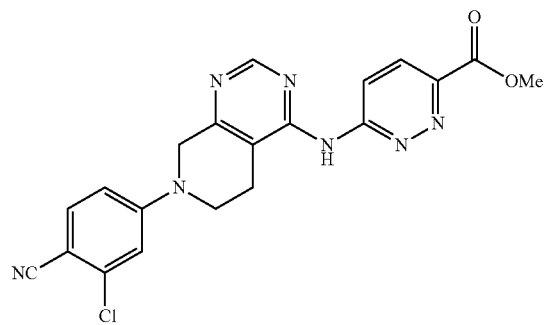 [SMILES: COC(=O)c1ccc(Nc2ncnc3c2CCN(c2ccc(C#N)c(Cl)c2)C3)nn1]

By performing the same operation as Reference Example 1-1 for the compound (260 mg) obtained from step 1 and using 2-chloro-4-fluorobenzonitrile (322 mg) instead of 4-fluoro-2-(trifluoromethyl)benzonitrile, the target compound was obtained (34 mg, 12%).

$^1$H-NMR (CDCl$_3$) δ9.01 (1H, d, J=8.8 Hz), 8.70 (1H, s), 8.24 (1H, d, J=8.8 Hz), 7.56 (1H, d, J=8.8 Hz), 7.40 (1H, s), 7.07 (1H, d, J=2.4 Hz), 6.94 (1H, dd, J=8.8, 2.4 Hz), 4.52 (2H, s), 4.06 (3H, s), 3.87 (2H, t, J=5.2 Hz), 3.04 (2H, t, J=5.2 Hz); LRMS (ESI) m/z 422 [M+H]+.

Step 3

Synthesis of 6-((7-(3-chloro-4-cyanophenyl)-5,6,7,8-tetrahydropyrido[3,4-d]pyrimidin-4-yl)amino)pyridazine-3-carboxylic acid

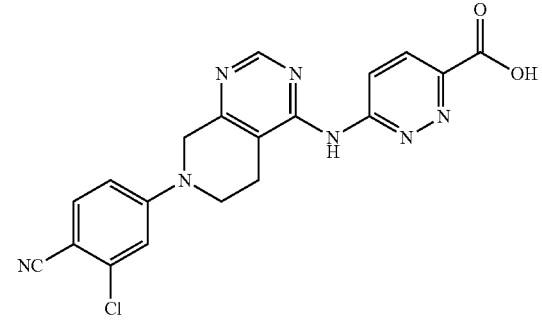 [SMILES: N#Cc1ccc(N2CCc3c(ncnc3Nc3ccc(C(=O)O)nn3)C2)cc1Cl]

By performing the same operation as Reference Example 2-2 and using the compound (34 mg) obtained from step 2, the target compound was obtained (27 mg, 82%).

$^1$H-NMR (DMSO-d$_6$) δ10.33 (1H, br-s), 8.65 (1H, s), 8.47 (1H, d, J=9.3 Hz), 8.16 (1H, d, J=9.3 Hz), 7.70 (1H, d, J=8.8 Hz), 7.33 (1H, d, J=2.4 Hz), 7.13 (1H, dd, J=8.8, 2.4 Hz), 4.55 (2H, s), 3.82 (2H, t, J=5.6 Hz), 2.97 (2H, t, J=5.6 Hz); LRMS (ESI) m/z 408 [M+H]+.

Step 4

Synthesis of 6-((7-(3-chloro-4-cyanophenyl)-5,6,7,8-tetrahydropyrido[3,4-d]pyrimidin-4-yl)amino)-N-((1r,4r)-4-hydroxycyclohexyl)pyridazine-3-carboxamide

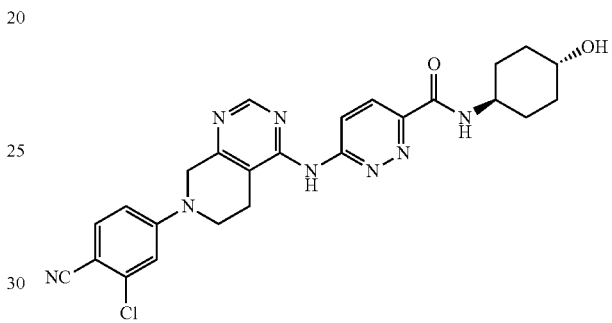

By reacting the compound obtained from step 3 and trans-4-aminocyclohexanol according to Example 11, the target compound was obtained (5.6 mg, 50%).

$^1$H-NMR (DMSO-d$_6$) δ10.14 (1H, br-s), 8.67 (1H, d, J=8.7 Hz), 8.63 (1H, s), 8.41 (1H, d, J=9.5 Hz), 8.12 (1H, d, J=9.5 Hz), 7.70 (1H, d, J=8.7 Hz), 7.33 (1H, d, J=2.2 Hz), 7.13 (1H, dd, J=8.7, 2.2 Hz), 4.60-4.52 (3H, m), 3.84-3.74 (3H, m), 2.95 (2H, t, J=5.3 Hz), 1.90-1.75 (4H, m), 1.56-1.45 (2H, m), 1.33-1.18 (3H, m); LRMS (ESI) m/z 505 [M+H]+.

Example 30

6-((7-(4-Cyano-3-(trifluoromethyl)phenyl)-5,6,7,8-tetrahydropyrido[3,4-d]pyrimidin-4-yl)amino)-N-((1-hydroxycyclopropyl)methyl)pyridazine-3-carboxamide

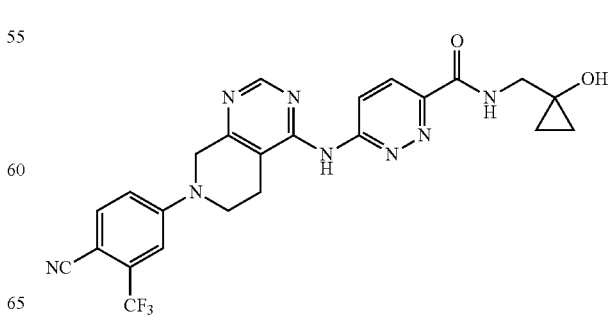

By performing the same operation as Example 11 and using the compound (20 mg) obtained from Production Example B and 1-(aminomethyl)cyclopropanol (34 mg), the target compound was obtained (3.6 mg, 16%).

$^1$H-NMR (CDCl$_3$) δ9.00 (1H, d, J=9.2 Hz), 8.74 (1H, s), 8.38 (1H, t, J=5.8 Hz), 8.31 (1H, d, J=9.2 Hz), 8.25-8.08 (1H, m), 7.72 (1H, d, J=8.8 Hz), 7.27 (1H, d, J=2.6 Hz), 7.10 (1H, dd, J=8.8, 2.6 Hz), 7.36 (1H, dd, J=8.8, 2.3 Hz), 4.57 (2H, s), 3.92 (2H, t, J=5.6 Hz), 3.69 (2H, d, J=5.8 Hz), 3.00 (2H, t, J=5.6 Hz), 0.95-0.89 (2H, m), 0.77-0.70 (2H, m); LRMS (ESI) m/z 511 [M+H]$^+$.

Example 31

2-((7-(4-Cyano-3-(trifluoromethyl)phenyl)-5,6,7,8-tetrahydropyrido[3,4-d]pyrimidin-4-yl)amino)-N-(2,2,2-trifluoroethyl) isonicotinamide

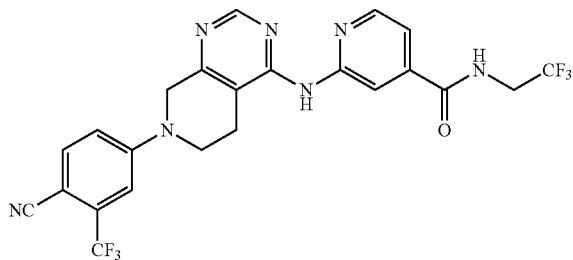 [SMILES: N#Cc1ccc(N2CCc3c(ncnc3Nc3cc(C(=O)NCC(F)(F)F)ccn3)C2)cc1C(F)(F)F]

Step 1

Synthesis of 2-((7-(4-cyano-3-(trifluoromethyl)phenyl)-5,6,7,8-tetrahydropyrido[3,4-d]pyrimidin-4-yl)amino)isonicotinic acid

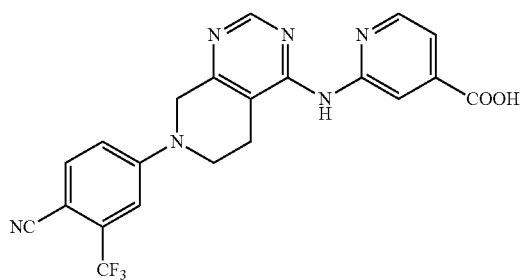 [SMILES: N#Cc1ccc(N2CCc3c(ncnc3Nc3cc(C(=O)O)ccn3)C2)cc1C(F)(F)F]

By performing the same operation as Reference Examples 2-1 and 2-2 and using ethyl 2-aminoisonicotinate (135 mg) instead of methyl 6-aminonicotinate, the target compound was obtained (147 mg, two step yield 45%).

$^1$H-NMR (DMSO-d$_6$) δ9.35 (1H, s) 8.62 (2H, s), 8.48 (1H, d, J=5.0 Hz), 7.86 (1H, d, J=8.9 Hz), 7.47 (1H, dd, J=5.0, 1.1 Hz), 7.43 (1H, d, J=2.0 Hz), 7.36 (1H, dd, J=8.9, 2.0 Hz), 4.57 (2H, s), 3.85 (2H, t, J=5.4 Hz), 2.90 (2H, t, J=5.4 Hz); LRMS (ESI) m/z 441 [M+H]$^+$.

Step 2

Synthesis of 2-((7-(4-cyano-3-(trifluoromethyl)phenyl)-5,6,7,8-tetrahydropyrido[3,4-d]pyrimidin-4-yl)amino)-N-(2,2,2-trifluoroethyl)isonicotinamide

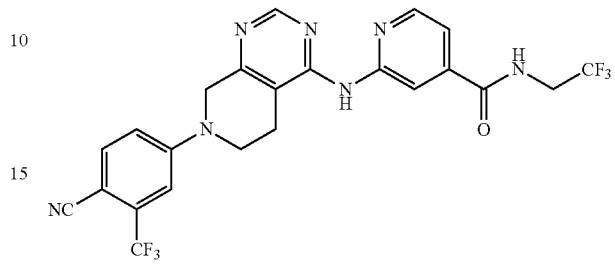

The compound (25 mg) obtained from step 1 and 2,2,2-trifluoroethylamine (11 mg) were dissolved in DMF (1 mL), and added with HATU (43 mg) and diisopropylethylamine (40 μL), followed by stirring for 3 hours at room temperature. The reaction solution was added with water and extraction with ethyl acetate was performed three times. The organic layer was washed with water and saturated brine, dried over sodium sulfate, and concentrated. The obtained residues were purified by silica gel column chromatography to obtain the target compound (22 mg, 73%).

$^1$H-NMR (CDCl$_3$) δ8.90 (1H, s), 8.74 (1H, s), 8.43 (1H, d, J=5.1 Hz), 7.70 (1H, d, J=8.8 Hz), 7.45 (1H, s), 7.40 (1H, dd, J=5.1, 1.5 Hz), 7.25 (1H, d, J=2.6 Hz), 7.08 (1H, dd, J=8.8, 2.6 Hz), 6.71 (1H, t, J=5.9 Hz), 4.53 (2H, s), 4.18 (2H, m), 3.89 (2H, t, J=5.8 Hz), 2.89 (2H, t, J=5.8 Hz); LRMS (ESI) m/z 522 [M+H]$^+$.

Example 32

6-((7-(4-Cyano-3-(trifluoromethyl)phenyl)-5,6,7,8-tetrahydropyrido[3,4-d]pyrimidin-4-yl)amino)-N-(2-hydroxy-2-methylpropyl)pyridazine-3-carboxamide

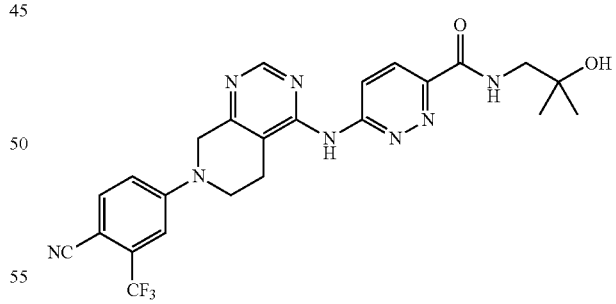

By performing the same operation as Example 11 and using the compound (20 mg) obtained from Production Example B instead of the compound obtained from Reference Example 2-2, 1-amino-2-methylpropan-2-ol (4 mg) instead of 2,2,2-trifluoroethylamine, and HATU (26 mg) and DIPEA (15 μL) instead of DMT-MM, the target compound was obtained (4.2 mg, 18%).

$^1$H-NMR (CD$_3$OD) δ8.81 (1H, d, J=9.2 Hz), 8.65 (1H, s), 8.22 (1H, d, J=9.2 Hz), 7.79 (1H, d, J=8.8 Hz), 7.41 (1H, d, J=2.6 Hz), 7.32 (1H, dd, J=2.6, 8.8 Hz), 4.64-4.54 (3H, m), 3.93 (2H, t, J=5.5 Hz), 3.47 (2H, s), 3.02 (2H, t, J=5.5 Hz), 1.26 (6H, s); LRMS (ESI) m/z 513 [M+H]⁺.

Example 33

5-((7-(4-Cyano-3-(trifluoromethyl)phenyl)-5,6,7,8-tetrahydropyrido[3,4-d]pyrimidin-4-yl)amino)-N-(2-hydroxy-2-methylpropyl) pyrazine-2-carboxamide

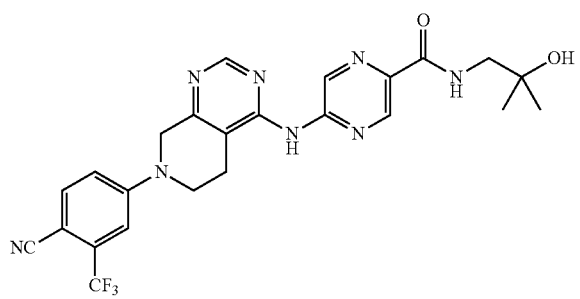 [SMILES: CC(C)(O)CNC(=O)c1cnc(Nc2ncnc3c2CCN(c2ccc(C#N)c(C(F)(F)F)c2)C3)cn1]

By performing the same operation as Example 11 and using the compound (10 mg) obtained from Production Example C instead of the compound obtained from Reference Example 2-2 and 1-amino-2-methylpropan-2-ol (8 mg) instead of 2,2,2-trifluoroethylamine, the target compound was obtained (6.4 mg, 55%).

¹H-NMR (DMSO-d₆) δ10.04 (1H, br-s), 9.35 (1H, s), 8.92 (1H, s), 8.67 (1H, s), 8.29 (1H, t, J=6.2 Hz), 7.88 (1H, d, J=8.9 Hz), 7.46 (1H, d, J=2.2 Hz), 7.39 (1H, dd, J=2.2, 8.9 Hz), 4.72 (1H, s), 4.62 (2H, s), 3.87 (2H, t, J=5.5 Hz), 3.34-3.30 (2H, m), 2.94 (2H, t, J=5.5 Hz), 1.12 (6H, s); LRMS (ESI) m/z 513 [M+H]⁺.

Example 34

2-((7-(4-Cyano-3-(trifluoromethyl)phenyl)-5,6,7,8-tetrahydropyrido[3,4-d]pyrimidin-4-ylamino)-N-(2-hydroxy-2-methylpropyl)pyrimidine-5-carboxamide

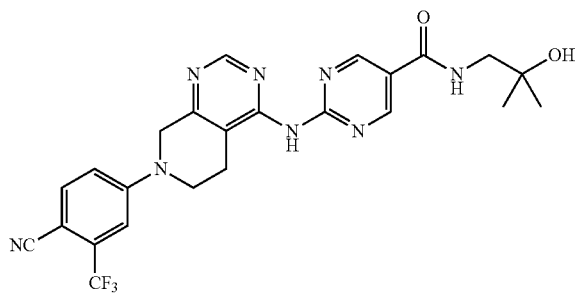 [SMILES: CC(C)(O)CNC(=O)c1cnc(Nc2ncnc3c2CCN(c2ccc(C#N)c(C(F)(F)F)c2)C3)nc1]

By performing the same operation as Example 11 and using the compound (5 mg) obtained from Production Example D instead of the compound obtained from Reference Example 2-2 and 1-amino-2-methylpropan-2-ol (4 mg) instead of 2,2,2-trifluoroethylamine, the target compound was obtained (3.2 mg, 53%).

¹H-NMR (DMSO-d₆) δ10.42 (1H, br-s), 8.95 (2H, s), 8.77 (1H, s), 8.42 (1H, t, J=6.2 Hz), 7.88 (1H, d, J=8.9 Hz), 7.43 (1H, d, J=2.1 Hz), 7.36 (1H, dd, J=2.1, 8.9 Hz), 4.67 (2H, s), 4.56 (1H, s), 3.79 (2H, t, J=5.5 Hz), 3.24 (2H, d, J=6.2 Hz), 2.77 (2H, t, J=5.5 Hz), 1.11 (6H, s); LRMS (ESI) m/z 513 [M+H]⁺.

Example 35

5-((7-(4-Cyano-3-(trifluoromethyl)phenyl)-5,6,7,8-tetrahydropyrido[3,4-d]pyrimidin-4-yl)amino)-N-(2-(1-methyl-1H-pyrazol-5-yl)ethyl)-1,3,4-thiadiazol-2-carboxamide

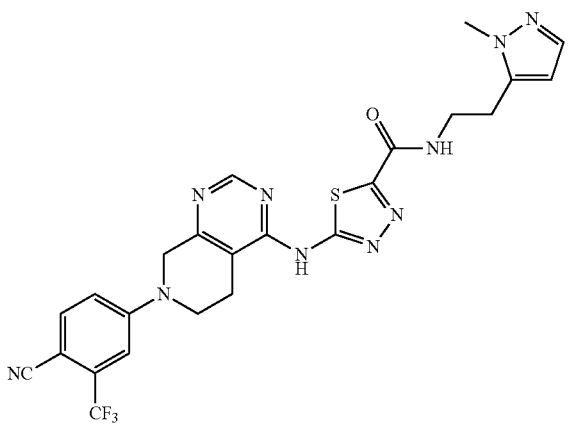 [SMILES: Cn1nccc1CCNC(=O)c1nnc(Nc2ncnc3c2CCN(c2ccc(C#N)c(C(F)(F)F)c2)C3)s1]

Step 1

Synthesis of 2-(1-methyl-1H-pyrazol-5-yl)ethyl methanesulfonate

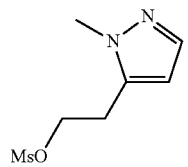

2-(1-Methyl-1H-pyrazol-5-yl)ethanol (537 mg) obtained from step 1 of Example 14 and triethylamine (0.89 mL) were dissolved in chloroform (10 mL) and added dropwise with methanesulfonyl chloride (0.4 mL) at 0° C. The reaction solution was stirred for 6 hours at room temperature. After adding water to the reaction solution and extraction three times with chloroform, it was dried over sodium sulfate and concentrated. The obtained residues were purified by silica gel column chromatography to obtain the target compound as a colorless oily product (930 mg).

¹H-NMR (CDCl₃) δ7.42 (1H, d, J=1.7 Hz), 6.14 (1H, d, J=1.7 Hz), 4.44 (2H, t, J=6.7 Hz), 3.85 (3H, s), 3.11 (2H, t, J=6.7 Hz), 2.95 (3H, s); LRMS (ESI) m/z 205 [M+H]⁺.

Step 2

Synthesis of
2-(1-methyl-1H-pyrazol-5-yl)ethanamine

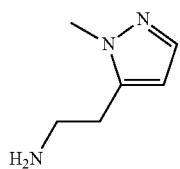

The compound (443 mg) obtained from step 1 was dissolved in DMF, and added with sodium azide (705 mg), followed by stirring at 60° C. for 3 hours. The reaction solution was added with water and extracted three times with ethyl acetate. The organic layer was washed with water and saturated brine, dried over sodium sulfate and then concentrated. The obtained residues were dissolved in methanol (8 mL), and added with 10% palladium/carbon (50 mg, containing 50% water), followed by stirring overnight at atmospheric pressure under hydrogen atmosphere. The reaction solution was filtered through Hyflo Super-Cel and the solvent was concentrated to obtain the target compound (180 mg, 76%).

$^1$H-NMR (CDCl$_3$) δ7.42 (1H, J=1.7 Hz), 6.10 (1H, d, J=1.7 Hz), 3.84 (3H, s), 3.57 (2H, t, J=7.1 Hz), 2.90 (2H, t, J=7.1 Hz); LRMS (ESI) m/z 126 [M+H]$^+$.

Step 3

Synthesis of 5-((7-(4-cyano-3-(trifluoromethyl)phenyl)-5,6,7,8-tetrahydropyrido[3,4-d]pyrimidin-4-yl)amino)-N-(2-(1-methyl-1H-pyrazol-5-yl)ethyl)-1,3,4-thiadiazol-2-carboxamide

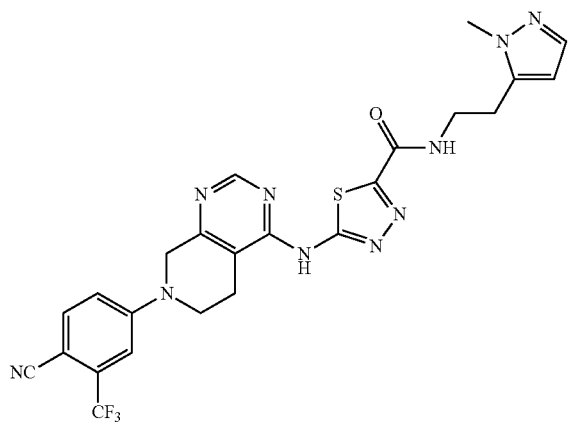 [SMILES: Cn1nccc1CCNC(=O)c1nnc(Nc2ncnc3c2CCN(c2ccc(C#N)c(C(F)(F)F)c2)C3)s1]

The compound (17 mg) obtained from step 2 and the compound (30 mg) obtained from Production Example E were dissolved in DMF, and added with EDC-HCl (25 mg) and 1-hydroxybenzotriazole (18 mg), followed by stirring overnight at room temperature. The reaction solution was added with water and extracted three times with ethyl acetate. The organic layer was washed with water and saturated brine, dried over sodium sulfate and then concentrated. The obtained residues were purified by silica gel column chromatography to obtain the target compound (17 mg, 46%).

$^1$H-NMR (CDCl$_3$) δ8.32 (1H, s), 7.70 (1H, d, J=8.8 Hz), 7.49 (1H, t, J=5.9 Hz), 7.39 (1H, d, J=1.8 Hz), 7.24 (1H, d, J=2.4 Hz), 7.09 (1H, dd, J=8.8, 2.4 Hz), 6.11 (1H, d, J=1.8 Hz), 4.59 (2H, s), 3.91-3.71 (4H, m), 3.83 (3H, s), 3.07-2.94 (4H, m); LRMS (ESI) m/z 555 [M+H]$^+$.

Example 36

6-((7-(4-Cyano-3-(trifluoromethyl)phenyl)-5,6,7,8-tetrahydropyrido[3,4-d]pyrimidin-4-yl)amino)-N-((4-(trifluoromethyl)thiazol-2-yl)methyl)nicotinamide

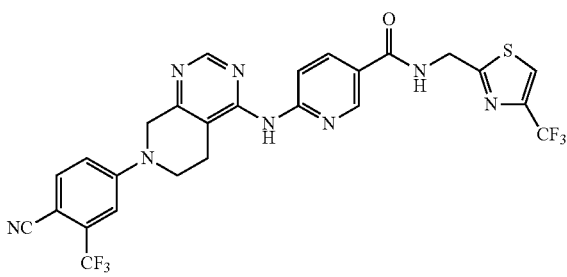 [SMILES: N#Cc1ccc(N2CCc3c(ncnc3Nc3ccc(C(=O)NCc4nc(C(F)(F)F)cs4)cn3)C2)cc1C(F)(F)F]

By performing the same operation as Example 11 and using the compound (30 mg) obtained from Reference Example 2-2 and 4-(trifluoromethyl)thiazol-2-yl)methanamine hydrochloride (16 mg) instead 2,2,2-trifluoroethylamine, and adding HATU (39 mg) and DIPEA (18 mg) instead of DMT-MM, 20 mg of the target compound was obtained (yield 48%).

$^1$H-NMR (DMSO-d$_6$) δ9.53 (1H, m), 8.84 (1H, s), 8.64 (1H, s), 8.41 (1H, s), 8.24 (2H, m), 8.11 (1H, s), 7.86 (1H, d, J=8.8 Hz), 7.43 (1H, d, J=2.2 Hz), 7.37 (1H, d, J=8.8 Hz), 4.78 (2H, d, J=6.2 Hz), 4.58 (2H, s), 3.84 (2H, t, J=5.7 Hz), 2.92 (2H, t, 5.5 Hz); LRMS (ESI) m/z 605 [M+H]$^+$.

Example 37

(R)—N-(1-(1,3,4-Oxadiazol-2-yl)ethyl)-2-((7-(4-cyano-3-(trifluoromethyl)phenyl)-5,6,7,8-tetrahydropyrido[3,4-d]pyrimidin-4-yl)amino)-4-(trifluoromethyl)thiazol-5-carboxamide

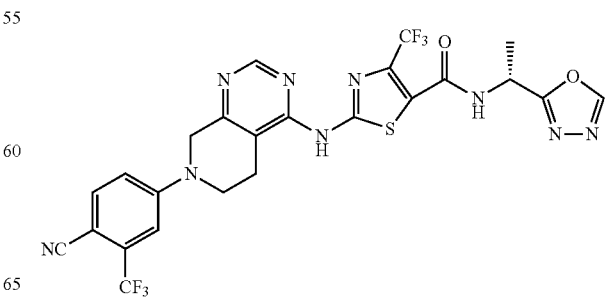

Step 1

Synthesis of (R)-tert-butyl (1-hydrazinyl-1-oxopropan-2-yl)carbamate

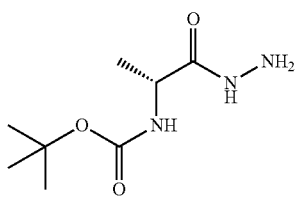

Boc-D-alanine methyl ester (2.0 g) was dissolved in ethanol (50 mL), and added with hydrazine monohydrate (0.6 mL), followed by stirring overnight. Upon the completion of the reaction, ethyl acetate and water were added for fractionation. The organic layer was washed with saturated brine, and dried over anhydrous sodium sulfate. The insoluble matters were separated by filtration, the filtrate was concentrated and dried, and the obtained residues were purified by silica gel column chromatography to obtain 500 mg of the target compound (yield 25%).

$^1$H-NMR (DMSO-$d_6$) δ8.96 (1H, br-s), 6.83 (1H, d, J=7.7 Hz), 4.16 (2H, br-s), 3.91 (1H, t, 7.2 Hz), 1.36 (9H, s), 1.13 (3H, d, J=7.0 Hz); LRMS (ESI) m/z 204 [M+H]$^+$.

Step 2

Synthesis of (R)-tert-butyl (1-(1,3,4-oxadiazol-2-yl)ethyl)carbamate

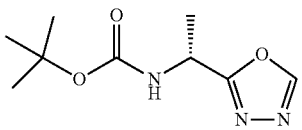

The compound obtained from step 1 was dissolved in triethyl orthoformate (11 mL) and stirred overnight at 150° C. After the reaction, it was purified by silica gel column chromatography to obtain the target compound (960 mg) (yield 82%).

$^1$H-NMR (DMSO-$d_6$) δ9.15 (1H, s), 7.62 (1H, m), 4.87 (1H, m), 1.45 (3H, d, J=7.1 Hz), 1.38 (9H, s); LRMS (ESI) m/z 157 [M-tert butyl+H]$^+$.

Step 3

Synthesis of (R)-1-(1,3,4-oxadiazol-2-yl)ethanamine

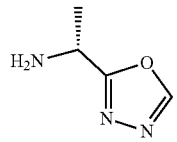

The compound (200 mg) obtained from step 2 was dissolved in 1,1,1,3,3,3-hexafluoro-2-propanol (4.7 mL) and stirred for 1 hour at 150° C. under irradiation of microwave. After cooling, it was concentrated under reduced pressure to obtain the target compound as an oily product (96 mg) (yield 91%).

$^1$H-NMR (DMSO-$d_6$) δ9.13 (1H, s), 4.18 (1H, m), 2.12 (2H, br-s), 1.38 (3H, d, J=6.8 Hz); LRMS (ESI) m/z 114 [M+H]$^+$.

Step 4

Synthesis of (R)—N-(1-(1,3,4-oxadiazol-2-yl)ethyl)-2-((7-(4-cyano-3-(trifluoromethyl)phenyl)-5,6,7,8-tetrahydropyrido[3,4-d]pyrimidin-4-yl)amino)-4-(trifluoromethyl)thiazol-5-carboxamide

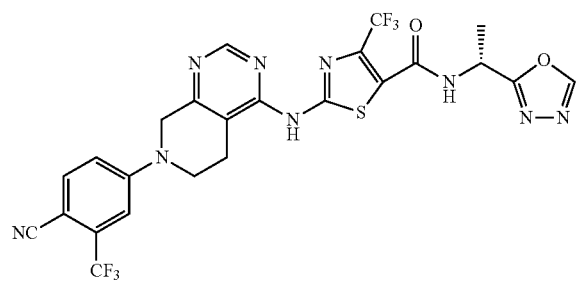 [SMILES: C[C@@H](NC(=O)c1sc(Nc2ncnc3c2CCN(c2ccc(C#N)c(C(F)(F)F)c2)C3)nc1C(F)(F)F)c1nnco1]

By performing the same operation as Example 11 and using the compound (45 mg) obtained from Example 26 (step 2) instead of the compound obtained from Reference Example 2-2 and (R)-1-(1,3,4-oxadiazol-2-yl)ethanamine (17 mg) obtained from step 3 instead of 2,2,2-trifluoroethylamine, 29 mg of the target compound was obtained (yield 55%).

$^1$H-NMR (DMSO-$d_6$) δ9.38 (1H, d, J=6.8 Hz), 9.19 (1H, s), 8.74 (1H, s), 8.11 (1H, s), 7.84 (1H, d, J=8.9 Hz), 7.43 (1H, s), 7.36 (1H, d, J=8.9 Hz), 5.33 (1H, t, J=7.2 Hz), 4.56 (2H, s), 3.84 (2H, t, J=5.5 Hz), 2.90 (2H, m), 1.55 (3H, d, J=7.5 Hz) LRMS (ESI) m/z 610 [M+H]$^+$.

Example 38

(R)—N-(1-(1,3,4-Oxadiazol-2-yl)ethyl)-6-((7-(4-cyano-3-(trifluoromethyl)phenyl)-5,6,7,8-tetrahydropyrido[3,4-d]pyrimidin-4-yl)amino)nicotinamide

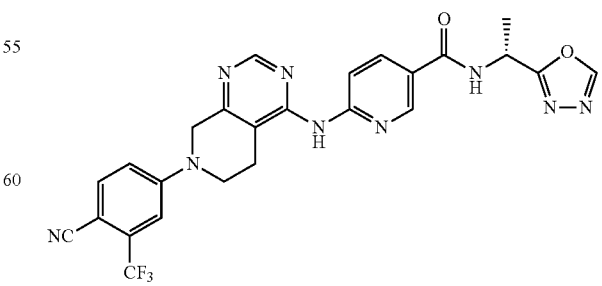

By performing the same operation as Example 11 and using the compound (30 mg) obtained from Reference Example 2-2 and the compound (15 mg) obtained from step 3 of Example 37 instead of 2,2,2-trifluoroethylamine, 12 mg of the target compound was obtained (yield 33%).

$^1$H-NMR (DMSO-d$_6$) δ9.50 (1H, s), 9.18-9.11 (2H, m), 8.80 (1H, s), 8.62 (1H, s), 8.24-8.17 (2H, m), 7.84 (1H, d, J=8.9 Hz), 7.42 (1H, s), 7.35 (1H, d, J=8.9 Hz), 5.42 (1H, m), 4.56 (2H, s), 3.83 (2H, t, J=5.5 Hz), 2.90 (2H, m), 1.60 (3H, d, J=6.8 Hz) LRMS (ESI) m/z 536 [M+H]$^+$.

Example 39

(R)—N-(1-(1,3,4-Oxadiazol-2-yl)ethyl)-5-((7-(4-cyano-3-(trifluoromethyl)phenyl)-5,6,7,8-tetrahydropyrido[3,4-d]pyrimidin-4-yl)amino)-1,3,4-thiadiazol-2-carboxamide

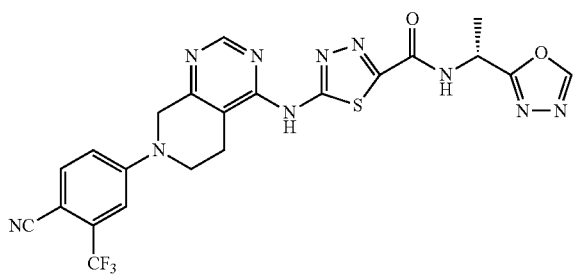 [SMILES: C[C@@H](NC(=O)c1nnc(Nc2ncnc3c2CCN(c2ccc(C#N)c(C(F)(F)F)c2)C3)s1)c1nnco1]

By performing the same operation as Example 11 and using the compound obtained from Production Example E instead of the compound obtained from Reference Example 2-2 and the compound obtained from step 3 of Example 37 instead of 2,2,2-trifluoroethylamine, the target compound was obtained (yield 44%).

$^1$H-NMR (DMSO-d$_6$) δ9.74 (1H, d, J=7.5 Hz), 9.15 (1H, s), 8.77 (1H, s), 8.10 (1H, s), 7.84 (1H, d, J=8.9 Hz), 7.43 (1H, s), 7.36 (1H, d, J=8.9 Hz), 5.41 (1H, m), 4.59 (2H, s), 3.85 (2H, t, J=5.5 Hz), 2.94 (2H, m), 1.62 (3H, d, J=7.5 Hz) LRMS (ESI) m/z 543 [M+H]$^+$.

Example 40

(R)-6-((7-(4-Cyano-3-(trifluoromethyl)phenyl)-5,6,7,8-tetrahydropyrido[3,4-d]pyrimidin-4-yl)amino)-N-(1-(5-(trifluoromethyl)-1,3,4-oxadiazol-2-yl)ethyl)nicotinamide

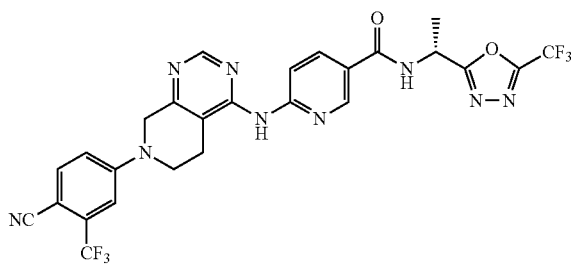 [SMILES: C[C@@H](NC(=O)c1ccc(Nc2ncnc3c2CCN(c2ccc(C#N)c(C(F)(F)F)c2)C3)nc1)c1nnc(C(F)(F)F)o1]

Step 1

Synthesis of (R)-tert-butyl (1-oxo-1-(2-(2,2,2-trifluoroacetyl)hydrazinyl)propan-2-yl)carbamate

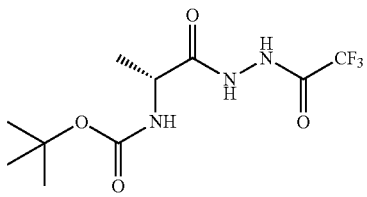 [SMILES: C[C@@H](NC(=O)OC(C)(C)C)C(=O)NNC(=O)C(F)(F)F]

The compound (400 mg) obtained from step 1 of Example 37 was dissolved in acetonitrile (10 mL) and then added with DIPEA (0.77 mL). Under nitrogen atmosphere, it was cooled to −45° C. and added with trifluoroacetic anhydride (0.56 mL). The temperature of the mixture solution was gradually increased and stirred for 30 minutes at room temperature. The solvent was removed by concentration under reduced pressure, and ethyl acetate and water were added for fractionation. The organic layer was washed with saturated brine, and dried over anhydrous sodium sulfate. The insoluble matters were separated by filtration, the filtrate was concentrated and dried, and the obtained residues were purified by silica gel column chromatography to obtain 236 mg of the target compound (yield 40%).

$^1$H-NMR (CDCl$_3$) δ4.90 (1H, m), 4.28 (1H, m), 1.46 (9H, s), 1.42 (3H, d, J=7.0 Hz); LRMS (ESI) m/z 243 [M-tert-butyl+H]$^+$.

Step 2

Synthesis of (R)-tert-butyl (1-(5-(trifluoromethyl)-1,3,4-oxadiazol-2-yl)ethyl)carbamate

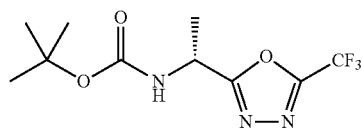 [SMILES: C[C@@H](NC(=O)OC(C)(C)C)c1nnc(C(F)(F)F)o1]

Acetonitrile suspension (7.7 mL) of the compound (230 mg) obtained from step 1 was added with DIPEA (780 μL) and triphenylphosphine (830 mg), followed by stirring for 5 minutes at room temperature. After being added with hexachloroethane (420 mg), it was stirred overnight at room temperature. The solvent was distilled off under reduced pressure and the residues were added with ethyl acetate and water for fractionation. After the extraction, it was washed with saturated brine, and dried over anhydrous sodium sulfate. The insoluble matters were separated by filtration, the filtrate was concentrated and dried, and the obtained residues were purified by silica gel column chromatography to obtain 142 mg of the target compound (yield 65%).

$^1$H-NMR (CDCl$_3$) δ5.18-5.11 (2H, m), 1.80-1.60 (3H, m), 1.45 (9H, s)

Step 3

Synthesis of (R)-1-(5-(trifluoromethyl)-1,3,4-oxadiazol-2-yl)ethanamine

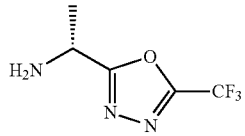

The compound (140 mg) obtained from step 2 was dissolved in 1,1,1,3,3,3-hexafluoro-2-propanol (2.5 mL) and stirred for 1 hour at 150° C. under irradiation of microwave. After cooling, concentration under reduced pressure was performed to obtain the target compound as an oily product (99 mg, yield 99%).

$^1$H-NMR (CDCl$_3$) δ4.47-4.36 (3H, m), 1.63 (3H, d, J=7.0 Hz)

Step 4

Synthesis of (R)-6-((7-(4-cyano-3-(trifluoromethyl) phenyl)-5,6,7,8-tetrahydropyrido[3,4-d]pyrimidin-4-yl)amino)-N-(1-(5-(trifluoromethyl)-1,3,4-oxadiazol-2-yl)ethyl)nicotinamide

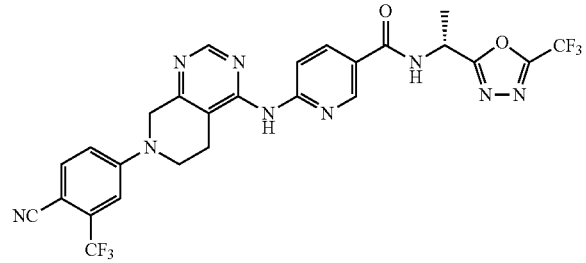 [SMILES: C[C@@H](NC(=O)c1ccc(Nc2ncnc3c2CCN(c2ccc(C#N)c(C(F)(F)F)c2)C3)nc1)c1nnc(C(F)(F)F)o1]

By performing the same operation as Example 11 and using the compound obtained from step 3 instead of 2,2,2-trifluoroethylamine, the target compound was obtained (41%).

$^1$H-NMR (DMSO-d$_6$) δ9.53 (1H, br-s), 9.22 (1H, d, J=7.3 Hz), 8.82 (1H, s), 8.64 (1H, s), 8.25-8.15 (2H, m), 7.86 (1H, d, J=9.0 Hz), 7.44 (1H, d, J=2.4 Hz), 7.36 (1H, dd, J=9.0 Hz, 2.4 Hz), 5.50 (1H, dq, J=7.3 Hz, 7.1 Hz), 4.58 (2H, s), 3.85 (2H, m), 2.92 (2H, m), 1.66 (3H, d, J=7.1 Hz), LRMS (ESI) m/z 604 [M+H]+

Example 41

4-(4-((4-(4-(2-Hydroxypropan-2-yl)piperidin-1-carbonyl)oxazol-2-yl)amino)-5,6-dihydropyrido[3,4-d]pyrimidin-7 (8H)-yl)-2-(trifluoromethyl)benzonitrile

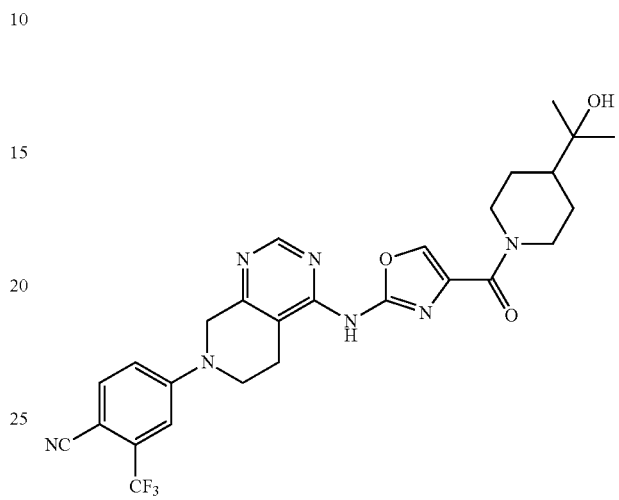

Step 1

Synthesis of ethyl 2-((7-(4-cyano-3-(trifluoromethyl)phenyl)-5,6,7,8-tetrahydropyrido[3,4-d]pyrimidin-4-yl)amino)oxazol-4-carboxylate

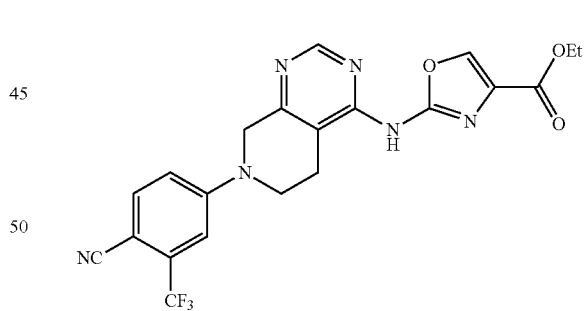

By performing the same operation as Reference Example 2-1 and using 2-aminooxazol-4-carboxylic acid ethyl ester (387 mg) instead of methyl 6-aminonicotinate, and having the reaction for 20 minutes at 160° C. under irradiation of microwave instead of overnight stirring at 80° C., the target compound was obtained (570 mg, 60%).

$^1$H-NMR (DMSO-d$_6$) δ8.30 (1H, s), 7.95 (1H, s), 7.69 (1H, d, 8.9 Hz), 7.23 (1H, d, J=2.4 Hz), 7.07 (1H, dd, J=2.4, 8.9 Hz), 4.47-4.34 (4H, m), 3.74 (2H, t, 5.5 Hz), 2.96 (2H, t, J=5.5 Hz), 1.39 (3H, t, J=7.2 Hz); LRMS (ESI) m/z 459 [M+H]$^+$.

Step 2

Synthesis of 2-((7-(4-cyano-3-(trifluoromethyl)phenyl)-5,6,7,8-tetrahydropyrido[3,4-d]pyrimidin-4-yl)amino)oxazol-4-carboxylic acid

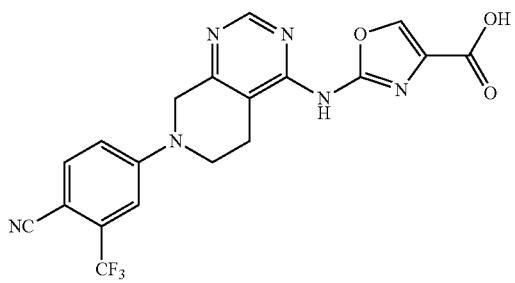 [SMILES: N#Cc1ccc(N2CCc3c(ncnc3Nc3nc(C(=O)O)co3)C2)cc1C(F)(F)F]

The compound (550 mg) obtained from step 1 was suspended in ethanol (10 mL), and added with 2.0 mol/L aqueous solution of sodium hydroxide (4.8 mL), followed by stirring for 6 hours at 60° C. The reaction solution was concentrated and diluted with distilled water. By using 2.0 mol/L hydrochloric acid, the pH was adjusted to about 5. The precipitated solid was collected by filtration to obtain the target compound (495 mg, 96%).

LRMS (ESI) m/z 431 [M+H]$^+$.

Step 3

Synthesis of 4-(4-((4-(4-(2-hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile

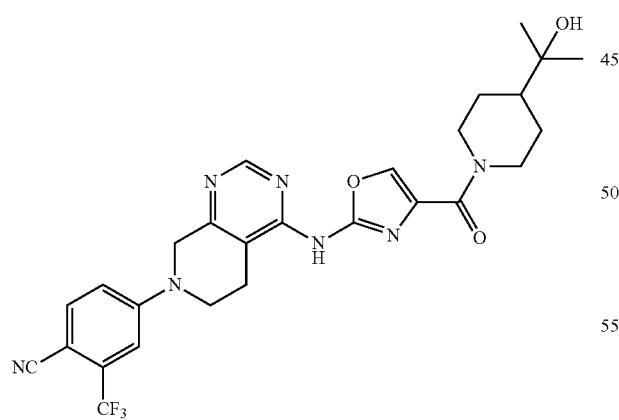

By performing the same operation as Example 11 and using the compound (15 mg) obtained from step 2 instead of the compound obtained from Reference Example 2-2, 2-(piperidin-4-yl)propan-2-ol (6 mg) instead of 2,2,2-trifluoroethylamine, and HATU (20 mg) and DIPEA (12 µL) instead of DMT-MM, the target compound was obtained (4.8 mg, 25%).

$^1$H-NMR (CD$_3$OD) δ8.40 (1H, s), 7.99 (1H, br-s), 7.95-7.85 (1H, m), 7.77 (1H, d, J=8.8 Hz), 7.38 (1H, d, J=2.3 Hz), 7.29 (1H, dd, J=2.3, 8.8 Hz), 4.75-4.60 (2H, m), 4.48 (2H, br-s), 3.84-3.80 (2H, m), 3.32-3.24 (2H, m), 2.90-2.65 (3H, m), 1.95-1.80 (2H, m), 1.66-1.58 (1H, m), 1.41-1.25 (2H, m), 1.17 (6H, s); LRMS (ESI) m/z 556 [M+H]$^+$.

Example 42

4-(4-((5-(4-(2-Hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile

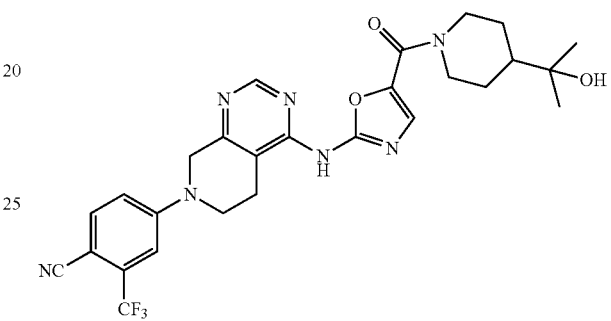

Step 1

Synthesis of ethyl 2-((7-(4-cyano-3-(trifluoromethyl)phenyl)-5,6,7,8-tetrahydropyrido[3,4-d]pyrimidin-4-yl)amino)oxazol-5-carboxylate

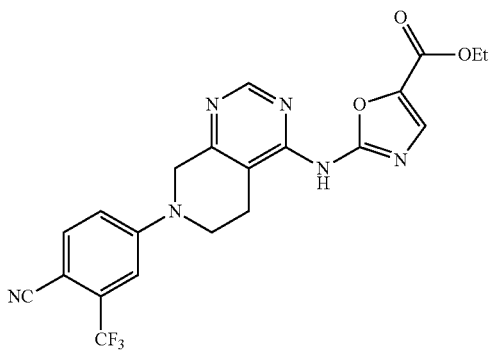 [SMILES: CCOC(=O)c1cnc(Nc2ncnc3c2CCN(c2ccc(C#N)c(C(F)(F)F)c2)C3)o1]

By performing the same operation as Reference Example 2-1 and using 2-aminooxazole-5-carboxylic acid ethyl ester (276 mg) instead of methyl 6-aminonicotinate, and having the reaction for 25 minutes at 160° C. under irradiation of microwave instead of overnight stirring at 80° C., the target compound was obtained (180 mg, 27%).

$^1$H-NMR (CDCl$_3$) δ8.28 (1H, s), 7.68-7.77 (3H, s), 7.23 (1H, d, 2.6 Hz), 7.08 (1H, dd, J=2.6, 8.8 Hz), 4.45-4.36 (4H, m), 3.75 (2H, t, 5.7 Hz), 2.98 (2H, t, J=5.7 Hz), 1.39 (3H, t, J=7.2 Hz); LRMS (ESI) m/z 459 [M+H]$^+$.

Step 2

Synthesis of 2-((7-(4-cyano-3-(trifluoromethyl)phenyl)-5,6,7,8-tetrahydropyrido[3,4-d]pyrimidin-4-yl)amino)oxazol-5-carboxylic acid

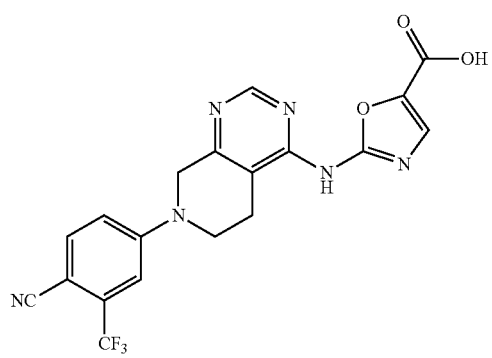 [SMILES: N#Cc1ccc(N2CCc3c(ncnc3Nc3ncc(C(=O)O)o3)C2)cc1C(F)(F)F]

By performing the same operation as step 2 of Example 41 and using the compound (180 mg) obtained from step 1 of this Example instead of the compound obtained from step 1 of Example 41, the target compound was obtained (137 mg, 81%).

LRMS (ESI) m/z 431 [M+H]$^+$.

Step 3

Synthesis of 4-(4-((5-(4-(2-hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile

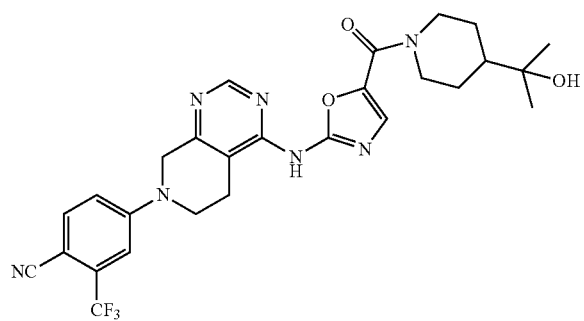 [SMILES: CC(C)(O)C1CCN(C(=O)c2cnc(Nc3ncnc4c3CCN(c3ccc(C#N)c(C(F)(F)F)c3)C4)o2)CC1]

By performing the same operation as Example 11 and using the compound (25 mg) obtained from step 2 instead of the compound obtained from Reference Example 2-2, 2-(piperidin-4-yl)propan-2-ol (10 mg) instead of 2,2,2-trifluoroethylamine, and HOBt (10 mg) and WSC (13 mg) instead of DMT-MM, the target compound was obtained (8.6 mg, 27%).

$^1$H-NMR (CDCl$_3$) δ8.26 (1H, s), 7.69 (1H, d, J=8.8 Hz), 7.60 (1H, s), 7.29-7.21 (1H, m), 7.07 (1H, dd, J=2.2, 8.8 Hz), 4.75-4.60 (2H, m), 4.42 (2H, s), 3.75 (2H, t, J=5.7 Hz), 3.06-2.92 (2H, m), 1.94-1.86 (2H, m), 1.61 (2H, dt, J=2.9, 12.1 Hz), 1.39-1.16 (9H, m); LRMS (ESI) m/z 556 [M+H]$^+$.

Example 43

4-(4-((5-(4-(2-Hydroxypropan-2-yl)piperidin-1-carbonyl)-1,3,4-oxadiazol-2-yl)amino)-5,6-dihydropyrido[3,4-d]pyrimidin-7 (8H)-yl)-2-(trifluoromethyl)benzonitrile

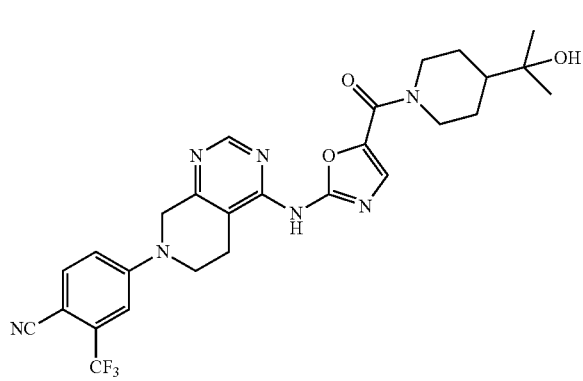 [SMILES: CC(C)(O)C1CCN(C(=O)c2cnc(Nc3ncnc4c3CCN(c3ccc(C#N)c(C(F)(F)F)c3)C4)o2)CC1]

Step 1

Synthesis of ethyl 5-((7-(4-cyano-3-(trifluoromethyl)phenyl)-5,6,7,8-tetrahydropyrido[3,4-d]pyrimidin-4-yl)amino)-1,3,4-oxadiazol-2-carboxylate

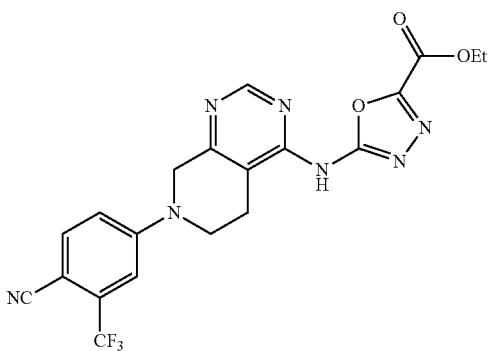 [SMILES: CCOC(=O)c1nnc(Nc2ncnc3c2CCN(c2ccc(C#N)c(C(F)(F)F)c2)C3)o1]

By performing the same operation as Reference Example 2-1 and using 5-amino-1,3,4-oxadiazol-2-carboxylic acid ethyl ester (418 mg) instead of methyl 6-aminonicotinate, and having the reaction for 30 minutes at 150° C. under irradiation of microwave instead of overnight stirring at 80° C., the target compound was obtained (120 mg, 15%).

$^1$H-NMR (DMSO-d$_6$) δ8.59 (1H, s), 7.88 (1H, d, 8.8 Hz), 7.46 (1H, d, 2.6 Hz), 7.38 (1H, dd, J=2.6, 8.8 Hz), 4.55 (2H, s), 4.40 (2H, q, 7.0 Hz), 3.83 (2H, t, J=5.9 Hz), 2.80 (2H, t, J=5.9 Hz), 1.34 (3H, t, J=7.0 Hz); LRMS (ESI) m/z 460 [M+H]$^+$.

Step 2

Synthesis of 4-(4-((5-(4-(2-hydroxypropan-2-yl)piperidin-1-carbonyl)-1,3,4-oxadiazol-2-yl)amino)-5,6-dihydropyrido[3,4-d]pyrimidin-7(8H)-yl)-2-(trifluoromethyl)benzonitrile

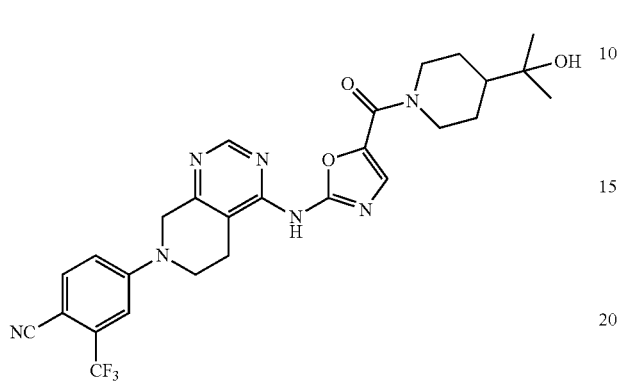

The compound (30 mg) obtained from step 1 was dissolved in ethanol (2 mL) and THF (2 mL), and added with 1.0 mol/L aqueous solution of sodium hydroxide (130 μL), followed by stirring for 5 minutes at room temperature. The reaction solution was ice-cooled and adjusted to have a pH of about 5 by using 1.0 mol/L hydrochloric acid, followed by concentration and drying. The obtained solid was dissolved in methanol (1 mL) and DMF (1 mL), and added with 2-(piperidin-4-yl)propan-2-ol (11 mg) and DMT-MM (21 mg), followed by stirring overnight at room temperature. The reaction solution was added with 2-(piperidin-4-yl)propan-2-ol (10 mg) and DMT-MM (88 mg) and further stirred at room temperature for 6 hours. The reaction solution was added with water, and the precipitates were collected by filtration. The obtained solid was purified by silica gel column chromatography to obtain the target compound (5.0 mg, 14%).

$^1$H-NMR (DMSO-$d_6$) δ8.56 (1H, br-s), 7.87 (1H, d, J=8.8 Hz), 7.46 (1H, d, J=2.2 Hz), 7.38 (1H, dd, J=2.2, 8.8 Hz), 4.69-4.43 (4H, m), 4.20 (1H, s), 3.81 (2H, t, J=5.7 Hz) 3.17-3.04 (1H, m), 2.85-2.61 (3H, m), 1.80 (2H, t, J=12.8 Hz), 1.57-1.45 (1H, m), 1.31-1.12 (2H, m), 1.03 (6H, s); LRMS (ESI) m/z 557 [M+H]$^+$.

Example 44

2-Bromo-4-(4-((5-(2-hydroxypropan-2-yl)pyridin-2-yl)amino)-5,6-dihydropyrido[3,4-d]pyrimidin-7(8H)-yl)benzonitrile

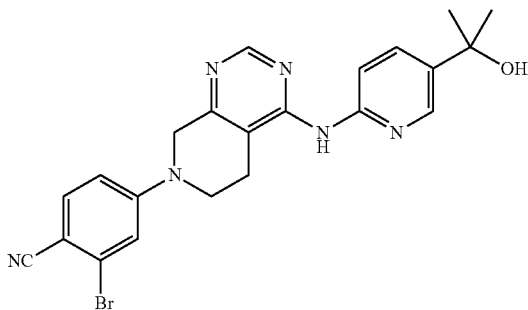

Step 1

Synthesis of methyl 6-((7-benzyl-5,6,7,8-tetrahydropyrodopyrido[3,4-d]pyrimidin-4-yl)amino)nicotinate

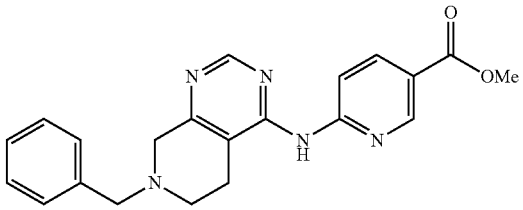 [SMILES: COC(=O)c1ccc(Nc2ncnc3c2CCN(Cc2ccccc2)C3)nc1]

According to Reference Example 2-1, commercially available 7-benzyl-4-chloro-5,6,7,8-tetrahydropyrido[3,4-d]pyrimidine (5.37 g), methyl 6-aminonicotinate (3.45 g), Pd(dba)$_2$ (1.19 g), dppf (1.15 g), and potassium carbonate (5.70 g) were suspended in 1,2-dimethoxyethane (100 mL) and stirred for 1 hour at 83° C. under nitrogen atmosphere. After the reaction solution was cooled to room temperature, it was added with water (400 mL). The resulting solid was collected by filtration and suspended and washed with methanol/water (3/1, 60 mL), followed by suspending and washing with toluene (60 mL). After drying by heating, the target compound was obtained (5.18 g, yield 67%).

$^1$H-NMR (DMSO-$d_6$) δ9.39 (1H, s), 8.84 (1H, s), 8.57 (1H, s), 8.32 (1H, d, J=8.0 Hz), 8.26 (1H, dd, J=8.0, 4.0 Hz), 7.40-7.20 (5H, m), 3.86 (3H, s), 3.69 (2H, s), 3.48 (2H, s), 2.80-2.70 (4H, m); LRMS (ESI) m/z 376 [M+H]$^+$.

Step 2

Synthesis of 2-(6-((7-benzyl-5,6,7,8-tetrahydropyridopyrodo[3,4-d]pyrimidin-4-yl)amino)pyridin-3-yl)propan-2-ol

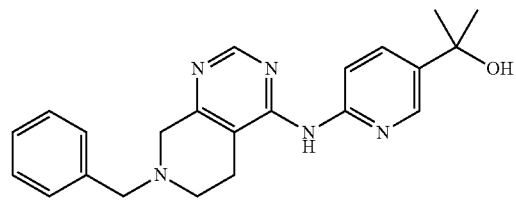 [SMILES: CC(C)(O)c1ccc(Nc2ncnc3c2CCN(Cc2ccccc2)C3)nc1]

Under nitrogen atmosphere, the compound (5.0 g) obtained from step 1 was suspended in THF (16 mL), and under ice cooling, a THF solution (47 mL) of 1 mol/L methyl magnesium bromide was added dropwise thereto over 5 minutes. After the dropwise addition was completed, the temperature was raised to room temperature and the reaction solution was stirred at the same temperature for 3.5 hours. The reaction solution was again cooled under ice cooling, and added with 2 mol/L hydrochloric acid (24 mL) at a temperature of 20° C. or less. The insoluble matters were removed by Celite, and the oil layer obtained by layer fractionation was dried over magnesium sulfate and the solvent was distilled off under reduced pressure. The obtained oily product was added with m-xylene (25 mL) and stirred under ice cooling to precipitate the solid. The precipitated product was collected by filtration, followed by drying by heating to obtain the target compound (2.44 g, yield 49%).

$^1$H-NMR (DMSO-$d_6$) δ8.78 (1H, s), 8.44 (1H, s), 8.40 (1H, d, J=4.0 Hz), 8.07 (1H, d, J=8.0 Hz), 7.82 (1H, dd, J=8.0, 4.0 Hz), 7.40-7.25 (5H, m), 5.14 (1H, s), 3.68 (2H, s), 3.43 (2H, s), 2.80-2.65 (4H, m), 1.45 (6H, s); LRMS (ESI) m/z 376 [M+H]+

Step 3

Synthesis of 2-(6-((5,6,7,8-tetrahydropyridopyrodo[3,4-d]pyrimidin-4-yl)amino)pyridin-3-yl)propan-2-ol

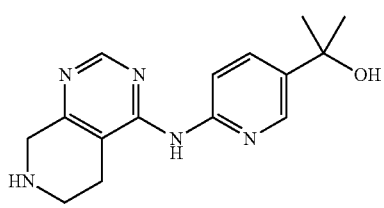 [SMILES: CC(C)(O)c1ccc(Nc2ncnc3c2CCNC3)nc1]

The compound (1.0 g) obtained from step 2 was dissolved in ethanol (10 mL), and added with 10% palladium/carbon (50% wet product, 600 mg), followed by stirring at 60° C. for 7 hours under hydrogen atmosphere. The insoluble matters were removed by Celite, and the filtrate was concentrated. The obtained oily product was added with methyl isobutyl ketone (12 mL) and the precipitates were obtained by cooling. The solid was collected by filtration, and dried and heated under reduced pressure to obtain the precipitates, which were collected by filtration to obtain the target compound (576 mg, yield 76%).

Step 4

Synthesis of 2-bromo-4-(4-((5-(2-hydroxypropan-2-yl)pyridin-2-yl)amino)-5,6-dihydropyrido[3,4-d]pyrimidin-7(8H)-yl)benzonitrile

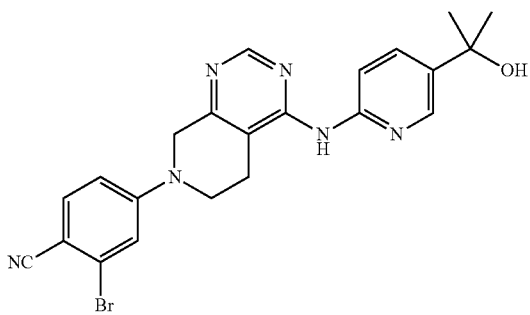 [SMILES: CC(C)(O)c1ccc(Nc2ncnc3c2CCN(c2ccc(C#N)c(Br)c2)C3)nc1]

The compound (20 mg) obtained from step 3, 2-bromo-4-fluorobenzonitrile (21 mg), and potassium carbonate (15 mg) were dissolved in DMSO (0.2 mL), and stirred at 125° C. for 25 minutes under microwave irradiation. The reaction mixture was purified by reverse phase preparative HPLC column chromatography, and the obtained fraction was concentrated under reduced pressure to obtain the target compound as a white amorphous product (15 mg, 46%).

$^1$H-NMR (CDCl$_3$) δ8.67 (1H, s), 8.47 (1H, d, J=8.8 Hz), 8.42 (1H, d, J=2.6 Hz), 7.87 (1H, dd, J=8.8, 2.6 Hz), 7.51 (1H, d, J=8.8 Hz), 7.36 (1H, br-s), 7.17 (1H, d, J=2.6 Hz), 6.89 (1H, dd, J=8.8, 2.6 Hz), 4.45 (2H, s), 3.81 (2H, t, J=5.9 Hz), 2.83 (2H, t, J=5.7 Hz), 1.62 (6H, s); LRMS (ESI) m/z 465 [M+H]$^+$.

Example 45

2-Chloro-4-(4-((4-fluoro-5-(2-hydroxypropan-2-yl)pyridin-2-yl)amino)-5,6-dihydropyrido[3,4-d]pyrimidin-7(8H)-yl)benzonitrile

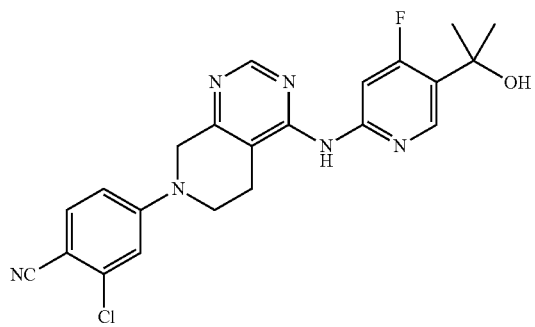 [SMILES: CC(C)(O)c1cnc(Nc2ncnc3c2CCN(c2ccc(C#N)c(Cl)c2)C3)cc1F]

Step 1

Synthesis of 4-fluoro-5-iodopyridin-2-amine

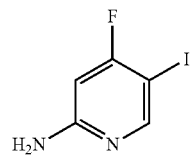

4-Fluoropyridin-2-amine (1.20 g) was dissolved in acetonitrile (24 mL), and added with N-iodosuccinimide (2.41 g) under ice cooling and light blocking conditions, followed by stirring overnight at room temperature. The obtained reaction solution was concentrated and purified by silica gel column chromatography to obtain 132 mg (5%) of the target compound as a pale yellow solid.

Step 2

Synthesis of ethyl 6-amino-4-fluoropyridin-3-carboxylate

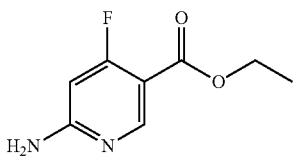

The compound (132 mg) obtained from step 1, palladium acetate (II) (31 mg), dppf (77 mg), and triethylamine (0.23 mL) were suspended in ethanol (26 mL), and stirred at 60° C. for two days and nights under carbon monoxide atmosphere (0.5 MPa). The reaction solution was concentrated under reduced pressure, and added with ethyl acetate (20 mL) and distilled water (20 mL), followed by filtration through Celite. The organic layer was washed with distilled water and saturated brine, and dried over anhydrous sodium sulfate. The insoluble matters were separated by filtration, and the filtrate was concentrated and dried. The obtained solid was purified by silica gel column chromatography to obtain 67 mg (66%) of the target compound as a grayish white solid.

Step 3

Synthesis of ethyl 6-((7-(3-chloro-4-cyanophenyl)-5,6,7,8-tetrahydropyridopyrodo[3,4-d]pyrimidin-4-yl)amino)-4-fluoronicotinate

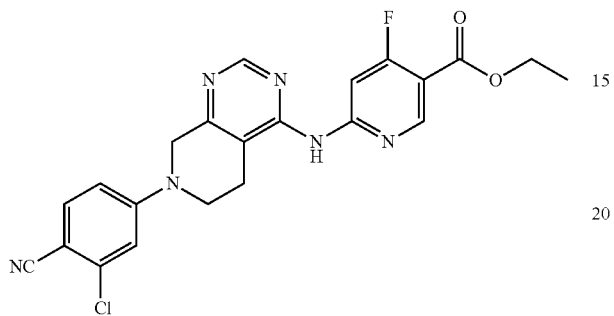

The compound (139 mg) obtained from Reference Example 1-3, the compound (60 mg) obtained from step 2, Pd$_2$(dba)$_3$ (30 mg), XantPhos (38 mg), and cesium carbonate (318 mg) were suspended in dioxane (1.2 mL), and stirred for 4 hours at 80° C. under nitrogen atmosphere. The reaction solution was cooled to room temperature and filtered through Celite. The filtrate was concentrated and the obtained solid was purified by silica gel column chromatography to obtain 14 mg (9%) of the target compound as a pale yellow solid.

Step 4

Synthesis of 2-chloro-4-(4-((4-fluoro-5-(2-hydroxypropan-2-yl)pyridin-2-yl)amino)-5,6-dihydropyrido[3,4-d]pyrimidin-7 (8H)-yl)benzonitrile

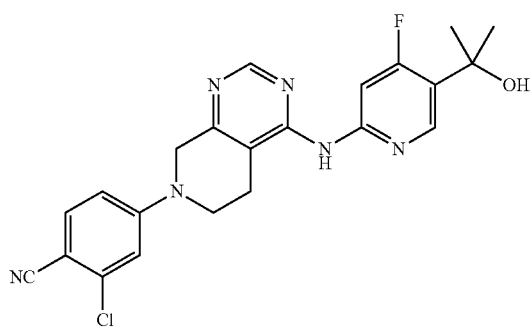 [SMILES: CC(C)(O)c1cnc(Nc2ncnc3c2CCN(c2ccc(C#N)c(Cl)c2)C3)cc1F]

The compound (14 mg) obtained from step 3 was dissolved in THF (1.4 mL), and added with methyl magnesium bromide (3 mol/L diethyl ether solution, 0.11 mL) in an ice bath, followed by stirring at room temperature for 1 hour. The reaction solution was added with a saturated aqueous solution of ammonium chloride (3 mL), followed by extracting three times with chloroform. The organic layer was combined, dried over magnesium sulfate, the insoluble matters were separated by filtration, and the filtrate was concentrated under reduced pressure. The obtained residues were purified by reverse phase preparative HPLC column chromatography to obtain 2.1 mg (16%) of the target compound as a yellow solid.

$^1$H-NMR (CDCl$_3$) δ8.70 (1H, s), 8.47 (1H, d, J=11.0 Hz), 8.37 (1H, d, J=14.3 Hz), 7.53 (1H, d, J=8.8 Hz), 7.45 (1H, br-s), 6.99 (1H, d, J=2.6 Hz), 6.85 (1H, dd, J=8.8, 2.6 Hz), 4.47 (2H, s), 3.81 (2H, t, J=5.9 Hz), 2.83 (2H, t, J=5.7 Hz), 1.67 (6H, s); LRMS (ESI) m/z 439 [M+H]$^+$.

Example 46

2-Chloro-4-(4-((6-fluoro-5-(2-hydroxypropan-2-yl)pyridin-2-yl)amino)-5,6-dihydropyrido[3,4-d]pyrimidin-7(8H)-yl)benzonitrile

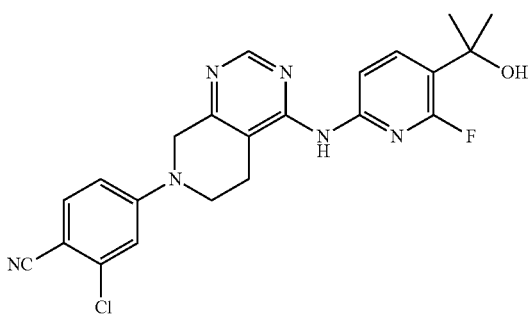 [SMILES: CC(C)(O)c1ccc(Nc2ncnc3c2CCN(c2ccc(C#N)c(Cl)c2)C3)nc1F]

Step 1

Synthesis of ethyl 6-amino-2-fluoronicotinate

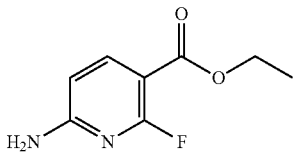

By performing the same operation as step 2 of Example 5 and using ethanol instead of methanol, the target compound was obtained.

Step 2

Ethyl 6-((7-(3-chloro-4-cyanophenyl)-5,6,7,8-tetrahydropyrido[3,4-d]pyrimidin-4-yl)amino)-2-fluoronicotinate

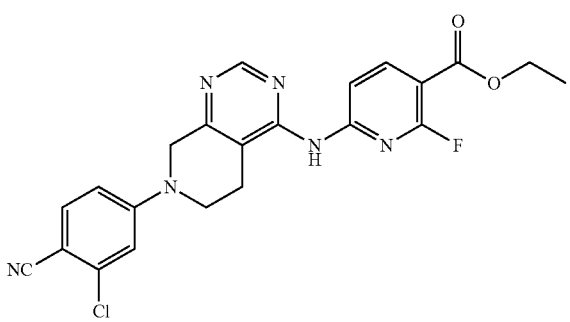 [SMILES: CCOC(=O)c1ccc(Nc2ncnc3c2CCN(c2ccc(C#N)c(Cl)c2)C3)nc1F]

By performing the same operation as Reference Example 2-1 and using the compound obtained from Reference Example 1-2 and the compound obtained from step 1, the target compound was obtained.

Step 3

2-Chloro-4-(4-((6-fluoro-5-(2-hydroxypropan-2-yl)pyridin-2-yl)amino)-5,6-dihydropyrido[3,4-d]pyrimidin-7(8H)-yl)benzonitrile

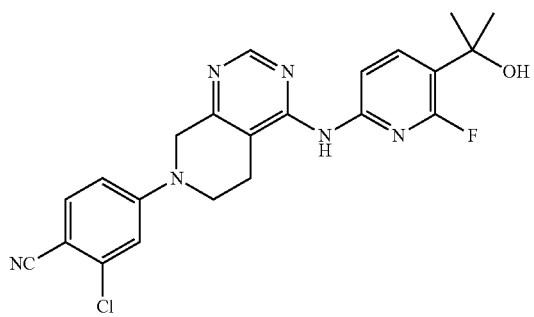 [SMILES: CC(C)(O)c1ccc(Nc2ncnc3c2CCN(c2ccc(C#N)c(Cl)c2)C3)nc1F]

By performing the same operation as step 4 of Example 45 and using the compound (30 mg) obtained from step 3, the target compound was obtained as a white solid (4.2 mg, 14%).

$^1$H-NMR (CDCl$_3$) δ8.70 (1H, s), 8.39 (1H, dd, J=8.4, 1.8 Hz), 8.06 (1H, dd, J=10.6, 8.4 Hz), 7.53 (1H, d, J=8.8 Hz), 7.00 (1H, d, J=2.6 Hz), 6.85 (1H, dd, J=8.8, 2.6 Hz), 4.47 (2H, s), 3.81 (2H, t, J=5.7 Hz), 2.80 (2H, t, J=5.7 Hz), 1.65 (6H, s); LRMS (ESI) m/z 439 [M+H]V.

Example 47

4-(4-((4-Fluoro-5-(2-hydroxypropan-2-yl)pyridin-2-yl)amino)-5,6-dihydropyrido[3,4-d]pyrimidin-7(8H)-yl)-2-(trifluoromethyl)benzonitrile

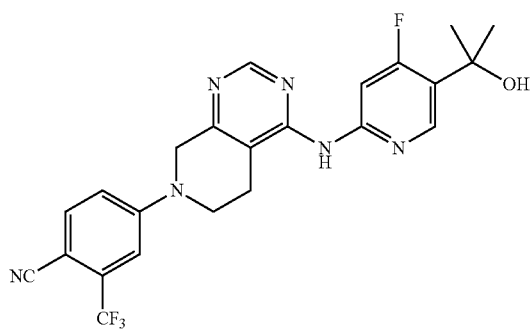 [SMILES: CC(C)(O)c1cnc(Nc2ncnc3c2CCN(c2ccc(C#N)c(C(F)(F)F)c2)C3)cc1F]

By performing the same operation as Example 46 and using ethyl 6-amino-4-fluoronicotinate, which had been synthesized according to step 2 of Example 5 by using 4-fluoropyridin-2-amine instead of 6-fluoropyridin-2-amine, and using the compound obtained from Reference Example 1-2 instead of the compound obtained from Reference Example 1-3, the target compound was obtained as a white solid (21.3 mg, 20%).

$^1$H-NMR (CDCl$_3$) δ8.70 (1H, s), 8.47 (1H, d, J=11.0 Hz), 8.37 (1H, d, J=14.3 Hz), 7.70 (1H, d, J=8.4 Hz), 7.45 (1H, br-s), 7.25 (1H, d, J=2.6 Hz), 7.08 (1H, dd, J=8.6, 2.6 Hz), 4.47 (2H, s), 3.80 (2H, t, J=6.0 Hz), 2.83 (2H, t, J=5.8 Hz), 1.67 (6H, s); LRMS (ESI) m/z 473 [M+H]$^+$.

Example 48

5-((7-(4-Cyano-3-(trifluoromethyl)phenyl)-5,6,7,8-tetrahydropyrido[3,4-d]pyrimidin-4-yl)amino)-N-(2,2-difluoroethyl)picolinamide

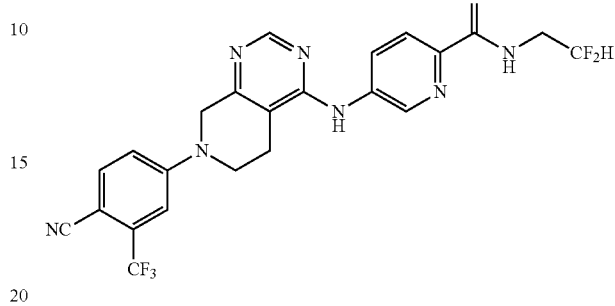

Step 1

Synthesis of 5-((7-(4-cyano-3-(trifluoromethyl)phenyl)-5,6,7,8-tetrahydropyrido[3,4-d]pyrimidin-4-yl)amino)pyridin-3-yl)picolinic acid

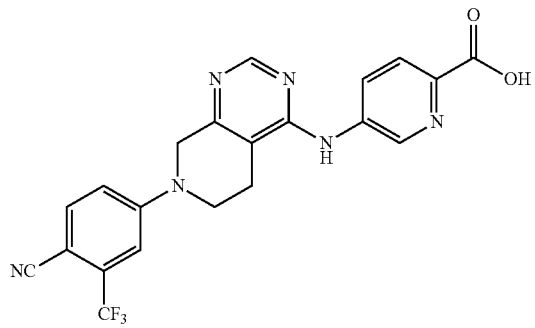 [SMILES: N#Cc1ccc(N2CCc3c(ncnc3Nc3ccc(C(=O)O)nc3)C2)cc1C(F)(F)F]

By performing the same operation as Reference Examples 2-1 and 2-2 and using methyl 5-aminopicolinate (540 mg) instead of methyl 6-aminonicotinate, the target compound was obtained (496 mg, two step yield 38%).

Step 2

Synthesis of 5-((7-(4-cyano-3-(trifluoromethyl)phenyl)-5,6,7,8-tetrahydropyrido[3,4-d]pyrimidin-4-yl)amino)-N-(2,2-difluoroethyl)pyridin-3-yl)picolinamide

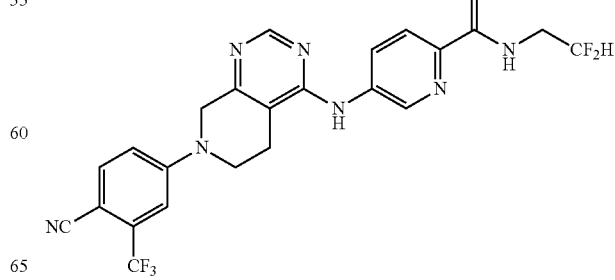

By performing the same operation as Example 11 and using the compound (40 mg) obtained from step 1 instead of the compound obtained from Reference Example 2-2, HATU (69 mg) and DIPEA (63 uL) instead of DMT-MM, and 2,2-difluoroethylamine instead of 2,2,2-trifluoroethylamine, the target compound was obtained (24 mg) (yield 52%).

¹H-NMR (DMSO-d₆) δ9.13 (br-s, 1H), 8.97 (d, J=2.2 Hz, 1H), 8.94 (t, J=6.2 Hz, 1H), 8.55 (s, 1H), 8.41 (dd, J=8.6, 2.4 Hz, 1H), 8.02 (d, J=8.6 Hz, 1H), 7.88 (d, J=9.1 Hz, 1H), 7.45 (brd, J=2.2 Hz, 1H), 7.39 (dd, J=9.1, 2.2 Hz, 1H), 5.94-6.33 (m, 1H), 4.57 (s, 2H), 3.90 (brt, J=5.5 Hz, 2H), 3.63-3.74 (m, 2H), 3.25 (br-s, 1H), 2.87 (t, J=5.5 Hz, 2H); LRMS (ESI) m/z 504 [M+H]⁺.

Example 49

6-((7-(3-Chloro-4-cyanophenyl)-5,6,7,8-tetrahydropyrido[3,4-d]pyrimidin-4-yl)amino)-N-(2,2,2-trifluoroethyl)pyridazine-3-carboxamide

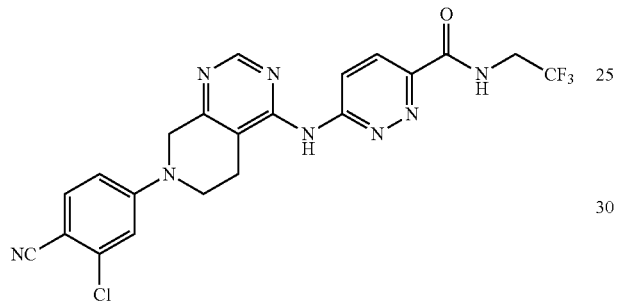

By reacting the compound (9.0 mg) obtained from step 3 of Example 29 with 2,2,2-trifluoroethylamine (4.4 mg) according to Example 29, the target compound was obtained (7.0 mg, 65%).

¹H-NMR (DMSO-d₆) δ10.27 (br-s, 1H), 9.58 (t, J=6.6 Hz, 1H), 8.65 (s, 1H), 8.47 (d, J=9.5 Hz, 1H), 8.18 (d, J=9.5 Hz, 1H), 7.70 (d, J=9.0 Hz, 1H), 7.33 (d, J=2.4 Hz, 1H), 7.13 (dd, J=9.0, 2.4 Hz, 1H), 4.56 (s, 2H), 4.06-4.17 (m, 2H), 3.82 (t, J=5.6 Hz, 2H), 2.97 (brt, J=5.6 Hz, 2H); LRMS (ESI) m/z 489 [M+H]⁺.

Example 50

4-(4-((5-Fluoro-6-(2-methyl-2-(1H-tetrazol-1-yl)propoxy)pyridin-3-yl)amino)-5,6-dihydropyrido[3,4-d]pyrimidin-7(8H)-yl)-2-(trifluoromethyl)benzonitrile

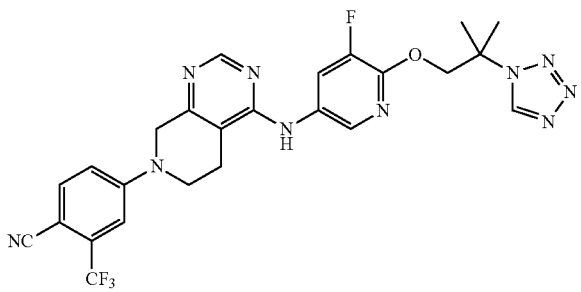

By performing the same operation as Example 15 and using 2-chloro-3-fluoro-5-nitropyridine (100 mg) instead of 2-chloro-5-nitropyridine and 2-methyl-2-(1H-tetrazol-1-yl)propan-1-ol (97 mg) obtained from step 1 of Example 16 instead of 2-(1H-1,2,3-triazol-1-yl)ethanol, the target compound was obtained (40 mg, 49%).

¹H-NMR (DMSO-d₆) δ9.59 (s, 1H), 8.82 (br-s, 1H), 8.43 (s, 1H), 8.14 (d, J=2.2 Hz, 1H), 8.05 (dd, J=12.1, 2.2 Hz, 1H), 7.87 (d, J=8.8 Hz, 1H), 7.44 (d, J=2.6 Hz, 1H), 7.38 (dd, J=8.8, 2.6 Hz, 1H), 4.67 (s, 2H), 4.52 (s, 2H), 3.88 (t, J=5.7 Hz, 2H), 2.78 (brt, J=5.5 Hz, 2H), 1.77 (s, 6H); LRMS (ESI) m/z 555 [M+H]⁺.

Example 51

4-(4-((5-Fluoro-6-(2-methyl-2-(1H-1,2,3-triazol-1-yl)propoxy)pyridin-3-yl)amino)-5,6-dihydropyrido[3,4-d]pyrimidin-7(8H)-yl)-2-(trifluoromethyl)benzonitrile

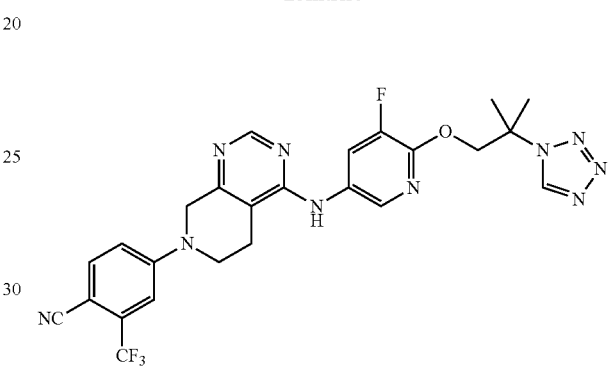

Step 1

Synthesis of ethyl 2-methyl-2-(1H-1,2,3-triazol-1-yl)propanoate

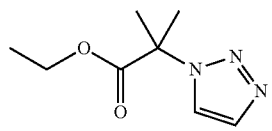

Ethyl 2-azide-2-methylpropanoate (3.1 g) was dissolved in toluene (190 mL), and added with ethynyltrimethylsilane (13 mL), followed by stirring at 130° C. for 36 hours. The reaction solution was concentrated and dried, and the obtained residues were purified by silica gel column chromatography to obtain a crude oily product (2.16 g). The obtained oily product was dissolved in THF (20 mL), and added with a THF solution (9.8 mL) of 1.0 mol/L tetrabutylammomnium fluoride, followed by stirring for 15 hours at room temperature. The reaction solution was added with a THF solution (3.0 mL) of 1.0 mol/L tetrabutylammomnium fluoride, followed by stirring for 7 hours at room temperature. The reaction mixture was added with a saturated aqueous solution of ammonium chloride, extracted with ethyl acetate, and dried over anhydrous sodium sulfate. The insoluble matters were separated by filtration, and the filtrate was concentrated and dried. The obtained residues were purified by silica gel column chromatography to obtain the target product (500 mg, 42%).

Step 2

Synthesis of 2-methyl-2-(1H-1,2,3-triazol-1-yl)propan-1-ol

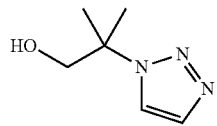

The compound (420 mg) obtained from step 1 was dissolved in THF (10 mL), and then added with a THF solution (10 mL) of lithium aluminum hydroxide (130 mg) under ice cooling. After stirring for 2 hours under ice cooling, water (132 μL), 1.0 mol/L aqueous solution of sodium hydroxide (132 μL), and water (400 μL) were added dropwise thereto. The reaction solution was filtered through Celite and washed with ethyl acetate. The filtrate was concentrated and dried, and the obtained residues were purified by silica gel column chromatography to obtain the target product (240 mg, 74%).

Step 3

Synthesis of 4-(4-((5-fluoro-6-(2-methyl-2-(1H-1,2,3-triazol-1-yl)propoxy)pyridin-3-yl)amino)-5,6-dihydropyrido[3,4-d]pyrimidin-7(8H)-yl)-2-(trifluoromethyl)benzonitrile

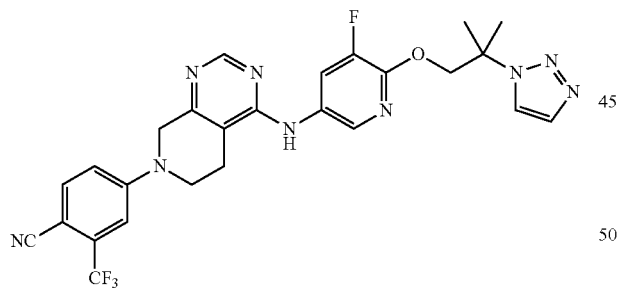

By performing the same operation as Example 15 and using 2-chloro-3-fluoro-5-nitropyridine (100 mg) instead of 2-chloro-5-nitropyridine and 2-methyl-2-(1H-1,2,3-triazol-1-yl)propan-1-ol (80 mg) obtained from step 2 instead of 2-(1H-1,2,3-triazol-1-yl)ethanol, the target compound was obtained (54 mg, 66%).

$^1$H-NMR (DMSO-d$_6$) δ8.82 (br-s, 1H), 8.43 (s, 1H), 8.26 (s, 1H), 8.17 (d, J=2.1 Hz, 1H), 8.05 (dd, J=12.3, 2.1 Hz, 1H), 7.87 (d, J=8.8 Hz, 1H), 7.71 (s, 1H), 7.44 (d, J=2.1 Hz, 1H), 7.38 (dd, J=8.8, 2.4 Hz, 1H), 4.66 (s, 2H), 4.52 (br-s, 2H), 3.89 (t, J=5.6 Hz, 2H), 2.78 (brt, J=5.6 Hz, 2H), 1.73 (s, 6H); LRMS (ESI) m/z 554 [M+H]$^+$.

Example 52

4-(4-((5-Chloro-6-(2-methyl-2-(1H-tetrazol-1-yl)propoxy)pyridin-3-yl)amino)-5,6-dihydropyrido[3,4-d]pyrimidin-7(8H)-yl)-2-(trifluoromethyl)benzonitrile

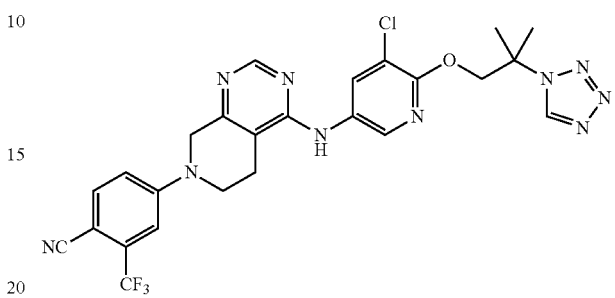

By performing the same operation as Example 15 and using 2,3-dichloro-5-nitropyridine (100 mg) instead of 2-chloro-5-nitropyridine and 2-methyl-2-(1H-tetrazol-1-yl)propan-1-ol (88 mg) obtained from step 1 of Example 16 instead of 2-(1H-1,2,3-triazol-1-yl)ethanol, the target compound was obtained (33 mg, 39%).

$^1$H-NMR (DMSO-d$_6$) δ9.58 (s, 1H), 8.79 (s, 1H), 8.44 (s, 1H), 8.30 (d, J=2.5 Hz, 1H), 8.22 (d, J=2.2 Hz, 1H), 7.87 (d, J=8.8 Hz, 1H), 7.44 (d, J=2.2 Hz, 1H), 7.39 (dd, J=8.8, 2.5 Hz, 1H), 4.64 (s, 2H), 4.52 (br-s, 2H), 3.89 (t, J=5.6 Hz, 2H), 2.78 (brt, J=5.6 Hz, 2H), 1.79 (s, 6H); LRMS (ESI) m/z 571 [M+H]$^+$.

Example 53

2-Chloro-4-(4-((5-(2-methyl-2-(1H-tetrazol-1-yl)propoxy)pyridin-2-yl)amino)-5,6-dihydropyrido[3,4-d]pyrimidin-7(8H)-yl)benzonitrile

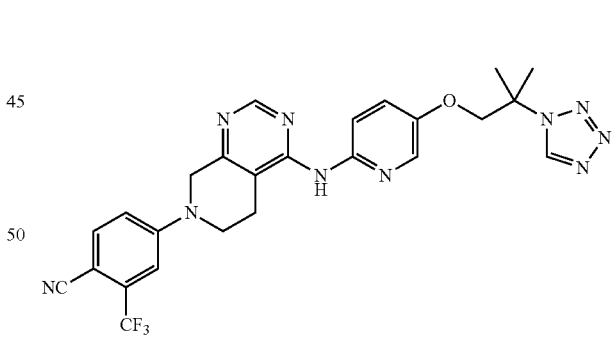

By performing the same operation as step 4 of Example 17 and using the compound (42 mg) obtained from step 3 of Example 17 and the compound (50 mg) obtained from Reference Example 1-3 instead of the compound obtained from Reference Example 1-2, the target compound was obtained (27 mg, 33%).

$^1$H-NMR (DMSO-d$_6$) δ9.61 (s, 1H), 8.97 (br-s, 1H), 8.47 (s, 1H), 7.97-8.02 (m, 2H), 7.67 (d, J=9.2 Hz, 1H), 7.40 (dd, J=9.0, 3.1 Hz, 1H), 7.29 (d, J=2.2 Hz, 1H), 7.09 (dd, J=9.2, 2.2 Hz, 1H), 4.45 (br-s, 2H), 4.36 (s, 2H), 3.78 (t, J=5.6 Hz, 2H), 2.80 (brt, J=5.6 Hz, 2H), 1.77 (s, 6H); LRMS (ESI) m/z 503 [M+H]$^+$.

Example 54

2-Chloro-4-(4-((4-methoxyphenyl)amino)-5,6-dihydropyrido[3,4-d]pyrimidin-7(8H)-yl)benzonitrile

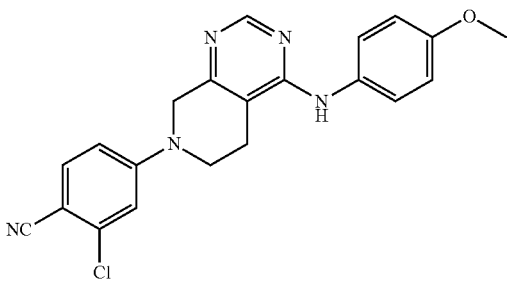 [SMILES: COc1ccc(Nc2ncnc3c2CCN(c2ccc(C#N)c(Cl)c2)C3)cc1]

The solid (5.0 mg) obtained from Reference Example 1-3, 4-methoxyaniline (11 g), and (+)-10-camphorsulfonic acid (3.8 mg) were suspended in 2-propanol (1 mL), and under microwave irradiation, stirred for 1 hour at 120° C. The reaction solution was concentrated and dried under nitrogen stream, and the residues were purified by reverse phase preparative HPLC column chromatography, and the obtained fraction was concentrated under reduced pressure to obtain the target compound (1.7 mg, 26%).

$^1$H-NMR (400 MHz, CDCl$_3$) δ: 8.54 (1H, s), 7.52 (1H, d, J=9.2 Hz), 7.41 (2H, brd, J=8.8 Hz), 6.99 (1H, s), 6.93 (2H, d, J=8.8 Hz), 6.84 (1H, brd, J=9.2 Hz), 6.34 (1H, br-s), 4.45 (2H, s), 3.82 (3H, s), 3.78-3.84 (2H, m), 2.73 (2H, br-s); LRMS (ESI) m/z 392 [M+H]$^+$.

Example 55

2-Chloro-4-(4-((3-methoxyphenyl)amino)-5,6-dihydropyrido[3,4-d]pyrimidin-7(8H)-yl)benzonitrile

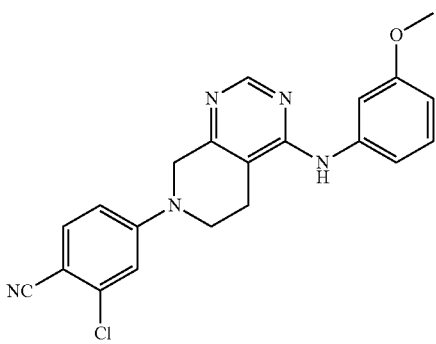 [SMILES: COc1cccc(Nc2ncnc3c2CCN(c2ccc(C#N)c(Cl)c2)C3)c1]

The solid (12 mg) obtained from Reference Example 1-3, 3-methoxyaniline (15 mg), and (+)-10-camphorsulfonic acid (5.3 mg) were suspended in tert-butanol (1 mL), and under microwave irradiation, stirred for 45 minutes at 115° C. The reaction solution was concentrated and dried under nitrogen stream, and the residues were purified by reverse phase preparative HPLC column chromatography, and the obtained fraction was concentrated under reduced pressure to obtain the target compound (5.5 mg, 36%).

$^1$H-NMR (DMSO-d$_6$) δ8.80 (1H, s), 7.52 (1H, d, J=9.2 Hz), 7.45-7.58 (2H, m), 7.07 (1H, brd, J=9.2 Hz), 6.99 (1H, s), 6.85 (1H, d, J=7.1 Hz), 6.72 (1H, d, J=7.2 Hz), 6.48 (1H, br-s), 4.45 (2H, s), 3.84 (3H, s), 3.78-3.84 (2H, m), 2.67-2.84 (2H, m); LRMS (ESI) m/z 392 [M+H]$^+$.

Example 56

2-Chloro-4-(4-((6-fluoro-5-(1-hydroxycyclobutyl)pyridin-2-yl)amino)-5,6-dihydropyrido[3,4-d]pyrimidin-7(8H)-yl)benzonitrile

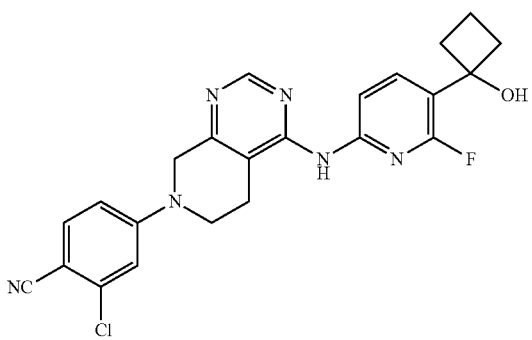 [SMILES: N#Cc1ccc(N2CCc3c(ncnc3Nc3ccc(C4(O)CCC4)c(F)n3)C2)cc1Cl]

Step 1

Synthesis of 1-(6-chloro-2-fluoro-3-pyridyl)cyclobutanol

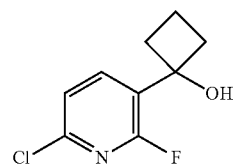 [SMILES: OC1(c2ccc(Cl)nc2F)CCC1]

A THF solution (15 mL) of 2-chloro-6-fluoropyridine (910 mg) was cooled to −78° C., and then added dropwise with LDA (2 mol/L THF solution, 5.2 mL). The reaction solution was stirred at −78° C. for 45 minutes, and added dropwise with cyclobutanone (480 mg), followed by stirring at −78° C. for 90 minutes. The reaction solution was added with ethyl acetate and water, and the organic layer was washed sequentially with a saturated aqueous solution of ammonium chloride and saturated brine, and dried over anhydrous sodium sulfate. The insoluble matters were separated by filtration, and the filtrate was concentrated and dried. The obtained residues were purified by silica gel column chromatography to obtain the target compound as a colorless oily product (1.5 g).

Step 2

Synthesis of
1-(6-amino-2-fluoro-3-pyridyl)cyclobutanol

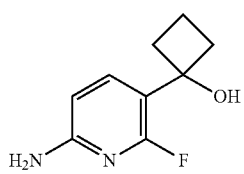

The compound (200 mg) obtained from step 1 and copper oxide (I) (30 mg) were suspended in a mixed solvent of NMP (2 mL) and 28% ammonia water, and stirred for 2 hours at 110° C. under irradiation of microwave. The solvent was distilled off under reduced pressure and the residues were purified by silica gel column chromatography to obtain the target compound (8.4 mg, 4.6%).

Step 3

Synthesis of 2-chloro-4-(4-((6-fluoro-5-(1-hydroxy-cyclobutyl)pyridin-2-yl)amino)-5,6-dihydropyrido[3,4-d]pyrimidin-7(8H)-yl)benzonitrile

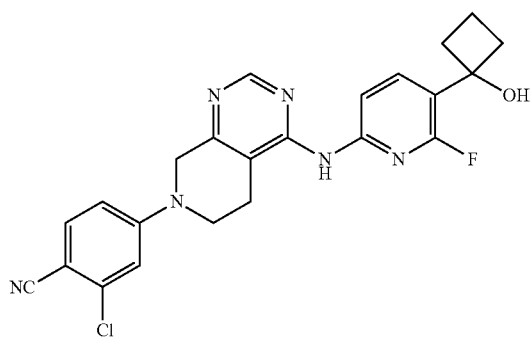 [SMILES: N#Cc1ccc(N2CCc3c(ncnc3Nc3ccc(C4(O)CCC4)c(F)n3)C2)cc1Cl]

By performing the same operation as Reference Example 2-1 and using the solid (7.2 mg) obtained from Reference Example 1-3 instead of the compound obtained from Reference Example 1-2 and the compound (4.2 mg) obtained from step 2 instead of methyl 6-aminonicotinate, the target compound was obtained as a yellow amorphous product (2.0 mg, 19%).

$^1$H-NMR (CDCl$_3$) δ 8.71 (1H, s), 8.40 (1H, dd, J=8.8, 2.2 Hz), 7.86 (1H, dd, J=11.0, 8.1 Hz), 7.53 (1H, d, J=8.1 Hz), 7.00 (1H, d, J=2.2 Hz), 6.85 (1H, dd, J=8.8, 2.2 Hz), 4.48 (2H, s), 3.75-3.86 (2H, m), 2.76-2.86 (2H, m), 2.56-2.72 (2H, m), 2.33-2.48 (2H, m), 2.07-2.22 (2H, m); LRMS (ESI) m/z 451 [M+H]$^+$.

Example 57

4-(4-((2-Hydroxypropan-2-yl)phenyl)amino)-5,6-dihydropyrido[3,4-d]pyrimidin-7(8H)-yl)-2-(trifluoromethyl)benzonitrile

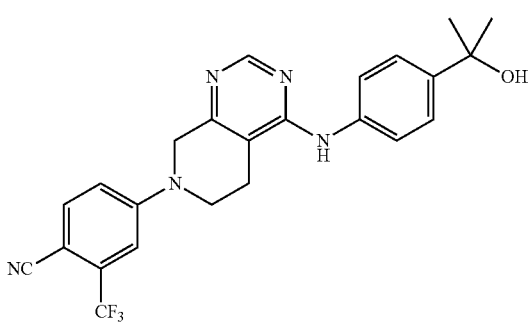

Step 1

Synthesis of 4-(4-((4-acetylphenyl)amino)-5,6-dihydropyrido[3,4-d]pyrimidin-7(8H)-yl)-2-(trifluoromethyl)benzonitrile The compound (8.2 mg) obtained from Reference Example 1-2, 1-(4-aminophenyl)ethanone (8.3 mg), and (+)-10-camphorsulfonic acid (2.9 mg) were suspended in tert-butanol (1 mL), and under microwave irradiation, stirred for 90 minutes at 135° C. The reaction solution was concentrated and dried under nitrogen stream, and the residues were purified by reverse phase preparative HPLC column chromatography, and the obtained fraction was concentrated under reduced pressure to obtain the target compound (7.9 mg, 75%).

Step 2

Synthesis of 4-(4-((2-hydroxypropan-2-yl)phenyl)amino)-5,6-dihydropyrido[3,4-d]pyrimidin-7(8H)-yl)-2-(trifluoromethyl)benzonitrile

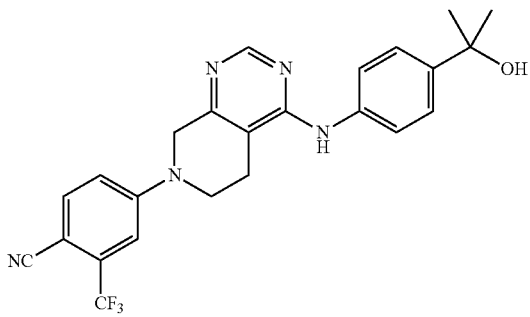 [SMILES: CC(C)(O)c1ccc(Nc2ncnc3c2CCN(c2ccc(C#N)c(C(F)(F)F)c2)C3)cc1]

A THF solution (0.5 mL) of the compound (2.5 mg) obtained from step 1 was added with methylmagnesium bromide (2 M THF solution, 0.1 mL) at room temperature, and the reaction solution was stirred for 15 minutes at room temperature. The reaction solution was concentrated and dried under nitrogen stream, and the residues were purified by reverse phase preparative HPLC column chromatography, and the obtained fraction was concentrated under reduced pressure to obtain the target compound as a white solid (1.8 mg, 69%).

$^1$H-NMR (CDCl$_3$) δ8.60 (1H, s), 7.70 (1H, d, J=8.8 Hz), 7.53 (4H, s), 7.24 (1H, d, J=2.0 Hz), 7.07 (1H, dd, J=8.8, 2.0 Hz), 6.42 (1H, s), 4.51 (2H, s), 3.89 (2H, t, J=5.6 Hz), 2.78 (2H, t, J=5.6 Hz), 1.61 (6H, s); LRMS (ESI) m/z 454 [M+H]$^+$.

Example 58

4-(4-((1-Hydroxyethyl)phenyl)amino)-5,6-dihydropyrido[3,4-d]pyrimidin-7(8H)-yl)-2-(trifluoromethyl)benzonitrile

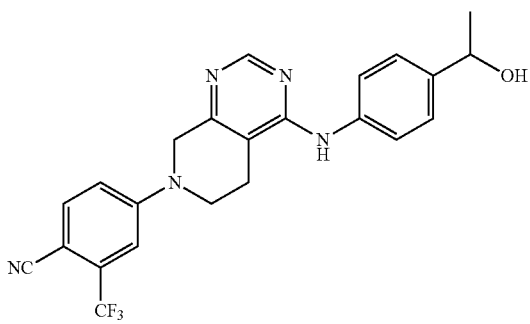 [SMILES: CC(O)c1ccc(Nc2ncnc3c2CCN(c2ccc(C#N)c(C(F)(F)F)c2)C3)cc1]

A methanol solution (0.5 mL) of the compound (1.7 mg) obtained from Example 57 (step 1) was added with sodium tetrahydroborate (3 mg) at room temperature, and the reaction solution was stirred for 15 minutes at room temperature. The reaction solution was concentrated and dried under nitrogen stream, and the residues were purified by reverse phase preparative HPLC column chromatography, and the obtained fraction was concentrated under reduced pressure to obtain the target compound as a white solid (1.6 mg, 94%).

$^1$H-NMR (CDCl$_3$) δ8.60 (1H, s), 7.70 (1H, d, J=8.8 Hz), 7.53-7.60 (2H, m), 7.38-7.46 (2H, m), 7.20-7.30 (1H, m), 7.03-7.13 (1H, m), 6.42 (1H, d, 9.2 Hz), 4.88-4.98 (1H, m), 4.51 (2H, s), 3.85-3.93 (2H, m), 2.75-2.85 (2H, m), 1.49-1.56 (3H, m); LRMS (ESI) m/z 440 [M+H]$^+$.

Comparative Example 1

N-(4-Cyano-3-(trifluoromethyl)phenyl)-3-((4-fluorophenyl)sulfonyl)-2-hydroxy-2-methylpropanamide (Bicalutamide)

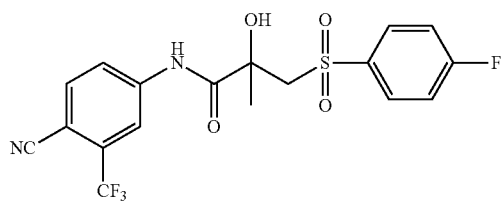 [SMILES: CC(O)(CS(=O)(=O)c1ccc(F)cc1)C(=O)Nc1ccc(C#N)c(C(F)(F)F)c1]

Synthesis was performed according to the method described in J. Org. Chem., 2003, 68 (26): 10181-2.

Comparative Example 2

4-(4-((4-Isopropoxyphenyl)amino)-7, 8-dihydropyrido[4,3-d]pyrimidin-6(5H)-yl)-2-(trifluoromethyl)benzonitrile

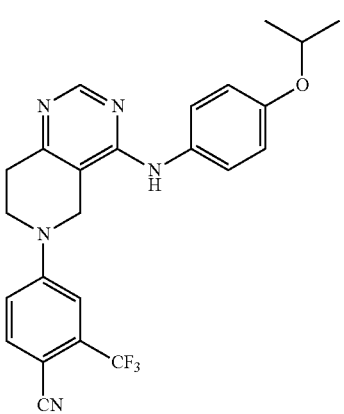 [SMILES: CC(C)Oc1ccc(Nc2ncnc3c2CN(c2ccc(C#N)c(C(F)(F)F)c2)CC3)cc1]

Step 1

Synthesis of 6-benzyl-5,6,7,8-tetrahydropyrido[4,3-d]pyrimidin-4-ol

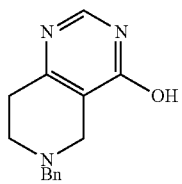 [SMILES: Oc1ncnc2c1CN(Cc1ccccc1)CC2]

Ethyl 1-benzyl-4-oxopiperidin-3-carboxylate hydrochloride (5.31 g) was added with formamidine hydrochloride (1.67 g) and sodium methoxide (30 mL, 28% methanol solution), and stirred overnight at 85° C. The reaction solution was added with water and extracted 5 times with chloroform, dried over sodium sulfate, and concentrated to obtain the target compound (3.16 g, 77%).

$^1$H-NMR (DMSO-$d_6$) δ7.81 (1H, s), 7.32-7.23 (5H, m), 3.58 (2H, s), 3.09 (2H, s), 2.58 (2H, t, J=5.7 Hz), 2.43 (2H, t, J=5.7 Hz); LRMS (ESI) m/z 242 [M+H]$^+$.

Step 2

Synthesis of (4-(4-Hydroxy-7,8-dihydropyrido[4,3-d]pyrimidin-6(5H)-yl)-2-(trifluoromethyl)benzonitrile

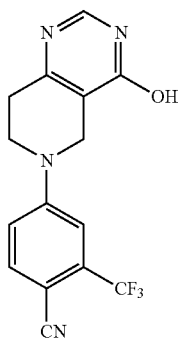 [SMILES: N#Cc1ccc(N2CCc3ncnc(O)c3C2)cc1C(F)(F)F]

The compound (3.16 g) obtained from step 1 was dissolved in methanol (8 mL), and added with 10% palladium/carbon (600 mg, containing 50% water) and ammonium formate (4.13 g), followed by stirring for 2 days at 60° C. The reaction solution was filtered through Hyflo Super-Cel, the residues were washed with methanol and DMSO, and the methanol in the filtrate was distilled off under reduced pressure. The obtained solution was added with 4-fluoro-2-(trifluoromethyl)benzonitrile (2.70 g), and stirred for 2 days at 40° C. The reaction solution was added with water, and extracted three times with ethyl acetate, and the organic layer was washed with water and saturated brine. The obtained solution was dried over sodium sulfate, followed by concentration under reduced pressure to obtain the target compound (4.03 g, 44%).

$^1$H-NMR (DMSO-$d_6$) δ8.07 (1H, s), 7.85 (1H, d, J=8.9 Hz), 7.34 (1H, d, J=2.2 Hz), 7.28 (1H, dd, J=8.9, 2.2 Hz), 4.20 (2H, s), 3.75 (2H, t, J=5.6 Hz), 2.72 (2H, t, J=5.6 Hz); LRMS (ESI) m/z 321 [M+H]$^+$.

Step 3

Synthesis of (4-(4-chloro-7,8-dihydropyrido[4,3-d]pyrimidin-6(5H)-yl)-2-(trifluoromethyl)benzonitrile

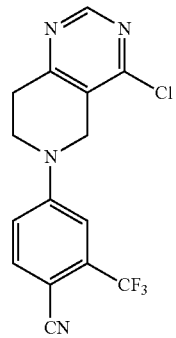 [SMILES: N#Cc1ccc(N2CCc3ncnc(Cl)c3C2)cc1C(F)(F)F]

The compound (1.82 g) obtained from step 2 was dissolved in 1,2-dichloroethane (10 mL), and added with phosphorus oxychloride (5.3 mL) and triethylamine (1.73 mL), followed by stirring for 2 hours at 90° C. The reaction solution was poured into ice water, and by carefully adding solid potassium carbonate, neutralization was carried out. The obtained solution was extracted three times with chloroform, dried over sodium sulfate, and concentrated under reduced pressure. The obtained residues were purified by silica gel column chromatography to obtain the target compound (1.09 g, 57%).

LRMS (ESI) m/z 339 [M+H]$^+$.

Step 4

Synthesis of 4-(4-((4-isopropoxyphenyl)amino)-7,8-dihydropyrido[4,3-d]pyrimidin-6(5H)-yl)-2-(trifluoromethyl)benzonitrile

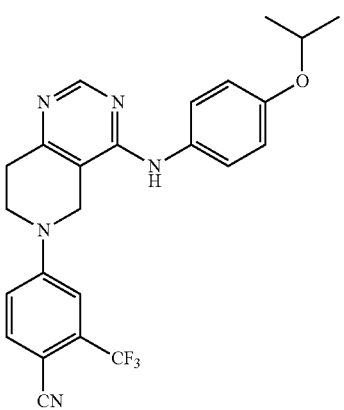 [SMILES: CC(C)Oc1ccc(Nc2ncnc3c2CN(c2ccc(C#N)c(C(F)(F)F)c2)CC3)cc1]

The compound (60 mg) obtained from step 3 was dissolved in acetonitrile (1.5 mL), and added with 4-isopropoxyaniline (40 mg), followed by stirring for 30 minutes at 180° C. under microwave irradiation. The reaction solution was added with a saturated aqueous solution of sodium hydrogen carbonate, extracted three times with chloroform, and the organic layer was dried over sodium sulfate and concentrated. The obtained residues were purified by silica gel column chromatography to obtain the target compound (82 mg, 100%).

$^1$H-NMR (DMSO-d$_6$) δ8.57 (1H, s), 7.69 (1H, d, J=8.8 Hz) 7.41-7.37 (2H, m), 7.23 (1H, d, J=2.6 Hz), 7.10 (1H, dd, J=8.8, 2.6 Hz), 6.95-6.90 (2H, m), 6.30 (1H, b-rs), 4.55 (1H, sept, J=6.1 Hz), 4.30 (2H, s), 3.82 (2H, t, J=5.9 Hz), 3.06 (2H, t, J=5.9 Hz), 1.36 (6H, d, J=6.1 Hz); LRMS (ESI) m/z 454 [M+H]$^+$.

Comparative Example 3

4-(3-((4-Isopropoxyphenyl)amino)-5,6-dihydro[1,2,4]triazolo[4,3-a]pyrazin-7 (8H)-yl)-2-(trifluoromethyl)benzonitrile

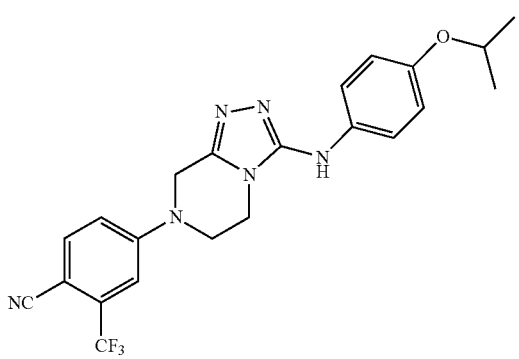 [SMILES: CC(C)Oc1ccc(Nc2nnc3n2CCN(c2ccc(C#N)c(C(F)(F)F)c2)C3)cc1]

Step 1

Synthesis of 2-chloro-3-hydrazinylpyrazine

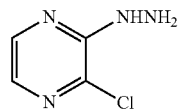

2,3-Dichloropyrazine (25 g) was dissolved in ethanol (500 mL), and added with hydrazine monohydrate (16.7 mL), followed by stirring for 1.5 hours under reflux. The reaction solution was added with water, and the precipitated solid was collected by filtration and dried under reduced pressure. By recrystallizing the obtained solid from ethanol, the target compound was obtained (18.12 g, 74%).

Step 2

Synthesis of 8-chloro-[1,2,4]triazolo[4,3-a]pyrazine

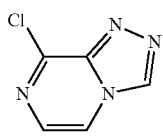

A mixture of the compound (8 g) obtained from step 1 and triethyl orthoformate (32 mL) was stirred for 4 hours under reflux. The reaction solution was cooled to room temperature, and the precipitated solid was filtered, washed with ethanol, and dried under reduced pressure to obtain the target compound (8.10 g, 95%).

$^1$H-NMR (DMSO-d$_6$) δ9.53 (1H, s), 8.62 (1H, d, J=4.6 Hz), 7.76 (1H, d, J=4.6 Hz); LRMS (ESI) m/z 155 [M+H]$^+$.

Step 3

Synthesis of tert-butyl 5,6-dihydro-[1,2,4]triazolo[4,3-a]pyrazin-7(8H)-carboxylate

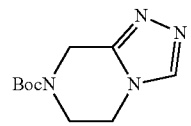

The compound (8.10 g) obtained from step 2, platinum oxide (IV), and 10% palladium/carbon (2 g, containing 50% water) were dissolved in methanol (8 mL), and stirred for 34 hours under hydrogen atmosphere of 50 psi (Parr). The reaction solution was filtered through Hyflo Super-Cel. The oily product obtained by concentrating the solvent was dissolved in dichloromethane (200 mL), and added with N,N-diisopropylethylamine (10 mL) and di-tert-butyl bicarbonate (11.4 g), followed by stirring for 3 hours at room temperature. The reaction solution was added with a saturated aqueous solution of sodium hydrogen carbonate, and extracted three times with chloroform. The organic layer was dried over sodium sulfate and concentrated. The obtained residues were purified by silica gel column chromatography to obtain the target compound (2.55 g, 22%).

$^1$H-NMR (CDCl$_3$) δ8.15 (1H, s), 4.84 (2H, s), 4.09 (1H, t, J=5.5 Hz), 3.88 (1H, t, J=5.5 Hz), 1.50 (9H, s); LRMS (ESI) m/z 225 [M+H]$^+$.

Step 4

Synthesis of tert-butyl 3-bromo-5,6-dihydro-[1,2,4]triazolo[4,3-a]pyrazin-7 (8H)-carboxylate

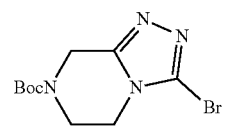

The compound (1 g) obtained from step 3 was dissolved in chloroform (20 mL), and added with sodium hydrogen carbonate (688 mg) and N-bromosuccinimide (873 mg) at 0° C., followed by stirring for 2.5 hours at room temperature. The reaction solution was added with water, and extracted three times with chloroform. The organic layer was dried over sodium sulfate and concentrated. The obtained residues were purified by silica gel column chromatography to obtain the target compound (693 mg, 51%).

LRMS (ESI) m/z 303 [M+H]$^+$.

Step 5

Synthesis of 4-(3-bromo-5,6-dihydro-[1,2,4]triazolo[4,3-a]pyrazin-7(8H)-yl)-2-(trifluoromethyl)benzonitrile

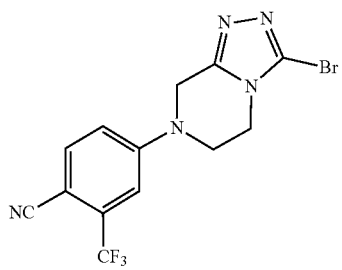 [SMILES: N#Cc1ccc(N2CCn3c(Br)nnc3C2)cc1C(F)(F)F]

The compound (53 mg) obtained from step 4 was dissolved in chloroform (2 mL), and added with trifluoroacetic acid (0.2 mL), followed by stirring overnight at room temperature. The oily product obtained by concentrating the reaction solution under reduced pressure was dissolved in N,N-dimethylformamide (1.5 mL), and added with cesium carbonate (111 mg) and 4-fluoro-2-(trifluoromethyl)benzonitrile (64 mg), followed by stirring at 200° C. for 2 hours. The reaction solution was added with water, and extracted three times with ethyl acetate. The organic layer was washed with water and saturated brine, dried over sodium sulfate and concentrated. The obtained residues were purified by silica gel column chromatography to obtain the target compound (19 mg, 30%).

LRMS (ESI) m/z 372 [M+H]$^+$.

Step 6

Synthesis of 4-(3-((4-isopropoxyphenyl)amino)-5,6-dihydro[1,2,4]triazolo[4,3-a]pyrazin-7(8H)-yl)-2-(trifluoromethyl)benzonitrile

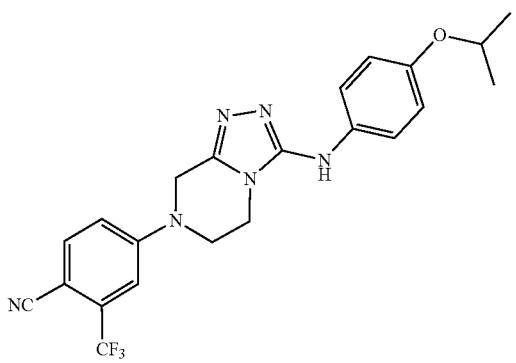 [SMILES: CC(C)Oc1ccc(Nc2nnc3n2CCN(c2ccc(C#N)c(C(F)(F)F)c2)C3)cc1]

The compound (19 mg) obtained from step 5 was dissolved in dioxane (1 mL), and added with 4-isopropoxyaniline (12 mg) and 4 N-hydrochloric acid-dioxane (64 μL), followed by stirring for 20 minutes at 180° C. under microwave irradiation. The reaction solution was added with a saturated aqueous solution of sodium hydrogen carbonate, and extracted three times with chloroform. The organic layer was dried over sodium sulfate and concentrated. The obtained residues were purified by silica gel column chromatography to obtain the target compound (13 mg, 57%).

$^1$H-NMR (CDCl$_3$) δ7.71 (1H, d, J=8.8 Hz), 7.29 (1H, s), 7.18-7.12 (3H, m), 7.03 (1H, dd, J=8.8, 2.7 Hz), 6.88-6.79 (2H, m), 4.66 (2H, s), 4.45 (1H, sept, J=6.1 Hz), 3.83 (4H, br-s), 1.31 (6H, d, J=6.1 Hz); LRMS (ESI) m/z 443 [M+H]$^+$.

Comparative Example 4

7-(3-Chloropyridin-2-yl)-N-(4-(trifluoromethyl)phenyl)-5,6,7,8-tetrahydropyrido[3,4-d]pyrimidin-4-amine

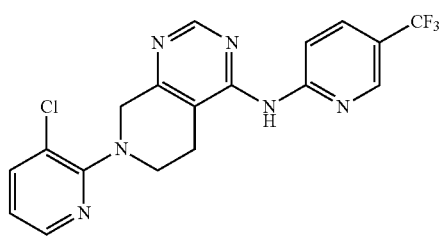 [SMILES: FC(F)(F)c1ccc(Nc2ncnc3c2CCN(c2ncccc2Cl)C3)nc1]

Synthesis was performed according to the method described in Patent Literature 1 or 3.

Comparative Example 5

3-Chloro-4-(4-((5-(2-hydroxypropan-2-yl)pyridin-2-yl)amino)-5,6-dihydropyrido[3,4-d]pyrimidin-7(8H)-yl)benzonitrile

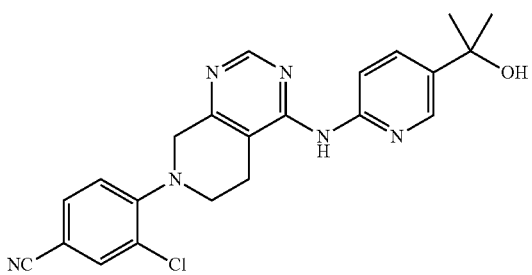 [SMILES: CC(C)(O)c1ccc(Nc2ncnc3c2CCN(c2ccc(C#N)cc2Cl)C3)nc1]

The compound (74 mg) obtained from step 3 of Example 44, 3-chloro-4-fluorobenzonitrile (40 mg), and sodium carbonate (82 mg) were added to DMSO (2 mL), and reacted for 3 hours at 120° C. The insoluble matters were filtered, and the target compound was obtained by reverse phase preparative HPLC column chromatography (26 mg, 24%).

$^1$H-NMR (DMSO-d6) δ8.92 (1H, s), 8.52 (1H, s), 8.42 (1H, d, J=2.4 Hz), 8.07 (1H, d, J=8.8 Hz), 8.01 (1H, d, J=2.4 Hz), 7.84 (1H, dd, J=8.8, 2.4 Hz), 7.79 (1H, dd, J=8.4, 2.0 Hz), 7.36 (1H, d, J=8.4 Hz), 5.14 (1H, s), 4.26 (2H, s), 3.53 (2H, t, J=5.6 Hz), 2.90 (2H, t, J=5.6 Hz), 1.46 (6H, s); LRMS (ESI) m/z 421 [M+H]$^+$

Comparative Example 6

3-Chloro-5-(4-((5-(2-hydroxypropan-2-yl)pyridin-2-yl)amino)-5,6-dihydropyrido[3,4-d]pyrimidin-7(8H)-yl)benzonitrile

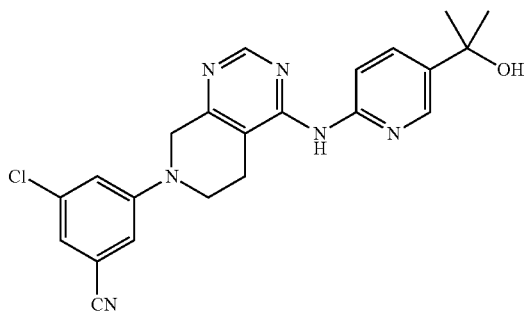 [SMILES: CC(C)(O)c1ccc(Nc2ncnc3c2CCN(c2cc(Cl)cc(C#N)c2)C3)nc1]

The compound (74 mg) obtained from step 3 of Example 44, 3-chloro-5-fluorobenzonitrile (40 mg), and sodium carbonate (82 mg) were added to DMSO (2 mL), and reacted for 15 hours at 120° C. The insoluble matters were filtered, and the target compound was obtained by reverse phase preparative HPLC column chromatography (17 mg, yield 15%).

$^1$H-NMR (DMSO-d6) δ8.99 (1H, s), 8.53 (1H, s), 8.42 (1H, d, J=2.4 Hz), 8.04 (1H, d, J=8.4 Hz), 7.83 (1H, dd, J=8.8, 2.8 Hz), 7.51 (1H, s), 7.43 (1H, t, J=2.4 Hz), 7.26 (1H, s), 5.13 (1H, s), 4.40 (2H, s), 3.73 (2H, t, J=5.6 Hz), 2.85 (2H, t, J=5.6 Hz), 1.46 (6H, s); LRMS (ESI) m/z 421 [M+H]$^+$

Comparative Example 7

2-Chloro-6-(4-((5-(2-hydroxypropan-2-yl)pyridin-2-yl)amino)-5,6-dihydropyrido[3,4-d]pyrimidin-7(8H)-yl)benzonitrile

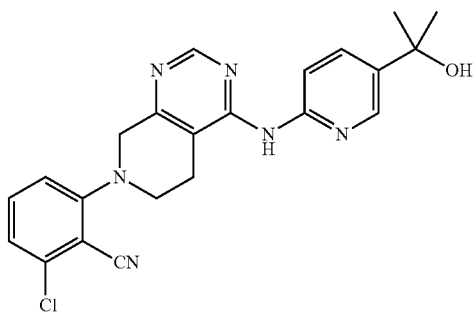 [SMILES: CC(C)(O)c1ccc(Nc2ncnc3c2CCN(c2cccc(Cl)c2C#N)C3)nc1]

The compound (74 mg) obtained from step 3 of Example 44, 2-chloro-6-fluorobenzonitrile (40 mg), and sodium carbonate (82 mg) were added to DMSO (2 mL), and reacted for 3 hours at 120° C. The insoluble matters were filtered, and the target compound was obtained by reverse phase preparative HPLC column chromatography (18 mg, yield 16%).

$^1$H-NMR (DMSO-d6) δ9.01 (1H, s), 8.52 (1H, s), 8.43 (1H, d, J=2.4 Hz), 8.04 (1H, d, J=8.8 Hz), 7.84 (1H, dd, J=8.8, 2.4 Hz), 7.62 (1H, t, J=8.4 Hz), 7.27 (2H, t, J=8.4 Hz), 5.14 (1H, s), 4.31 (2H, s), 3.66 (2H, t, J=5.6 Hz), 2.94 (2H, t, J=5.6 Hz), 1.46 (6H, s); LRMS (ESI) m/z 421 [M+H]$^+$

Comparative Example 8

6-((7-(2-Cyano-4-(trifluoromethyl)phenyl)-5,6,7,8-tetrahydropyrido[3,4-d]pyrimidin-4-yl)amino)-N-(2,2,2-trifluoroethyl)nicotinamide

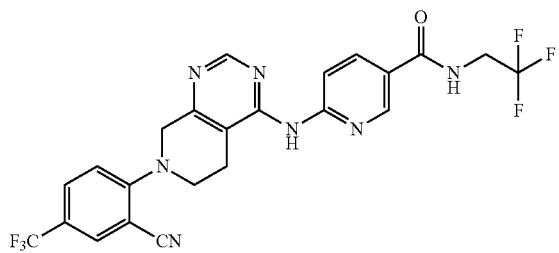 [SMILES: N#Cc1cc(C(F)(F)F)ccc1N1CCc2c(ncnc2Nc2ccc(C(=O)NCC(F)(F)F)cn2)C1]

Step 1

Synthesis of 6-((7-benzyl-5,6,7,8-tetrahydropyrido[3,4-d]pyrimidin-4-yl)amino)nicotinic acid

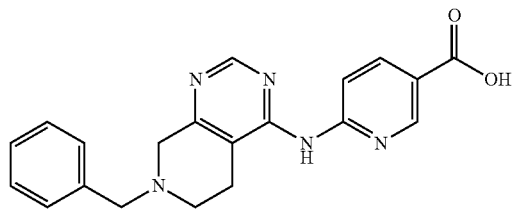 [SMILES: O=C(O)c1ccc(Nc2ncnc3c2CCN(Cc2ccccc2)C3)nc1]

The compound (150 mg) obtained from step 1 of Example 44 was suspended in methanol (1 mL) and 6 mol/L aqueous solution of sodium hydroxide (0.2 mL), and under microwave irradiation, reacted for 10 minutes at 120° C. Subsequently, the solid formed by adding 5 N-HCl (0.24 mL) was collected by filtration and dried to obtain the target product with pale brown color (120 mg, 83%). It was used for the next reaction without any purification.

Step 2

Synthesis of 6-((7-benzyl-5,6,7,8-tetrahydropyrido[3,4-d]pyrimidin-4-yl)amino)-N-(2,2,2-trifluoroethyl)nicotinamide

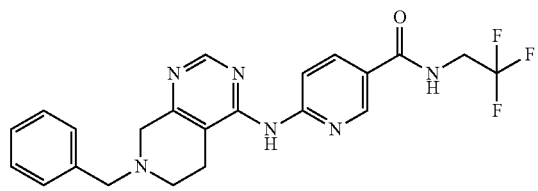 [SMILES: O=C(NCC(F)(F)F)c1ccc(Nc2ncnc3c2CCN(Cc2ccccc2)C3)nc1]

The compound (120 mg) obtained from step 1 was added to DMF (3 mL), and it was further added with DIPEA (N,N-diisopropylethylamine, 76 µL) and HATU (162 mg). Next, 2,2,2-trifluoroethanamine (43 mg) was added thereto, and the mixture was stirred for 2 hours at room temperature. Subsequently, water (3 mL) was added under ice cooling, followed by stirring for 1 hour. The precipitated solid was collected by filtration and dried to obtain the target compound (70 mg, yield 92%).

¹H-NMR (DMSO-d6) δ9.28 (1H, s), 9.14 (1H, t, J=6.4 Hz), 8.23 (1H, s), 8.54 (1H, s), 8.29 (1H, d, J=8.8 Hz), 8.22 (1H, d, J=8.8 Hz), 7.40-7.30 (5H, m), 4.13-4.09 (2H, m), 3.68 (2H, s), 3.46 (2H, s), 2.76-2.72 (4H, m); LRMS (ESI) m/z 443 [M+H]⁺

Step 3

Synthesis of 6-((5,6,7,8-tetrahydropyridopyrodo[3,4-d]pyrimidin-4-yl)amino)-N-(2,2,2-trifluoroethyl)nicotinamide

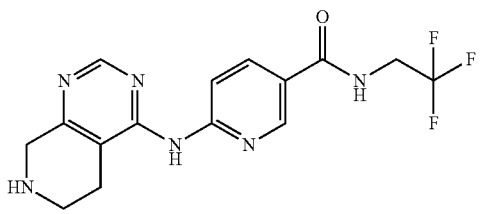 [SMILES: O=C(NCC(F)(F)F)c1ccc(Nc2ncnc3c2CCNC3)nc1]

The compound (640 mg) obtained from step 2 was dissolved in ethanol (30 mL), and added with 10% palladium/carbon (50% wet product, 300 mg), followed by stirring at 70° C. for 5 hours under hydrogen atmosphere. The insoluble matters were removed by Celite, and the filtrate was concentrated. The obtained crude product was added with methyl isobutyl ketone (1 mL) and hexane (1 mL) to precipitate a solid. The solid was collected by filtration, and dried to obtain the target compound (440 mg, yield 86%).

¹H-NMR (DMSO-d6) δ9.16-9.10 (2H, m), 8.80 (1H, s), 8.52 (1H, s), 8.24 (1H, d, J=8.8 Hz), 8.20 (1H, d, J=8.8 Hz), 4.13-4.04 (2H, m), 3.71 (2H, s), 2.94 (2H, t, J=5.6 Hz), 2.62-2.60 (2H, m); LRMS (ESI) m/z 353 [M+H]⁺.

Step 4

Synthesis of 6-((7-(2-cyano-4-(trifluoromethyl)phenyl)-5,6,7,8-tetrahydropyrido[3,4-d]pyrimidin-4-yl)amino)-N-(2,2,2-trifluoroethyl)nicotinamide

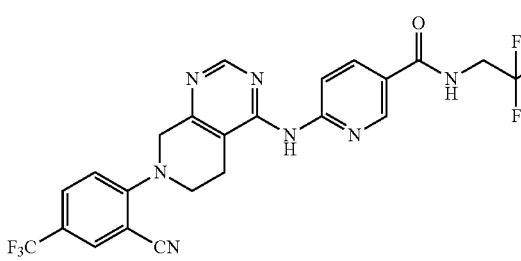

The compound (74 mg) obtained from step 3, 2-fluoro-5-(trifluoromethyl)benzonitrile (50 mg), sodium carbonate (82 mg) were added to DMSO (2 mL), and reacted for 3 hours at 120° C. The insoluble matters were filtered, and the target compound was obtained by reverse phase preparative HPLC column chromatography (31 mg, 28%).

¹H-NMR (DMSO-d6) δ9.56 (1H, s), 9.12 (1H, t, J=6.4 Hz), 8.84 (1H, t, J=5.6 Hz), 8.67 (1H, s), 8.30-8.20 (3H, m), 7.61 (1H, d, J=8.8 Hz), 7.48 (1H, dd, J=8.8, 2.4 Hz), 6.23 (2H, s), 4.23 (2H, t, J=6.4 Hz), 4.20-4.05 (2H, m), 3.23 (2H, t, J=6.4 Hz); LRMS (ESI) m/z 522 [M+H]⁺.

Comparative Example 9

6-((7-(2-Cyano-5-(trifluoromethyl)phenyl)-5,6,7,8-tetrahydropyrido[3,4-d]pyrimidin-4-yl)amino)-N-(2,2,2-trifluoroethyl)nicotinamide

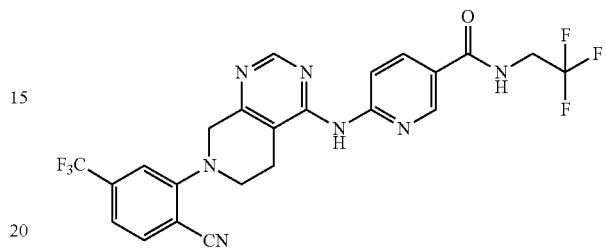

The compound (74 mg) obtained from step 3 of Comparative Example 8, 2-fluoro-4-(trifluoromethyl)benzonitrile (50 mg), and sodium carbonate (82 mg) were added to DMSO (2 mL), and reacted for 3 hours at 120° C. The insoluble matters were filtered, and the target compound was obtained by reverse phase preparative HPLC column chromatography (32 mg, yield 29%).

¹H-NMR (DMSO-d6) δ9.57 (1H, s), 9.13 (1H, t, J=6.4 Hz), 8.85 (1H, s), 8.69 (1H, s), 8.24 (2H, S), 7.94 (1H, d, J=8.0 Hz), 7.87 (1H, s), 7.22 (1H, d, J=8.8 Hz), 6.12 (2H, s), 4.26 (2H, t, J=6.4 Hz), 4.18-4.06 (2H, m), 3.24 (2H, t, J=6.4 Hz); LRMS (ESI) m/z 522 [M+H]⁺.

Comparative Example 10

6-((7-(3-Cyano-2-(trifluoromethyl)phenyl)-5,6,7,8-tetrahydropyrido[3,4-d]pyrimidin-4-yl)amino)-N-(2,2,2-trifluoroethyl)nicotinamide

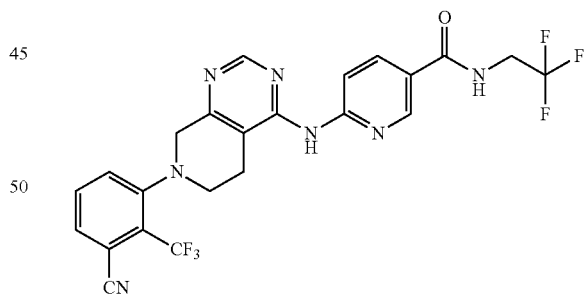

The compound (148 mg) obtained from step 3 of Comparative Example 8, 3-fluoro-2-(trifluoromethyl)benzonitrile (100 mg), and sodium carbonate (164 mg) were added to DMSO (2 mL), and reacted for 15 hours at 120° C. The insoluble matters were filtered, and the target compound was obtained by reverse phase preparative HPLC column chromatography (18 mg, yield 17%).

¹H-NMR (DMSO-d6) δ9.41 (1H, s), 9.14 (1H, t, J=6.4 Hz), 8.86 (1H, d, J=2.4 Hz), 8.62 (1H, s), 8.31 (1H, d, J=8.4 Hz), 8.25 (1H, dd, J=8.8, 2.4 Hz), 8.05-8.00 (1H, m), 7.95-7.85 (2H, m), 4.18-4.06 (4H, m), 3.29 (2H, t, J=5.6 Hz), 2.92 (2H, t, J=5.6 Hz); LRMS (ESI) m/z 522 [M+H]⁺.

Comparative Example 11

4-(4-((5-(2-Hydroxypropan-2-yl)pyridin-2-yl)amino)-5,6-dihydropyrido[3,4-d]pyrimidin-7(8H)-yl)benzonitrile

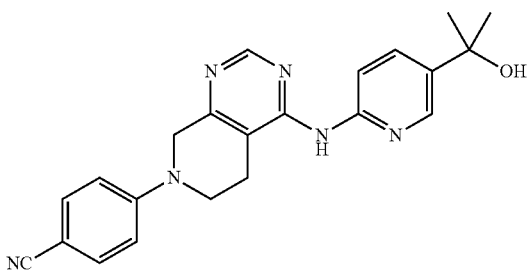 [SMILES: CC(C)(O)c1ccc(Nc2ncnc3c2CCN(c2ccc(C#N)cc2)C3)nc1]

The compound (20 mg) obtained from step 3 of Example 44, 4-fluorobenzonitrile (11 mg), and potassium carbonate (15 mg) were dissolved in DMSO (0.2 mL), and stirred for 25 minutes at 125° C. under irradiation of microwave. The reaction mixture was purified by reverse phase preparative HPLC column chromatography to obtain the target compound (4.4 mg, 16%).

$^1$H-NMR (DMSO-$d_6$) δ8.67 (1H, s), 8.47 (1H, d, J=8.4 Hz), 8.42 (1H, d, J=2.2 Hz), 7.86 (1H, dd, J=8.8, 2.2 Hz), 7.56 (2H, d, J=9.2 Hz), 6.97 (2H, d, J=9.2 Hz), 4.46 (2H, s), 3.82 (2H, t, J=5.7 Hz), 2.82 (2H, t, J=5.7 Hz), 1.62 (6H, s); LRMS (ESI) m/z 387 [M+H]$^+$.

Biological Evaluation Test

Test Example 1

Antagonist Activity for AR

Antagonist activity for AR was evaluated according to the following method. COS-7 cells (ATCC) were transfected with pMMTV-luc vector (reporter plasmid having, as an androgen response element, murine mouse mammary virus long terminal repeat) and pEX-hAR vector (human androgen receptor expression vector: which expresses human AR gene under control of CMV promoter) by using Nucleofector (registered trademark) Kit R (Lonza) as a transfection reagent and Amaxa (Lonza). The COS-7 cells obtained after transfection were seeded in a clear bottom 96 well microplate (BD) at 1.5×10$^4$/well with phenol red free RPMI1640 containing 10% charcoal-treated fetal bovine serum (hereinbelow, DCC-FBS) (hereinbelow, the medium is referred to as an evaluation medium), and then cultured overnight. The culture was added with the evaluation medium containing dihydrotestosterone (DHT) (final concentration of DHT: 1 nmol/L) or the evaluation medium containing the compound of Examples or the compound of Comparative Examples (final concentration of the compound of Examples or the compound of Comparative Examples: 5, 14, 41, 123, 370, 1111, 3333, or 10000 nmol/L), followed by culture for 24 hours. Then, the transcription activity value was measured. The transcription activity was measured by using Bright-Glo™ Luciferase Assay System (Promega). From the measured transcription activity, 50% transcription activity inhibition concentration (IC$_{50}$ value) was calculated by logistic regression when the transcription activity value obtained by using 1 nmol/L DHT was 100% and the transcription activity value obtained by using the evaluation medium only was 0%.

The results are shown in Table 1. Even when compared with Bicalutamide (Comparative Example 1), the compounds of the present invention exhibited an antagonist activity for AR equal to or higher than that of Bicalutamide. Meanwhile, the compound of Comparative Example 4 described in Patent Literatures 1 and 3 exhibited no antagonist activity for AR, which was observed for the compounds of Examples of the present invention. Furthermore, unlike the compounds of Examples having 5,6,7,8-tetrahydropyrido[3,4-d]pyrimidine skeleton, the compound having 5,6,7,8-tetrahydropyrido[4,3-d]pyrimidine skeleton of Comparative Example 2, the compound having 5,6,7,8-tetrahydro[1,2,4]triazolo[4,3-a]pyrazine skeleton of Comparative Example 3, and the compound of Comparative Example 4 described in Patent Literatures 2 and 3 exhibited no antagonist activity for AR. In addition, the compounds described in Comparative Examples 5 to 10 having cyanobenzene which has a substituent group X but is different from the compounds of the present invention also did not show the antagonist activity for AR. Furthermore, the compound described in Comparative Example 11 not having a substituent group X also did not show the antagonist activity for AR.

TABLE 1

TABLE 1-1

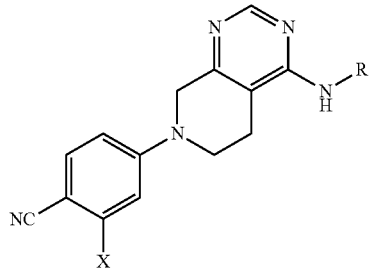

| Example | X | —R | IC$_{50}$ value (μM) |
|---|---|---|---|
| 1 | CF$_3$ |  | 0.08 |

TABLE 1-continued

| # | R | Structure | Value |
|---|---|---|---|
| 2 | CF₃ | 4-methylphenyl isopropyl ether | 0.37 |
| 3 | CF₃ | 4-methylphenyl methyl ether | 0.53 |
| 4 | CF₃ | 3-methylbiphenyl | 0.62 |
| 5 | CF₃ | 2-(2-fluoro-6-methylpyridin-3-yl)propan-2-ol | 0.19 |
| 6 | Cl | 2-(6-methylpyridazin-3-yl)propan-2-ol | 0.07 |
| 7 | CF₃ | 2-(6-methylpyridin-3-yl)propan-2-ol | 0.16 |
| 8 | CF₃ | 2-(2-methyl-4-(trifluoromethyl)thiazol-5-yl)propan-2-ol | 0.25 |

TABLE 1-2

| # | R | Structure | Value |
|---|---|---|---|
| 9 | Cl | 2-(6-methylpyridin-3-yl)propan-2-ol | 0.25 |
| 10 | CF₃ | 2-(6-methylpyridazin-3-yl)propan-2-ol | 0.09 |
| 11 | CF₃ | 6-methyl-N-(2,2,2-trifluoroethyl)nicotinamide | 0.03 |

TABLE 1-continued
| 12 | CF$_3$ | 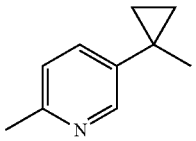 | 0.17 |
| 13 | CF$_3$ | 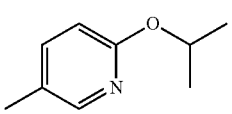 | 0.11 |
| 14 | CF$_3$ | 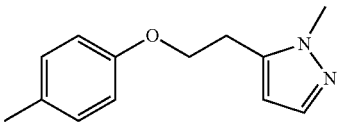 [SMILES: Cc1ccc(OCCc2ccnn2C)cc1] | 0.30 |
| 15 | CF$_3$ | 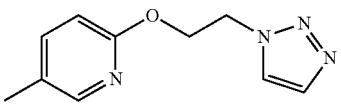 | 0.13 |
| 16 | CF$_3$ | 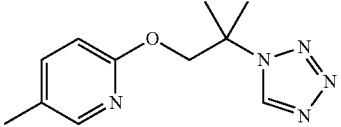 [SMILES: Cc1ccc(OCC(C)(C)n2cnnn2)nc1] | 0.21 |
| 17 | CF$_3$ | 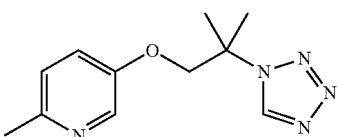 | 0.17 |
| 18 | CF$_3$ | 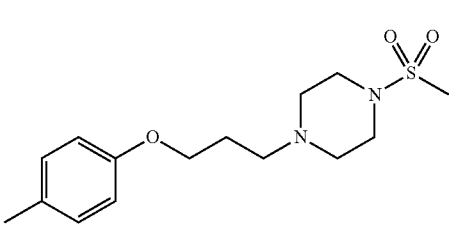 | 0.36 |
TABLE 1-3
| 19 | CF$_3$ | 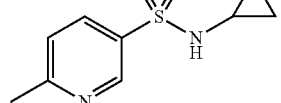 | 0.13 |
| 20 | CF$_3$ | 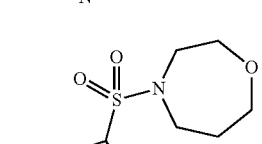 | 0.10 |
| 21 | CF$_3$ | 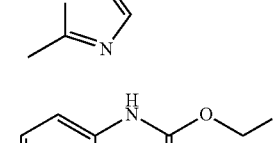 | 0.38 |

TABLE 1-continued
| | | | |
|---|---|---|---|
| 22 | CF$_3$ | 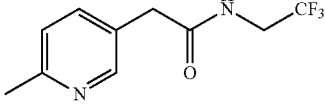 | 0.37 |
| 23 | CF$_3$ | 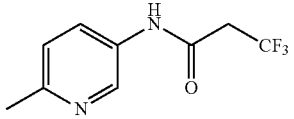 | 0.80 |
| 24 | CF$_3$ | 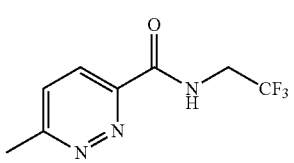 | 0.07 |
| 25 | CF$_3$ | 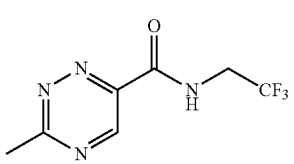 | 3.32 |
| 26 | CF$_3$ | 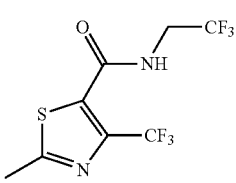 [SMILES: Cc1nc(C(F)(F)F)c(C(=O)NCC(F)(F)F)s1] | 0.06 |
| 27 | CF$_3$ | 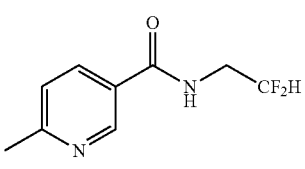 | 0.09 |
| 28 | CF$_3$ | 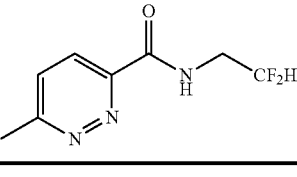 | 0.02 |
TABLE 1-4
| | | | |
|---|---|---|---|
| 29 | Cl | 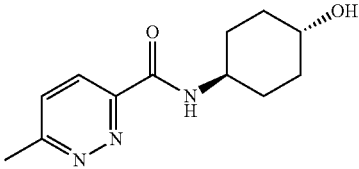 [SMILES: Cc1ccc(C(=O)N[C@H]2CC[C@H](O)CC2)nn1] | 0.02 |
| 30 | CF$_3$ | 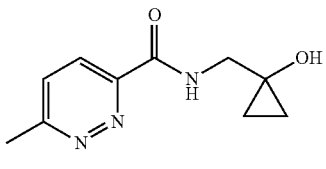 | ND |
| 31 | CF$_3$ | 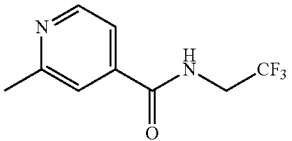 | 0.39 |

TABLE 1-continued
| 32 | CF₃ | 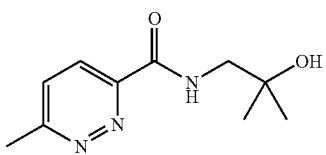 | 0.06 |
| 33 | CF₃ | 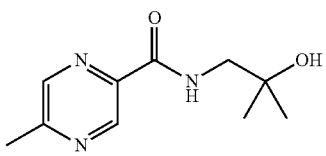 | 0.31 |
| 34 | CF₃ | 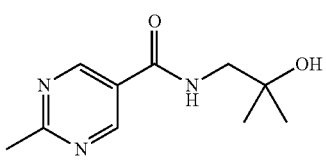 | 0.70 |
| 35 | CF₃ | 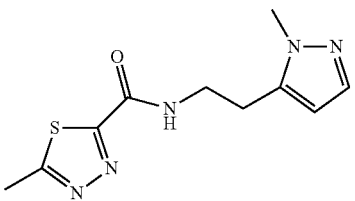 [SMILES: Cc1nnc(C(=O)NCCc2ccnn2C)s1] | 0.19 |
| 36 | CF₃ | 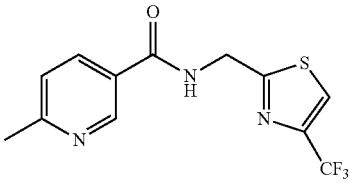 [SMILES: Cc1ccc(C(=O)NCc2nc(C(F)(F)F)cs2)cn1] | 0.17 |
| 37 | CF₃ | 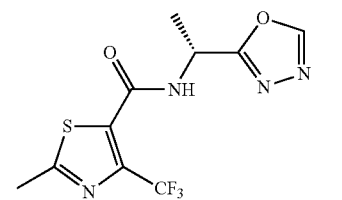 | 0.17 |
| 38 | CF₃ | 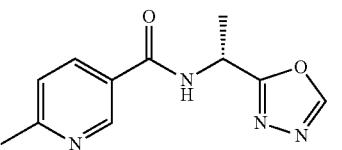 [SMILES: Cc1ccc(C(=O)N[C@H](C)c2nnco2)cn1] | 0.56 |
TABLE 1-5
| 39 | CF₃ | 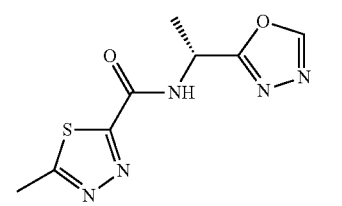 [SMILES: Cc1nnc(C(=O)N[C@H](C)c2nnco2)s1] | 2.05 |

TABLE 1-continued

| | | | |
|---|---|---|---|
| 40 | CF₃ | (structure) | 0.26 |
| 41 | CF₃ | (structure) | 1.94 |
| 42 | CF₃ | (structure) | 0.34 |
| 43 | CF₃ | (structure) | 0.79 |
| 44 | Br | (structure) | 0.05 |
| 45 | Cl | (structure) | 0.94 |
| 46 | Cl | (structure) | 0.25 |
| 47 | CF₃ | (structure) | 0.07 |

TABLE 1-6

| | | | |
|---|---|---|---|
| 48 | CF₃ | (structure) | 0.49 |

TABLE 1-continued

| # | R | Structure | Value |
|---|---|---|---|
| 49 | Cl | 6-methyl-N-(2,2,2-trifluoroethyl)pyridazine-3-carboxamide | 0.002 |
| 50 | CF₃ | 2-((3-fluoro-5-methylpyridin-2-yl)oxy)-2-methyl-1-(1H-tetrazol-1-yl)propane | 0.32 |
| 51 | CF₃ | 2-((3-fluoro-5-methylpyridin-2-yl)oxy)-2-methyl-1-(1H-1,2,3-triazol-1-yl)propane | 1.1 |
| 52 | CF₃ | 2-((3-chloro-5-methylpyridin-2-yl)oxy)-2-methyl-1-(1H-tetrazol-1-yl)propane | 0.15 |
| 53 | Cl | 2-((5-methylpyridin-2-yl)oxy)-2-methyl-1-(1H-tetrazol-1-yl)propane | 0.055 |
| 54 | Cl | 4-methoxy-methylbenzene | NT |
| 55 | Cl | 3-methoxy-methylbenzene | NT |
| 56 | Cl | 1-(2-fluoro-6-methylpyridin-3-yl)cyclobutan-1-ol | 0.84 |

TABLE 1-continued

TABLE 1-7

| 57 | CF$_3$ | ![structure: 2-(4-methylphenyl)propan-2-ol group] | NT |
| 58 | CF$_3$ | ![structure: 1-(4-methylphenyl)ethan-1-ol group] | NT |

| Comparative Example | Structural formula or Compound name | IC$_{50}$ value (μM) |
|---|---|---|
| 1 | Bicalutamide | 1.27 |
| 2 | ![structure] | >10 |
| 3 | ![structure] | >10 |
| 4 | ![structure] | >10 |
| 5 | ![structure] | >10 |

TABLE 1-continued
TABLE 1-8
| 6 | 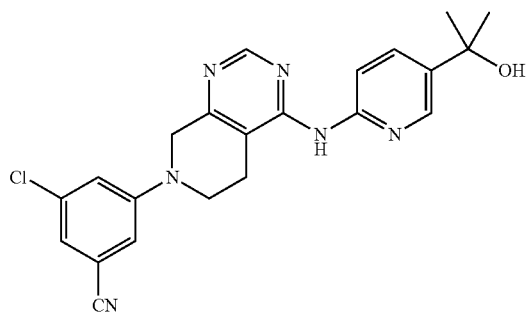 [SMILES: CC(C)(O)c1ccc(Nc2ncnc3c2CCN(c2cc(Cl)cc(C#N)c2)C3)nc1] | >10 |
| --- | --- | --- |
| 7 | 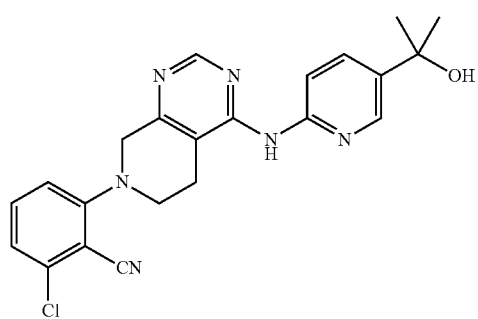 [SMILES: CC(C)(O)c1ccc(Nc2ncnc3c2CCN(c2cccc(Cl)c2C#N)C3)nc1] | >10 |
| 8 | 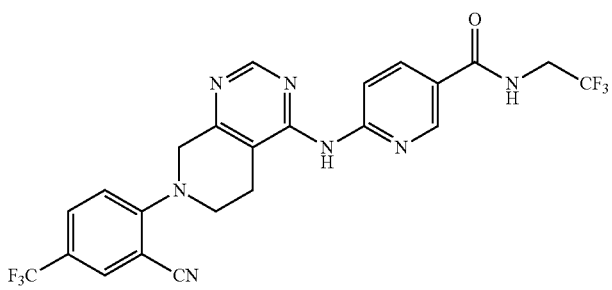 [SMILES: N#Cc1cc(C(F)(F)F)ccc1N1CCc2c(ncnc2Nc2ccc(C(=O)NCC(F)(F)F)cn2)C1] | >10 |
| 9 | 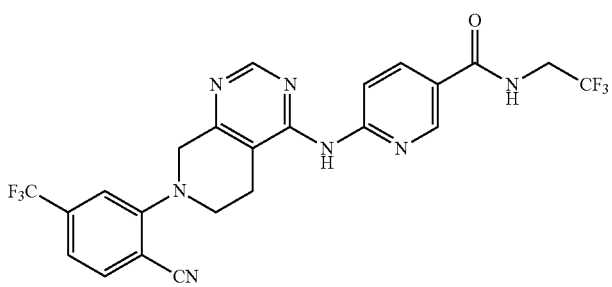 [SMILES: N#Cc1ccc(C(F)(F)F)cc1N1CCc2c(ncnc2Nc2ccc(C(=O)NCC(F)(F)F)cn2)C1] | >10 |
| 10 | 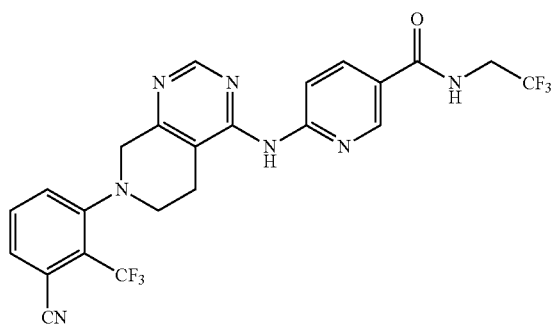 [SMILES: N#Cc1cccc(N2CCc3c(ncnc3Nc3ccc(C(=O)NCC(F)(F)F)cn3)C2)c1C(F)(F)F] | >10 |

TABLE 1-continued

| 11 | 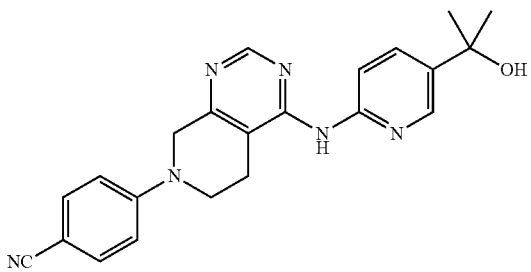 [SMILES: CC(C)(O)c1ccc(Nc2ncnc3c2CCN(c2ccc(C#N)cc2)C3)nc1] | >10 |
|---|---|---|

Test Example 2

Androgen-Dependent Inhibitory Activity on Proliferation of Prostate Cancer Cells Human prostate cancer cells LNCaP (Non-Patent Literature 5) having amplified androgen receptor gene were seeded in a clear bottom 96 well microplate (BD) at $4.0\times10^3$/well with phenol red free RPMI1640 containing 5% DCC-FBS (hereinbelow, the medium is referred to as an evaluation medium), and then cultured overnight. The culture was added with the evaluation medium containing DHT (final concentration of DHT: 10 nmol/L) or the evaluation medium containing the compound of Examples or the compound of Comparative Examples (final concentration of the compound of Examples or the compound of Comparative Examples: 10, 30, 100, 300, 1000, 3000, 10000, or 30000 nmol/L), followed by culture for 72 hours. Then, the number of viable cells was counted. The number of viable cells was measured by using Cell Counting Kit-8 (DOJINDO LABORATORIES). From the measured number of viable cells, 50% proliferation inhibition concentration (GI50 value) was calculated by logistic regression when the cell proliferation activity obtained by using 10 nmol/L DHT was 100% and the cell proliferation activity obtained by using the evaluation medium only was 0%.

The results are shown in Table 2. When compared to Bicalutamide (Comparative Example 1), the compounds of the present invention exhibited an androgen-dependent inhibitory activity on proliferation of prostate cancer cells equal to or higher than that of Bicalutamide.

TABLE 2

| Example | GI$_{50}$ value (μM) |
|---|---|
| 1 | 3.0 |
| 2 | 1.0 |
| 5 | 0.6 |
| 6 | 0.4 |
| 7 | 0.5 |
| 9 | 0.5 |
| 10 | 0.8 |
| 11 | 0.38 |
| 13 | 0.6 |
| 14 | 1.4 |
| 16 | 0.7 |
| 17 | 0.7 |
| 18 | 1.9 |
| 19 | 3.0 |
| 20 | 2.5 |
| 23 | 1.5 |
| 24 | 3.5 |
| 27 | 2.8 |
| 28 | 3.2 |
| 29 | 0.2 |

TABLE 2-continued

| Example | GI$_{50}$ value (μM) |
|---|---|
| 30 | 3.2 |
| 32 | 3.1 |
| 33 | 2.1 |
| 34 | 3.8 |
| 35 | 1.6 |
| 36 | 0.3 |
| 38 | 1.1 |
| 40 | 0.4 |
| 41 | 2.4 |
| 42 | 1.1 |
| Comparative Example 1 | 3.5 |

Test Example 3

Agonist Activity for AR

AR positive human prostate cancer cells VCaP (In Vivo 15:163-168, 2001) were seeded in a clear bottom 96 well microplate (BD) at $1.5\times10^4$/well with phenol red free RPMI1640 containing 5% DCC-FBS (hereinbelow, the medium is referred to as an evaluation medium), and then cultured overnight. The culture was added with the evaluation medium containing the compound of Examples or the compound of Comparative Examples (final concentration of the compound of Examples or the compound of Comparative Examples: 2, 5, 14, 41, 123, 370, 1111, 3333, or 10000 nmol/L), followed by culture for 72 hours. Then, the number of viable cells was counted (test group). As a control, the cells were cultured after being added with the evaluation medium only, and the number of viable cells was counted (control group). The number of viable cells was measured by using CellTiter-Glo™ Luminescent Cell Viability Assay (Promega). From the measured number of viable cells, cell proliferation rate with respect to the compound of Examples or the compound of Comparative Examples was calculated based on the number of viable cells measured in the case of using the evaluation medium only.

Cell proliferation rate (%)=(Number of viable cells in test group−Number of viable cells in control group)/(Number of viable cells in control group)×100

By considering an error in the number of viable cells measured in the case of using the evaluation medium only, when the cell proliferation rate was more than 10% at any concentration of the 9 concentrations which had been evaluated, it was determined to have an agonist activity for AR.

The results are shown in Table 3. Unlike Bicalutamide (Comparative Example 1), no agonist activity for AR was observed for the compounds of the present invention.

TABLE 3

| Example | Cell proliferation rate (%) |
|---|---|
| 1 | 8.7 |
| 2 | 3.8 |
| 3 | 1.0 |
| 5 | -5.5 |
| 6 | -0.7 |
| 7 | 4.9 |
| 9 | -0.7 |
| 10 | 2.8 |
| 11 | 2.9 |
| 13 | 2.8 |
| 15 | 0.3 |
| 16 | -1.5 |
| 17 | 0.6 |
| 18 | -4.6 |
| 20 | 0.0 |
| 21 | -0.6 |
| 23 | 5.1 |
| 25 | 6.3 |
| 26 | 5.7 |
| 27 | -0.2 |
| 32 | -2.2 |
| 33 | 4.4 |
| 34 | 6.4 |
| 35 | 0.1 |
| 36 | -1.9 |
| 37 | 0.9 |
| 38 | -2.7 |
| 39 | 5.5 |
| 40 | 0.0 |
| 42 | -17.2 |
| 44 | 5.2 |
| 46 | 1.0 |
| 47 | 1.9 |
| 48 | -2.6 |
| 50 | -3.7 |
| 51 | -5.4 |
| 52 | -3.4 |
| 54 | 3.4 |
| 55 | 1.0 |
| 56 | 8.0 |
| 57 | 5.0 |
| 58 | 2.0 |
| Comparative Example 1 | 39.7 |

Test Example 4

Evaluation of Activity of Reducing Expression Level of Androgen Receptor

AR positive human prostate cancer cells LNCaP were seeded in a clear bottom 6 well microplate (BD) at $3.5 \times 10^5$/well with phenol red free RPMI1640 containing 5% FBS (hereinbelow, the medium is referred to as an evaluation medium), and then cultured overnight. The culture was added with the evaluation medium containing the compound of Examples or the compound of Comparative Examples such that the final concentration of the compound of Examples or the compound of Comparative Examples was 10000 nmol/L, followed by culture for 48 hours. After culture for 48 hours, the medium was removed and the cells were washed with PBS and added with 0.1 mL of Lysis buffer (M-PER added with Protease Inhibitor Cocktail), followed by keeping at 4° C. for 20 minutes. After cell lysis, the cell solution was centrifuged to recover the supernatant as cell lysate. The cell lysates were adjusted to have the same protein concentration and subjected to SDS-PAGE and Western blotting using anti AR antibody (Santa Cruz Biotechnology, N-20). The antibody-reacting band (anti AR receptor) was quantified by LAS-3000 (FUJIFILM) using Super Signal West Pico Substrate (Thermo Scientific) as a detection reagent. For the quantification, when the AR expression in LNCaP was reduced by 50% or more compared with the evaluation medium control, it was determined to have an AR expression inhibitory activity.

The results are shown in Table 4. When the AR expression reducing activity is 50% or more, it is described as "reduced". For Comparative Examples 1 to 4, the AR expression reducing activity was less than 10% at 10 μM, and thus the activity was not observed at all. In contrast, the compounds of the present invention were confirmed to have AR expression reducing activity of 50% or more at 10 μM.

TABLE 4

| Example | 10 μM AR expression reducing activity |
|---|---|
| 1 | reduced |
| 2 | reduced |
| 3 | reduced |
| 4 | reduced |
| 5 | reduced |
| 6 | reduced |
| 7 | reduced |
| 8 | reduced |
| 9 | reduced |
| 10 | reduced |
| 11 | reduced |
| 12 | reduced |
| 13 | reduced |
| 14 | reduced |
| 16 | reduced |
| 17 | reduced |
| 18 | reduced |
| 20 | reduced |
| 24 | reduced |
| 26 | reduced |
| 28 | reduced |
| 30 | reduced |
| 32 | reduced |
| 34 | reduced |
| 36 | reduced |
| 37 | reduced |
| 38 | reduced |
| 39 | reduced |
| 40 | reduced |
| 41 | reduced |
| 42 | reduced |
| 44 | reduced |
| 46 | reduced |
| 47 | reduced |
| 49 | reduced |
| 50 | reduced |
| 51 | reduced |
| 52 | reduced |
| 57 | reduced |
| Comparative Example 1 | <10% |
| Comparative Example 2 | <10% |
| Comparative Example 3 | <10% |
| Comparative Example 4 | <10% |

Test Example 5

Evaluation of Anti-Tumor Activity in In Vivo Model of Castration Resistant Prostate Cancer From the AR positive human prostate cancer cells LNCaP, castration resistant prostate cancer cells, LNCaP-Xeno-IL-6 cells, were established based on the scientific paper (Clin Cancer Res, 2001 7:2941-8) (in the paper, the cells have been reported as LNCaP-IL-6+ cells) and used for the in vivo test. The LNCaP-Xeno-IL-6 cells were implanted subcutaneously in male nude mice, and the castration treatment was performed when the tumor volume reached about 200 mm³. After the castration, the vehicle only (0.5% HPMC) or the compound of Examples suspended in the vehicle was orally administered to the mice every day for 2 weeks. The compound of Examples was administered such that there was no difference in an exposure amount between the compounds. After the administration for 2 weeks, the tumor volume of each mouse was recorded and the average tumor volume of the group administered with the evaluation compound relative to the average tumor volume of the group administered only with the vehicle, that is, T/C (%), was calculated based on the following formula.

T/C (%)=(Average tumor volume of evaluation compound group)/(Average tumor volume of vehicle administration group)

The results are shown in Table 5. The compounds of the present invention exhibited an anti-tumor effect in an in vivo model of castration resistant prostate cancer.

TABLE 5

| Example | Daily dose (mg/kg/day) | T/C (%) |
| --- | --- | --- |
| 6 | 100 | 29 |
| 7 | 30 | 49 |
| 9 | 15 | 40 |
| 11 | 200 | 47 |

The invention claimed is:

1. A method for treating prostate cancer and breast cancer, comprising:
administering an effective amount of a tetrahydropyridopyrimidine compound of formula (I) or a pharmaceutically acceptable salt thereof to a subject in need thereof,

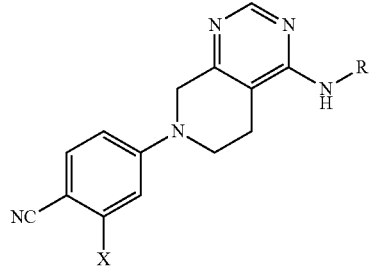

(I)

wherein, in the formula (I),
X is a halogen atom or a halogeno-$C_{1-3}$ alkyl group;
R is a $C_{6-14}$ aryl group which is substituted with $R^1$ and is simultaneously substituted or unsubstituted with $R^2$, or a 5- or 6-membered heteroaryl group which is substituted with $R^1$ and is simultaneously substituted or unsubstituted with $R^2$;
$R^1$ is a hydrogen atom, a phenyl group, a hydroxy-$C_{1-6}$ alkyl group, a hydroxy-$C_{3-7}$ cycloalkyl group, a $C_{1-6}$ alkoxy group which is substituted or unsubstituted with Ra, a $C_{3-7}$ cycloalkylaminosulfonyl group, a 3-to 7-membered monocyclic heterocycloalkylsulfonyl group, a halogeno-$C_{1-3}$ alkoxycarbonylamino group, a halogeno-$C_{1-3}$ alkylcarbonylamino group, a 3-to 7-membered monocyclic heterocycloalkanecarbonyl group substituted with a hydroxy-$C_{1-6}$ alkyl group, or —$(CH_2)_n$—C(=O)—NHRf;
$R^2$ is a hydrogen atom, a halogen atom, or a halogeno-$C_{1-3}$ alkyl group;
Ra is a $C_{1-6}$ alkylpyrazolyl group, a triazolyl group, a tetrazolyl group, or a $C_{1-6}$ alkylsulfonylpiperazinyl group;
Rf is a halogeno-$C_{1-3}$ alkyl group, a hydroxy-$C_{1-6}$ alkyl group, a hydroxy-$C_{3-7}$ cycloalkyl group, a hydroxy-$C_{3-7}$ cycloalkyl-$C_{1-6}$ alkyl group, or a $C_{1-6}$ alkyl group substituted with Rfa;
Rfa is a $C_{1-6}$ alkylpyrazolyl group, a halogeno-$C_{1-3}$ alkylthiazolyl group, an oxadiazolyl group, or a halogeno-$C_{1-3}$ alkyloxadiazolyl group; and
n is an integer of from 0 to 3.

2. The method of claim 1, wherein, in the formula (I), X is a chlorine atom, a bromine atom, or a trifluoromethyl group.

3. The method of claim 1, wherein, in the formula (I), n is 0 or 1.

4. The method of claim 1, wherein, in the formula (I), R is selected from the group consisting of:

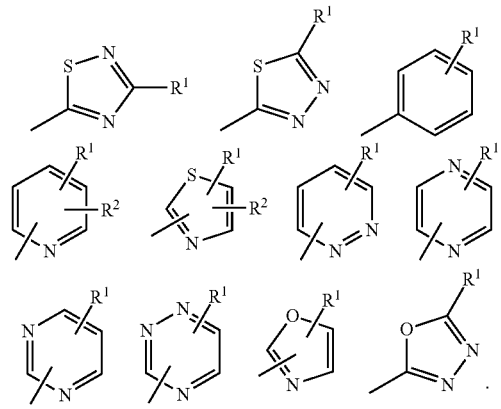

5. The method of claim 1, wherein, in the formula (I), $R^1$ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanyl sulfonyl group, a 2,2,2-trifluoroethoxycarbonylamino group, a 2,2,2-trifluoroethylcarbonylamino group, a piperidinecarbonyl group substituted with a hydroxy-isopropyl group, or —$(CH_2)_n$—C(=O)—NHRf;
Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with a trifluoromethyloxazolyl group; and
n is 0 or 1.

6. The method of claim 1, wherein, in the formula (I), R is selected from the group consisting of:

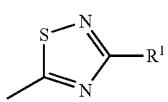

where R¹ is a hydrogen atom;

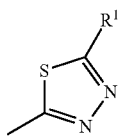

where R¹ is —(CH$_2$)$_n$—C(=O)—NHRf,
Rf is a methyl group substituted with Rfa or an ethyl group substituted with Rfa,
Rfa is a methylpyrazolyl group or an oxadiazolyl group, and
n is 0;

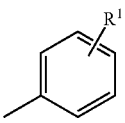

where R¹ is a phenyl group, a hydroxy-ethyl group, a hydroxy-isopropyl group, a methoxy group, an isopropoxy group, an ethoxy group substituted with a methylpyrazolyl group, or an n-propoxy group substituted with a methylsulfonylpiperazinyl group;

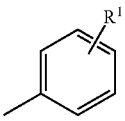

where R¹ is a hydroxy-isopropyl group, a hydroxy-cyclopropyl group, a hydroxy-cyclobutyl group, an isopropoxy group, an ethoxy group substituted with a triazolyl group, a 2-methylpropoxy group substituted with a triazolyl group, a 2-methylpropoxy group substituted with a tetrazolyl group, a cyclopropylaminosulfonyl group, a 2,2,2-trifluoroethoxycarbonylamino group, a 2,2,2-trifluoroethylcarbonylamino group, or —(CH$_2$)—C(=O)$_n$—NHRf,
R² is a hydrogen atom, a fluorine atom, or a chlorine atom,
Rf is a 2,2-difluoroethyl group, a 2,2,2-trifluoroethyl group, a methyl group substituted with Rfa, or an ethyl group substituted with Rfa,
Rfa is a trifluoromethylthiazolyl group, an oxadiazolyl group, or a trifluoromethyloxadiazolyl group, and
n is 0 or 1;

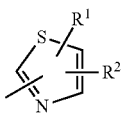

where R¹ is a hydroxy-isopropyl group, a 1,4-oxazepanylsulfonyl group, or —(CH$_2$)$_n$—C(=O)—NHRf,
R² is a hydrogen atom or a trifluoromethyl group,
Rf is a 2,2,2-trifluoroethyl group or an ethyl group substituted with Rfa,
Rfa is an oxadiazolyl group, and
n is 0;

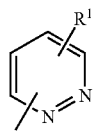

where R¹ is a hydroxy-isopropyl group or —(CH$_2$)$_n$—C(=O)—NHRf,
Rf is a 2,2-difluoroethyl group, a 2,2,2-trifluoroethyl group, a hydroxy-2-methylpropyl group,
a hydroxycyclohexyl group, a hydroxycyclopropylmethyl group, and
n is 0;

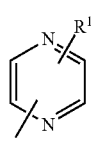

where R¹ is —(CH$_2$)$_n$—C(=O)—NHRf,
Rf is a hydroxy-2-methylpropyl group, and
n is 0;

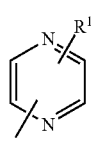

where R¹ is —(CH$_2$)$_n$—C(=O)—NHRf,
Rf is a hydroxy-2-methylpropyl group, and
n is 0;

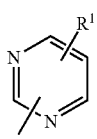

where R¹ is —(CH$_2$)$_n$—C(=O)—NHRf,
Rf is a 2,2,2-trifluoroethyl group, and
n is 0;

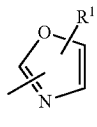

where R¹ is a piperidinecarbonyl group substituted with a hydroxy-isopropyl group; and

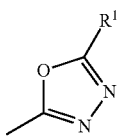

where $R^1$ is a piperidinecarbonyl group substituted with a hydroxy-isopropyl group.

7. The method of claim 1, wherein, in the formula (I), X is a chlorine atom, a bromine atom, or a trifluoromethyl group, and
R is selected from the group consisting of:

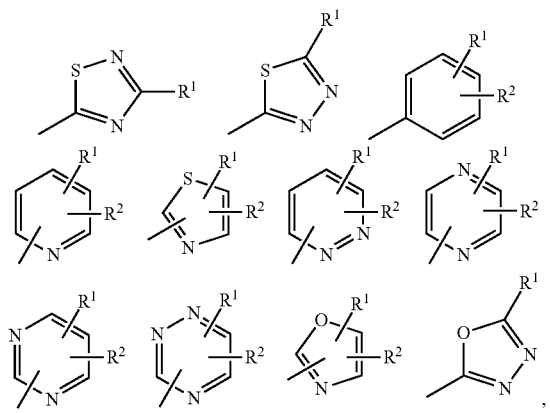

where $R^1$ is a hydrogen atom, a phenyl group, a hydroxy-$C_{1-4}$ alkyl group, a hydroxy-$C_{3-5}$ cycloalkyl group, a $C_{1-4}$ alkoxy group which is substituted or unsubstituted with Ra, a $C_{3-5}$ cycloalkylaminosulfonyl group, a 7-membered monocyclic heterocycloalkylsulfonyl group, a fluoro-$C_{1-3}$ alkoxycarbonylamino group, a fluoro-$C_{1-3}$ alkylcarbonylamino group, a 6-membered monocyclic heterocycloalkanecarbonyl group substituted with a hydroxy-$C_{1-4}$ alkyl group, or —$(CH_2)_n$—C(=O)—NHRf, $R^2$ is a hydrogen atom, a fluorine atom, a chlorine atom, or a trifluoromethyl group;

Ra is a $C_{1-4}$ alkylpyrazolyl group, a triazolyl group, a tetrazolyl group, or a $C_{1-4}$ alkylsulfonylpiperazinyl group, Rf is a fluoro-$C_{1-3}$ alkyl group, a hydroxy-$C_{1-4}$ alkyl group, a hydroxy-$C_{3-5}$ cycloalkyl group, a hydroxy-$C_{3-5}$ cycloalkyl-$C_{1-4}$ alkyl group, or a $C_{1-4}$ alkyl group substituted with Rfa, Rfa is a $C_{1-4}$ alkylpyrazolyl group, a fluoro-$C_{1-3}$ alkylthiazolyl group, an oxadiazolyl group, or a fluoro-$C_{1-3}$ alkyloxadiazolyl group, and n is 0 or 1.

8. The method of claim 7, wherein, in the formula (I), R is selected from the group consisting of:

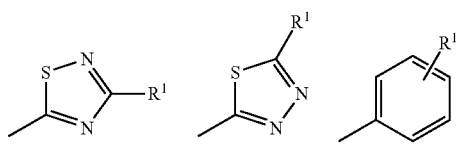

-continued

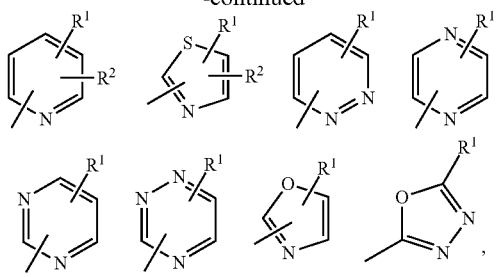

where $R^1$ is a hydrogen atom, a phenyl group, a hydroxy-ethyl group, a hydroxy-isopropyl group, a hydroxy-cyclopropyl group, a hydroxy-cyclobutyl group, a methoxy group, an isopropoxy group, an ethoxy group substituted with a methylpyrazolyl group, an ethoxy group substituted with a triazolyl group, a 2-methylpropoxy group substituted with a triazolyl group, a 2-methylpropoxy group substituted with a tetrazolyl group, an n-propoxy group substituted with a methylsulfonylpiperazinyl group, a cyclopropylaminosulfonyl group, a 1,4-oxazepanyl sulfonyl group, a 2,2,2-trifluoroethoxycarbonylamino group, a 2,2,2-trifluoroethylcarbonylamino group, a piperidinecarbonyl group substituted with a hydroxy-isopropyl group, or —$(CH_2)_n$—C(=O)—NHRf, $R^2$ is a hydrogen atom, a fluorine atom, a chlorine atom, or a trifluoromethyl group; Rf is a 2,2-difluoroethyl group, a 2,2,2-trifluoroethyl group, a hydroxy-2-methylpropyl group, a hydroxycyclohexyl group, a hydroxycyclopropylmethyl group, a methyl group substituted with a trifluoromethylthiazolyl group, an ethyl group substituted with a methylthiazolyl group, an ethyl group substituted with an oxadiazolyl group, or an ethyl group substituted with a trifluoromethyl group, and n is 0 or 1.

9. The method of claim 8, wherein, in the formula (I), X is a chlorine atom or a trifluoromethyl group, and
R is selected from the group consisting of:

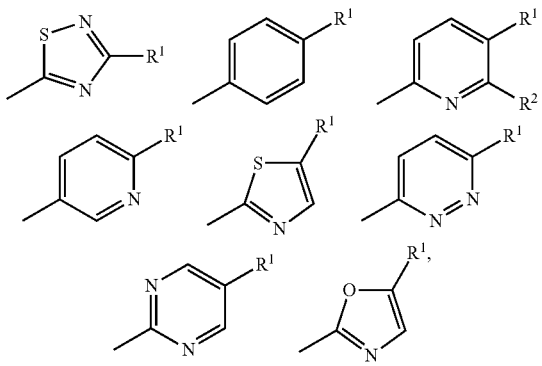

where $R^1$ is a hydrogen atom, a hydroxy-isopropyl group, an isopropoxy group, a 2-methylpropoxy group substituted with a tetrazolyl group, an n-propoxy group substituted with a methylsulfonylpiperazinyl group, a 1,4-oxazepanylsulfonyl group, a piperidinecarbonyl group substituted with a hydroxy-isopropyl group, or —$(CH_2)_n$—C(=O)—NHRf, $R^2$ is a hydrogen atom or a fluorine atom, Rf is a 2,2,2-trifluoroethyl group, a hydroxy-2-methylpropyl group, a methyl group substituted with a trifluoromethylthiazolyl group, an ethyl group substituted with an oxadiazolyl group, or an ethyl group substituted with a trifluoromethyloxadiazolyl group, and n is 0.

10. The method of claim 1, wherein the tetrahydropyridopyrimidine compound is at least one selected from the group consisting of:
- 4-(4-((1,2,4-thiadiazol-5-yl)amino)-5,6-dihydropyrido[3,4-d]pyrimidin-7(8H)-yl)-2-(trifluoromethyl)benzonitrile;
- 4-(4-((4-isopropoxyphenyl)amino)-5,6-dihydropyrido[3,4-d]pyrimidin-7(8H)-yl)-2-(trifluoromethyl)benzonitrile,
- 4-(4-((6-fluoro-5-(2-hydroxypropan-2-yl)pyridin-2-yl)amino)-5,6-dihydropyrido[3,4-d]pyrimidin-7(8H)-yl)-2-(trifluoromethyl)benzonitrile;
- 2-chloro-4-(4-((6-(2-hydroxypropan-2-yl)pyridazin-3-yl)amino)-5,6-dihydropyrido[3,4-d]pyrimidin-7(8H)-yl)benzonitrile;
- 4-(4-4-((5-(2-hydroxypropan-2-yl)pyridin-2-yl)amino)-5,6-dihydropyrido[3,4-d]pyrimidin-7(8H)-yl)-2-(trifluoromethyl)benzonitrile;
- 2-chloro-4-(4-((5-(2-hydroxypropan-2-yl)pyridin-2-yl)amino)-5,6-dihydropyrido[3,4-d]pyrimidin-7(8H)-yl)benzonitrile;
- 4-(4-((6-(2-hydroxypropan-2-yl)pyridazin-3-yl)amino)-5,6-dihydropyrido[3,4-d]pyrimidin-7(8H)-yl)-2-(trifluoromethyl)benzonitrile;
- 6-((7-(4-cyano-3-(trifluoromethyl)phenyl)-5,6,7,8,-tetrahydropyrido[3,4-d]pyrimidin-4-yl)amino)-N-(2,2,2-trifluoroethyl)nicotinamide;
- 4-(4-((6-isopropoxypyridin-3-yl)amino)-5,6-dihydropyrido[3,4-d]pyrimidin-7(8H)-yl)-2-(trifluoromethyl)benzonitrile;
- 4-(4-((6-(2-methyl-2-(1H-tetrazol-1-yl)propoxy)pyridin-3 -yl)amino)-5,6-dihydropyrido[3,4-d]pyrimidin-7(8H)-yl)-2-(trifluoromethyl)benzonitrile;
- 4-(4-((5-(2-methyl-2-(1H-tetrazol-1-yl)propoxy)pyridin-2-yl)amino)-5,6-dihydropyrido[3,4-d]pyrimidin-7(8H)-yl)-2-(trifluoromethyl)benzonitrile;
- 4-(4-((4-(3-(4-(methylsulfonyl)piperazin-1-yl)propoxy)phenyl)amino)-5,6-dihydropyrido[3,4-d]pyrimidin-7(8H)-yl)-2-(trifluoromethyl)benzonitrile;
- 4-(4-((5-((1,4-oxazepan-4-yl)sulfonyl)thiazol-2-yl)amino)-5,6-dihydropyrido[3,4-d]pyrimidin-7(8H)-yl)-2-(trifluoromethyl)benzonitrile;
- 6-((7-(4-cyano-3-(trifluoromethyl)phenyl)-5,6,7,8-tetrahydropyrido[3,4-d]pyrimidin-4-yl)amino)-N-(2-hydroxy-2-methylpropyl)pyridazine-3-carboxamide;
- 2-((7-(4-cyano-3-(trifluoromethyl)phenyl)-5,6,7,8-tetrahydropyrido[3,4-d]pyrimidin-4-yl)amino)-N-(2-hydroxy-2-methylpropyl)pyrimidine-5-carboxamide;
- 6((7-(4-cyano-3-(trifluoromethyl)phenyl)-5,6,7,8-tetrahydropyrido[3,4-d]pyrimidin-4-yl)amino)-N-((4-(trifluoromethyl)thiazol-2-yl)methyl)nicotinamide;
- (R)-N-(1-(1,3,4-oxadiazol-2-yl)ethyl)-6-((7-(4-cyano-3-(trifluoromethyl)phenyl)-5,6,7,8-tetrahydropyrido[3,4-d]pyrimidin-4-yl)amino)nicotinamide;
- (R)-6-((7-(4-cyano-3-(trifluoromethyl)phenyl)-5,6,7,8-tetrahydropyrido[3,4-d]pyrimidin-4-yl)amino)-N-(1-(5-(trifluoromethyl)-1,3,4-oxadiazol-2-yl)ethyl)nicotinamide; and
- 4-(4-((5-(4-(2-hydroxypropan-2-yl)piperidin-1-carbonyl)oxazol-2-yl)amino)-5,6-dihydropyrido[3,4-d]pyrimidin-7(8H)-yl)-2-(trifluoromethyl)benzonitrile.

11. The method of claim 1, wherein the subject has breast cancer.

12. The method of claim 10, wherein the subject has prostate cancer.

13. The method of claim 1, wherein the subject has prostate cancer.

14. The method of claim 13, wherein the prostate cancer is at least one selected from the group consisting of castration resistant prostate cancer, hormone resistant prostate cancer, PSA recurrent prostate cancer, taxan resistant prostate cancer, and radiation resistant prostate cancer.

15. The method of claim 1, wherein the tetrahydropyridopyrimidine compound or the pharmaceutically acceptable salt thereof is orally administered to the subject.

16. The method of claim 1, wherein the tetrahydropyridopyrimidine compound or the pharmaceutically acceptable salt thereof is administered to the subject in an amount of 0.05 to 5,000 mg per day.

17. The method of claim 1, wherein the tetrahydropyridopyrimidine compound or the pharmaceutically acceptable salt thereof is administered to the subject once, twice, three times, or four times a day.

18. The method of claim 10,
wherein
the tetrahydropyridopyrimidine compound or the pharmaceutically acceptable salt thereof is orally administered to the subject.

19. The method of claim 10, wherein the subject has breast cancer.

* * * * *

UNITED STATES PATENT AND TRADEMARK OFFICE
CERTIFICATE OF CORRECTION

PATENT NO. : 9,889,136 B2
APPLICATION NO. : 15/203059
DATED : February 13, 2018
INVENTOR(S) : Kazuhisa Minamiguchi et al.

It is certified that error appears in the above-identified patent and that said Letters Patent is hereby corrected as shown below:

In the Claims

Column 157, Line 36, Claim 1, "prostate cancer and breast cancer" should read -- prostate cancer or breast cancer --

Column 159, Line 52, Claim 6, "-(CH$_2$)-C(=O)$_n$-NHRf" should read -- -(CH$_2$)$_n$-C(=O)-NHRf --

Column 162, Line 24, Claim 8, "1,4-oxazepanyl sulfonyl group" should read -- 1,4-oxazepanylsulfonyl group --

Column 163, Lines 22-24, Claim 10, "4-(4-4-((5-(2-hydroxypropan-2-yl)pyridin-2-yl)amino)-5,6-dihydropyrido[3,4-d]pyrimidin-7(8H)-yl)-2-(trifluoromethyl)benzonitrile;" should read -- 4-(4-((5-(2-hydroxypropan-2-yl)pyridin-2-yl)amino)-5,6-dihydropyrido[3,4-d]pyrimidin-7(8H)-yl)-2-(trifluoromethyl)benzonitrile --

Column 163, Lines 37-39, Claim 10, "4-(4-((6-(2-methyl-2-(1H-tetrazol-1-yl)propoxy)pyridin-3- yl)amino)-5,6-dihydropyrido[3,4-d]pyrimidin-7(8H)-yl)-2-(trifluoromethyl)benzonitrile;" should read -- 4-(4-((6-(2-methyl-2-(1H-tetrazol-1-yl)propoxy)pyridin-3-yl)amino)-5,6-dihydropyrido[3,4-d]pyrimidin-7(8H)-yl)-2-(trifluoromethyl)benzonitrile; --

Signed and Sealed this
Eleventh Day of June, 2019

Andrei Iancu
*Director of the United States Patent and Trademark Office*